(12) United States Patent
Xiong et al.

(10) Patent No.: US 11,655,239 B2
(45) Date of Patent: May 23, 2023

(54) FUSED RING PYRIMIDINE AMINO COMPOUND AND PREPARATION METHOD, PHARMACEUTICAL COMPOSITION, AND USE THEREOF

(71) Applicant: SHANGHAI INSTITUTE OF MATERIAL MEDICA, CHINESE ACADEMY OF SCIENCES, Shanghai (CN)

(72) Inventors: Bing Xiong, Shanghai (CN); Jia Li, Shanghai (CN); Meiyu Geng, Shanghai (CN); Jingkang Shen, Shanghai (CN); Yi Zang, Shanghai (CN); Jing Ai, Shanghai (CN); Danqi Chen, Shanghai (CN); Qi Wang, Shanghai (CN); Ying Dong, Shanghai (CN); Xia Peng, Shanghai (CN); Yinchun Ji, Shanghai (CN); Qian Tan, Shanghai (CN)

(73) Assignee: Shanghai Institute Of Material Medica, Chinese Academy of Sciences, Shanghai (CN)

(*) Notice: Subject to any disclaimer, the term of this patent is extended or adjusted under 35 U.S.C. 154(b) by 0 days.

(21) Appl. No.: 17/628,246

(22) PCT Filed: Jul. 17, 2020

(86) PCT No.: PCT/CN2020/102653
§ 371 (c)(1),
(2) Date: Jan. 19, 2022

(87) PCT Pub. No.: WO2021/013084
PCT Pub. Date: Jan. 28, 2021

(65) Prior Publication Data
US 2022/0274962 A1   Sep. 1, 2022

(30) Foreign Application Priority Data

Jul. 19, 2019  (CN) .......................... 201910654591.7
Jul. 13, 2020  (CN) .......................... 202010667271.8

(51) Int. Cl.
| | | |
|---|---|---|
| C07D 239/84 | (2006.01) |
| C07D 401/14 | (2006.01) |
| C07D 403/12 | (2006.01) |
| C07D 417/14 | (2006.01) |
| A61P 11/00 | (2006.01) |
| A61K 31/517 | (2006.01) |
| A61K 45/06 | (2006.01) |
| C07D 403/14 | (2006.01) |

(52) U.S. Cl.
CPC .......... C07D 403/12 (2013.01); A61K 31/517 (2013.01); A61K 45/06 (2013.01); A61P 11/00 (2018.01); C07D 239/84 (2013.01); C07D 401/14 (2013.01); C07D 403/14 (2013.01); C07D 417/14 (2013.01)

(58) Field of Classification Search
CPC .. C07D 239/84; C07D 401/14; C07D 403/12; C07D 417/14
See application file for complete search history.

(56) References Cited

FOREIGN PATENT DOCUMENTS

| CN | 109305944 A | 2/2019 |
| EP | 1878727 A1 | 1/2008 |
| EP | 1836174 B1 | 2/2013 |
| WO | 2006039718 A2 | 4/2006 |
| WO | 2016051186 A1 | 4/2016 |

OTHER PUBLICATIONS

Japanese Office Action for Japanese Patent Application No. 2022-503815, dated Jul. 5, 2022.
International Search Report for International Patent Application No. PCT/CN2020/102653, dated Sep. 22, 2020.
Written Opinion of the International Searching Authority for International Patent Application No. PCT/CN2020/102653, dated Sep. 22, 2020.
Chinese Office Action for Chinese Patent Application No. 202010667271.8, dated Jun. 8, 2021.

(Continued)

*Primary Examiner* — Brian E McDowell
(74) *Attorney, Agent, or Firm* — Pilloff Passino & Cosenza LLP; Sean A. Passino; Rachel K. Pilloff

(57) ABSTRACT

The present disclosure relates to a fused ring pyrimidine amino compound and a preparation method, a pharmaceutical composition, and a use thereof. Specifically disclosed in the present disclosure are the compound shown in formula I, a pharmaceutically acceptable salt thereof, a tautomer thereof, a stereoisomer thereof, a metabolite thereof, a metabolic precursor thereof, or a prodrug thereof. The fused ring pyrimidine amino compound of the present application has good inhibitory activity against DDRs, particularly DDR2, and has a good therapeutic effect on tumors and fibrotic diseases, especially pulmonary inflammation and pulmonary fibrosis. Also disclosed in the present disclosure are a preparation method for the compound shown in formula I, and a use thereof.

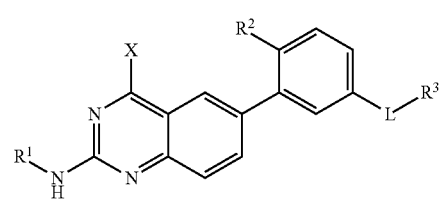

16 Claims, 12 Drawing Sheets

(56) References Cited

OTHER PUBLICATIONS

Brad Herberich et al., "Discovery of Highly Selective and Potent p38 Inhibitors Based on a Phthalazine Scaffold," Journal of Medicinal Chemistry, Sep. 26, 2008, pp. 6271-6279, vol. 51, No. 20.

Martin Golkowski et al., "Rapid profiling of protein kinase inhibitors by quantitative proteomics," Med. Chem. Comm., Dec. 11, 2013, pp. 363-369, vol. 5, No. 3.

Notification to Grant Patent Right for Invention for Chinese Patent Application No. 202010667271.8, dated Nov. 3, 2021.

Canadian Office Action issued in Canadian Patent Application No. 3,147,852, dated Mar. 23, 2022.

Nov. 22, 2022 Japanese Decision of Rejection issued in Japanese Patent Application No. 2022503815.

FUSED RING PYRIMIDINE AMINO COMPOUND AND PREPARATION METHOD, PHARMACEUTICAL COMPOSITION, AND USE THEREOF

The present application claims the priority of the Chinese patent application CN 201910654591.7 with the filing date of Jul. 19, 2019, and the Chinese patent application CN 202010667271.8 with the filing date of Jul. 13, 2020. The entirety of the above Chinese patent application is cited by the present application.

TECHNICAL FIELD

The present disclosure belongs to the technical field of biomedicine, and relates to a fused ring pyrimidine amino compound, preparation method, pharmaceutical composition and use thereof.

BACKGROUND

Various types of fibrosis such as pulmonary fibrosis (PF) are characterized by the proliferation of fibroblasts (Fb) and the accumulation of large amounts of extracellular matrix (ECM). A variety of factors can cause pulmonary fibrosis, such as occupational dust ($SiO_2$, etc.), radiation damage and certain drugs (bleomycin). There is also a type of pulmonary fibrosis of unknown etiology—idiopathic pulmonary fibrosis (IPF). Although the causes are different, the development and outcome of fibrosis are basically similar, that is, it starts from the infiltration of inflammatory cells in lower respiratory tract; damage to alveolar epithelial cells and vascular endothelial cells is gradually caused; and the release of myofibroblasts (MF) and type II alveolar epithelial cell proliferating cytokines is accompanied, resulting in the deposition of extracellular matrix protein and collagen and ultimately causing damage to the lung structure. The late stage of pulmonary fibrosis often causes heart and lung failure and death, which is extremely harmful to humans. At present, the exact mechanism of pulmonary fibrosis is unclear, and no breakthrough progress has been made in early prevention and treatment.

Discoidindomain receptors (DDRs) are receptor-type protein tyrosine kinases (RTKs). It has been found that the family contains two members: DDR1 and DDR2.

Discoidindomain receptors are closely related to the normal development of the body. After knocking out the mouse systemic discoidindomain receptor gene, although the mouse embryo develops normally, the gene knockout would cause a wide range of tissue and organ defects. The most obvious phenotype directly caused by the deletion of the discoidindomain receptor gene is the change in body size, including the size of the bones, the body weight, and the amount of fat. Knockout of the DDR1 gene would result in that fibula calcification is decreased, the morphology of the mammary glands is changed and consequently cause lactation disorders, and blastocysts can not be implanted in the uterine wall and consequently cause reproductive disorders. Knockout of the DDR2 gene would result in that the proliferation of chondrocytes is decreased and consequently cause defects in bone growth, and the proliferation of fibroblasts is decreased and consequently cause wounds that cannot heal. Therefore, the discoidindomain receptors are very important for the normal development of bones, the differentiation of mammary glands and the implantation of blastocysts. Discoidindomain receptors play an important role in the various stages of the body's development to maturity. DDR1 and DDR2 have obvious specificity in the distribution of cells and tissues. The expression of DDR1 is mainly restricted to epithelial cells, while the expression of DDR2 is mainly restricted to mesenchymal cells. In addition to the widespread expression of discoidindomain receptors in immune cells and the developing nervous system, DDR1 is only highly expressed in mouse and human brain, lung, kidney, spleen, placenta tissues, etc., while DDR2 is highly expressed in bone, heart, muscle, kidney and lung. In addition, in different tissues, the distribution of different subtypes also has obvious differences. DDR1b is mainly expressed in embryonic and adult tissues, while DDR1a is highly expressed in human breast cancer cells and glioma cells. It is precisely because of the widespread expression of discoidindomain receptors in the human body that discoidindomain receptors play an important role in regulating the development of organs, influencing cell adhesion, differentiation, proliferation and migration, regulating the expression of matrix metalloproteinases and epithelial-mesenchymal transition, remodeling the extracellular matrix, etc. Abnormal activation of discoidindomain receptors can lead to diseases. Current studies have shown that discoidindomain receptors regulate the occurrence and development of tumors, fibrosis, atherosclerosis, osteoarthritis and other diseases through activation of signal pathways.

The mutations and expression level change of discoidindomain receptors are common in the occurrence and development of tumors, which suggests that they may play a key role in promoting tumor development in different stages of the same tumor or in different tumor types. As shown in the figure, discoidindomain receptors play different roles in tumor cell proliferation and apoptosis. DDR1 can promote the proliferation and growth of tumor cells in both malignant and non-malignant tumor cells. For example, it can promote tumor cell proliferation and apoptosis in human colorectal cancer, human glioma cells, breast cancer and other malignant tumor cells. However, there are also some reports in the literature that DDR1 can inhibit the proliferation and growth of tumor cells in some tumor cells. DDR2 can promote the proliferation and growth of human squamous cell carcinoma cells, colon cancer cells and other cells. Epithelial-mesenchymal transition plays an important role in embryonic development, tissue reconstruction, chronic inflammatory response, various fibrotic diseases and cancer metastasis. Through epithelial-mesenchymal transition, epithelial cells would lose cell polarity and at the same time lose epithelial phenotypes such as the link with the matrix membrane, thereby gaining the ability to migrate and invade, and at the same time gaining the ability to resist apoptosis and degrade the extracellular matrix. Discoidindomain receptors play an important role in epithelial-mesenchymal transition. Knockout of discoidindomain receptors (DDR1 and DDR2) in human lung cancer cells can inhibit the occurrence of epithelial-mesenchymal transition. [38]A very important function of the discoidindomain receptors is the regulation of cell adhesion. Discoidindomain receptors cause tumor cells to spread by promoting the adhesion of tumor cells to the collagen in the extracellular matrix, initiating signal pathways and amplifying the cascade reaction, and then causing the contraction of myosin and the polymerization of actin. [39, 40]Changes in the microenvironment of tumor extracellular matrix can make tumor cells acquire an aggressive phenotype. The invasion of tumor cells into the extracellular matrix is a complex process involving multiple genes, but the process ultimately depends on the receptors of the extracellular matrix and the matrix metalloproteinases in the extracellular matrix. Tumor cells need to destroy the extracellular matrix to break through the tissue barrier. In tumor cells, discoidindomain receptors can disrupt the signal transduction between normal cells and the matrix, thereby promoting tumor cell migration and invasion.

Through the analysis of tissue samples of different types of fibrosis clinical samples from patients at home and abroad, the distribution and content of collagen receptors in various pulmonary fibrotic tissues are determined. In fibrotic tissues, the mRNA expression levels of the four collagen receptor genes, including DDR1, DDR2, integrin α1, and integrin α10, were significantly higher than those in normal lung tissue. The most significant was that the average expression level of DDR2 exceeds nearly a hundred times. According to the amount of mRNA expression, the order is DDR1, integrin α1, and integrin α10. The expression levels of DDR1 and DDR2 in the discoidindomain receptor family in normal lung tissue are very low. The difference is that in idiopathic pulmonary fibrosis, the expression of DDR2 is extremely significant. In all cases, compared with normal lung tissue, the mRNA content of DDR2 is significantly elevated, and the protein level is also significantly elevated. DDR1 varies greatly among individuals, and the expression levels of integrin α1 and integrin α10 mRNA are lower in lung tissues of patients with idiopathic pulmonary fibrosis than in normal lung tissues.

At present, the research on the mechanism of pulmonary fibrosis for discoidindomain receptors mainly focuses on the establishment of gene-deletion mouse models. In the idiopathic pulmonary fibrosis model, DDR2 is a key factor in promoting pulmonary fibrosis. The protein level and mRNA level of DDR2 can be significantly up-regulated in the pulmonary fibrosis model induced by type I collagen and bleomycin, and the deletion of DDR2 gene would significantly reduce the degree of pulmonary fibrosis damage. The expression of DDR1 is mainly concentrated in epithelial cells and macrophages, while DDR2 is highly expressed in mesenchymal cells, such as lung fibroblasts stimulated by TGF-β and myofibroblasts in pulmonary fibrosis. In pulmonary fibrosis, the expression of DDR1 induced by type I collagen is mainly dependent on the signal transduction effect of DDR2 receptor activation, which implies that DDR2 plays a more important role in both early and late stages.

DDR2 can regulate the activation of myofibroblasts via activation and non-activation manners. TGF-β is one of the most important cytokines that can induce the activation of myofibroblasts. Throughout the process of fibrosis, the expression level of TGF-β1 shows a trend of first increasing and then decreasing. In the most severe period of inflammation, TGF-β expression reaches its highest point. However, collagen begins to be expressed in large quantities in the later stage of inflammation, that is, the fibrosis stage. In the case of TGF-β induction or collagen stimulation, DDR2 regulates the process of fibrosis through different signal transduction pathways. In the early and middle stages of inflammation, the DDR2 receptor itself can promote the formation of myofibroblasts in an activation-independent manner by regulating the phosphorylation of p38/Akt induced by TGF-β1. In the fibrosis phase, DDR2 activates the downstream Erk1/2 pathway to activate myofibroblasts and accelerate the process of pulmonary fibrosis by sensing a large amount of collagen in the extracellular matrix in an activation-dependent manner.

DDR2 is an important regulator of endothelial cell activity and angiogenesis.

In the process of fibrosis, the overexpression of DDR2 can promote the proliferation and migration of umbilical vein endothelial cells in vitro and promote the angiogenesis induced by VEGFR. DDR2 can regulate the angiogenesis process in the process of pulmonary fibrosis by participating in the regulation of the expression of vascular endothelial growth factor, human angiopoietin, and fibroblast growth factor that promote angiogenesis. At the same time, DDR2 can also regulate the tissue repair process of pulmonary fibrosis.

Atherosclerosis is one of the common cardiovascular and cerebrovascular diseases, and has gradually attracted people's attention because of its high morbidity and high fatality rate. Inflammatory response plays an important role in the occurrence and development of atherosclerosis, and discoidindomain receptors are involved in regulating the inflammatory response in atherosclerosis. DDR1 can regulate the infiltration and accumulation of inflammatory cells, cause the pseudopodia to extend to increase the migration rate through the three-dimensional collagen network, increase the adhesion of the discoidindomain receptors to collagen and invasion to promote the aggregation of macrophages under the endothelium and the infiltration of inflammatory cells, and eventually lead to the occurrence of atherosclerosis.

In addition, DDR1 promotes the progression of atherosclerosis by regulating cell differentiation, producing chemokines and cytokines to continuously activate the DDR1 signaling pathway. DDR2 can specifically mediate the activation of human dendritic cell functions, and improve the ability of antigen uptake and activate the infiltration of T lymphocytes by increasing the levels of cytokines such as TNF-α, IL-12 and IFN-α. In the model of atherosclerosis, the expression level of DDR2 in macrophages is significantly elevated, proving that DDR2 also plays an important role in the occurrence and development of atherosclerosis. Smooth muscle cells play an important role in atherosclerosis. Mature arterial vascular smooth muscle cells would dedifferentiate under inflammatory stimuli and transform from contractile smooth muscle cells into secretory smooth muscle cells with a lower degree of differentiation, and dedifferentiate through continuous proliferation and migrate into the inner membrane to synthesize large amounts of extracellular matrix proteins, leading to the occurrence of atherosclerosis. The type I collagen and type III collagen produced by smooth muscle cells promote the phenotypic transformation of smooth muscle cells and the aggregation of inflammatory cells by maintaining elastic resilience, tensile strength, and plaque stability. In atherosclerotic plaques, the discoidindomain receptors on smooth muscle cells can bind to a variety of collagen, which means that the discoidindomain receptors would participate in regulating the phenotypic transformation of smooth muscle cells and plays a key role in promoting proliferation, migration and the synthesis of extracellular matrix in which smooth muscle cells involve. The stability of atherosclerotic plaque is an important factor to prevent end-stage events such as myocardial infarction, sudden cardiac death and stroke. The accumulation of extracellular matrix isan important feature for stabilizing atherosclerotic plaques. In the late stage of atherosclerosis, the stability of plaque would be affected by collagen-degrading enzymes, extracellular matrix metalloproteinases (MMPs). Discoidindomain receptors can cause plaque rupture by regulating smooth muscle cells and macrophages to produce matrix metalloproteinases such as MMP-1, MMP-2, MMP-8 and MMP-9 to degrade the extracellular matrix so as to destroy the stability of atherosclerotic plaque.

Rheumatoid arthritis is an autoimmune disease with synovitis of the joints as the main feature and with the destruction of articular cartilage and bone due to excessive synovial hyperplasia and recurrent severe inflammation. The discoidindomain receptor DDR2 is specifically and highly expressed in the synovial tissue of rheumatoid arthritis. Under the stimulation of type II collagen, DDR2 can make synovial cells highly express a matrix metalloproteinase-1 or -13 that can destroy cartilage. Experiments have shown that the interstitial component of articular cartilage is type II collagen. Under abnormal immune state, disintegration in the joint cavity produces a very small amount of type II collagen. The collagen acts on DDR2, causes the overexpression of the matrix metalloproteinase-1 or -13 and causes damage to articular cartilage. The dissolved type II collagen would stimulate the overexpression of DDR2 and the secretion of MMP-1 again, and this would go back and forth, forming a vicious circle with a cascade amplification effect. Studies have shown that a suitable receptor blocker can effectively block the binding of type II collagen to DDR2, thereby reducing cartilage damage. This provides new ideas for the treatment of rheumatoid arthritis.

Patent application WO2016/051186A1 discloses a class of fused ring pyrimidine amino compounds, and specifically discloses compounds with the following structures. The compound is a p38MAPK inhibitor and can be used to treat diseases caused by inflammation.

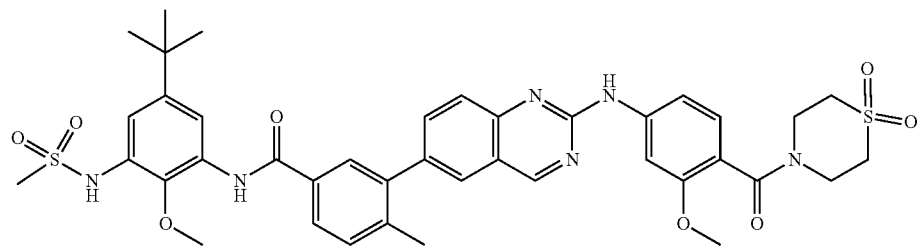

CONTENT OF THE PRESENT INVENTION

The technical problem to be solved in the present disclosure is to overcome the defect of the existing DDR inhibitors having a single structure, and the present disclosure provides a fused ring pyrimidine amino compound and a preparation method, a pharmaceutical composition, and a use thereof. The fused ring pyrimidine amino compound of the present disclosure has good inhibitory activity against DDRs, particularly DDR2, and has a good therapeutic effect on pulmonary inflammation and pulmonary fibrosis.

The present disclosure solves the above-mentioned technical problem through the following technical solutions.

The present disclosure provides a compound shown in formula I, a pharmaceutically acceptable salt thereof, a tautomer thereof, a stereoisomer thereof, a metabolite thereof, a metabolic precursor thereof or a prodrug thereof, the structure thereof is as follows:

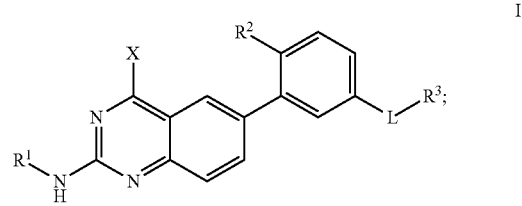

wherein, X is hydrogen or amino;
$R^3$ is unsubstituted or $R^{3-1}$-substituted-$C_{1-10}$ aryl, unsubstituted or $R^{3-2}$ substituted 5 to 10 membered heteroaryl with 1 to 4 heteroatoms selected from one or more of N, O and S, unsubstituted or $R^{3-3}$ substituted $C_{6-10}$ aryl-fused $C_{3-8}$ cycloalkyl, or, $C_{6-10}$ aryl-fused 3 to 8 membered heterocycloalkyl with 1 to 3 heteroatoms selected from one or more of N, O and S, the $C_{6-10}$ aryl-fused 3 to 8 membered heterocycloalkyl is unsubstituted or substituted by $R^{3-4}$;

$R^{3-1}$ and $R^{3-2}$ are independently deuterium, hydroxyl, unsubstituted or $R^{3-1-1}$ substituted $C_{1-6}$ alkyl, $C_{1-6}$ alkoxy, unsubstituted or $R^{3-1-2}$ substituted $C_{3-10}$ cycloalkyl, unsubstituted or $R^{3-1}$-3 substituted 3 to 10 membered heterocycloalkyl with 1 to 3 heteroatoms selected from one or more of N, O and S, unsubstituted or $R^{3-1-4}$ substituted $C_{6-10}$ aryl, or, unsubstituted or $R^{3-1-5}$ substituted 5 to 6 membered heteroaryl with 1 to 3 heteroatoms selected from one or more of N, O and S;

$R^{3-3}$ and $R^{3-4}$ are independently hydrogen or $C_{1-6}$ alkyl substituted with one or more halogens;

$R^{3-1-1}$ to $R^{3-1-5}$ are independently hydroxyl, cyano, halogen, $C_{1-6}$ alkyl, $C_{3-10}$ cycloalkyl, or, unsubstituted or $R^{3-1-1-1}$ substituted 3 to 10 membered heterocycloalkyl with 1 to 3 heteroatoms selected from one or more of N, O and S;

$R^{3-1-1-1}$ is hydroxyl,

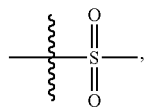

$C_{1-4}$ alkyl, $C_{3-6}$ cycloalkyl, $C_{1-4}$ alkylcarbonyl, or, $-NR^{3-1-1-1'}R^{3-1-1-1''}$; $R^{3-1-1-1'}$ and $R^{3-1-1-1''}$ are independently hydrogen or $C_{1-4}$ alkyl;

when $R^2$ is methyl or ethyl, then L is $-NH-CO-NH-$, $-CHR^{4-1}-CO-NH-$, $-CHR^{4-2}-NH-CO-$, —NH—CO—CHR$^{4-3}$—, —CO—NH—CHR$^{4-4}$—, —CHR$^4$—S—NH—CO—NH—, —NH—CO—NH—CHR$^{4-6}$—, or —CO—NH—CR$^{4-7}$R$^{4-8}$—;

when R$^2$ is methyl or ethyl, then R$^1$ is unsubstituted or R$^{1-1}$ substituted C$_{6-10}$ aryl, or unsubstituted or R$^{1-2}$ substituted 5 to 10 membered heteroaryl with 1 to 4 heteroatoms selected from one or more of N, O and S;

when R$^2$ is isopropyl or cyclopropyl, then L is —CO—NH—, —NH—CO—, —NH—CO—NH—, —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, —NH—CO—NH—CHR$^{4-6}$—, or —CO—NH—CR$^{4-7}$R$^{4-8}$—;

when R$^2$ is isopropyl or cyclopropyl, then R$^1$ is hydrogen, C$_{1-10}$ alkyl, C$_{1-6}$ haloalkyl, unsubstituted or R$^{1-1}$ substituted C$_{6-10}$ aryl, unsubstituted or R$^{1-2}$ substituted 5 to 10 membered heteroaryl with 1 to 3 heteroatoms selected from one or more of N, O and S, unsubstituted or R$^{1-3}$ substituted heterocycloalkyl, unsubstituted or R$^{1-4}$ substituted heterocycloalkyl-C$_{1-6}$ alkyl, unsubstituted or R$^{1-5}$ substituted C$_{3-7}$ cycloalkyl, unsubstituted or R$^{1-6}$ substituted C$_{3-7}$ cycloalkyl-C$_{1-6}$ alkyl, unsubstituted or R$^{1-7}$ substituted C$_{1-6}$ heteroalkyl with 1 to 3 heteroatoms selected from one or more of N, O and S and 1 to 6 carbon atoms; the heterocycloalkyl is a 3 to 10 membered heterocycloalkyl with 1 to 3 heteroatoms selected from one or more of N, O and S;

the left end of L is connected to

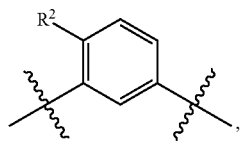

and the right end is connected to R$^3$;

R$^{4-1}$ to R$^{4-8}$ are independently hydrogen, C$_{1-4}$ alkyl, C$_{1-4}$ heteroalkyl with 1 to 2 heteroatoms are selected from one or more of N, O and S and 1 to 4 carbon atoms, C$_{3-6}$ cycloalkyl, 3 to 7 membered heterocycloalkyl with 1 to 2 heteroatoms selected from one or more of N, O and S, or R$^{4-7}$ and R$^{4-8}$ together with the carbon atom therebetween form C$_{3-6}$ cycloalkyl;

R$^{1-1}$ and R$^{1-2}$ are independently deuterium, unsubstituted or R$^{1-1-1}$ substituted C$_{1-6}$ alkyl, C$_{1-6}$ alkoxy, unsubstituted or R$^{1-1-2}$ substituted C$_{3-10}$ cycloalkyl, unsubstituted or R$^{1-1-3}$ substituted 3 to 10 membered heterocycloalkyl with 1 to 3 heteroatoms selected from one or more of N, O and S, or NR$^{1-1-4}$R$^{1-1-5}$;

R$^{1-1-1}$ to R$^{1-1-5}$ are independently hydroxyl, C$_{1-6}$ alkyl, C$_{3-10}$ cycloalkyl, or 3 to 10 membered heterocycloalkyl with 1 to 3 heteroatoms selected from one or more of N, O and S;

R$^{1-3}$ to R$^{1-7}$ are independently halogen, hydroxyl, C$_{6-10}$ aryl, C$_{1-6}$ alkyl, C$_{1-6}$ haloalkyl, C$_{1-3}$ alkoxy, C$_{1-4}$ acyloxy-C$_{1-3}$ alkyl or C$_{1-3}$ hydroxyalkyl.

In the present disclosure, when R$^3$ is unsubstituted or R$^{3-1}$ substituted C$_{6-10}$ aryl, the number of the R$^{3-1}$ can be one or more (the number meets the following criteria: the substituted group conforms to the valence bond theory and exists stably. For example, the number is 1, 2, 3, or 4), when more than one R$^{3-1}$ occurs, the R$^{3-1}$ can be the same or different.

In the present disclosure, when R$^3$ is unsubstituted or R$^{3-1}$ substituted C$_{6-10}$ aryl, the C$_{6-10}$ aryl is preferably phenyl.

In the present disclosure, when R$^3$ is unsubstituted or R$^{3-1}$ substituted C$_{6-10}$ aryl, the R$^{3-1}$ substituted C$_{6-10}$ aryl is preferably

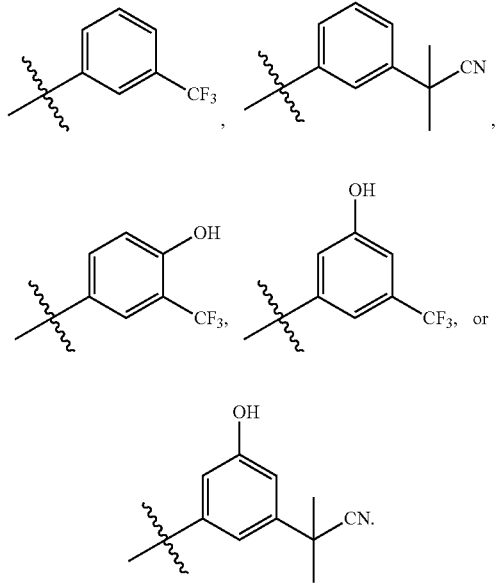

In the present disclosure, when R$^3$ is unsubstituted or R$^{3-2}$ substituted 5 to 10 membered heteroaryl with 1 to 4 heteroatoms selected from one or more of N, O and S, the number of the R$^{3-2}$ can be one or more (the number meets the following criteria: the substituted group conforms to the valence bond theory and exists stably. For example, the number is 1, 2, or 3), when more than one R$^{3-2}$ occurs, the R$^{3-2}$ can be the same or different.

In the present disclosure, when R$^3$ is unsubstituted or R$^{3-2}$ substituted 5 to 10 membered heteroaryl with 1 to 4 heteroatoms selected from one or more of N, O and S, the heteroaryl is preferably 5 to 6 membered heteroaryl with 1 to 4 heteroatoms selected from one or more of N, O and S, for example, pyrrolyl, furyl, thienyl, imidazolyl, pyrazolyl, oxazolyl, isoxazolyl, thiazolyl, isothiazolyl, 1,2,3-triazolyl, 1,2,4-triazolyl, furazanyl, 1,2,3-oxadiazolyl, 1,2,4-oxadiazolyl, 1,2,5-oxadiazolyl, 1,3,4-oxadiazolyl, thiadiazolyl, dithiazolyl, tetrazolyl, pyridyl, pyranyl, thiopyranyl, diazinyl, pyrazinyl, pyrimidinyl, pyridazinyl, oxazinyl, thiazinyl, dioxinyl, dithiinyl, 1,2,3-triazinyl, 1,2,4-triazinyl, 1,3,5-triazinyl or tetrazinyl, more preferably pyrazolyl (for example,

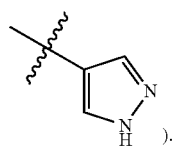

).

In the present disclosure, when R$^3$ is unsubstituted or R$^{3-2}$ substituted 5 to 10 membered heteroaryl with 1 to 4 heteroatoms selected from one or more of N, O and S, the R$^{3-2}$ substituted 5 to 10 membered heteroaryl with 1 to 4 heteroatoms selected from one or more of N, O and S is preferably

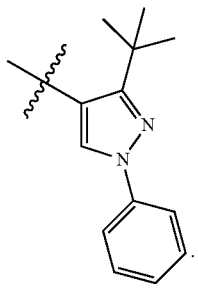 [SMILES: *c1cn(-c2ccccc2)nc1C(C)(C)C]

In the present disclosure, when $R^3$ is unsubstituted or $R^{3-3}$ substituted $C_{6-10}$ aryl-fused $C_{3-8}$ cycloalkyl, the number of the $R^{3-3}$ can be one or more (the number meets the following criteria: the substituted group conforms to the valence bond theory and exists stably. For example, the number is 1, 2, 3, or 4), when more than one $R^{3-3}$ occurs, the $R^{3-3}$ can be the same or different.

In the present disclosure, when $R^3$ is unsubstituted or $R^{3-3}$ substituted $C_{6-10}$ aryl-fused $C_{3-8}$ cycloalkyl, the $C_{6-10}$ aryl can be phenyl.

In the present disclosure, when $R^3$ is unsubstituted or $R^{3-3}$ substituted $C_{6-10}$ aryl-fused $C_{3-8}$ cycloalkyl, the $C_{3-8}$ cycloalkyl can be $C_{3-6}$ cycloalkyl, or can be cyclopropyl, cyclobutyl, cyclopentyl or cyclohexyl, for example cyclopentyl.

In the present disclosure, when $R^3$ is unsubstituted or $R^{3-3}$ substituted $C_{6-10}$ aryl-fused $C_{3-8}$ cycloalkyl, the $R^{3-3}$ substituted $C_{6-10}$ aryl-fused $C_{3-8}$ cycloalkyl can be

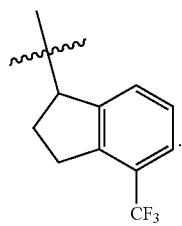

In the present disclosure, when $R^{3-1}$ is unsubstituted or $R^{3-1-1}$ substituted $C_{1-6}$ alkyl, the number of the $R^{3-1-1}$ can be one or more (the number meets the following criteria: the substituted group conforms to the valence bond theory and exists stably. For example, the number is 1, 2, or 3), when more than one $R^{3-1-1}$ occurs, the $R^{3-1-1}$ can be the same or different.

In the present disclosure, when $R^{3-1}$ is unsubstituted or $R^{3-1-1}$ substituted $C_{1-6}$ alkyl, the $C_{1-6}$ alkyl is preferably $C_{1-4}$ alkyl, for example methyl, ethyl, propyl, isopropyl, n-butyl, isobutyl, sec-butyl or tert-butyl, more preferably methyl, isopropyl or tert-butyl.

In the present disclosure, when $R^{3-1}$ is unsubstituted or $R^{3-1-1}$ substituted $C_{1-6}$ alkyl, the $R^{3-1-1}$ substituted $C_{1-6}$ alkyl is preferably —$CF_3$, or

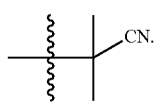 [SMILES: *C(C)(C)C#N]

In the present disclosure, when $R^{3-1}$ is unsubstituted or $R^{3-1-4}$ substituted $C_{6-10}$ aryl, the number of the $R^{3-1-4}$ can be one or more (the number meets the following criteria: the substituted group conforms to the valence bond theory and exists stably. For example, the number is 1, 2, 3, or 4), when more than one $R^{3-1-4}$ occurs, the $R^{3-1-4}$ can be the same or different.

In the present disclosure, when $R^{3-1}$ is unsubstituted or $R^{3-1-4}$ substituted $C_{6-10}$ aryl, the $C_{6-10}$ aryl is preferably phenyl.

In the present disclosure, when $R^{3-2}$ is unsubstituted or $R^{3-1-1}$ substituted $C_{1-6}$ alkyl, the number of the $R^{3-1-1}$ can be one or more (the number meets the following criteria: the substituted group conforms to the valence bond theory and exists stably. For example, the number is 1, 2, or 3), when more than one $R^{3-1-1}$ occurs, the $R^{3-1-1}$ can be the same or different.

In the present disclosure, when $R^{3-2}$ is unsubstituted or $R^{3-1-1}$ substituted $C_{1-6}$ alkyl, the $C_{1-6}$ alkyl is preferably $C_{1-4}$ alkyl, for example methyl, ethyl, propyl, isopropyl, n-butyl, isobutyl, sec-butyl or tert-butyl, more preferably methyl, isopropyl or tert-butyl.

In the present disclosure, when $R^{3-2}$ is unsubstituted or $R^{3-1-1}$ substituted $C_{1-6}$ alkyl, the $R^{3-1-1}$ substituted $C_{1-6}$ alkyl is preferably —$CF_3$,

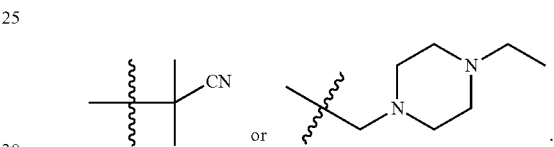

In the present disclosure, when $R^{3-2}$ is unsubstituted or $R^{3-1-4}$ substituted $C_{6-10}$ aryl, the number of the $R^{3-1-4}$ can be one or more (the number meets the following criteria: the substituted group conforms to the valence bond theory and exists stably. For example, the number is 1, 2, 3, or 4), when more than one $R^{3-1-4}$ occurs, the $R^{3-1-4}$ can be the same or different.

In the present disclosure, when $R^{3-2}$ is unsubstituted or $R^{3-1-4}$ substituted $C_{6-10}$ aryl, the $C_{6-10}$ aryl is preferably phenyl.

In the present disclosure, when $R^{3-3}$ is $C_{1-6}$ alkyl substituted with one or more halogens, the number of the halogen is 1, 2 or 3.

In the present disclosure, when $R^{3-3}$ is $C_{1-6}$ alkyl substituted with one or more halogens, the halogens can be fluorine, chlorine, bromine or iodine, preferably fluorine.

In the present disclosure, when $R^{3-3}$ is $C_{1-6}$ alkyl substituted with one or more halogens, the $C_{1-6}$ alkyl can be $C_{1-4}$ alkyl, for example methyl, ethyl, propyl, isopropyl, n-butyl, isobutyl, sec-butyl or tert-butyl, more preferably methyl.

In the present disclosure, when $R^{3-3}$ is $C_{1-6}$ alkyl substituted with one or more halogens, the $C_{1-6}$ alkyl substituted with one or more halogens is —$CF_3$.

In the present disclosure, when $R^{3-1-1}$ is halogen, the halogen can be fluorine, chlorine, bromine or iodine, preferably fluorine.

In the present disclosure, when $R^{3-1-1}$ is unsubstituted or $R^{3-1-1-1}$ substituted 3 to 10 membered heterocycloalkyl with 1 to 3 heteroatoms selected from one or more of N, O and S, the number of the $R^{3-1-1-1}$ can be one or more (the number meets the following criteria: the substituted group conforms to the valence bond theory and exists stably. For example, the number is 1, 2, 3, or 4), when more than one $R^{3-1-1-1}$ occurs, the $R^{3-1-1-1}$ can be the same or different.

In the present disclosure, when $R^{3-1-1}$ is unsubstituted or $R^{3-1-1-1}$ substituted 3 to 10 membered heterocycloalkyl with 1 to 3 heteroatoms selected from one or more of N, O and S, the heterocycloalkyl can be 5 to 6 membered heterocycloalkyl with 1 or 2 heteroatoms selected from N and can also be piperazinyl.

In the present disclosure, when $R^{3-1-4}$ is halogen, the halogen can be fluorine, chlorine, bromine or iodine, preferably fluorine.

In the present disclosure, when $R^{3-1-1}$ is $C_{1-4}$ alkyl, the $C_{1-4}$ alkyl is for example methyl, ethyl, propyl, isopropyl, n-butyl, isobutyl, sec-butyl or tert-butyl and can also be ethyl.

In the present disclosure, when $R^2$ is methyl or ethyl, L is preferably

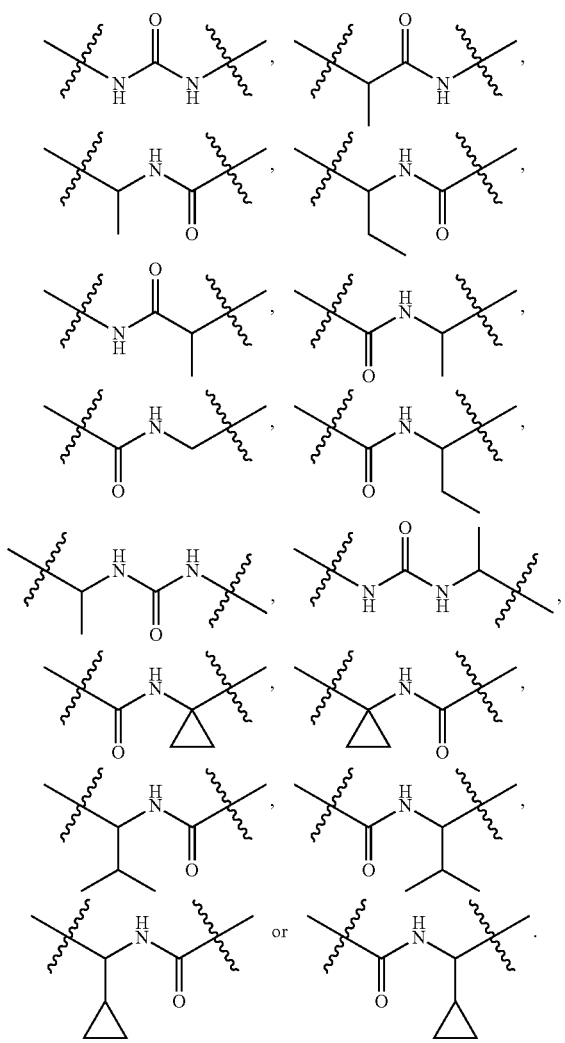

In the present disclosure, when $R^2$ is isopropyl or cyclopropyl, L is preferably

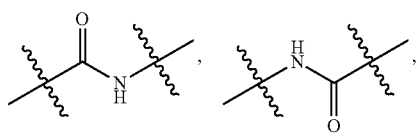

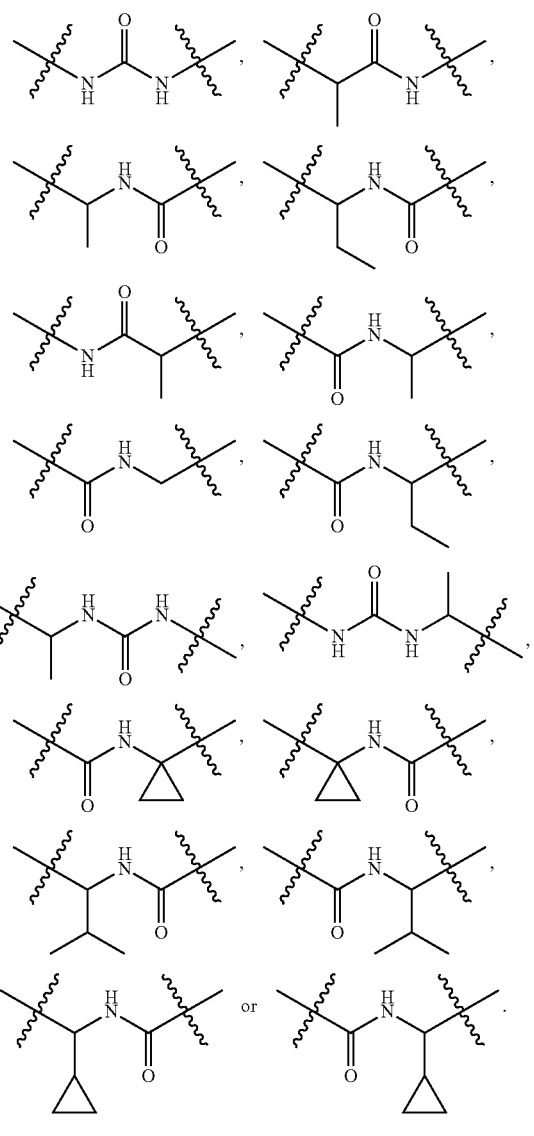

In the present disclosure, when $R^1$ is unsubstituted or $R^{1-1}$ substituted $C_{6-10}$ aryl, the number of the $R^{1-1}$ can be one or more (the number meets the following criteria: the substituted group conforms to the valence bond theory and exists stably. For example, the number is 1, 2, 3, or 4), when more than one $R^{1-1}$ occurs, the $R^{1-1}$ can be the same or different.

In the present disclosure, when $R^1$ is unsubstituted or $R^{1-1}$ substituted $C_{6-10}$ aryl, the $C_{6-10}$ aryl is preferably phenyl.

In the present disclosure, when $R^1$ is unsubstituted or $R^{1-1}$ substituted $C_{6-10}$ aryl, the $R^{1-1}$ substituted $C_{6-10}$ aryl is preferably

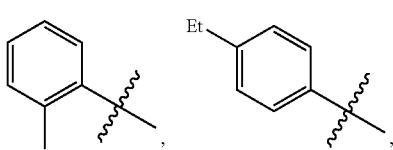

-continued

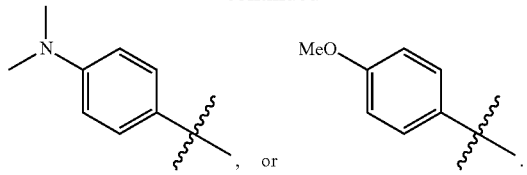

In the present disclosure, when R¹ is unsubstituted or R¹⁻² substituted 5 to 10 membered heteroaryl with 1 to 4 heteroatoms selected from one or more of N, O and S, the number of the R¹⁻² can be one or more (the number meets the following criteria: the substituted group conforms to the valence bond theory and exists stably. For example, the number is 1, 2, or 3), when more than one R¹⁻² occurs, the R¹⁻² can be the same or different.

In the present disclosure, when R¹ is unsubstituted or R¹⁻² substituted 5 to 10 membered heteroaryl with 1 to 4 heteroatoms selected from one or more of N, O and S, the heteroaryl is preferably 5 to 6 membered heteroaryl with 1 to 4 heteroatoms selected from one or more of N, O and S, for example, pyrrolyl, furyl, thienyl, imidazolyl, pyrazolyl, oxazolyl, isoxazolyl, thiazolyl, isothiazolyl, 1,2,3-triazolyl, 1,2,4-triazolyl, furazanyl, 1,2,3-oxadiazolyl, 1,2,4-oxadiazolyl, 1,2,5-oxadiazolyl, 1,3,4-oxadiazolyl, thiadiazolyl, dithiazolyl, tetrazolyl, pyridyl, pyranyl, thiopyranyl, diazinyl, pyrazinyl, pyrimidinyl, pyridazinyl, oxazinyl, thiazinyl, dioxinyl, dithiinyl, 1,2,3-triazinyl, 1,2,4-triazinyl, 1,3,5-triazinyl or tetrazinyl, more preferably pyrazolyl (for example,

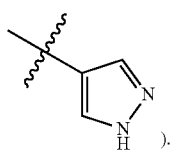 [SMILES: *c1cn[nH]c1]

).

In the present disclosure, when R¹ is unsubstituted or R¹⁻² substituted 5 to 10 membered heteroaryl with 1 to 4 heteroatoms selected from one or more of N, O and S, the R¹⁻² substituted heteroaryl is preferably

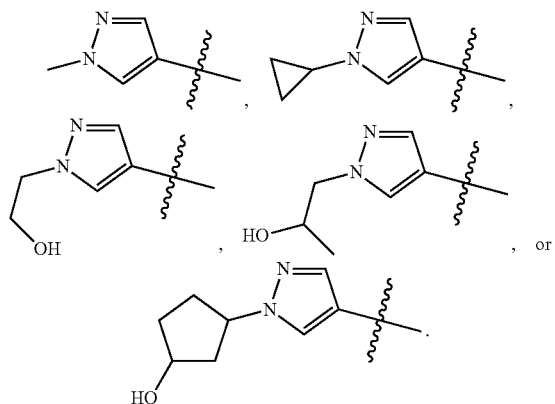

In the present disclosure, when R¹⁻¹ is unsubstituted or R¹⁻¹⁻¹ substituted C$_{1-6}$ alkyl, the number of the R¹⁻¹⁻¹ can be one or more (the number meets the following criteria: the substituted group conforms to the valence bond theory and exists stably. For example, the number is 1, 2, or 3), when more than one R¹⁻¹⁻¹ occurs, the R¹⁻¹⁻¹ can be the same or different.

In the present disclosure, when R¹⁻¹ is unsubstituted or R¹⁻¹⁻¹ substituted C$_{1-6}$ alkyl, the C$_{1-6}$ alkyl is preferably C$_{1-4}$ alkyl, for example methyl, ethyl, propyl, isopropyl, n-butyl, isobutyl, sec-butyl or tert-butyl, more preferably methyl, ethyl or isopropyl.

In the present disclosure, when R¹⁻¹ is unsubstituted or R¹⁻¹⁻¹ substituted C$_{1-6}$ alkyl, the R¹⁻¹⁻¹ substituted C$_{1-6}$ alkyl is preferably

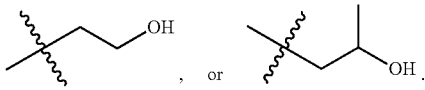

In the present disclosure, when R¹⁻¹ is C$_{1-6}$ alkoxy, the C$_{1-6}$ alkoxy is preferably C$_{1-4}$ alkoxy, for example methoxy, ethoxy, propoxy, isopropoxy, n-butoxy, isobutoxy, sec-butoxy or tert-butoxy, more preferably methoxy.

In the present disclosure, when R¹⁻¹ is unsubstituted or R¹⁻¹⁻² substituted C$_{3-10}$ cycloalkyl, the number of the R¹⁻¹⁻² can be one or more (the number meets the following criteria: the substituted group conforms to the valence bond theory and exists stably. For example, the number is 1, 2, or 3), when more than one R¹⁻¹⁻² occurs, the R¹⁻¹⁻² can be the same or different.

In the present disclosure, when R¹⁻¹ is unsubstituted or R¹⁻¹⁻² substituted C$_{3-10}$ cycloalkyl, the C$_{3-10}$ cycloalkyl is preferably C$_{3-6}$ cycloalkyl, for example cyclopropyl, cyclobutyl, cyclopentyl or cyclohexyl, more preferably cyclopropyl or cyclopentyl.

In the present disclosure, when R¹⁻¹ is unsubstituted or R¹⁻¹⁻² substituted C$_{3-10}$ cycloalkyl, the R¹⁻¹⁻² substituted C$_{3-10}$ cycloalkyl is preferably

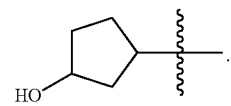 [SMILES: *C1CCC(O)C1]

In the present disclosure, when R¹⁻¹ is —NR¹⁻¹⁻⁴R¹⁻¹⁻⁵, the —NR¹⁻¹⁻⁴R¹⁻¹⁻⁵ is preferably —N(Me)$_2$.

In the present disclosure, when R¹⁻² is unsubstituted or R¹⁻¹⁻¹ substituted C$_{1-6}$ alkyl, the number of the R¹⁻¹⁻¹ can be one or more (the number meets the following criteria: the substituted group conforms to the valence bond theory and exists stably. For example, the number is 1, 2, or 3), when more than one R¹⁻¹⁻¹ occurs, the R¹⁻¹⁻¹ can be the same or different.

In the present disclosure, when R¹⁻² is unsubstituted or R¹⁻¹⁻¹ substituted C$_{1-6}$ alkyl, the C$_{1-6}$ alkyl is preferably C$_{1-4}$ alkyl, for example methyl, ethyl, propyl, isopropyl, n-butyl, isobutyl, sec-butyl or tert-butyl, more preferably methyl, ethyl or isopropyl.

In the present disclosure, when R¹⁻² is unsubstituted or R¹⁻¹⁻¹ substituted C$_{1-6}$ alkyl, the R¹⁻¹⁻¹ substituted C$_{1-6}$ alkyl is preferably

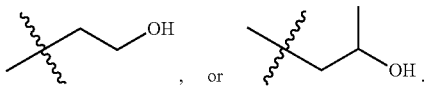

In the present disclosure, when $R^{1-2}$ is $C_{1-6}$ alkoxy, the $C_{1-6}$ alkoxy preferably $C_{1-4}$ alkoxy, for example methoxy, ethoxy, propoxy, isopropoxy, n-butoxy, isobutoxy, sec-butoxy or tert-butoxy, more preferably methoxy.

In the present disclosure, when $R^{1-2}$ is unsubstituted or $R^{1-1-2}$ substituted $C_{3-10}$ cycloalkyl, the number of the $R^{1-1-2}$ can be one or more (the number meets the following criteria: the substituted group conforms to the valence bond theory and exists stably. For example, the number is 1, 2, or 3), when more than one $R^{1-1-2}$ occurs, the $R^{1-1-2}$ can be the same or different.

In the present disclosure, when $R^{1-2}$ is unsubstituted or $R^{1-1-2}$ substituted $C_{3-10}$ cycloalkyl, the $C_{3-10}$ cycloalkyl is preferably $C_{3-6}$ cycloalkyl, for example cyclopropyl, cyclobutyl, cyclopentyl or cyclohexyl, more preferably cyclopropyl or cyclopentyl.

In the present disclosure, when $R^{1-2}$ is unsubstituted or $R^{1-1-2}$ substituted $C_{3-10}$ cycloalkyl, the $R^{1-1-2}$ substituted $C_{3-10}$ cycloalkyl is preferably

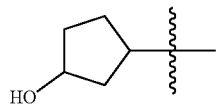

.

In the present disclosure, when $R^{1-2}$ is unsubstituted or $R^{1-1-3}$ substituted 3 to 10 membered heterocycloalkyl with 1 to 3 heteroatoms selected from one or more of N, O and S, the number of the $R^{1-1-3}$ can be one or more (the number meets the following criteria: the substituted group conforms to the valence bond theory and exists stably. For example, the number is 1, 2, or 3), when more than one $R^{1-1-3}$ occurs, the $R^{1-1-3}$ can be the same or different.

In the present disclosure, when $R^{1-2}$ is unsubstituted or $R^{1-1-3}$ substituted 3 to 10 membered heterocycloalkyl with 1 to 3 heteroatoms selected from one or more of N, O and S, the 3 to 10 membered heterocycloalkyl with 1 to 3 heteroatoms selected from one or more of N, O and S can be 5 to 6 membered heterocycloalkyl with 1 or 2 heteroatoms selected from N and can also be piperidyl.

In the present disclosure, when $R^{1-2}$ is $-NR^{1-1-4}R^{1-1-5}$, the $-NR^{1-1-4}R^{1-1-5}$ is preferably $-N(Me)_2$.

In the present disclosure, when $R^{1-2}$ is $C_{1-6}$ alkyl, the $C_{1-6}$ alkyl is preferably $C_{1-4}$ alkyl, for example methyl, ethyl, propyl, isopropyl, n-butyl, isobutyl, sec-butyl or tert-butyl.

In the present disclosure, when $R^{1-1-3}$ is $C_{1-6}$ alkyl, the $C_{1-6}$ alkyl is preferably $C_{1-4}$ alkyl, for example methyl, ethyl, propyl, isopropyl, n-butyl, isobutyl, sec-butyl or tert-butyl, and can also be methyl.

In the present disclosure, when $R^{1-1-4}$ is $C_{1-6}$ alkyl, the $C_{1-6}$ alkyl is preferably $C_{1-4}$ alkyl, for example methyl, ethyl, propyl, isopropyl, n-butyl, isobutyl, sec-butyl or tert-butyl, more preferably methyl.

In the present disclosure, when $R^{1-1-5}$ is $C_{1-6}$ alkyl, the $C_{1-6}$ alkyl is preferably $C_{1-4}$ alkyl, for example methyl, ethyl, propyl, isopropyl, n-butyl, isobutyl, sec-butyl or tert-butyl, more preferably methyl.

In the present disclosure, when $R^{4-1}$—$R^{4-6}$ are independently $C_{1-4}$ alkyl, the $C_{1-4}$ alkyl is for example methyl, ethyl, propyl, isopropyl, n-butyl, isobutyl, sec-butyl or tert-butyl, more preferably methyl or ethyl.

In the present disclosure, when $R^{4-7}$ and $R^{4-8}$ together with the carbon atom therebetween form $C_{3-6}$ cycloalkyl, the $C_{3-6}$ cycloalkyl can be cyclopropyl, cyclobutyl, cyclopentyl or cyclohexyl, preferably cyclopropyl.

In a certain scheme, some groups of the compound represented by formula I are defined as follows (undefined groups are as described in any of the previous schemes): $R^1$ is unsubstituted or $R^{1-2}$ substituted 5 to 10 membered heteroaryl with 1 to 4 heteroatoms selected from one or more of N, O and S.

In a certain scheme, some groups of the compound represented by formula I are defined as follows (undefined groups are as described in any of the previous schemes): $R^2$ is cyclopropyl.

In a certain scheme, some groups of the compound represented by formula I are defined as follows (undefined groups are as described in any of the previous schemes): $R^2$ is isopropyl.

In a certain scheme, some groups of the compound represented by formula I are defined as follows (undefined groups are as described in any of the previous schemes):

X is hydrogen;

$R^3$ is unsubstituted or $R^{3-1}$ substituted $C_{6-10}$ aryl, or unsubstituted or $R^{3-2}$ substituted 5 to 10 membered heteroaryl with 1 to 4 heteroatoms selected from one or more of N, O and S;

$R^{3-1}$ and $R^{3-2}$ are independently hydroxyl, unsubstituted or $R^{3-1-1}$ substituted $C_{1-6}$ alkyl, or unsubstituted or $R^{3-1-4}$ substituted $C_{6-10}$ aryl;

$R^{3-1-1}$ and $R^{3-1-4}$ are independently cyano or halogen;

$R^1$ is unsubstituted or $R^{1-1}$ substituted $C_{6-10}$ aryl, or unsubstituted or $R^{1-2}$ substituted 5 to 10 membered heteroaryl with 1 to 4 heteroatoms selected from one or more of N, O and S;

$R^{1-1}$ and $R^{1-2}$ are independently unsubstituted or $R^{1-1-1}$ substituted $C_{1-6}$ alkyl, $C_{1-6}$ alkoxy, unsubstituted or $R^{1-1-2}$ substituted $C_{3-10}$ cycloalkyl, or $NR^{1-1-4}R^{1-1-5}$;

$R^{1-1-1}$, $R^{1-1-2}$, $R^{1-1-4}$ and $R^{1-1-5}$ are independently hydroxyl, or $C_{1-6}$ alkyl;

when $R^2$ is methyl or ethyl, L is $-NH-CO-NH-$, $-CHR^{4-1}-CO-NH-$, $-CHR^{4-2}-NH-CO-$, $-NH-CO-CHR^{4-3}-$, $-CO-NH-CHR^{4-4}-$, $-CHR^{4-5}-NH-CO-NH-$, $-NH-CO-NH-CHR^{4-6}-$, or $-CO-NH-CR^{4-7}R^{4-8}-$;

when $R^2$ is isopropyl or cyclopropyl, L is $-CO-NH-$, $-NH-CO-$, $-NH-CO-NH-$, $-CHR^{4-1}-CO-NH-$, $-CHR^{4-2}-NH-CO-$, $-NH-CO-CHR^{4-3}-$, $-CO-NH-CHR^{4-4}-$, $-CHR^{4-5}-NH-CO-NH-$, $-NH-CO-NH-CHR^{4-6}-$, or $-CO-NH-CR^{4-7}R^{4-8}-$;

$R^{4-1}$—$R^{4-8}$ are independently hydrogen, $C_{1-4}$ alkyl, or $R^{4-7}$ and $R^{4-8}$ together with the carbon atom therebetween form $C_{3-6}$ cycloalkyl.

In a certain scheme, some groups of the compound represented by formula I are defined as follows (undefined groups are as described in any of the previous schemes):

X is hydrogen;

$R^3$ is unsubstituted or $R^{3-1}$ substituted $C_{6-10}$ aryl, or unsubstituted or $R^{3-2}$ substituted 5 to 10 membered heteroaryl with 1 to 4 heteroatoms selected from one or more of N, O and S;

$R^{3-1}$ and $R^{3-2}$ are independently hydroxyl, unsubstituted or $R^{3-1-1}$ substituted $C_{1-6}$ alkyl, or unsubstituted or $R^{3-1-4}$ substituted $C_{6-10}$ aryl;

$R^{3-1-1}$ and $R^{3-1-4}$ are independently cyano or halogen;

$R^1$ is unsubstituted or $R^{1-2}$ substituted 5 to 10 membered heteroaryl with 1 to 4 heteroatoms selected from one or more of N, O and S;

$R^{1-2}$ is unsubstituted or $R^{1-1-1}$ substituted $C_{1-6}$ alkyl, $C_{1-6}$ alkoxy, unsubstituted or $R^{1-1-2}$ substituted $C_{3-10}$ cycloalkyl, or $NR^{1-1-4}R^{1-1-5}$;

$R^{1-1-1}$, $R^{1-1-2}$, $R^{1-1-4}$ and $R^{1-1-5}$ are independently hydroxyl, or $C_{1-6}$ alkyl;

when $R^2$ is methyl or ethyl, L is —NH—CO—NH—, —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, —NH—CO—NH—CHR$^{4-6}$—, or —CO—NH—CR$^{4-7}$R$^{4-8}$—;

when $R^2$ is isopropyl or cyclopropyl, L is —CO—NH—, —NH—CO—, —NH—CO—NH—, —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, —NH—CO—NH—CHR$^{4-6}$—, or —CO—NH—CR$^{4-7}$R$^{4-8}$—;

$R^{4-1}$—$R^{4-8}$ are independently hydrogen, unsubstituted or $R^{4-1-1}$ substituted $C_{1-4}$ alkyl, or $R^{4-7}$ and $R^{4-8}$ together with the carbon atom therebetween form $C_{3-6}$ cycloalkyl.

In a certain scheme, some groups of the compound represented by formula I are defined as follows (undefined groups are as described in any of the previous schemes):

X is hydrogen;

$R^3$ is unsubstituted or $R^{3-1}$ substituted $C_{6-10}$ aryl, or unsubstituted or $R^{3-2}$ substituted 5 to 10 membered heteroaryl with 1 to 4 heteroatoms selected from one or more of N, O and S;

$R^{3-1}$ and $R^{3-2}$ are independently hydroxyl, unsubstituted or $R^{3-1-1}$ substituted $C_{1-6}$ alkyl, or unsubstituted or $R^{3-1-4}$ substituted $C_{6-10}$ aryl;

$R^{3-1-1}$ and $R^{3-1-4}$ are independently cyano or halogen;

$R^1$ is unsubstituted or $R^{1-1}$ substituted $C_{6-10}$ aryl, or unsubstituted or $R^{1-2}$ substituted 5 to 10 membered heteroaryl with 1 to 4 heteroatoms selected from one or more of N, O and S;

$R^{1-1}$ and $R^{1-2}$ are independently unsubstituted or $R^{1-1-1}$ substituted $C_{1-6}$ alkyl, $C_{1-6}$ alkoxy, unsubstituted or $R^{1-1-2}$ substituted $C_{3-10}$ cycloalkyl, or NR$^{1-1-4}$R$^{1-1-5}$;

$R^{1-1-1}$, $R^{1-1-2}$, $R^{1-1-4}$ and $R^{1-1-5}$ are independently hydroxyl, or $C_{1-6}$ alkyl;

when $R^2$ is methyl or ethyl, L is —CHR$^{4-2}$—NH—CO—;

when $R^2$ is isopropyl or cyclopropyl, L is —CHR$^{4-2}$—NH—CO—;

$R^{4-2}$ is hydrogen, unsubstituted or $R^{4-1-1}$ substituted $C_{1-4}$ alkyl.

In a certain scheme, some groups of the compound represented by formula I are defined as follows (undefined groups are as described in any of the previous schemes):

X is hydrogen;

$R^3$ is unsubstituted or $R^{3-1}$ substituted $C_{6-10}$ aryl, or unsubstituted or $R^{3-2}$ substituted 5 to 10 membered heteroaryl with 1 to 4 heteroatoms selected from one or more of N, O and S;

$R^{3-1}$ and $R^{3-2}$ are independently hydroxyl, unsubstituted or $R^{3-1-1}$ substituted $C_{1-6}$ alkyl, or unsubstituted or $R^{3-1-4}$ substituted $C_{6-10}$ aryl;

$R^{3-1-1}$ and $R^{3-1-4}$ are independently cyano or halogen;

$R^1$ is unsubstituted or $R^{1-1}$ substituted $C_{6-10}$ aryl, or unsubstituted or $R^{1-2}$ substituted 5 to 10 membered heteroaryl with 1 to 4 heteroatoms selected from one or more of N, O and S;

$R^{1-1}$ and $R^{1-2}$ are independently unsubstituted or $R^{1-1-1}$ substituted $C_{1-6}$ alkyl, $C_{1-6}$ alkoxy, unsubstituted or $R^{1-1-2}$ substituted $C_{3-10}$ cycloalkyl, or NR$^{1-4}$R$^{1-1-5}$;

$R^{1-1-1}$, $R^{1-1-2}$, $R^{1-1-4}$ and $R^{1-1-5}$ are independently hydroxyl, or $C_{1-6}$ alkyl;

$R^2$ is cyclopropyl;

L is —CO—NH—, —NH—CO—, —NH—CO—NH—, —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, —NH—CO—NH—CHR$^{4-6}$—, or —CO—NH—CR$^{4-7}$R$^{4-8}$—.

$R^{4-1}$ to $R^{4-8}$ are independently hydrogen, unsubstituted or $R^{4-1-1}$ substituted $C_{1-4}$ alkyl, or $R^{4-7}$ and $R^{4-8}$ together with the carbon atom therebetween form $C_{3-6}$ cycloalkyl.

In a certain scheme, some groups of the compound represented by formula I are defined as follows (undefined groups are as described in any of the previous schemes):

X is hydrogen;

$R^3$ is unsubstituted or $R^{3-1}$ substituted $C_{6-10}$ aryl, or unsubstituted or $R^{3-2}$ substituted 5 to 10 membered heteroaryl with 1 to 4 heteroatoms selected from one or more of N, O and S;

$R^{3-1}$ and $R^{3-2}$ are independently hydroxyl, unsubstituted or $R^{3-1-1}$ substituted $C_{1-6}$ alkyl, or unsubstituted or $R^{3-1-4}$ substituted $C_{6-10}$ aryl;

$R^{3-1-1}$ and $R^{3-1-4}$ are independently cyano or halogen;

$R^1$ is unsubstituted or $R^{1-1}$ substituted $C_{6-10}$ aryl, or unsubstituted or $R^{1-2}$ substituted 5 to 10 membered heteroaryl with 1 to 4 heteroatoms selected from one or more of N, O and S;

$R^{1-1}$ and $R^{1-2}$ are independently unsubstituted or $R^{1-1-1}$ substituted $C_{1-6}$ alkyl, $C_{1-6}$ alkoxy, unsubstituted or $R^{1-1-2}$ substituted $C_{3-10}$ cycloalkyl, or NR$^{1-1-4}$R$^{1-1-5}$;

$R^{1-1-1}$, $R^{1-1-2}$, $R^{1-1-4}$ and $R^{1-1-5}$ are independently hydroxyl, or $C_{1-6}$ alkyl;

$R^2$ is isopropyl;

L is —CO—NH—, —NH—CO—, —NH—CO—NH—, —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, —NH—CO—NH—CHR$^{4-6}$—, or —CO—NH—CR$^{4-7}$R$^{4-8}$—.

$R^{4-1}$ to $R^{4-8}$ are independently hydrogen, unsubstituted or $R^{4-1-1}$ substituted $C_{1-4}$ alkyl, or $R^{4-7}$ and $R^{4-8}$ together with the carbon atom therebetween form $C_{3-6}$ cycloalkyl.

In a certain scheme, some groups of the compound represented by formula I are defined as follows (undefined groups are as described in any of the previous schemes):

X is hydrogen;

$R^3$ is unsubstituted or $R^{3-1}$ substituted $C_{6-10}$ aryl, unsubstituted or $R^{3-2}$ substituted 5 to 10 membered heteroaryl with 1 to 4 heteroatoms selected from one or more of N, O and S, or unsubstituted or $R^{3-3}$ substituted $C_{6-10}$ aryl-fused $C_{3-8}$ cycloalkyl;

$R^{3-1}$ and $R^{3-2}$ are independently unsubstituted or $R^{3-1-1}$ substituted $C_{1-6}$ alkyl, or unsubstituted or $R^{3-1-4}$ substituted $C_{6-10}$ aryl;

$R^{3-3}$ is hydrogen or $C_{1-6}$ alkyl substituted with one or more halogens;

$R^{3-1-1}$ and $R^{3-1-4}$ are independently cyano, halogen, or unsubstituted or $R^{3-1-1-1}$ substituted 3 to 10 membered heterocycloalkyl with 1 to 3 heteroatoms selected from one or more of N, O and S;

$R^{3-1-1-1}$ is $C_{1-4}$ alkyl;

$R^1$ is unsubstituted or $R^{1-2}$ substituted 5 to 10 membered heteroaryl with 1 to 4 heteroatoms selected from one or more of N, O and S;

$R^{1-2}$ is unsubstituted or $R^{1-1-1}$ substituted $C_{1-6}$ alkyl, unsubstituted or $R^{1-1-2}$ substituted $C_{3-10}$ cycloalkyl, unsubstituted or $R^{1-1-3}$ substituted 3 to 10 membered heterocycloalkyl with 1 to 3 heteroatoms selected from one or more of N, O and S, or NR$^{1-1-4}$R$^{1-1-5}$;

$R^{1-1-1}$, $R^{1-1-2}$, $R^{1-1-3}$, $R^{1-1-4}$ and $R^{1-1-5}$ are independently $C_{1-6}$ alkyl;

when $R^2$ is methyl or ethyl, L is —NH—CO—NH—, —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, —NH—CO—NH—CHR$^{4-6}$—, or —CO—NH—CR$^{4-7}$R$^{4-8}$—;

when R$^2$ is isopropyl or cyclopropyl, L is —CO—NH—, —NH—CO—, —NH—CO—NH—, —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, —NH—CO—NH—CHR$^{4-6}$—, or —CO—NH—CR$^{4-7}$R$^{4-8}$—;

R$^{4-1}$ to R$^{4-8}$ are independently hydrogen, unsubstituted or R$^{4-1-1}$ substituted C$_{1-4}$ alkyl, or R$^{4-7}$ and R$^{4-8}$ together with the carbon atom attached thereto form C$_{3-6}$ cycloalkyl.

In a certain scheme, some groups of the compound represented by formula I are defined as follows (undefined groups are as described in any of the previous schemes):

X is hydrogen;

R$^3$ is unsubstituted or R$^{3-1}$ substituted C$_{6-10}$ aryl, or unsubstituted or R$^{3-2}$ substituted 5 to 10 membered heteroaryl with 1 to 4 heteroatoms selected from one or more of N, O and S;

R$^{3-1}$ and R$^{3-2}$ are independently unsubstituted or R$^{3-1-1}$ substituted C$_{1-6}$ alkyl, or unsubstituted or R$^{3-1-4}$ substituted C$_{6-10}$ aryl;

R$^{3-1-1}$ and R$^{3-1-4}$ are independently cyano or halogen;

R$^1$ is unsubstituted or R$^{1-2}$ substituted 5 to 10 membered heteroaryl with 1 to 4 heteroatoms selected from one or more of N, O and S;

R$^{1-1}$ and R$^{1-2}$ are independently unsubstituted or R$^{1-1-1}$ substituted C$_{1-6}$ alkyl, unsubstituted or R$^{1-1-2}$ substituted C$_{3-10}$ cycloalkyl, or NR$^{1-1-4}$R$^{1-1-5}$;

R$^{1-1-1}$, R$^{1-1-2}$, R$^{1-1-4}$ and R$^{1-1-5}$ are independently C$_{1-6}$ alkyl;

when R$^2$ is methyl or ethyl, L is —NH—CO—NH—, —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, —NH—CO—NH—CHR$^{4-6}$—, or —CO—NH—CR$^{4-7}$R$^{4-8}$—;

when R$^2$ is isopropyl or cyclopropyl, L is —CO—NH—, —NH—CO—, —NH—CO—NH—, —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, —NH—CO—NH—CHR$^{4-6}$—, or —CO—NH—CR$^{4-7}$R$^{4-8}$—;

R$^{4-1}$ to R$^{4-8}$ are independently hydrogen, unsubstituted or R$^{4-1-1}$ substituted C$_{1-4}$ alkyl, or R$^{4-7}$ and R$^{4-8}$ together with the carbon atom attached thereto form C$_{3-6}$ cycloalkyl.

In a certain scheme, some groups of the compound represented by formula I are defined as follows (undefined groups are as described in any of the previous schemes):

X is hydrogen;

R$^3$ is unsubstituted or R$^{3-1}$ substituted C$_{6-10}$ aryl, or unsubstituted or R$^{3-2}$ substituted 5 to 10 membered heteroaryl with 1 to 4 heteroatoms selected from one or more of N, O and S, or unsubstituted or R$^{3-3}$ substituted C$_{6-10}$ aryl-fused C$_{3-8}$ cycloalkyl;

R$^{3-1}$ and R$^{3-2}$ are independently unsubstituted or R$^{3-1-1}$ substituted C$_{1-6}$ alkyl, or unsubstituted or R$^{3-1-4}$ substituted C$_{6-10}$ aryl;

R$^{3-3}$ is hydrogen or C$_{1-6}$ alkyl substituted with one or more halogens;

R$^{3-1-1}$ and R$^{3-1-4}$ are independently cyano, halogen, or unsubstituted or R$^{3-1-1-1}$ substituted 3 to 10 membered heterocycloalkyl with 1 to 3 heteroatoms selected from one or more of N, O and S;

R$^{3-1-1-1}$ is C$_{1-4}$ alkyl;

R$^1$ is unsubstituted or R$^{1-2}$ substituted 5 to 10 membered heteroaryl with 1 to 4 heteroatoms selected from one or more of N, O and S;

R$^{1-1}$ and R$^{1-2}$ are independently unsubstituted or R$^{1-1-1}$ substituted C$_{1-6}$ alkyl, unsubstituted or R$^{1-1-2}$ substituted C$_{3-10}$ cycloalkyl, unsubstituted or R$^{1-1-3}$ substituted 3 to 10 membered heterocycloalkyl with 1 to 3 heteroatoms selected from one or more of N, O and S, or NR$^{1-1-4}$R$^{1-1-5}$;

R$^{1-1-1}$, R$^{1-1-2}$, R$^{1-1-3}$, R$^{1-1-4}$ and R$^{1-1-5}$ are independently C$_{1-6}$ alkyl;

R$^2$ is isopropyl or cyclopropyl;

L is —CO—NH—, —NH—CO—, —NH—CO—NH—, —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, —NH—CO—NH—CHR$^{4-6}$—, or —CO—NH—CR$^{4-7}$R$^{4-8}$—.

R$^{4-1}$ to R$^{4-8}$ are independently hydrogen, unsubstituted or R$^{4-1-1}$ substituted C$_{1-4}$ alkyl, or R$^{4-7}$ and R$^{4-8}$ together with the carbon atom therebetween form C$_{3-6}$ cycloalkyl.

In a certain scheme, some groups of the compound represented by formula I are defined as follows (undefined groups are as described in any of the previous schemes):

X is hydrogen;

R$^3$ is unsubstituted or R$^{3-1}$ substituted C$_{6-10}$ aryl, or unsubstituted or R$^{3-2}$ substituted 5 to 10 membered heteroaryl with 1 to 4 heteroatoms selected from one or more of N, O and S;

R$^{3-1}$ and R$^{3-2}$ are independently unsubstituted or R$^{3-1-1}$ substituted C$_{1-6}$ alkyl, or unsubstituted or R$^{3-1-4}$ substituted C$_{6-10}$ aryl;

R$^{3-1-1}$ and R$^{3-1-4}$ are independently cyano or halogen;

R$^1$ is unsubstituted or R$^{1-2}$ substituted 5 to 10 membered heteroaryl with 1 to 4 heteroatoms selected from one or more of N, O and S;

R$^{1-1}$ and R$^{1-2}$ are independently unsubstituted or R$^{1-1-1}$ substituted C$_{1-6}$ alkyl, unsubstituted or R$^{1-1-2}$ substituted C$_{3-10}$ cycloalkyl, or NR$^{1-1-4}$R$^{1-1-5}$;

R$^{1-1-1}$, R$^{1-1-2}$, R$^{1-1-4}$ and R$^{1-1-5}$ are independently C$_{1-6}$ alkyl;

R$^2$ is isopropyl or cyclopropyl;

L is —CO—NH—, —NH—CO—, —NH—CO—NH—, —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, —NH—CO—NH—CHR$^{4-6}$—, or —CO—NH—CR$^{4-7}$R$^{4-8}$—.

R$^{4-1}$ to R$^{4-8}$ are independently hydrogen, unsubstituted or R$^{4-1-1}$ substituted C$_{1-4}$ alkyl, or R$^{4-7}$ and R$^{4-8}$ together with the carbon atom therebetween form C$_{3-6}$ cycloalkyl.

In a certain scheme, some groups of the compound represented by formula I are defined as follows (undefined groups are as described in any of the previous schemes):

X is hydrogen;

R$^3$ is unsubstituted or R$^{3-1}$ substituted C$_{6-10}$ aryl, or unsubstituted or R$^{3-2}$ substituted 5 to 10 membered heteroaryl with 1 to 4 heteroatoms selected from one or more of N, O and S;

R$^{3-1}$ and R$^{3-2}$ are independently unsubstituted or R$^{3-1-1}$ substituted C$_{1-6}$ alkyl, or unsubstituted or R$^{3-1-4}$ substituted C$_{6-10}$ aryl;

R$^{3-1-1}$ and R$^{3-1-4}$ are independently cyano, halogen, or unsubstituted or R$^{3-1-1-1}$ substituted 3 to 10 membered heterocycloalkyl with 1 to 3 heteroatoms selected from one or more of N, O and S;

R$^{3-1-1-1}$ is C$_{1-4}$ alkyl;

R$^1$ is unsubstituted or R$^{1-2}$ substituted 5 to 10 membered heteroaryl with 1 to 4 heteroatoms selected from one or more of N, O and S;

R$^{1-1}$ and R$^{1-2}$ are independently unsubstituted or R$^{1-1-1}$ substituted C$_{1-6}$ alkyl, unsubstituted or R$^{1-1-2}$ substituted C$_{3-10}$ cycloalkyl, unsubstituted or R$^{1-1-3}$ substituted 3 to 10 membered heterocycloalkyl with 1 to 3 heteroatoms selected from one or more of N, O and S, or $NR^{1-1-4}R^{1-1-5}$;

$R^{1-1-1}$, $R^{1-1-2}$, $R^{1-1-3}$, $R^{1-1-4}$ and $R^{1-1-5}$ are independently $C_{1-6}$ alkyl;

when $R^2$ is methyl or ethyl, L is —$CHR^{4-1}$—CO—NH—, —$CHR^{4-2}$—NH—CO—, —NH—CO—$CHR^{4-3}$—, —CO—NH—$CHR^{4-4}$—, —$CHR^{4-5}$—NH—CO—NH—, or —NH—CO—NH—$CHR^{4-6}$—;

when $R^2$ is isopropyl or cyclopropyl, L is —$CHR^{4-1}$—CO—NH—, —$CHR^{4-2}$—NH—CO—, —NH—CO—$CHR^{4-3}$—, —CO—NH—$CHR^{4-4}$—, —$CHR^{4-5}$—NH—CO—NH—, or —NH—CO—NH—$CHR^{4-6}$—;

$R^{4-1}$ to $R^{4-6}$ are independently hydrogen, unsubstituted or $R^{4-1-1}$ substituted $C_{1-4}$ alkyl.

In a certain scheme, some groups of the compound represented by formula I are defined as follows (undefined groups are as described in any of the previous schemes):

X is hydrogen;

$R^3$ is unsubstituted or $R^{3-1}$ substituted $C_{6-10}$ aryl, or unsubstituted or $R^{3-2}$ substituted 5 to 10 membered heteroaryl with 1 to 4 heteroatoms selected from one or more of N, O and S;

$R^{3-1}$ and $R^{3-2}$ are independently unsubstituted or $R^{3-1-1}$ substituted $C_{1-6}$ alkyl, or unsubstituted or $R^{3-1-4}$ substituted $C_{6-10}$ aryl;

$R^{3-1-1}$ and $R^{3-1-4}$ are independently cyano or halogen;

$R^1$ is unsubstituted or $R^{1-2}$ substituted 5 to 10 membered heteroaryl with 1 to 4 heteroatoms selected from one or more of N, O and S;

$R^{1-1}$ and $R^{1-2}$ are independently unsubstituted or $R^{1-1-1}$ substituted $C_{1-6}$ alkyl, unsubstituted or $R^{1-1-2}$ substituted $C_{3-10}$ cycloalkyl, or $NR^{1-1-4}R^{1-1-5}$;

$R^{1-1-1}$, $R^{1-1-2}$, $R^{1-1-4}$ and $R^{1-1-5}$ are independently $C_{1-6}$ alkyl;

when $R^2$ is methyl or ethyl, L is —$CHR^{4-1}$—CO—NH—, —$CHR^{4-2}$—NH—CO—, —NH—CO—$CHR^{4-3}$—, —CO—NH—$CHR^{4-4}$—, —$CHR^{4-5}$—NH—CO—NH—, or —NH—CO—NH—$CHR^{4-6}$—;

when $R^2$ is isopropyl or cyclopropyl, L is —$CHR^{4-1}$—CO—NH—, —$CHR^{4-2}$—NH—CO—, —NH—CO—$CHR^{4-3}$—, —CO—NH—$CHR^{4-4}$—, —$CHR^{4-5}$—NH—CO—NH—, or —NH—CO—NH—$CHR^{4-6}$—;

$R^{4-1}$ to $R^{4-6}$ are independently hydrogen, unsubstituted or $R^{4-1-1}$ substituted $C_{1-4}$ alkyl.

In a certain scheme, some groups of the compound represented by formula I are defined as follows (undefined groups are as described in any of the previous schemes):

X is hydrogen;

$R^3$ is unsubstituted or $R^{3-1}$ substituted $C_{6-10}$ aryl, or unsubstituted or $R^{3-2}$ substituted 5 to 10 membered heteroaryl with 1 to 4 heteroatoms selected from one or more of N, O and S;

$R^{3-1}$ and $R^{3-2}$ are independently unsubstituted or $R^{3-1-1}$ substituted $C_{1-6}$ alkyl, or unsubstituted or $R^{3-1-4}$ substituted $C_{6-10}$ aryl;

$R^{3-1-1}$ and $R^{3-1-4}$ are independently cyano or halogen;

$R^1$ is unsubstituted or $R^{1-2}$ substituted 5 to 10 membered heteroaryl with 1 to 4 heteroatoms selected from one or more of N, O and S;

$R^{1-1}$ and $R^{1-2}$ are independently unsubstituted or $R^{1-1-1}$ substituted $C_{1-6}$ alkyl, unsubstituted or $R^{1-1-3}$ substituted 3 to 10 membered heterocycloalkyl with 1 to 3 heteroatoms selected from one or more of N, O and S, or unsubstituted or $R^{1-1-2}$ substituted $C_{3-10}$ cycloalkyl;

$R^{1-1-1}$, $R^{1-1-2}$, $R^{1-1-3}$, $R^{1-1-4}$ and $R^{1-1-5}$ are independently $C_{1-6}$ alkyl;

when $R^2$ is methyl, L is —NH—CO—NH—, —$CHR^{4-1}$—CO—NH—, —$CHR^{4-2}$—NH—CO—, —NH—CO—$CHR^{4-3}$—, —CO—NH—$CHR^{4-4}$— or —$CHR^{4-5}$—NH—CO—NH—;

when $R^2$ is isopropyl or cyclopropyl, L is —CO—NH—, —NH—CO—$CHR^{4-3}$—, —$CHR^{4-5}$—NH—CO—NH— or —CO—NH—$CR^{4-7}R^{4-8}$—;

$R^{4-1}$ to $R^{4-8}$ are independently hydrogen, unsubstituted or $R^{4-1-1}$ substituted $C_{1-4}$ alkyl, or $R^{4-7}$ and $R^{4-8}$ together with the carbon atom therebetween form $C_{3-6}$ cycloalkyl.

In a certain scheme, some groups of the compound represented by formula I are defined as follows (undefined groups are as described in any of the previous schemes): X is hydrogen.

In a certain scheme, some groups of the compound represented by formula I are defined as follows (undefined groups are as described in any of the previous schemes):

$R^3$ is unsubstituted or $R^{3-1}$ substituted $C_{6-10}$ aryl, or unsubstituted or $R^{3-2}$ substituted 5 to 10 membered heteroaryl with 1 to 4 heteroatoms selected from one or more of N, O and S.

In a certain scheme, some groups of the compound represented by formula I are defined as follows (undefined groups are as described in any of the previous schemes):

$R^{3-1}$ and $R^{3-2}$ are independently hydroxyl, unsubstituted or $R^{3-1-1}$ substituted $C_{1-6}$ alkyl, or unsubstituted or $R^{3-1-4}$ substituted phenyl.

In a certain scheme, some groups of the compound represented by formula I are defined as follows (undefined groups are as described in any of the previous schemes):

$R^{3-1}$ and $R^{3-2}$ are independently unsubstituted or $R^{3-1-1}$ substituted $C_{1-6}$ alkyl, or unsubstituted or $R^{3-1-4}$ substituted phenyl.

In a certain scheme, some groups of the compound represented by formula I are defined as follows (undefined groups are as described in any of the previous schemes):

$R^{3-1-1}$ and $R^{3-1-4}$ are independently cyano, halogen, or unsubstituted or $R^{3-1-1-1}$ substituted 3 to 10 membered heterocycloalkyl with 1 to 3 heteroatoms selected from one or more of N, O and S.

In a certain scheme, some groups of the compound represented by formula I are defined as follows (undefined groups are as described in any of the previous schemes):

$R^{3-1-1}$ and $R^{3-1-4}$ are independently cyano or halogen.

In a certain scheme, some groups of the compound represented by formula I are defined as follows (undefined groups are as described in any of the previous schemes):

$R^{3-1-1-1}$ is $C_{1-4}$ alkyl.

In a certain scheme, some groups of the compound represented by formula I are defined as follows (undefined groups are as described in any of the previous schemes):

$R^1$ is unsubstituted or $R^{1-1}$ substituted $C_{6-10}$ aryl, or unsubstituted or $R^{1-2}$ substituted 5 to 10 membered heteroaryl with 1 to 4 heteroatoms selected from one or more of N, O and S.

In a certain scheme, some groups of the compound represented by formula I are defined as follows (undefined groups are as described in any of the previous schemes):

$R^1$ is unsubstituted or $R^{1-2}$ substituted 5 to 10 membered heteroaryl with 1 to 4 heteroatoms selected from one or more of N, O and S.

In a certain scheme, some groups of the compound represented by formula I are defined as follows (undefined groups are as described in any of the previous schemes):

$R^{1-2}$ is unsubstituted or $R^{1-1-1}$ substituted $C_{1-6}$ alkyl, unsubstituted or $R^{1-1-2}$ substituted $C_{3-10}$ cycloalkyl, unsubstituted or $R^{1-1-3}$ substituted 3 to 10 membered heterocycloalkyl with 1 to 3 heteroatoms selected from one or more of N, O and S, or $NR^{1-1-4}R^{1-1-5}$.

In a certain scheme, some groups of the compound represented by formula I are defined as follows (undefined groups are as described in any of the previous schemes): $R^{1-1}$ and $R^{1-2}$ are independently unsubstituted or $R^{1-1-1}$ substituted $C_{1-6}$ alkyl, $C_{1-6}$ alkoxy, unsubstituted or $R^{1-1-2}$ substituted $C_{3-10}$ cycloalkyl, or $NR^{1-1-4}R^{1-1-5}$.

In a certain scheme, some groups of the compound represented by formula I are defined as follows (undefined groups are as described in any of the previous schemes): $R^{1-1-1}$, $R^{1-1-2}$, $R^{1-1-3}$, $R^{1-1-4}$ and $R^{1-1-5}$ are independently $C_{1-6}$ alkyl.

In a certain scheme, some groups of the compound represented by formula I are defined as follows (undefined groups are as described in any of the previous schemes): $R^{1-1-1}$, $R^{1-1-2}$, $R^{1-1-4}$ and $R^{1-1-5}$ are independently hydroxyl, or $C_{1-6}$ alkyl.

In a certain scheme, some groups of the compound represented by formula I are defined as follows (undefined groups are as described in any of the previous schemes): $R^{1-1-1}$, $R^{1-1-2}$, $R^{1-1-4}$ and $R^{1-1-5}$ are independently $C_{1-6}$ alkyl.

In a certain scheme, some groups of the compound represented by formula I are defined as follows (undefined groups are as described in any of the previous schemes): when $R^2$ is methyl or ethyl, L is —NH—CO—NH—, —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, —NH—CO—NH—CHR$^{4-6}$—, or —CO—NH—CR$^{4-7}$R$^{4-8}$—.

In a certain scheme, some groups of the compound represented by formula I are defined as follows (undefined groups are as described in any of the previous schemes): when $R^2$ is methyl or ethyl, L is —CHR$^{4-1}$—CO—NH—, —CHR$^{4-2}$—NH—CO—, —NH—CO—CHR$^{4-3}$—, —CO—NH—CHR$^{4-4}$—, —CHR$^4$—NH—CO—NH—, or —NH—CO—NH—CHR$^{4-6}$—.

In a certain scheme, some groups of the compound represented by formula I are defined as follows (undefined groups are as described in any of the previous schemes): when $R^2$ is methyl or ethyl, L is —CHR$^{4-2}$—NH—CO—.

In a certain scheme, some groups of the compound represented by formula I are defined as follows (undefined groups are as described in any of the previous schemes): when $R^2$ is isopropyl or cyclopropyl, L is —CO—NH—, —NH—CO—, —NH—CO—NH—, —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, —NH—CO—NH—CHR$^{4-6}$—, or —CO—NH—CR$^{4-7}$R$^{4-8}$—.

In a certain scheme, some groups of the compound represented by formula I are defined as follows (undefined groups are as described in any of the previous schemes): when $R^2$ is isopropyl or cyclopropyl, L is —CHR$^{4-1}$—CO—NH—, —CHR$^{4-2}$—NH—CO—, —NH—CO—CHR$^{4-3}$—, —CO—NH—CHR$^{4-4}$—, —CHR$^4$—NH—CO—NH—, or —NH—CO—NH—CHR$^{4-6}$—.

In a certain scheme, some groups of the compound represented by formula I are defined as follows (undefined groups are as described in any of the previous schemes): when $R^2$ is isopropyl or cyclopropyl, L is —CHR$^{4-2}$—NH—CO—.

In a certain scheme, some groups of the compound represented by formula I are defined as follows (undefined groups are as described in any of the previous schemes): $R^2$ is isopropyl or cyclopropyl.

In a certain scheme, some groups of the compound represented by formula I are defined as follows (undefined groups are as described in any of the previous schemes): $R^2$ is cyclopropyl.

In a certain scheme, some groups of the compound represented by formula I are defined as follows (undefined groups are as described in any of the previous schemes): $R^2$ is isopropyl.

In a certain scheme, some groups of the compound represented by formula I are defined as follows (undefined groups are as described in any of the previous schemes):

$R^{4-1}$ to $R^{4-8}$ are independently hydrogen, unsubstituted or $R^{4-1-1}$ substituted $C_{1-4}$ alkyl, or $R^{4-7}$ and $R^{4-8}$ together with the carbon atom therebetween form $C_{3-6}$ cycloalkyl.

In a certain scheme, some groups of the compound represented by formula I are defined as follows (undefined groups are as described in any of the previous schemes):

$R^{4-1}$ to $R^{4-6}$ are independently hydrogen, unsubstituted or $R^{4-1-1}$ substituted $C_{1-4}$ alkyl.

In a certain scheme, some groups of the compound represented by formula I are defined as follows (undefined groups are as described in any of the previous schemes):

$R^{4-2}$ is hydrogen, unsubstituted or $R^{4-1-1}$ substituted $C_{1-4}$ alkyl.

In a certain scheme, when the compound shown in formula I contains a chiral C atom, the C atom can be in the S configuration or R configuration.

In a certain scheme, when L is —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH— or —NH—CO—NH—CHR$^{4-6}$—, the —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH— or —NH—CO—NH—CHR$^{4-6}$— can be

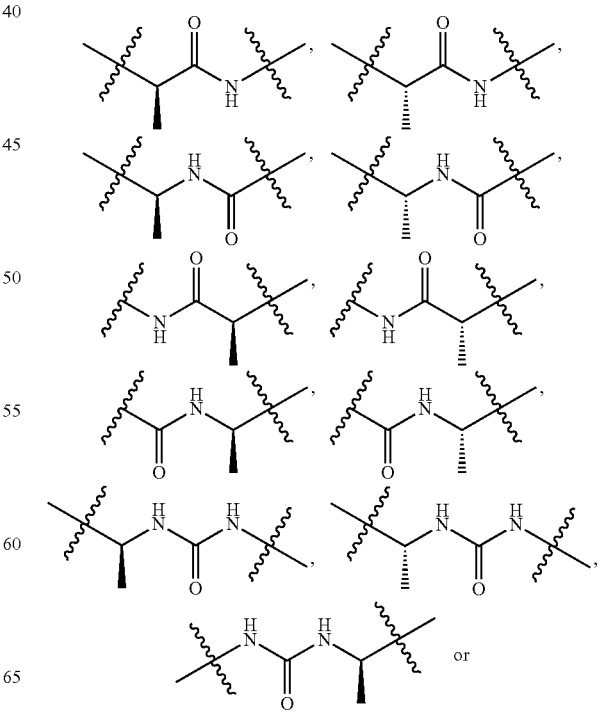

25
-continued
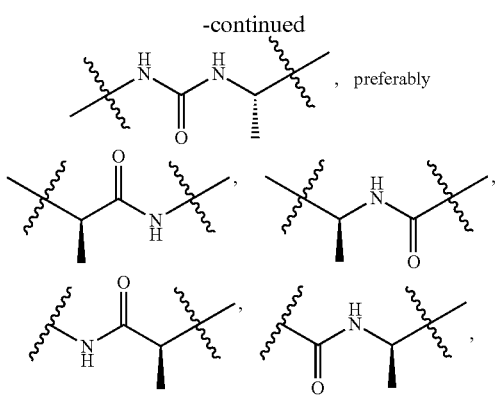, preferably
26
-continued
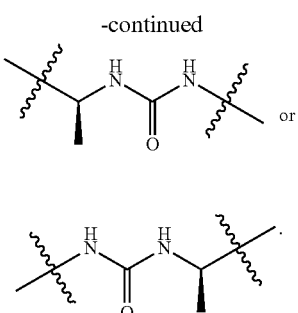 or
In a certain scheme, the compound represented by formula I can have any of the following structures:
S1
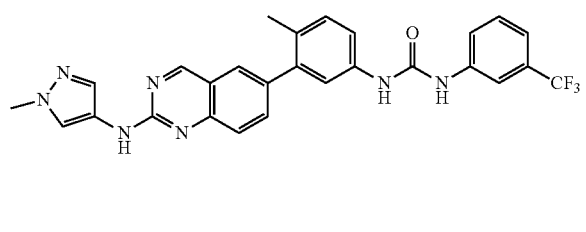
S2
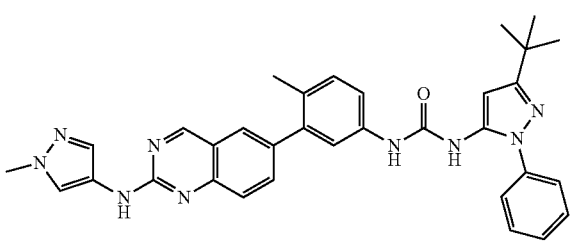
S4
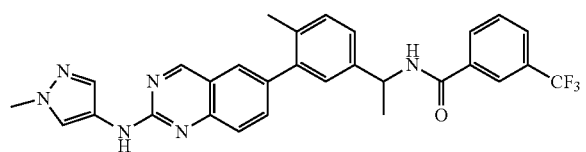
S5
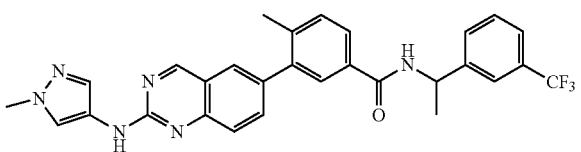
S6
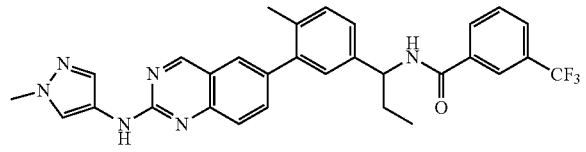
S7
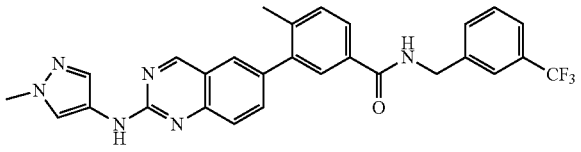
S8
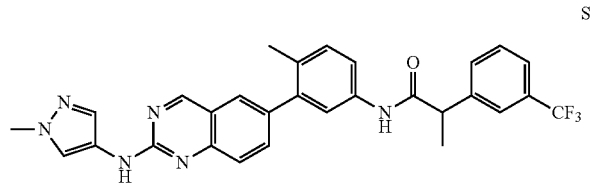
S9
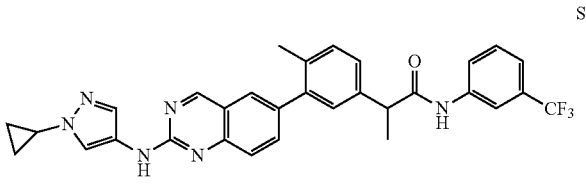
S10
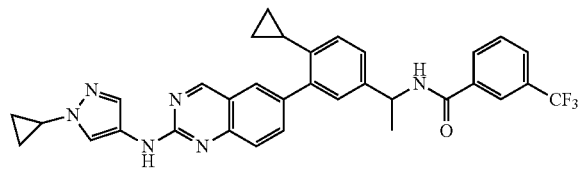
S11
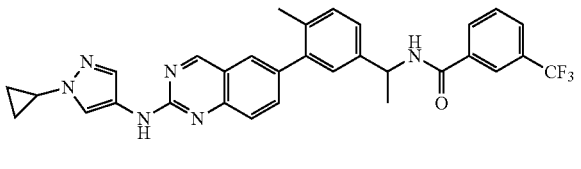
S12
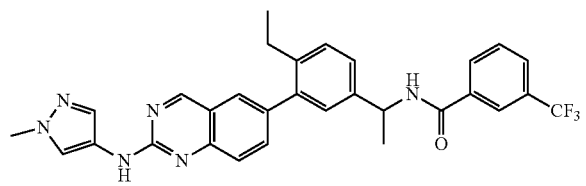
S13
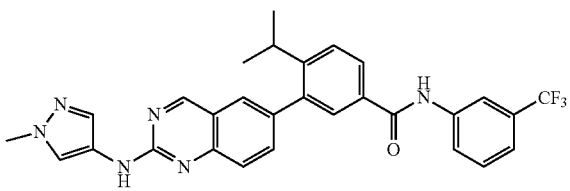

-continued

S28 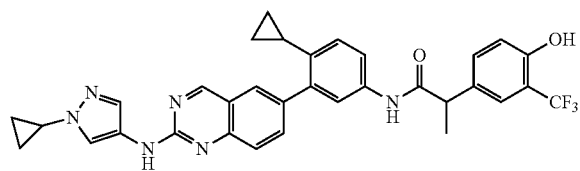
S29 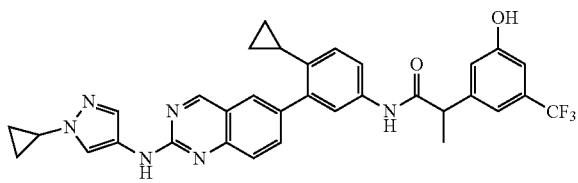
S30 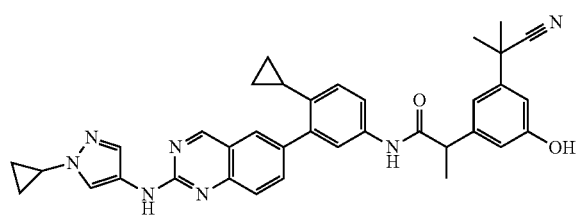
S31 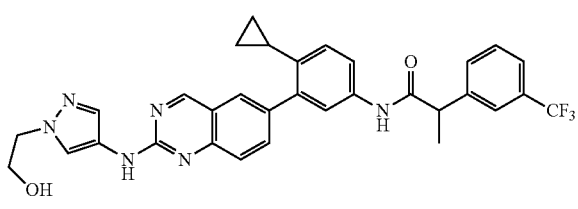
S32 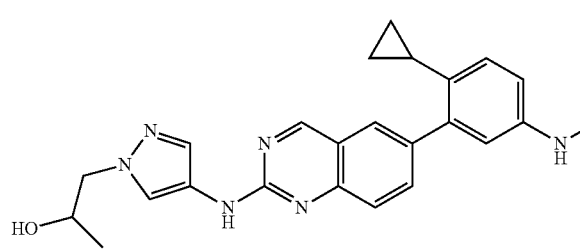
S33 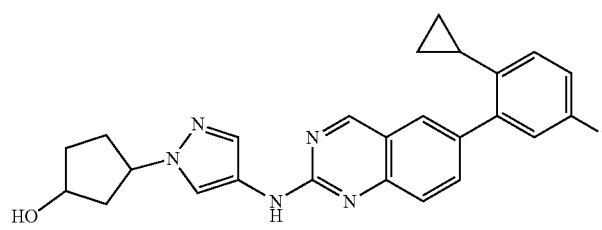
S34 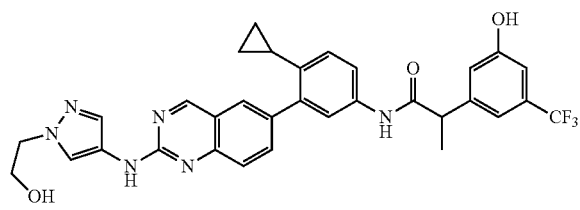
S35 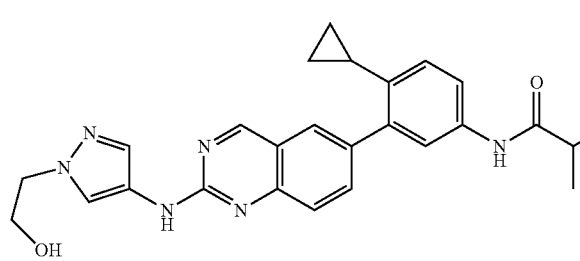
S36 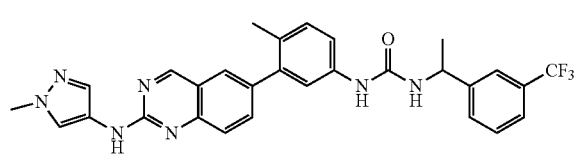
S11-A 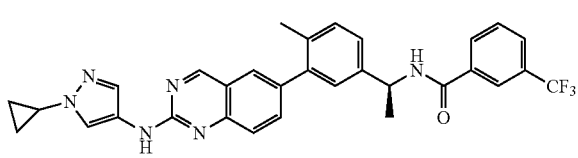

-continued
S11-B
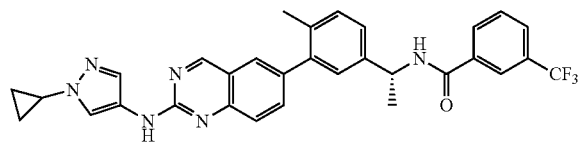
S37
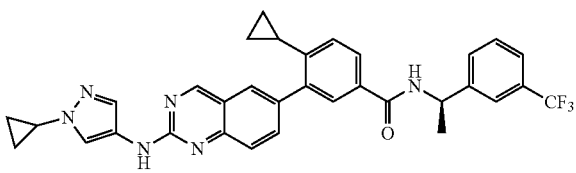
S38
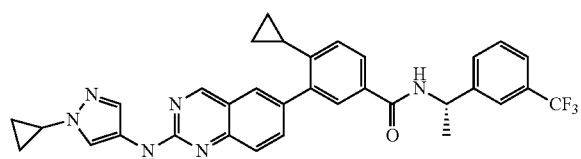
S39
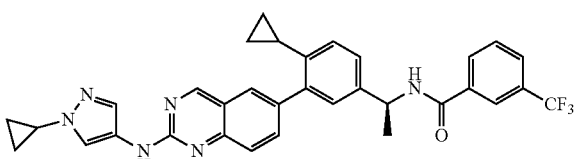
S40
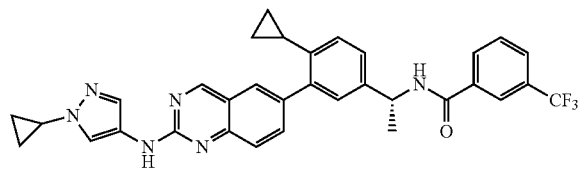
S41
S42
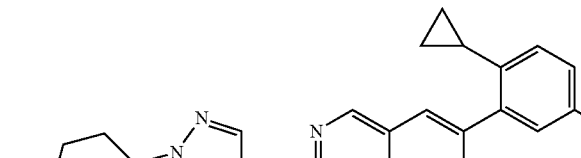
S43
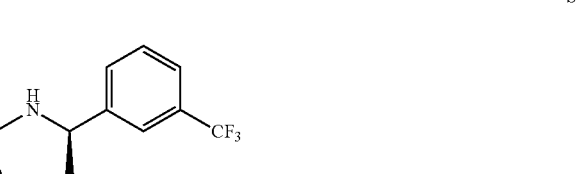
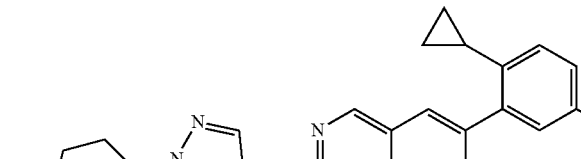
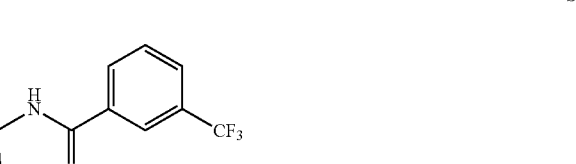
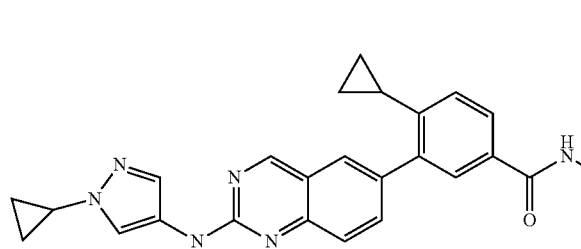
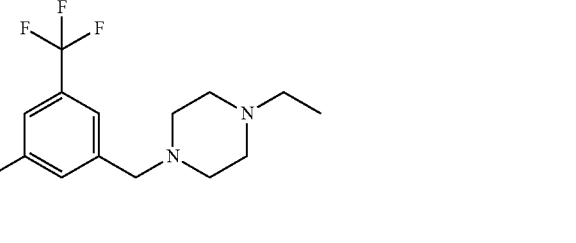
S44
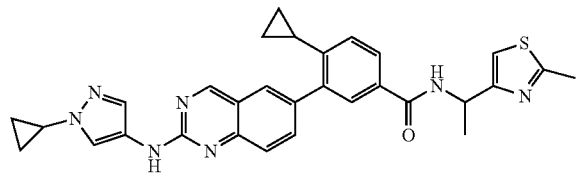
S45
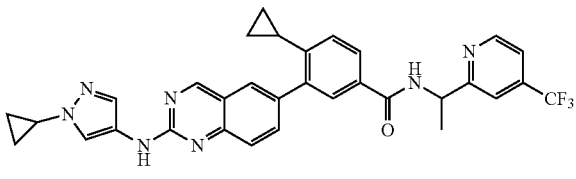

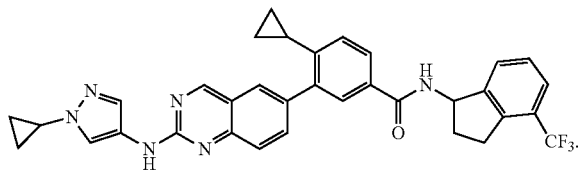

S46

The present disclosure also provides a method for preparing the compound shown in formula I, the method comprises the following steps: In a solvent, under the action of a base and a palladium catalyst, the compound represented by formula II and the compound represented by formula III are subjected to the coupling reaction shown below;

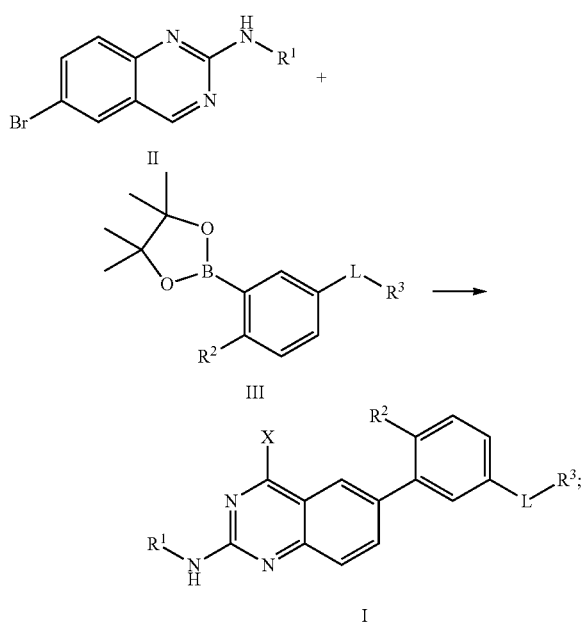

wherein, X, L, $R^1$, $R^2$ and $R^3$ are as defined above.

In the present disclosure, the coupling reaction is preferably carried out under a protective gas atmosphere, and the protective gas may be a conventional protective gas in the art, such as argon and/or nitrogen.

In the present disclosure, the solvent can be a conventional solvent in the art, preferably water and/or ether solvents. The ether solvents are preferably dioxane.

In the present disclosure, the base can be a conventional base in the art, preferably an alkali metal carbonate, such as potassium carbonate.

In the present disclosure, the palladium catalyst can be a conventional palladium catalyst in the art, preferably a zero-valent palladium catalyst, such as [1,1'-bis(diphenylphosphine)ferrocene]palladium dichloride dichloromethane complex.

In the present disclosure, the molar concentration of the compound represented by formula II in the solvent can be a molar concentration conventional in the art, preferably 0.01-0.05 mol/L, such as 0.0186 mol/L, 0.01925 mol/L and 0.03285 mol/L.

In the present disclosure, the molar ratio of the compound shown in formula III and the compound shown in formula II can be a conventional molar ratio in the art, preferably 0.8:1 to 1.5:1, such as 1:1 and 1.1:1.

In the present disclosure, the molar ratio of the base and the compound represented by formula II can be a conventional molar ratio in the art, preferably 1:1-3:1, such as 2:1.

In the present disclosure, the molar ratio of the palladium catalyst and the compound represented by formula II can be a conventional molar ratio in the art, preferably 1:30-1:35, such as 1:30.8, 1:31.8 and 1:32.85.

In the present disclosure, the temperature of the coupling reaction can be a conventional temperature in the art, preferably 70-90° C.

In the present disclosure, the progress of the coupling reaction can be monitored by conventional means in the art (such as TLC, HPLC or LCMS), and the time is preferably 2 to 4 hours, such as 3 hours.

In the present disclosure, after the coupling reaction is completed, preferably, a post-treatment step may be further included. The conditions and operations for the post-treatment can be conventional conditions and operations for the post-treatment in the art, and include the following steps: the reaction solution is cooled, a solvent is added, an organic layer is extracted, dried and filtered, and the solvent in the filtrate is removed to obtain a residue, and then the residue was separated and purified. Said cooling is preferably cooling to room temperature.

The solvent is preferably saline, such as saturated saline. The extraction conditions and operations can be conventional conditions and operations in the art, and the extraction solvent is preferably an ester solvent, such as ethyl acetate. The drying conditions and operations can be conventional conditions and operations in the art, and the drying reagent can be a conventional reagent in the art, such as anhydrous sodium sulfate. The filtering conditions and operations can be conventional conditions and operations in the field. The conditions and operations for removing the solvent can be conventional conditions and operations in the art, such as evaporating the solvent to dryness. The separation and purification are preferably column chromatography separation.

Unless otherwise specified, the "room temperature" in the present disclosure refers to 20-30° C.

The present disclosure also provides a pharmaceutical composition comprising the compound shown in formula I, the pharmaceutically acceptable salt thereof, the tautomer thereof, the stereoisomer thereof, the metabolite thereof, the metabolic precursor thereof or the prodrug thereof as described above, and pharmaceutical excipients.

In the pharmaceutical composition, the amount of the compound shown in formula I, the pharmaceutically acceptable salt thereof, the tautomer thereof, the stereoisomer thereof, the metabolite thereof, the metabolic precursor thereof or the prodrug thereof can be a therapeutically effective amount.

The present disclosure also provides the use of the compound shown in formula I, the pharmaceutically acceptable salt thereof, the tautomer thereof, the stereoisomer thereof, the metabolite thereof, the metabolic precursor thereof or the prodrug thereof or the pharmaceutical composition as described above in the preparation of DDR (Discoidindomain receptor) inhibitors.

In the present disclosure, the DDR inhibitors are preferably DDR1 and/or DDR2 inhibitors, and more preferably DDR2 inhibitors.

The present disclosure also provides the use of the compound shown in formula I, the pharmaceutically acceptable salt thereof, the tautomer thereof, the stereoisomer thereof, the metabolite thereof, the metabolic precursor thereof or the prodrug thereof or the pharmaceutical composition as described above in the preparation of a medicine.

The present disclosure also provides the use of the compound shown in formula I, the pharmaceutically acceptable salt thereof, the tautomer thereof, the stereoisomer thereof, the metabolite thereof, the metabolic precursor thereof or the prodrug thereof or the pharmaceutical composition as described above in the preparation of a medicine, the medicine can be used to treat fibrosis, arthritis, atherosclerosis or tumors, preferably fibrosis, tumors or arthritis, and the fibrosis is preferably pulmonary fibrosis.

The present disclosure also provides a use of the compound shown in formula I, the pharmaceutically acceptable salt thereof, the tautomer thereof, the stereoisomer thereof, the metabolite thereof, the metabolic precursor thereof or the prodrug thereof or the pharmaceutical composition as described above in the preparation of a medicine for treating DDR-related diseases.

In the present disclosure, the DDR-related diseases include but are not limited to fibrosis, arthritis, atherosclerosis or tumors, preferably fibrosis, tumors or arthritis, and the fibrosis is preferably pulmonary fibrosis.

The present disclosure also provides a method for treating fibrosis, arthritis, atherosclerosis or tumors, which comprises administering a therapeutically effective amount of the compound shown in formula I, the pharmaceutically acceptable salt thereof, the tautomer thereof, the stereoisomer thereof, the metabolite thereof, the metabolic precursor thereof or the prodrug thereof as described above to a patient.

The present disclosure also provides a pharmaceutical combination, which comprises: the compound shown in formula I, the pharmaceutically acceptable salt thereof, the tautomer thereof, the stereoisomer thereof, the metabolite thereof, the metabolic precursor thereof or the prodrug thereof, and a PD-1/PD-L1 inhibitor. The compound shown in formula I, the pharmaceutically acceptable salt thereof, the tautomer thereof, the stereoisomer thereof, the metabolite thereof, the metabolic precursor thereof or the prodrug thereof and the PD-1/PD-L1 inhibitor can be administered simultaneously or separately.

The present disclosure also provides a use of the above-mentioned medicine combination in the preparation of a medicine for treating tumors.

The present disclosure also provides a pharmaceutical composition comprising the compound shown in formula I, the pharmaceutically acceptable salt thereof, the tautomer thereof, the stereoisomer thereof, the metabolite thereof, the metabolic precursor thereof or the prodrug thereof as described above, a PD-1/PD-L1 inhibitor, and pharmaceutical excipients. The compound shown in formula I, the pharmaceutically acceptable salt thereof, the tautomer thereof, the stereoisomer thereof, the metabolite thereof, the metabolic precursor thereof or the prodrug thereof and the PD-1/PD-L1 inhibitor can be administered simultaneously or separately.

The present disclosure also provides a use of the above-mentioned pharmaceutical composition in the preparation of a medicine for treating tumors.

The present disclosure also provides an use of the compound shown in formula I, the pharmaceutically acceptable salt thereof, the tautomer thereof, the stereoisomer thereof, the metabolite thereof, the metabolic precursor thereof or the prodrug thereof as described above in the preparation of a medicine for treating tumors, the compound shown in formula I, the pharmaceutically acceptable salt thereof, the tautomer thereof, the stereoisomer thereof, the metabolite thereof, the metabolic precursor thereof or the prodrug thereof is used in combination with a PD-1/PD-L1 inhibitor. The compound shown in formula I, the pharmaceutically acceptable salt thereof, the tautomer thereof, the stereoisomer thereof, the metabolite thereof, the metabolic precursor thereof or the prodrug thereof and the PD-1/PD-L1 inhibitor can be administered simultaneously or separately.

The present disclosure also provides an use of the compound shown in formula I, the pharmaceutically acceptable salt thereof, the tautomer thereof, the stereoisomer thereof, the metabolite thereof, the metabolic precursor thereof or the prodrug thereof as described above and a PD-1/PD-L1 inhibitor in the preparation of a medicine for treating tumors, the compound shown in formula I, the pharmaceutically acceptable salt thereof, the tautomer thereof, the stereoisomer thereof, the metabolite thereof, the metabolic precursor thereof or the prodrug thereof is used in combination with the PD-1/PD-L1 inhibitor. The compound shown in formula I, the pharmaceutically acceptable salt thereof, the tautomer thereof, the stereoisomer thereof, the metabolite thereof, the metabolic precursor thereof or the prodrug thereof and the PD-1/PD-L1 inhibitor can be administered simultaneously or separately.

The present disclosure also provides a use of a PD-1/PD-L1 inhibitor in the preparation of a medicine for the treating tumors, the PD-1/PD-L1 inhibitor is used in combination with the compound shown in formula I, the pharmaceutically acceptable salt thereof, the tautomer thereof, the stereoisomer thereof, the metabolite thereof, the metabolic precursor thereof or the prodrug thereof as described above. The PD-1/PD-L1 inhibitor and the compound shown in formula I, the pharmaceutically acceptable salt thereof, the tautomer thereof, the stereoisomer thereof, the metabolite thereof, the metabolic precursor thereof or the prodrug thereof can be administered simultaneously or separately.

In the present disclosure, the tumors comprise but not limited to lung cancer, breast cancer, head and neck squamous cell carcinoma, liver cancer, gastric cancer or colorectal cancer.

The present disclosure provides a compound shown in formula I, a pharmaceutically acceptable salt thereof, a tautomer thereof, a stereoisomer thereof, a metabolite thereof, a metabolic precursor thereof or a prodrug thereof, the structure thereof is as follows:

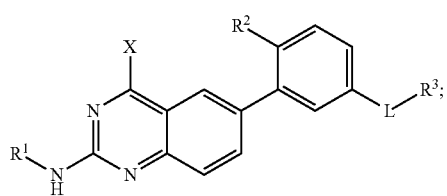

wherein, X is hydrogen or amino;

$R^3$ is unsubstituted or $R^{3-1}$ substituted $C_{1-10}$ aryl, or unsubstituted or $R^{3-2}$ substituted 5 to 10 membered heteroaryl with 1 to 4 heteroatoms selected from one or more of N, O and S;

$R^{3-1}$ and $R^{3-2}$ are independently deuterium, hydroxyl, unsubstituted or $R^{3-1-1}$ substituted $C_{1-6}$ alkyl, $C_{1-6}$ alkoxy, unsubstituted or $R^{3-1-2}$ substituted $C_{3-10}$ cycloalkyl, unsubstituted or $R^{3-1}$-3 substituted 3 to 10 membered heterocycloalkyl with 1 to 3 heteroatoms selected from one or more of N, O and S, unsubstituted or $R^{3-1-4}$ substituted $C_{6-10}$ aryl, or, unsubstituted or $R^{3-1-5}$ substituted 5 to 6 membered heteroaryl with 1 to 3 heteroatoms selected from one or more of N, O and S;

$R^{3-1-1}$ to $R^{3-1-5}$ are independently hydroxyl, cyano, halogen, $C_{1-6}$ alkyl, $C_{3-10}$ cycloalkyl, or, unsubstituted or $R^{3-1-1-1}$ substituted 3 to 10 membered heterocycloalkyl with 1 to 3 heteroatoms selected from one or more of N, O and S;

$R^{3-1-1-1}$ is hydroxyl,

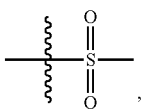 [SMILES: *S(C)(=O)=O]

$C_{1-4}$ alkyl, $C_{3-6}$ cycloalkyl, $C_{1-4}$ alkylcarbonyl, or, —$NR^{3-1-1-1'}R^{3-1-1-1''}$; $R^{3-1-1-1'}$ and $R^{3-1-1-1''}$ are independently hydrogen or $C_{1-4}$ alkyl;

when $R^2$ is methyl or ethyl, L is —NH—CO—NH—, —$CHR^{4-1}$—CO—NH—, —$CHR^{4-2}$—NH—CO—, —NH—CO—$CHR^{4-3}$—, —CO—NH—$CHR^{4-4}$—, —$CHR^{4-5}$—NH—CO—NH—, —NH—CO—NH—$CHR^{4-6}$—, or —CO—NH—$CR^{4-7}R^{4-8}$—.

when $R^2$ is methyl or ethyl, $R^1$ is unsubstituted or $R^{1-1}$ substituted $C_{6-10}$ aryl, or unsubstituted or $R^{1-2}$ substituted 5 to 10 membered heteroaryl with 1 to 4 heteroatoms selected from one or more of N, O and S;

when $R^2$ is isopropyl or cyclopropyl, L is —CO—NH—, —NH—CO—, —NH—CO—NH—, —$CHR^{4-1}$—CO—NH—, —$CHR^{4-2}$—NH—CO—, —NH—CO—$CHR^{4-3}$—, —CO—NH—$CHR^{4-4}$—, —$CHR^{4-5}$—NH—CO—NH—, —NH—CO—NH—$CHR^{4-6}$—, or —CO—NH—$CR^{4-7}R^{4-8}$—;

when $R^2$ is isopropyl or cyclopropyl, $R^1$ is hydrogen, $C_{1-10}$ alkyl, $C_{1-6}$ haloalkyl, unsubstituted or $R^{1-1}$ substituted $C_{6-10}$ aryl, unsubstituted or $R^{1-2}$ substituted 5 to 10 membered heteroaryl with 1 to 3 heteroatoms selected from one or more of N, O and S, unsubstituted or $R^{1-3}$ substituted heterocycloalkyl, unsubstituted or $R^{1-4}$ substituted heterocycloalkyl-$C_{1-6}$ alkyl, unsubstituted or $R^{1-5}$ substituted $C_{3-7}$ cycloalkyl, unsubstituted or $R^{1-6}$ substituted $C_{3-7}$ cycloalkyl-$C_{1-6}$ alkyl, unsubstituted or $R^{1-7}$ substituted $C_{1-6}$ heteroalkyl with 1 to 3 heteroatoms selected from one or more of N, O and S and 1 to 6 carbon atoms; the heterocycloalkyl is a 3 to 10 membered heterocycloalkyl with 1 to 3 heteroatoms selected from one or more of N, O and S;

the left end of L is connected to

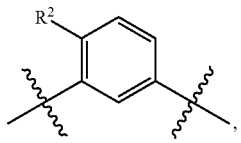

and the right end is connected to $R^3$;

$R^{4-1}$ to $R^{4-8}$ are independently hydrogen, $C_{1-4}$ alkyl, $C_{1-4}$ heteroalkyl with 1 to 2 heteroatoms are selected from one or more of N, O and S and 1 to 4 carbon atoms, $C_{3-6}$ cycloalkyl, 3 to 7 membered heterocycloalkyl with 1 to 2 heteroatoms selected from one or more of N, O and S, or $R^{4-7}$ and $R^{4-8}$ together with the carbon atom therebetween form $C_{3-6}$ cycloalkyl;

$R^{1-1}$ and $R^{1-2}$ are independently deuterium, unsubstituted or $R^{1-1-1}$ substituted $C_{1-6}$ alkyl, $C_{1-6}$ alkoxy, unsubstituted or $R^{1-1-2}$ substituted $C_{3-10}$ cycloalkyl, unsubstituted or $R^{1-1-3}$ substituted 3 to 10 membered heterocycloalkyl with 1 to 3 heteroatoms selected from one or more of N, O and S, or $NR^{1-1-4}R^{1-1-5}$;

$R^{1-1-1}$ to $R^{1-1-5}$ are independently hydroxyl, $C_{1-6}$ alkyl, $C_{3-10}$ cycloalkyl, or 3 to 10 membered heterocycloalkyl with 1 to 3 heteroatoms selected from one or more of N, O and S;

$R^{1-3}$ to $R^{1-7}$ are independently halogen, hydroxyl, $C_{6-10}$ aryl, $C_{1-6}$ alkyl, $C_{1-6}$ haloalkyl, $C_{1-3}$ alkoxy, $C_{1-4}$ acyloxy-$C_{1-3}$ alkyl or $C_{1-3}$ hydroxyalkyl.

In the present disclosure, when $R^3$ is unsubstituted or $R^{3-1}$ substituted $C_{6-10}$ aryl, the number of the $R^{3-1}$ can be one or more (the number meets the following criteria: the substituted group conforms to the valence bond theory and exists stably. For example, the number is 1, 2, 3, or 4), when more than one $R^{3-1}$ occurs, the $R^{3-1}$ can be the same or different.

In the present disclosure, when $R^3$ is unsubstituted or $R^{3-1}$ substituted $C_{6-10}$ aryl, the $C_{6-10}$ aryl is preferably phenyl.

In the present disclosure, when $R^3$ is unsubstituted or $R^{3-1}$ substituted $C_{6-10}$ aryl, the $R^{3-1}$ substituted $C_{6-10}$ aryl is preferably

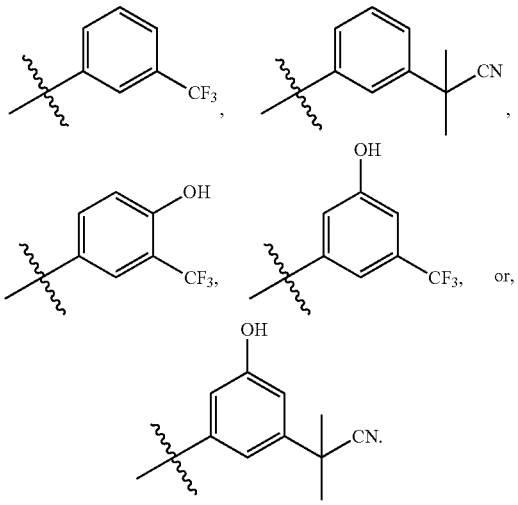

In the present disclosure, when $R^3$ is unsubstituted or $R^{3-2}$ substituted 5 to 10 membered heteroaryl with 1 to 4 heteroatoms selected from one or more of N, O and S, the number of the $R^{3-2}$ can be one or more (the number meets the following criteria: the substituted group conforms to the valence bond theory and exists stably. For example, the number is 1, 2, or 3), when more than one $R^{3-2}$ occurs, the $R^{3-2}$ can be the same or different.

In the present disclosure, when $R^3$ is unsubstituted or $R^{3-2}$ substituted 5 to 10 membered heteroaryl with 1 to 4 heteroatoms selected from one or more of N, O and S, the heteroaryl is preferably 5 to 6 membered heteroaryl with 1 to 4 heteroatoms selected from one or more of N, O and S, for example, pyrrolyl, furyl, thienyl, imidazolyl, pyrazolyl, oxazolyl, isoxazolyl, thiazolyl, isothiazolyl, 1,2,3-triazolyl, 1,2,4-triazolyl, furazanyl, 1,2,3-oxadiazolyl, 1,2,4-oxadiazolyl, 1,2,5-oxadiazolyl, 1,3,4-oxadiazolyl, thiadiazolyl, dithiazolyl, tetrazolyl, pyridyl, pyranyl, thiopyranyl, diazinyl, pyrazinyl, pyrimidinyl, pyridazinyl, oxazinyl, thiazinyl, dioxinyl, dithiinyl, 1,2,3-triazinyl, 1,2,4-triazinyl, 1,3,5-triazinyl or tetrazinyl, more preferably pyrazolyl (for example,

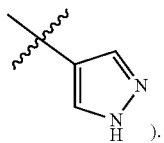

).

In the present disclosure, when $R^3$ is unsubstituted or $R^{3-2}$ substituted 5 to 10 membered heteroaryl with 1 to 4 heteroatoms selected from one or more of N, O and S, the $R^{3-2}$ substituted 5 to 10 membered heteroaryl with 1 to 4 heteroatoms selected from one or more of N, O and S is preferably

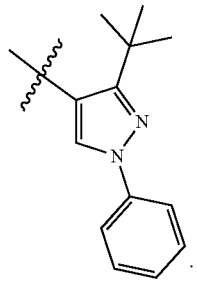 [SMILES: *c1cn(-c2ccccc2)nc1C(C)(C)C]

.

In the present disclosure, when $R^{3-1}$ is unsubstituted or $R^{3-1-1}$ substituted $C_{1-6}$ alkyl, the number of the $R^{3-1-1}$ can be one or more (the number meets the following criteria: the substituted group conforms to the valence bond theory and exists stably. For example, the number is 1, 2, or 3), when more than one $R^{3-1-1}$ occurs, the $R^{3-1-1}$ can be the same or different.

In the present disclosure, when $R^{3-1}$ is unsubstituted or $R^{3-1-1}$ substituted $C_{1-6}$ alkyl, the $C_{1-6}$ alkyl is preferably $C_{1-4}$ alkyl, for example methyl, ethyl, propyl, isopropyl, n-butyl, isobutyl, sec-butyl or tert-butyl, more preferably methyl, isopropyl or tert-butyl.

In the present disclosure, when $R^{3-1}$ is unsubstituted or $R^{3-1-1}$ substituted $C_{1-6}$ alkyl, the $R^{3-1-1}$ substituted $C_{1-6}$ alkyl is preferably —$CF_3$, or

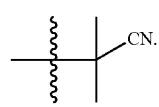 [SMILES: *C(C)(C)C#N]

In the present disclosure, when $R^{3-1}$ is unsubstituted or $R^{3-1-4}$ substituted $C_{6-10}$ aryl, the number of the $R^{3-1-4}$ can be one or more (the number meets the following criteria: the substituted group conforms to the valence bond theory and exists stably. For example, the number is 1, 2, 3, or 4), when more than one $R^{3-1-4}$ occurs, the $R^{3-1-4}$ can be the same or different.

In the present disclosure, when $R^{3-1}$ is unsubstituted or $R^{3-1-4}$ substituted $C_{6-10}$ aryl, the $C_{6-10}$ aryl is preferably phenyl.

In the present disclosure, when $R^{3-2}$ is unsubstituted or $R^{3-1-1}$ substituted $C_{1-6}$ alkyl, the number of the $R^{3-1-1}$ can be one or more (the number meets the following criteria: the substituted group conforms to the valence bond theory and exists stably. For example, the number is 1, 2, or 3), when more than one $R^{3-1-1}$ occurs, the $R^{3-1-1}$ can be the same or different.

In the present disclosure, when $R^{3-2}$ is unsubstituted or $R^{3-1-1}$ substituted $C_{1-6}$ alkyl, the $C_{1-6}$ alkyl is preferably $C_{1-4}$ alkyl, for example methyl, ethyl, propyl, isopropyl, n-butyl, isobutyl, sec-butyl or tert-butyl, more preferably methyl, isopropyl or tert-butyl.

In the present disclosure, when $R^{3-2}$ is unsubstituted or $R^{3-1-1}$ substituted $C_{1-6}$ alkyl, the $R^{3-1-1}$ substituted $C_{1-6}$ alkyl is preferably —$CF_3$, or

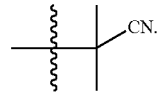 [SMILES: *C(C)(C)C#N]

In the present disclosure, when $R^{3-2}$ is unsubstituted or $R^{3-1-4}$ substituted $C_{6-10}$ aryl, the number of the $R^{3-1-4}$ can be one or more (the number meets the following criteria: the substituted group conforms to the valence bond theory and exists stably. For example, the number is 1, 2, 3, or 4), when more than one $R^{3-1-4}$ occurs, the $R^{3-1-4}$ can be the same or different.

In the present disclosure, when $R^{3-2}$ is unsubstituted or $R^{3-1-4}$ substituted $C_{6-10}$ aryl, the $C_{6-10}$ aryl is preferably phenyl.

In the present disclosure, when $R^{3-1-1}$ is halogen, the halogen can be fluorine, chlorine, bromine or iodine, preferably fluorine.

In the present disclosure, when $R^{3-1-4}$ is halogen, the halogen can be fluorine, chlorine, bromine or iodine, preferably fluorine.

In the present disclosure, when $R^2$ is methyl or ethyl, L is preferably

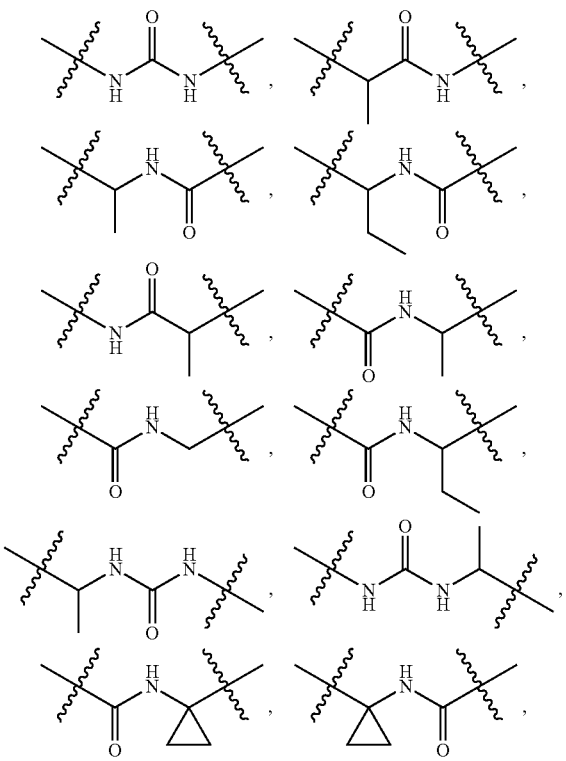

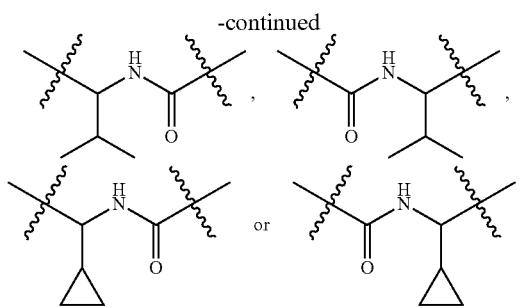

In the present disclosure, when R² is isopropyl or cyclopropyl, L is preferably

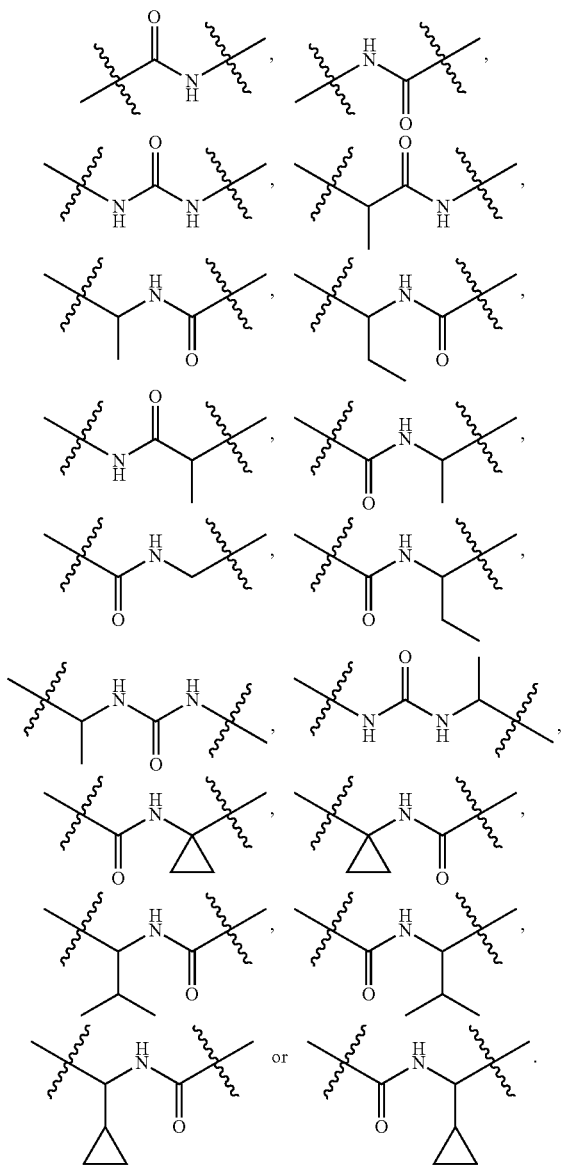

In the present disclosure, when R¹ is unsubstituted or R$^{1-1}$ substituted C$_{6-10}$ aryl, the number of the R$^{1-1}$ can be one or more (the number meets the following criteria: the substituted group conforms to the valence bond theory and exists stably. For example, the number is 1, 2, 3, or 4), when more than one R$^{1-1}$ occurs, the R$^{1-1}$ can be the same or different.

In the present disclosure, when R¹ is unsubstituted or R$^{1-1}$ substituted C$_{6-10}$ aryl, the C$_{6-10}$ aryl is preferably phenyl.

In the present disclosure, when R¹ is unsubstituted or R$^{1-1}$ substituted C$_{6-10}$ aryl, the R$^{1-1}$ substituted C$_{6-10}$ aryl is preferably

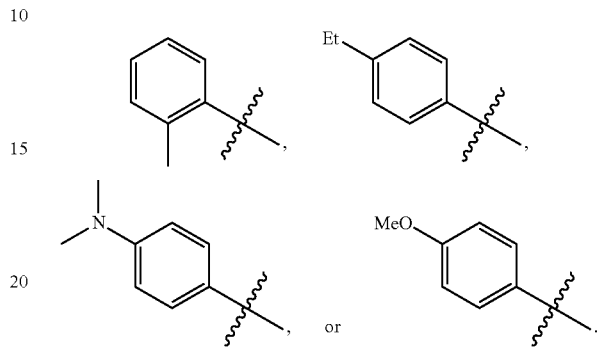

In the present disclosure, when R¹ is unsubstituted or R$^{1-2}$ substituted 5 to 10 membered heteroaryl with 1 to 4 heteroatoms selected from one or more of N, O and S, the number of the R$^{1-2}$ can be one or more (the number meets the following criteria: the substituted group conforms to the valence bond theory and exists stably. For example, the number is 1, 2, or 3), when more than one R$^{1-2}$ occurs, the R$^{1-2}$ can be the same or different.

In the present disclosure, when R¹ is unsubstituted or R$^{1-2}$ substituted 5 to 10 membered heteroaryl with 1 to 4 heteroatoms selected from one or more of N, O and S, the heteroaryl is preferably 5 to 6 membered heteroaryl with 1 to 4 heteroatoms selected from one or more of N, O and S, for example, pyrrolyl, furyl, thienyl, imidazolyl, pyrazolyl, oxazolyl, isoxazolyl, thiazolyl, isothiazolyl, 1,2,3-triazolyl, 1,2,4-triazolyl, furazanyl, 1,2,3-oxadiazolyl, 1,2,4-oxadiazolyl, 1,2,5-oxadiazolyl, 1,3,4-oxadiazolyl, thiadiazolyl, dithiazolyl, tetrazolyl, pyridyl, pyranyl, thiopyranyl, diazinyl, pyrazinyl, pyrimidinyl, pyridazinyl, oxazinyl, thiazinyl, dioxinyl, dithiinyl, 1,2,3-triazinyl, 1,2,4-triazinyl, 1,3,5-triazinyl or tetrazinyl, more preferably pyrazolyl (for example,

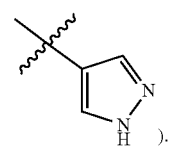 [SMILES: *c1cn[nH]c1]

).

In the present disclosure, when R¹ is unsubstituted or R$^{1-2}$ substituted 5 to 10 membered heteroaryl with 1 to 4 heteroatoms selected from one or more of N, O and S, the R$^{1-2}$ substituted heteroaryl is preferably

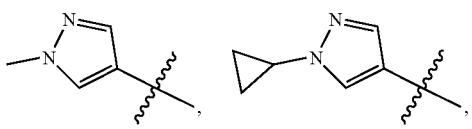

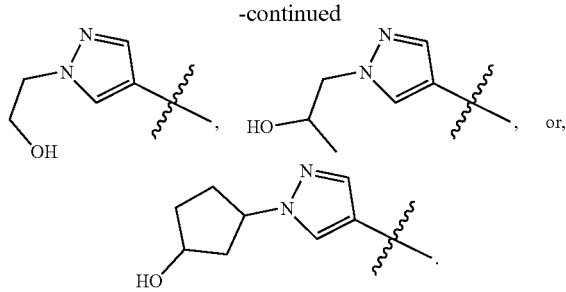

In the present disclosure, when $R^{1-1}$ is unsubstituted or $R^{1-1-1}$ substituted $C_{1-6}$ alkyl, the number of the $R^{1-1-1}$ can be one or more (the number meets the following criteria: the substituted group conforms to the valence bond theory and exists stably. For example, the number is 1, 2, or 3), when more than one $R^{1-1-1}$ occurs, the $R^{1-1-1}$ can be the same or different.

In the present disclosure, when $R^{1-1}$ is unsubstituted or $R^{1-1-1}$ substituted $C_{1-6}$ alkyl, the $C_{1-6}$ alkyl is preferably $C_{1-4}$ alkyl, for example methyl, ethyl, propyl, isopropyl, n-butyl, isobutyl, sec-butyl or tert-butyl, more preferably methyl, ethyl or isopropyl.

In the present disclosure, when $R^{1-1}$ is unsubstituted or $R^{1-1-1}$ substituted $C_{1-6}$ alkyl, the $R^{1-1-1}$ substituted $C_{1-6}$ alkyl is preferably

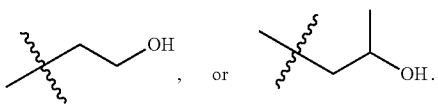

In the present disclosure, when $R^{1-1}$ is $C_{1-6}$ alkoxy, the $C_{1-6}$ alkoxy is preferably $C_{1-4}$ alkoxy, for example methoxy, ethoxy, propoxy, isopropoxy, n-butoxy, isobutoxy, sec-butoxy or tert-butoxy, more preferably methoxy.

In the present disclosure, when $R^{1-1}$ is unsubstituted or $R^{1-1-2}$ substituted $C_{3-10}$ cycloalkyl, the number of the $R^{1-1-2}$ can be one or more (the number meets the following criteria: the substituted group conforms to the valence bond theory and exists stably. For example, the number is 1, 2, or 3), when more than one $R^{1-1-2}$ occurs, the $R^{1-1-2}$ can be the same or different.

In the present disclosure, when $R^{1-1}$ is unsubstituted or $R^{1-1-2}$ substituted $C_{3-10}$ cycloalkyl, the $C_{3-10}$ cycloalkyl is preferably $C_{3-6}$ cycloalkyl, for example cyclopropyl, cyclobutyl, cyclopentyl or cyclohexyl, more preferably cyclopropyl or cyclopentyl.

In the present disclosure, when $R^{1-1}$ is unsubstituted or $R^{1-1-2}$ substituted $C_{3-10}$ cycloalkyl, the $R^{1-1-2}$ substituted $C_{3-10}$ cycloalkyl is preferably

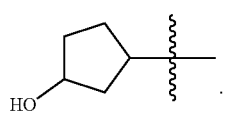

In the present disclosure, when $R^{1-1}$ is $-NR^{1-1-4}R^{1-1-5}$, the $-NR^{1-1-4}R^{1-1-5}$ is preferably $-N(Me)_2$.

In the present disclosure, when $R^{1-2}$ is unsubstituted or $R^{1-1-1}$ substituted $C_{1-6}$ alkyl, the number of the $R^{1-1-1}$ can be one or more (the number meets the following criteria: the substituted group conforms to the valence bond theory and exists stably. For example, the number is 1, 2, or 3), when more than one $R^{1-1-1}$ occurs, the $R^{1-1-1}$ can be the same or different.

In the present disclosure, when $R^{1-2}$ is unsubstituted or $R^{1-1-1}$ substituted $C_{1-6}$ alkyl, the $C_{1-6}$ alkyl is preferably $C_{1-4}$ alkyl, for example methyl, ethyl, propyl, isopropyl, n-butyl, isobutyl, sec-butyl or tert-butyl, more preferably methyl, ethyl or isopropyl.

In the present disclosure, when $R^{1-2}$ is unsubstituted or $R^{1-1-1}$ substituted $C_{1-6}$ alkyl, the $R^{1-1-1}$ substituted $C_{1-6}$ alkyl is preferably

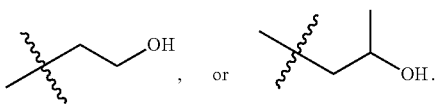

In the present disclosure, when $R^{1-2}$ is $C_{1-6}$ alkoxy, the $C_{1-6}$ alkoxy preferably $C_{1-4}$ alkoxy, for example methoxy, ethoxy, propoxy, isopropoxy, n-butoxy, isobutoxy, sec-butoxy or tert-butoxy, more preferably methoxy.

In the present disclosure, when $R^{1-2}$ is unsubstituted or $R^{1-1-2}$ substituted $C_{3-10}$ cycloalkyl, the number of the $R^{1-1-2}$ can be one or more (the number meets the following criteria: the substituted group conforms to the valence bond theory and exists stably. For example, the number is 1, 2, or 3), when more than one $R^{1-1-2}$ occurs, the $R^{1-1-2}$ can be the same or different.

In the present disclosure, when $R^{1-2}$ is unsubstituted or $R^{1-1-2}$ substituted $C_{3-10}$ cycloalkyl, the $C_{3-10}$ cycloalkyl is preferably $C_{3-6}$ cycloalkyl, for example cyclopropyl, cyclobutyl, cyclopentyl or cyclohexyl, more preferably cyclopropyl or cyclopentyl.

In the present disclosure, when $R^{1-2}$ is unsubstituted or $R^{1-1-2}$ substituted $C_{3-10}$ cycloalkyl, the $R^{1-1-2}$ substituted $C_{3-10}$ cycloalkyl is preferably

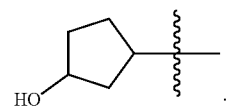

In the present disclosure, when $R^{1-2}$ is $-NR^{1-1-4}R^{1-1-5}$, the $-NR^{1-1-4}R^{1-1-5}$ is preferably $-N(Me)_2$.

In the present disclosure, when $R^{1-1-2}$ is $C_{1-6}$ alkyl, the $C_{1-6}$ alkyl is preferably $C_{1-4}$ alkyl, for example methyl, ethyl, propyl, isopropyl, n-butyl, isobutyl, sec-butyl or tert-butyl.

In the present disclosure, when $R^{1-1-4}$ is $C_{1-6}$ alkyl, the $C_{1-6}$ alkyl is preferably $C_{1-4}$ alkyl, for example methyl, ethyl, propyl, isopropyl, n-butyl, isobutyl, sec-butyl or tert-butyl, more preferably methyl.

In the present disclosure, when $R^{1-1-5}$ is $C_{1-6}$ alkyl, the $C_{1-6}$ alkyl is preferably $C_{1-4}$ alkyl, for example methyl, ethyl, propyl, isopropyl, n-butyl, isobutyl, sec-butyl or tert-butyl, more preferably methyl.

In the present disclosure, when $R^{4-1}-R^{4-6}$ are independently $C_{1-4}$ alkyl, the $C_{1-4}$ alkyl is for example methyl, ethyl, propyl, isopropyl, n-butyl, isobutyl, sec-butyl or tert-butyl, more preferably methyl or ethyl.

In the present disclosure, when $R^{4-7}$ and $R^{4-8}$ together with the carbon atom therebetween form $C_{3-6}$ cycloalkyl, the $C_{3-6}$ cycloalkyl can be cyclopropyl, cyclobutyl, cyclopentyl or cyclohexyl, preferably cyclopropyl.

In a certain scheme, some groups of the compound represented by formula I are defined as follows (undefined groups are as described in any of the previous schemes):

X is hydrogen;

$R^3$ is unsubstituted or $R^{3-1}$ substituted $C_{6-10}$ aryl, or unsubstituted or $R^{3-2}$ substituted 5 to 10 membered heteroaryl with 1 to 4 heteroatoms selected from one or more of N, O and S;

$R^{3-1}$ and $R^{3-2}$ are independently hydroxyl, unsubstituted or $R^{3-1-1}$ substituted $C_{1-6}$ alkyl, or unsubstituted or $R^{3-1-4}$ substituted $C_{6-10}$ aryl;

$R^{3-1-1}$ and $R^{3-1-4}$ are independently cyano or halogen;

$R^1$ is unsubstituted or $R^{1-1}$ substituted $C_{6-10}$ aryl, or unsubstituted or $R^{1-2}$ substituted 5 to 10 membered heteroaryl with 1 to 4 heteroatoms selected from one or more of N, O and S;

$R^{1-1}$ and $R^{1-2}$ are independently unsubstituted or $R^{1-1-1}$ substituted $C_{1-6}$ alkyl, $C_{1-6}$ alkoxy, unsubstituted or $R^{1-1-2}$ substituted $C_{3-10}$ cycloalkyl, or $NR^{1-1-4}R^{1-1-5}$;

$R^{1-1-1}$, $R^{1-1-2}$, $R^{1-1-4}$ and $R^{1-1-5}$ are independently hydroxyl, or $C_{1-6}$ alkyl;

when $R^2$ is methyl or ethyl, L is —NH—CO—NH—, —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, —NH—CO—NH—CHR$^{4-6}$—, or —CO—NH—CR$^{4-7}$R$^{4-8}$—;

when $R^2$ is isopropyl or cyclopropyl, L is —CO—NH—, —NH—CO—, —NH—CO—NH—, —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, —NH—CO—NH—CHR$^{4-6}$—, or —CO—NH—CR$^{4-7}$R$^{4-8}$—;

$R^{4-1}$ to $R^{4-8}$ are independently hydrogen, $C_{1-4}$ alkyl, or $R^{4-7}$ and $R^{4-8}$ together with the carbon atom therebetween form $C_{3-6}$ cycloalkyl.

In a certain scheme, some groups of the compound represented by formula I are defined as follows (undefined groups are as described in any of the previous schemes):

X is hydrogen;

$R^3$ is unsubstituted or $R^{3-1}$ substituted $C_{6-10}$ aryl, or unsubstituted or $R^{3-2}$ substituted 5 to 10 membered heteroaryl with 1 to 4 heteroatoms selected from one or more of N, O and S;

$R^{3-1}$ and $R^{3-2}$ are independently hydroxyl, unsubstituted or $R^{3-1-1}$ substituted $C_{1-6}$ alkyl, or unsubstituted or $R^{3-1-4}$ substituted $C_{6-10}$ aryl;

$R^{3-1-1}$ and $R^{3-1-4}$ are independently cyano or halogen;

$R^1$ is unsubstituted or $R^{1-2}$ substituted 5 to 10 membered heteroaryl with 1 to 4 heteroatoms selected from one or more of N, O and S;

$R^{1-2}$ is unsubstituted or $R^{1-1-1}$ substituted $C_{1-6}$ alkyl, $C_{1-6}$ alkoxy, unsubstituted or $R^{1-1-2}$ substituted $C_{3-10}$ cycloalkyl, or $NR^{1-1-4}R^{1-1-5}$;

$R^{1-1-1}$, $R^{1-1-2}$, $R^{1-1-4}$ and $R^{1-1-5}$ are independently hydroxyl, or $C_{1-6}$ alkyl;

when $R^2$ is methyl or ethyl, L is —NH—CO—NH—, —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, —NH—CO—NH—CHR$^{4-6}$—, or —CO—NH—CR$^{4-7}$R$^{4-8}$—;

when $R^2$ is isopropyl or cyclopropyl, L is —CO—NH—, —NH—CO—, —NH—CO—NH—, —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, —NH—CO—NH—CHR$^{4-6}$—, or —CO—NH—CR$^{4-7}$R$^{4-8}$—;

$R^{4-1}$ to $R^{4-8}$ are independently hydrogen, unsubstituted or $R^{4-1-1}$ substituted $C_{1-4}$ alkyl, or $R^{4-7}$ and $R^{4-8}$ together with the carbon atom therebetween form $C_{3-6}$ cycloalkyl.

In a certain scheme, some groups of the compound represented by formula I are defined as follows (undefined groups are as described in any of the previous schemes):

X is hydrogen;

$R^3$ is unsubstituted or $R^{3-1}$ substituted $C_{6-10}$ aryl, or unsubstituted or $R^{3-2}$ substituted 5 to 10 membered heteroaryl with 1 to 4 heteroatoms selected from one or more of N, O and S;

$R^{3-1}$ and $R^{3-2}$ are independently hydroxyl, unsubstituted or $R^{3-1-1}$ substituted $C_{1-6}$ alkyl, or unsubstituted or $R^{3-1-4}$ substituted $C_{6-10}$ aryl;

$R^{3-1-1}$ and $R^{3-1-4}$ are independently cyano or halogen;

$R^1$ is unsubstituted or $R^{1-1}$ substituted $C_{6-10}$ aryl, or unsubstituted or $R^{1-2}$ substituted 5 to 10 membered heteroaryl with 1 to 4 heteroatoms selected from one or more of N, O and S;

$R^{1-1}$ and $R^{1-2}$ are independently unsubstituted or $R^{1-1-1}$ substituted $C_{1-6}$ alkyl, $C_{1-6}$ alkoxy, unsubstituted or $R^{1-1-2}$ substituted $C_{3-10}$ cycloalkyl, or $NR^{1-1-4}R^{1-1-5}$;

$R^{1-1-1}$, $R^{1-1-2}$, $R^{1-1-4}$ and $R^{1-1-5}$ are independently hydroxyl, or $C_{1-6}$ alkyl;

when $R^2$ is methyl or ethyl, L is —CHR$^{4-2}$—NH—CO—;

when $R^2$ is isopropyl or cyclopropyl, L is —CHR$^{4-2}$—NH—CO—;

$R^{4-2}$ is hydrogen, unsubstituted or $R^{4-1-1}$ substituted $C_{1-4}$ alkyl.

In a certain scheme, some groups of the compound represented by formula I are defined as follows (undefined groups are as described in any of the previous schemes):

X is hydrogen;

$R^3$ is unsubstituted or $R^{3-1}$ substituted $C_{6-10}$ aryl, or unsubstituted or $R^{3-2}$ substituted 5 to 10 membered heteroaryl with 1 to 4 heteroatoms selected from one or more of N, O and S;

$R^{3-1}$ and $R^{3-2}$ are independently hydroxyl, unsubstituted or $R^{3-1-1}$ substituted $C_{1-6}$ alkyl, or unsubstituted or $R^{3-1-4}$ substituted $C_{6-10}$ aryl;

$R^{3-1-1}$ and $R^{3-1-4}$ are independently cyano or halogen;

$R^1$ is unsubstituted or $R^{1-1}$ substituted $C_{6-10}$ aryl, or unsubstituted or $R^{1-2}$ substituted 5 to 10 membered heteroaryl with 1 to 4 heteroatoms selected from one or more of N, O and S;

$R^{1-1}$ and $R^{1-2}$ are independently unsubstituted or $R^{1-1-1}$ substituted $C_{1-6}$ alkyl, $C_{1-6}$ alkoxy, unsubstituted or $R^{1-1-2}$ substituted $C_{3-10}$ cycloalkyl, or $NR^{1-1-4}R^{1-1-5}$;

$R^{1-1-1}$, $R^{1-1-2}$, $R^{1-1-4}$ and $R^{1-1-5}$ are independently hydroxyl, or $C_{1-6}$ alkyl;

$R^2$ is cyclopropyl;

L is —CO—NH—, —NH—CO—, —NH—CO—NH—, —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, —NH—CO—NH—CHR$^{4-6}$—, or —CO—NH—CR$^{4-7}$R$^{4-8}$—.

$R^{4-1}$ to $R^{4-8}$ are independently hydrogen, unsubstituted or $R^{4-1-1}$ substituted $C_{1-4}$ alkyl, or $R^{4-7}$ and $R^{4-8}$ together with the carbon atom therebetween form $C_{3-6}$ cycloalkyl.

In a certain scheme, some groups of the compound represented by formula I are defined as follows (undefined groups are as described in any of the previous schemes):

X is hydrogen;

$R^3$ is unsubstituted or $R^{3-1}$ substituted $C_{6-10}$ aryl, or unsubstituted or $R^{3-2}$ substituted 5 to 10 membered heteroaryl with 1 to 4 heteroatoms selected from one or more of N, O and S;

$R^{3-1}$ and $R^{3-2}$ are independently hydroxyl, unsubstituted or $R^{3-1-1}$ substituted $C_{1-6}$ alkyl, or unsubstituted or $R^{3-1-4}$ substituted $C_{6-10}$ aryl;

$R^{3-1-1}$ and $R^{3-1-4}$ are independently cyano or halogen;

$R^1$ is unsubstituted or $R^{1-1}$ substituted $C_{6-10}$ aryl, or unsubstituted or $R^{1-2}$ substituted 5 to 10 membered heteroaryl with 1 to 4 heteroatoms selected from one or more of N, O and S;

$R^{1-1}$ and $R^{1-2}$ are independently unsubstituted or $R^{1-1-1}$ substituted $C_{1-6}$ alkyl, $C_{1-6}$ alkoxy, unsubstituted or $R^{1-1-2}$ substituted $C_{3-10}$ cycloalkyl, or $NR^{1-1-4}R^{1-1-5}$;

$R^{1-1-1}$, $R^{1-1-2}$, $R^{1-1-4}$ and $R^{1-1-5}$ are independently hydroxyl, or $C_{1-6}$ alkyl;

$R^2$ is isopropyl;

L is —CO—NH—, —NH—CO—, —NH—CO—NH—, —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, —NH—CO—NH—CHR$^{4-6}$—, or —CO—NH—CR$^{4-7}$R$^{4-8}$—.

$R^{4-1}$ to $R^{4-8}$ are independently hydrogen, unsubstituted or $R^{4-1-1}$ substituted $C_{1-4}$ alkyl, or $R^{4-7}$ and $R^{4-8}$ together with the carbon atom therebetween form $C_{3-6}$ cycloalkyl.

In a certain scheme, some groups of the compound represented by formula I are defined as follows (undefined groups are as described in any of the previous schemes):

X is hydrogen;

$R^3$ is unsubstituted or $R^{3-1}$ substituted $C_{6-10}$ aryl, or unsubstituted or $R^{3-2}$ substituted 5 to 10 membered heteroaryl with 1 to 4 heteroatoms selected from one or more of N, O and S;

$R^{3-1}$ and $R^{3-2}$ are independently unsubstituted or $R^{3-1-1}$ substituted $C_{1-6}$ alkyl, or unsubstituted or $R^{3-1-4}$ substituted $C_{6-10}$ aryl;

$R^{3-1-1}$ and $R^{3-1-4}$ are independently cyano or halogen;

$R^1$ is unsubstituted or $R^{1-2}$ substituted 5 to 10 membered heteroaryl with 1 to 4 heteroatoms selected from one or more of N, O and S;

$R^{1-1}$ and $R^{1-2}$ are independently unsubstituted or $R^{1-1-1}$ substituted $C_{1-6}$ alkyl, unsubstituted or $R^{1-1-2}$ substituted $C_{3-10}$ cycloalkyl, or $NR^{1-1-4}R^{1-1-5}$;

$R^{1-1-1}$, $R^{1-1-2}$, $R^{1-1-4}$ and $R^{1-1-5}$ are independently $C_{1-6}$ alkyl;

when $R^2$ is methyl or ethyl, L is —NH—CO—NH—, —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, —NH—CO—NH—CHR$^{4-6}$—, or —CO—NH—CR$^{4-7}$R$^{4-8}$—;

when $R^2$ is isopropyl or cyclopropyl, L is —CO—NH—, —NH—CO—, —NH—CO—NH—, —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, —NH—CO—NH—CHR$^{4-6}$—, or —CO—NH—CR$^{4-7}$R$^{4-8}$—;

$R^{4-1}$ to $R^{4-8}$ are independently hydrogen, unsubstituted or $R^{4-1-1}$ substituted $C_{1-4}$ alkyl, or $R^{4-7}$ and $R^{4-8}$ together with the carbon atom attached thereto form $C_{3-6}$ cycloalkyl.

In a certain scheme, some groups of the compound represented by formula I are defined as follows (undefined groups are as described in any of the previous schemes):

X is hydrogen;

$R^3$ is unsubstituted or $R^{3-1}$ substituted $C_{6-10}$ aryl, or unsubstituted or $R^{3-2}$ substituted 5 to 10 membered heteroaryl with 1 to 4 heteroatoms selected from one or more of N, O and S;

$R^{3-1}$ and $R^{3-2}$ are independently unsubstituted or $R^{3-1-1}$ substituted $C_{1-6}$ alkyl, or unsubstituted or $R^{3-1-4}$ substituted $C_{6-10}$ aryl;

$R^{3-1-1}$ and $R^{3-1-4}$ are independently cyano or halogen;

$R^1$ is unsubstituted or $R^{1-2}$ substituted 5 to 10 membered heteroaryl with 1 to 4 heteroatoms selected from one or more of N, O and S;

$R^{1-1}$ and $R^{1-2}$ are independently unsubstituted or $R^{1-1-1}$ substituted $C_{1-6}$ alkyl, unsubstituted or $R^{1-1-2}$ substituted $C_{3-10}$ cycloalkyl, or $NR^{1-1-4}R^{1-1-5}$;

$R^{1-1-1}$, $R^{1-1-2}$, $R^{1-1-4}$ and $R^{1-1-5}$ are independently $C_{1-6}$ alkyl;

$R^2$ is isopropyl or cyclopropyl;

L is —CO—NH—, —NH—CO—, —NH—CO—NH—, —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, —NH—CO—NH—CHR$^{4-6}$—, or —CO—NH—CR$^{4-7}$R$^{4-8}$—.

$R^{4-1}$ to $R^{4-8}$ are independently hydrogen, unsubstituted or $R^{4-1-1}$ substituted $C_{1-4}$ alkyl, or $R^{4-7}$ and $R^{4-8}$ together with the carbon atom therebetween form $C_{3-6}$ cycloalkyl.

In a certain scheme, some groups of the compound represented by formula I are defined as follows (undefined groups are as described in any of the previous schemes):

X is hydrogen;

$R^3$ is unsubstituted or $R^{3-1}$ substituted $C_{6-10}$ aryl, or unsubstituted or $R^{3-2}$ substituted 5 to 10 membered heteroaryl with 1 to 4 heteroatoms selected from one or more of N, O and S;

$R^{3-1}$ and $R^{3-2}$ are independently unsubstituted or $R^{3-1-1}$ substituted $C_{1-6}$ alkyl, or unsubstituted or $R^{3-1-4}$ substituted $C_{6-10}$ aryl;

$R^{3-1-1}$ and $R^{3-1-4}$ are independently cyano or halogen;

$R^1$ is unsubstituted or $R^{1-2}$ substituted 5 to 10 membered heteroaryl with 1 to 4 heteroatoms selected from one or more of N, O and S;

$R^{1-1}$ and $R^{1-2}$ are independently unsubstituted or $R^{1-1-1}$ substituted $C_{1-6}$ alkyl, unsubstituted or $R^{1-1-2}$ substituted $C_{3-10}$ cycloalkyl, or $NR^{1-1-4}R^{1-1-5}$;

$R^{1-1-1}$, $R^{1-1-2}$, $R^{1-1-4}$ and $R^{1-1-5}$ are independently $C_{1-6}$ alkyl;

when $R^2$ is methyl or ethyl, L is —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, or —NH—CO—NH—CHR$^{4-6}$—;

when $R^2$ is isopropyl or cyclopropyl, L is —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, or —NH—CO—NH—CHR$^{4-6}$—;

$R^{4-1}$ to $R^{4-6}$ are independently hydrogen, unsubstituted or $R^{4-1-1}$ substituted $C_{1-4}$ alkyl.

In a certain scheme, some groups of the compound represented by formula I are defined as follows (undefined groups are as described in any of the previous schemes): X is hydrogen.

In a certain scheme, some groups of the compound represented by formula I are defined as follows (undefined groups are as described in any of the previous schemes):

$R^3$ is unsubstituted or $R^{3-1}$ substituted $C_{6-10}$ aryl, or unsubstituted or $R^{3-2}$ substituted 5 to 10 membered heteroaryl with 1 to 4 heteroatoms selected from one or more of N, O and S.

In a certain scheme, some groups of the compound represented by formula I are defined as follows (undefined groups are as described in any of the previous schemes):

$R^{3-1}$ and $R^{3-2}$ are independently hydroxyl, unsubstituted or $R^{3-1-1}$ substituted $C_{1-6}$ alkyl, or unsubstituted or $R^{3-1-4}$ substituted phenyl.

In a certain scheme, some groups of the compound represented by formula I are defined as follows (undefined groups are as described in any of the previous schemes):
$R^{3-1}$ and $R^{3-2}$ are independently unsubstituted or $R^{3-1-1}$ substituted $C_{1-6}$ alkyl, or unsubstituted or $R^{3-1-4}$ substituted phenyl.

In a certain scheme, some groups of the compound represented by formula I are defined as follows (undefined groups are as described in any of the previous schemes):
$R^{3-1-1}$ and $R^{3-1-4}$ are independently cyano or halogen.

In a certain scheme, some groups of the compound represented by formula I are defined as follows (undefined groups are as described in any of the previous schemes):
$R^1$ is unsubstituted or $R^{1-1}$ substituted $C_{6-10}$ aryl, or unsubstituted or $R^{1-2}$ substituted 5 to 10 membered heteroaryl with 1 to 4 heteroatoms selected from one or more of N, O and S.

In a certain scheme, some groups of the compound represented by formula I are defined as follows (undefined groups are as described in any of the previous schemes):
$R^1$ is unsubstituted or $R^{1-2}$ substituted 5 to 10 membered heteroaryl with 1 to 4 heteroatoms selected from one or more of N, O and S.

In a certain scheme, some groups of the compound represented by formula I are defined as follows (undefined groups are as described in any of the previous schemes):
$R^{1-1}$ and $R^{1-2}$ are independently unsubstituted or $R^{1-1-1}$ substituted $C_{1-6}$ alkyl, $C_{1-6}$ alkoxy, unsubstituted or $R^{1-1-2}$ substituted $C_{3-10}$ cycloalkyl, or $NR^{1-1-4}R^{1-1-5}$.

In a certain scheme, some groups of the compound represented by formula I are defined as follows (undefined groups are as described in any of the previous schemes):
$R^{1-1-1}$, $R^{1-1-2}$, $R^{1-1-4}$ and $R^{1-1-5}$ are independently hydroxyl, or $C_{1-6}$ alkyl.

In a certain scheme, some groups of the compound represented by formula I are defined as follows (undefined groups are as described in any of the previous schemes):
$R^{1-1-1}$, $R^{1-1-2}$, $R^{1-1-4}$ and $R^{1-1-5}$ are independently $C_{1-6}$ alkyl.

In a certain scheme, some groups of the compound represented by formula I are defined as follows (undefined groups are as described in any of the previous schemes):
when $R^2$ is methyl or ethyl, L is —NH—CO—NH—, —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, —NH—CO—NH—CHR$^{4-6}$—, or —CO—NH—CR$^{4-7}$R$^{4-8}$—.

In a certain scheme, some groups of the compound represented by formula I are defined as follows (undefined groups are as described in any of the previous schemes):
when $R^2$ is methyl or ethyl, L is —CHR$^{4-1}$—CO—NH—, —CHR$^{4-2}$—NH—CO—, —NH—CO—CHR$^{4-3}$—, —CO—NH—CHR$^{4-4}$—, —CHR$^4$—NH—CO—NH—, or —NH—CO—NH—CHR$^{4-6}$—.

In a certain scheme, some groups of the compound represented by formula I are defined as follows (undefined groups are as described in any of the previous schemes):
when $R^2$ is methyl or ethyl, L is —CHR$^{4-2}$—NH—CO—.

In a certain scheme, some groups of the compound represented by formula I are defined as follows (undefined groups are as described in any of the previous schemes):
when $R^2$ is isopropyl or cyclopropyl, L is —CO—NH—, —NH—CO—, —NH—CO—NH—, —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, —NH—CO—NH—CHR$^{4-6}$—, or —CO—NH—CR$^{4-7}$R$^{4-8}$—.

In a certain scheme, some groups of the compound represented by formula I are defined as follows (undefined groups are as described in any of the previous schemes):
when $R^2$ is isopropyl or cyclopropyl, L is —CHR$^{4-1}$—CO—NH—, —CHR$^{4-2}$—NH—CO—, —NH—CO—CHR$^{4-3}$—, —CO—NH—CHR$^{4-4}$—, —CHR$^4$—NH—CO—NH—, or —NH—CO—NH—CHR$^{4-6}$—.

In a certain scheme, some groups of the compound represented by formula I are defined as follows (undefined groups are as described in any of the previous schemes):
when $R^2$ is isopropyl or cyclopropyl, L is —CHR$^{4-2}$—NH—CO—.

In a certain scheme, some groups of the compound represented by formula I are defined as follows (undefined groups are as described in any of the previous schemes): $R^2$ is isopropyl or cyclopropyl.

In a certain scheme, some groups of the compound represented by formula I are defined as follows (undefined groups are as described in any of the previous schemes): $R^2$ is cyclopropyl.

In a certain scheme, some groups of the compound represented by formula I are defined as follows (undefined groups are as described in any of the previous schemes): $R^2$ is isopropyl.

In a certain scheme, some groups of the compound represented by formula I are defined as follows (undefined groups are as described in any of the previous schemes):
$R^{4-1}$ to $R^{4-8}$ are independently hydrogen, unsubstituted or $R^{4-1-1}$ substituted $C_{1-4}$ alkyl, or $R^{4-7}$ and $R^{4-8}$ together with the carbon atom therebetween form $C_{3-6}$ cycloalkyl.

In a certain scheme, some groups of the compound represented by formula I are defined as follows (undefined groups are as described in any of the previous schemes):
$R^{4-1}$ to $R^{4-6}$ are independently hydrogen, unsubstituted or $R^{4-1-1}$ substituted $C_{1-4}$ alkyl.

In a certain scheme, some groups of the compound represented by formula I are defined as follows (undefined groups are as described in any of the previous schemes):
$R^{4-2}$ is hydrogen, unsubstituted or $R^{4-1-1}$ substituted $C_{1-4}$ alkyl.

In a certain scheme, the compound represented by formula I can have any of the following structures:

-continued
S4
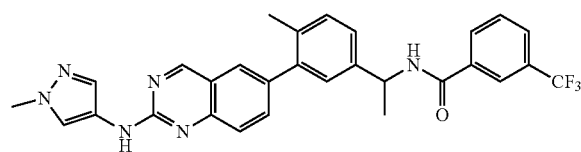
S5
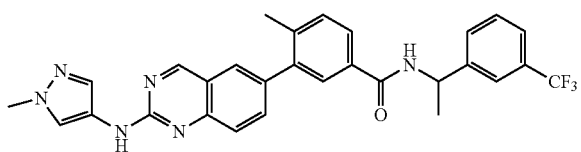
S6
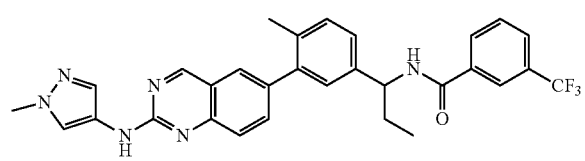
S7
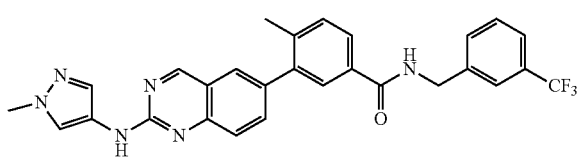
S8
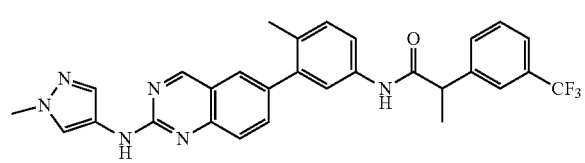
S9
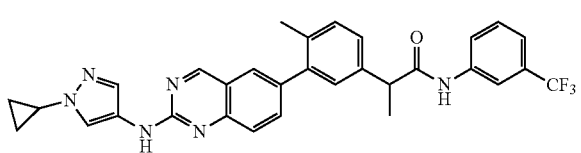
S10
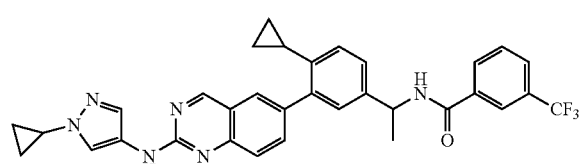
S11
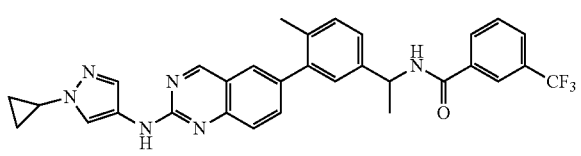
S12
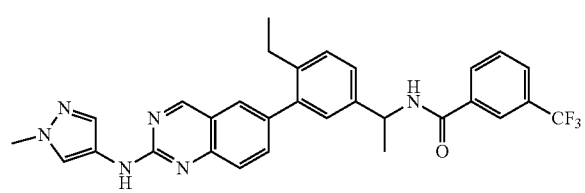
S13
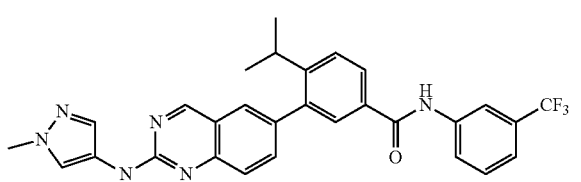
S14
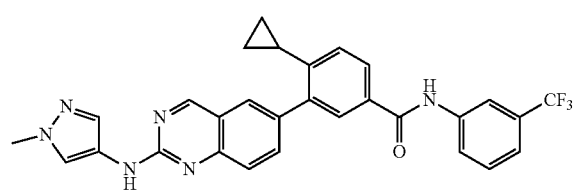
S15
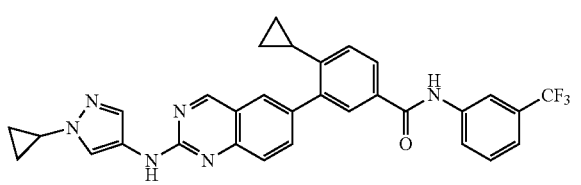
S16
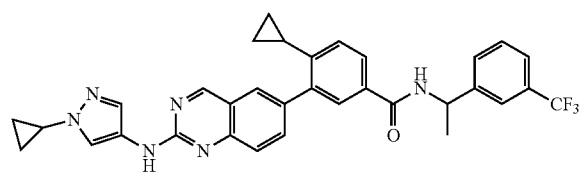
S17
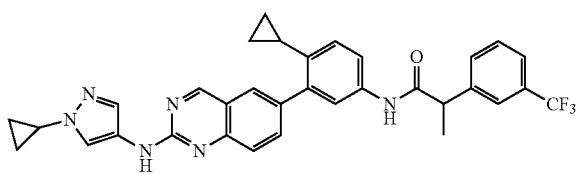
S18
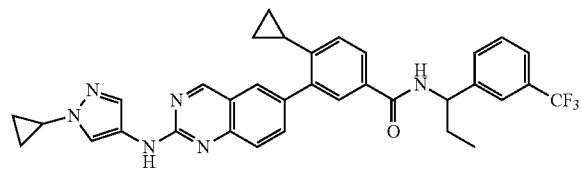
S19
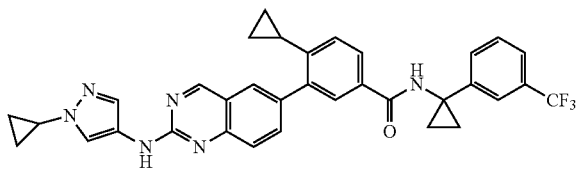

-continued
S20
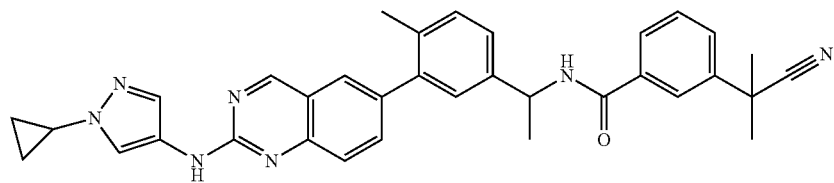
S21
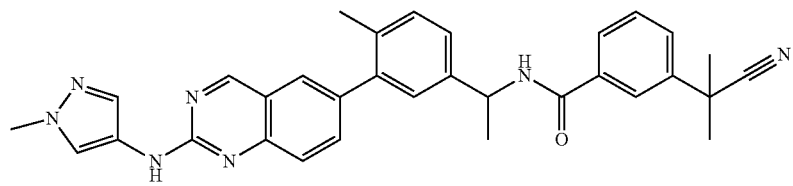
S22
S23
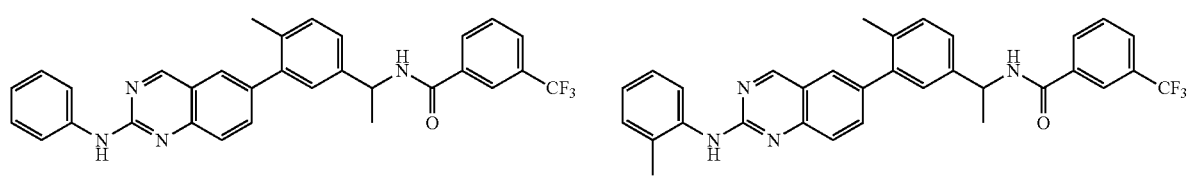
S24
S25
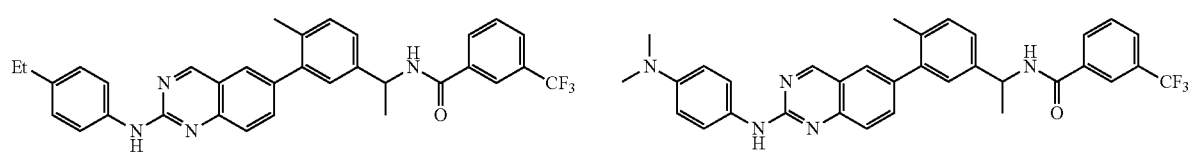
S26
S27
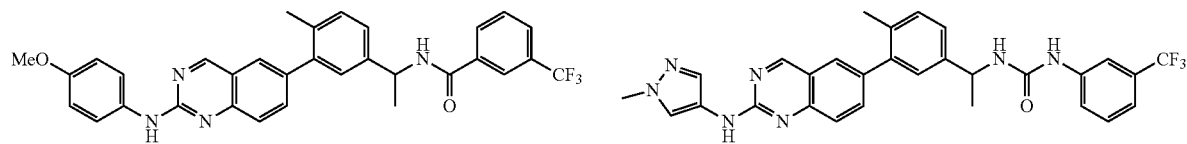
S28
S29
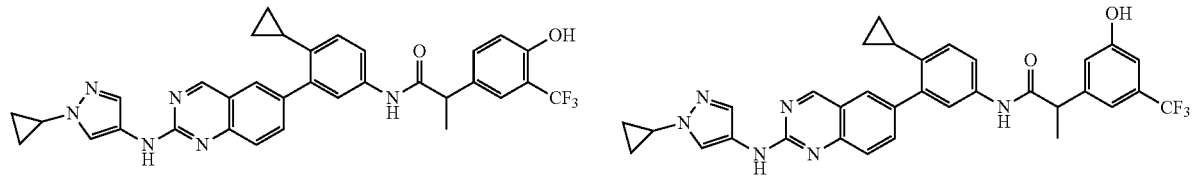
S30
S31
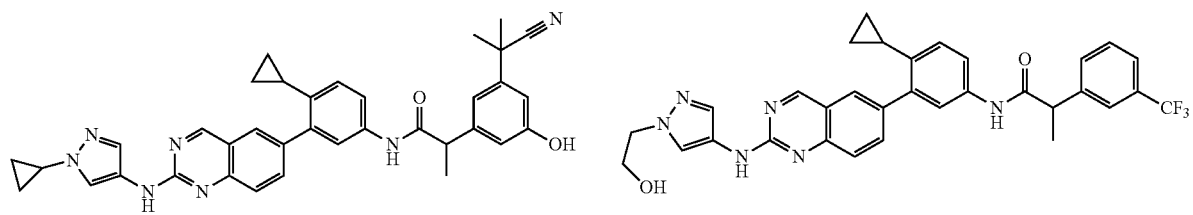
S32
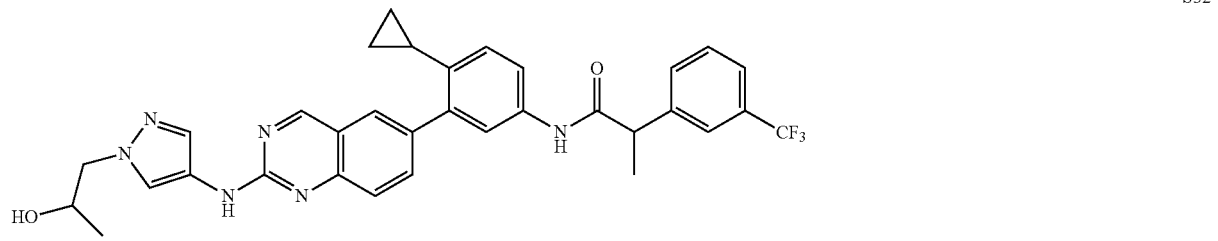

-continued
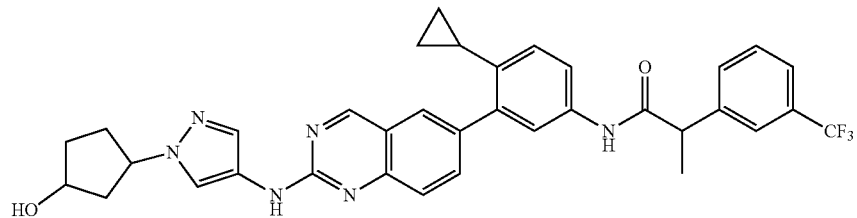
S33
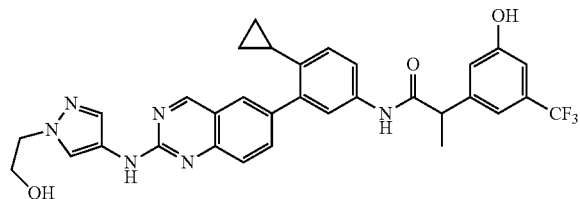
S34
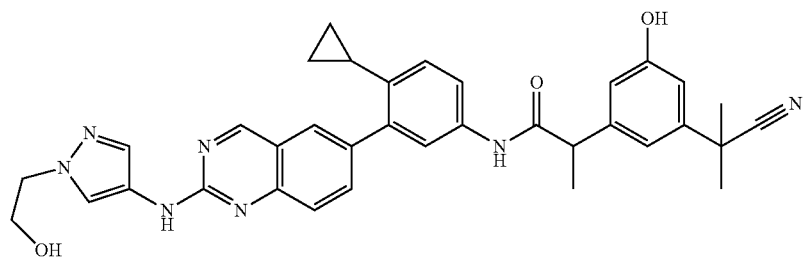
S35
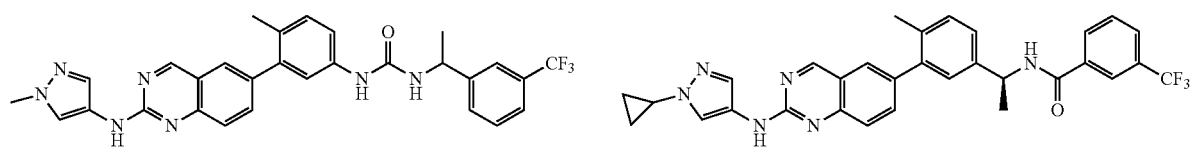
S36    S11-A
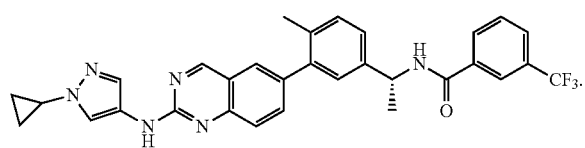
S11-B The present disclosure also provides a method for preparing the compound shown in formula I, the method comprises the following steps: In a solvent, under the action of a base and a palladium catalyst, the compound represented by formula II and the compound represented by formula III are subjected to the coupling reaction shown below;

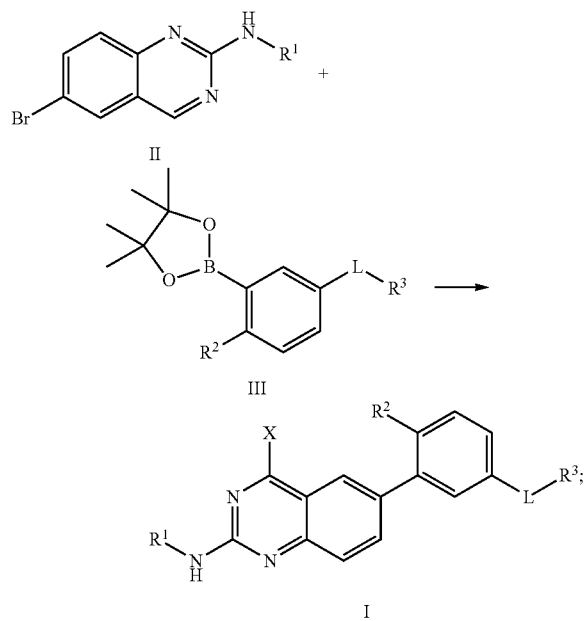

wherein, X, L, $R^1$, $R^2$ and $R^3$ are as defined above.

In the present disclosure, the coupling reaction is preferably carried out under a protective gas atmosphere, and the protective gas may be a conventional protective gas in the art, such as argon and/or nitrogen.

In the present disclosure, the solvent can be a conventional solvent in the art, preferably water and/or ether solvents. The ether solvents are preferably dioxane.

In the present disclosure, the base can be a conventional base in the art, preferably an alkali metal carbonate, such as potassium carbonate.

In the present disclosure, the palladium catalyst can be a conventional palladium catalyst in the art, preferably a zero-valent palladium catalyst, such as [1,1'-bis(diphenylphosphine)ferrocene]palladium dichloride dichloromethane complex.

In the present disclosure, the molar concentration of the compound represented by formula II in the solvent can be a molar concentration conventional in the art, preferably 0.01-0.05 mol/L, such as 0.0186 mol/L, 0.01925 mol/L and 0.03285 mol/L.

In the present disclosure, the molar ratio of the compound represented by formula III and the compound represented by formula II can be a conventional molar ratio in the art, preferably 0.8:1 to 1.5:1, such as 1:1 and 1.1:1.

In the present disclosure, the molar ratio of the base and the compound represented by formula II can be a conventional molar ratio in the art, preferably 1:1-3:1, such as 2:1.

In the present disclosure, the molar ratio of the palladium catalyst and the compound represented by formula II can be a conventional molar ratio in the art, preferably 1:30-1:35, such as 1:30.8, 1:31.8 and 1:32.85.

In the present disclosure, the temperature of the coupling reaction can be a conventional temperature in the art, preferably 70-90° C.

In the present disclosure, the progress of the coupling reaction can be monitored by conventional means in the art (such as TLC, HPLC or LCMS), and the time is preferably 2 to 4 hours, such as 3 hours.

In the present disclosure, after the coupling reaction is completed, preferably, a post-treatment step may be further included. The conditions and operations for the post-treatment can be conventional conditions and operations for the post-treatment in the art, and include the following steps: the reaction solution is cooled, a solvent is added, an organic layer is extracted, dried and filtered, and the solvent in the filtrate is removed to obtain a residue, and then the residue was separated and purified. Said cooling is preferably cooling to room temperature. The solvent is preferably saline, such as saturated saline. The extraction conditions and operations can be conventional conditions and operations in the art, and the extraction solvent is preferably an ester solvent, such as ethyl acetate. The drying conditions and operations can be conventional conditions and operations in the art, and the drying reagent can be a conventional reagent in the art, such as anhydrous sodium sulfate. The filtering conditions and operations can be conventional conditions and operations in the field. The conditions and operations for removing the solvent can be conventional conditions and operations in the art, such as evaporating the solvent to dryness. The separation and purification are preferably column chromatography separation.

Unless otherwise specified, the "room temperature" in the present disclosure refers to 20-30° C.

The present disclosure also provides a pharmaceutical composition comprising the compound shown in formula I, the pharmaceutically acceptable salt thereof, the tautomer thereof, the stereoisomer thereof, the metabolite thereof, the metabolic precursor thereof or the prodrug thereof as described above, and pharmaceutical excipients.

In the pharmaceutical composition, the amount of the compound shown in formula I, the pharmaceutically acceptable salt thereof, the tautomer thereof, the stereoisomer thereof, the metabolite thereof, the metabolic precursor thereof or the prodrug thereof can be a therapeutically effective amount.

The present disclosure also provides the use of the compound shown in formula I, the pharmaceutically acceptable salt thereof, the tautomer thereof, the stereoisomer thereof, the metabolite thereof, the metabolic precursor thereof or the prodrug thereof or the pharmaceutical composition as described above in the preparation of DDR inhibitors.

In the present disclosure, the DDR inhibitors are preferably DDR1 and/or DDR2 inhibitors, and more preferably DDR2 inhibitors.

The present disclosure also provides the use of the compound shown in formula I, the pharmaceutically acceptable salt thereof, the tautomer thereof, the stereoisomer thereof, the metabolite thereof, the metabolic precursor thereof or the prodrug thereof or the pharmaceutical composition as described above in the preparation of a medicine.

The present disclosure also provides the use of the compound shown in formula I, the pharmaceutically acceptable salt thereof, the tautomer thereof, the stereoisomer thereof, the metabolite thereof, the metabolic precursor thereof or the prodrug thereof or the pharmaceutical composition as described above in the preparation of a medicine, the medicine can be used to treat fibrosis, arthritis, atherosclerosis or tumors, preferably fibrosis, tumors or arthritis, and the fibrosis is preferably pulmonary fibrosis.

The present disclosure also provides a use of the compound shown in formula I, the pharmaceutically acceptable salt thereof, the tautomer thereof, the stereoisomer thereof, the metabolite thereof, the metabolic precursor thereof or the prodrug thereof or the pharmaceutical composition as described above in the preparation of a medicine for treating DDR-related diseases.

In the present disclosure, the DDR-related diseases include but are not limited to fibrosis, arthritis, atherosclerosis or tumors, preferably fibrosis, tumors or arthritis, and the fibrosis is preferably pulmonary fibrosis.

The present disclosure also provides a pharmaceutical combination, which comprises: the compound shown in formula I, the pharmaceutically acceptable salt thereof, the tautomer thereof, the stereoisomer thereof, the metabolite thereof, the metabolic precursor thereof or the prodrug thereof, and a PD-1/PD-L1 inhibitor. The compound shown in formula I, the pharmaceutically acceptable salt thereof, the tautomer thereof, the stereoisomer thereof, the metabolite thereof, the metabolic precursor thereof or the prodrug thereof and the PD-1/PD-L1 inhibitor can be administered simultaneously or separately.

The present disclosure also provides a use of the above-mentioned medicine combination in the preparation of a medicine for treating tumors.

This present disclosure also provides a pharmaceutical composition comprising the compound shown in formula I, the pharmaceutically acceptable salt thereof, the tautomer thereof, the stereoisomer thereof, the metabolite thereof, the metabolic precursor thereof or the prodrug thereof as described above, a PD-1/PD-L1 inhibitor, and pharmaceutical excipients.

The compound shown in formula I, the pharmaceutically acceptable salt thereof, the tautomer thereof, the stereoisomer thereof, the metabolite thereof, the metabolic precursor thereof or the prodrug thereof and the PD-1/PD-L1 inhibitor can be administered simultaneously or separately.

The present disclosure also provides a use of the above-mentioned pharmaceutical composition in the preparation of a medicine for treating tumors.

The present disclosure also provides an use of the compound shown in formula I, the pharmaceutically acceptable salt thereof, the tautomer thereof, the stereoisomer thereof, the metabolite thereof, the metabolic precursor thereof or the prodrug thereof as described above in the preparation of a medicine for treating tumors, the compound shown in formula I, the pharmaceutically acceptable salt thereof, the tautomer thereof, the stereoisomer thereof, the metabolite thereof, the metabolic precursor thereof or the prodrug thereof is used in combination with a PD-1/PD-L1 inhibitor. The compound shown in formula I, the pharmaceutically acceptable salt thereof, the tautomer thereof, the stereoisomer thereof, the metabolite thereof, the metabolic precursor thereof or the prodrug thereof and the PD-1/PD-L1 inhibitor can be administered simultaneously or separately.

The present disclosure also provides an use of the compound shown in formula I, the pharmaceutically acceptable salt thereof, the tautomer thereof, the stereoisomer thereof, the metabolite thereof, the metabolic precursor thereof or the prodrug thereof as described above and a PD-1/PD-L1 inhibitor in the preparation of a medicine for treating tumors, the compound shown in formula I, the pharmaceutically acceptable salt thereof, the tautomer thereof, the stereoisomer thereof, the metabolite thereof, the metabolic precursor thereof or the prodrug thereof is used in combination with the PD-1/PD-L1 inhibitor. The compound shown in formula I, the pharmaceutically acceptable salt thereof, the tautomer thereof, the stereoisomer thereof, the metabolite thereof, the metabolic precursor thereof or the prodrug thereof and the PD-1/PD-L1 inhibitor can be administered simultaneously or separately.

In the present disclosure, the tumors comprise but not limited to lung cancer, breast cancer, head and neck squamous cell carcinoma, liver cancer, gastric cancer or colorectal cancer.

The term "PD-1/PD-L1 inhibitor" refers to a substance that can block the binding of PD-1 to PD-L1, block negative regulatory signals, and restore the activity of T cells, thereby enhancing the immune response.

The term "simultaneous administration" refers to administration at the same time point, for example, administration of a single pharmaceutical composition comprising both of the compound represented by formula I, the pharmaceutically acceptable salt thereof, the tautomer thereof, the stereoisomer thereof, the metabolite thereof, the metabolic precursor thereof or the prodrug thereof and the PD-1/PD-L1 inhibitor; or, at the same time point, administration of a separate pharmaceutical composition comprising the compound represented by formula I, the pharmaceutically acceptable salt thereof, the tautomer thereof, the stereoisomer thereof, the metabolite thereof, the metabolic precursor thereof or the prodrug thereof and a separate pharmaceutical composition comprising the PD-1/PD-L1 inhibitor.

The term "separate administration" refers to administration at different time points, for example, administration of a separate pharmaceutical composition comprising the compound represented by formula I, the pharmaceutically acceptable salt thereof, the tautomer thereof, the stereoisomer thereof, the metabolite thereof, the metabolic precursor thereof or the prodrug thereof and a separate pharmaceutical composition comprising the PD-1/PD-L1 inhibitor at different time points; or, for example, first administration one of a separate pharmaceutical composition comprising the compound represented by formula I, the pharmaceutically acceptable salt thereof, the tautomer thereof, the stereoisomer thereof, the metabolite thereof, the metabolic precursor thereof or the prodrug thereof and a separate pharmaceutical composition comprising the PD-1/PD-L1 inhibitor and then administration of the other. Separate administration can be close in time or separated by a long time, but it is necessary to ensure that the compound represented by formula I, the pharmaceutically acceptable salt thereof, the tautomer thereof, the stereoisomer thereof, the metabolite thereof, the metabolic precursor thereof or the prodrug thereof and the PD-1/PD-L1 inhibitor can work together to provide the desired therapeutic effect. For example, the compound represented by formula I, the pharmaceutically acceptable salt thereof, the tautomer thereof, the stereoisomer thereof, the metabolite thereof, the metabolic precursor thereof or the prodrug thereof is preferentially administered prior to the administration of the PD-1/PD-L1 inhibitor (for example, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks prior to the administration), or is administered after the administration of the PD-L1 inhibitor (for example, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after the administration).

The pharmaceutical excipients can be those that are widely used in the art of pharmaceutical production. Excipients are mainly used to provide a safe, stable and functional pharmaceutical composition. A method can also be provided to dissolve active ingredients at a desired rate after the subject is administrated, or to promote the effective absorption of active ingredients after the subject is administrated with the composition. The pharmaceutical excipients may be inert fillers or provide certain functions, such as stabilizing the overall pH of the composition or preventing degradation of active ingredients in the composition. The pharmaceutical excipients may include one or more of the following excipients: binders, suspending agents, emulsifiers, diluents, fillers, granulating agents, adhesives, disintegrating agents, lubricants, anti-adhesives, glidants, wetting agents, gelling agents, absorption delaying agents, dissolution inhibitors, enhancers, adsorbents, buffers, chelating agents, preservatives, coloring agents, flavoring agents and sweetening agents.

The pharmaceutical composition of the present disclosure can be prepared according to the disclosure using any method known to those skilled in the art. For example, conventional mixing, dissolving, granulating, emulsifying, grinding, encapsulating, embedding or freeze-drying processes.

The pharmaceutical composition of the present disclosure can be administered in any form, including injection (intravenous), mucosal, oral (solid and liquid preparations), inhalation, ocular, rectal, topical or parenteral (infusion, injection, implantation, subcutaneous, intravenous, intraarterial, intramuscular) administration. The pharmaceutical composition of the present disclosure can also be a controlled release or delayed release dosage form (for example, liposomes or microspheres). Examples of solid oral preparations include, but are not limited to, powders, capsules, caplets, soft capsules, and tablets. Examples of liquid preparations for oral or mucosal administration include, but are not limited to, suspensions, emulsions, elixirs, and solutions. Examples of topical preparations include, but are not limited to, emulsions, gels, ointments, creams, patches, pastes, foams, lotions, drops, or serum preparations. Examples of preparations for parenteral administration include, but are not limited to, solutions for injection, dry preparations that can be dissolved or suspended in a pharmaceutically acceptable carrier, suspensions for injection, and emulsions for injection. Examples of other suitable preparations of the pharmaceutical composition include, but are not limited to, eye drops and other ophthalmic preparations; aerosol: such as nasal sprays or inhalants; liquid dosage form suitable for parenteral administration; Suppositories and lozenges.

The term "pharmaceutically acceptable salt" refers to a salt of the compound of the present disclosure, which is prepared from the compound having specific substituents found in the present disclosure with relatively non-toxic acids or bases. When compounds of the present disclosure contain relatively acidic functional groups, base addition salts can be obtained by contacting the neutral form of such compounds with a sufficient amount of base, either in pure solution or a suitable inert solvent. Pharmaceutically acceptable base addition salts include sodium, potassium, calcium, ammonium, organic amine or magnesium salts or similar salts. When compounds of the present disclosure contain relatively basic functional groups, acid addition salts can be obtained by contacting the neutral form of such compounds with a sufficient amount of acid, either in pure solution or a suitable inert solvent. Examples of pharmaceutically acceptable acid addition salts include salts of inorganic acids, which include, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid and phosphorous acid; and salts of organic acids, which include, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid; also include salts of amino acids (such as arginine, etc.), and salts of organic acids such as glucuronic acid (see Berge et al., "Pharmaceutical Salts", *Journal of Pharmaceutical Science* 66: 1-19 (1977)). Certain specific compounds of the present disclosure contain basic and acidic functional groups and thus can be converted to any base or acid addition salt. Preferably, the salt is contacted with a base or acid in a conventional manner, and then the parent compound is separated, thereby regenerating the neutral form of the compound. The parent form of the compound differs from its various salt forms in certain physical properties, such as solubility in polar solvents.

The "pharmaceutically acceptable salts" of the present disclosure can be synthesized from a parent compound containing acid radicals or base radicals by conventional chemical methods. In general, the method for preparing such salts comprises: in water or an organic solvent or a mixture of both, reacting these compounds in free acid or base forms with a stoichiometric amount of a suitable base or acid to prepare the salts. Generally, non-aqueous media such as ether, ethyl acetate, ethanol, isopropanol, or acetonitrile are preferred.

The term "tautomer" refers to functional group isomers produced by the rapid movement of an atom in two positions in a molecule, which can be converted to each other with different energies through a low energy barrier.

The term "stereoisomer" refers to the isomers produced by the different arrangements of atoms in the molecule in space and can be divided into three types: cis-trans isomers, enantiomers and conformational isomers and can also be divided into two categories: enantiomers and diastereomers. The cis-trans isomers are isomers caused by the inability of free rotation of double bonds or single bonds of ring-forming carbon atoms, such as cis-2-butene and trans-2-butene. The enantiomers refer to stereoisomers that are mirror images of each other and cannot be superimposed, such as L-lactic acid and D-lactic acid. The conformational isomers refer to stereoisomers caused by the rotation of single bonds, such as chair-type cyclohexane and boat-type cyclohexane.

The term "metabolite" refers to the pharmacologically active product produced by the in vivo metabolism of the compound represented by formula I or its salt. Such product can be produced, for example, from oxidation, reduction, hydrolysis, amidation, deamidation, esterification, deesterification, glucoronidation, enzymatic cleavage, etc. of the administered compound. Therefore, the present disclosure includes the metabolites of the compounds of the present disclosure, including compounds produced by contacting the compounds of the present disclosure with mammals for a period of time sufficient to obtain their metabolites.

The identification of metabolites is typically performed by preparing radiolabeled (e.g., $^{14}C$ or $^{3}H$) isotopes of the compounds of the present disclosure, and administering them to animals (for example, rats, mice, guinea pigs, monkeys, or humans) parenterally at a detectable dose (e.g., greater than about 0.5 mg/kg) for sufficient time to undergo metabolism (typically about 30 seconds to 30 hours) and separating their conversion products from urine, blood, or other biological samples. These products are easy to separate because they are labeled (others are separated by using antibodies capable of binding epitopes present in the metabolite). The metabolite structure is determined in a conventional manner, for example, by MS, LC/MS or NMR analysis. Generally, analysis of metabolites is performed in the same way as conventional drug metabolism studies well known to those skilled in the art. As long as the metabolite products are not otherwise unable to be found in the body, they can be used in assays for the therapeutic dose administration of the compounds of the present disclosure. The compounds of the present disclosure may contain unnatural proportions of atomic isotopes at one or more of the atoms constituting the compound. For example, the compounds may be radiolabeled with radioactive isotopes, such as tritium ($^3$H), iodine-125 ($^{125}$I) or C-14 ($^{14}$C).

All isotopic variations of the compounds of the present disclosure, whether radioactive or not, are intended to be encompassed within the scope of the present disclosure.

In addition to salt forms, the compounds provided by the present disclosure also exist in prodrug forms. The prodrugs of the compounds described herein are prone to chemical changes under physiological conditions, and thus are converted into the compounds of the present disclosure. Any compound that can be converted in the body to provide a biologically active substance (i.e., the compound represented by formula I) is a prodrug within the scope and spirit of the present disclosure. For example, a compound containing carboxyl can form a physiologically hydrolyzable ester, which serves as a prodrug for obtaining the compound represented by formula I itself by hydrolysis in vivo. The prodrug is preferably administered orally, because hydrolysis occurs mainly under the influence of digestive enzymes in many cases. When the ester itself is active or hydrolysis occurs in the blood, parenteral administration can be used. For specific preparation methods of prodrugs, please refer to Saulnier, M. G., et al., Bioorg. Med. Chem. Lett. 1994, 4, 1985-1990; Greenwald, R. B., et al., J. Med. Chem. 2000, 43, 475.

The term "active ingredient", "therapeutic agent", or "active substance" refers to a chemical entity that can effectively treat the target disorders, diseases, or conditions.

When the exemplified linking group does not indicate its linking direction, its linking direction is connection in the same direction as the reading order from left to right. For example, the linking group L in

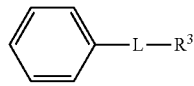

is —CO—NH—, at this time —CO— is connected to

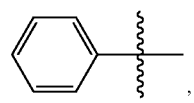

and —NH— is connected to R$^3$.

Those skilled in the art can understand that, according to the conventions used in the art, the

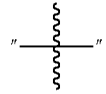

used in the structural formula of the group described in this application means that the corresponding group is connected to other fragments and groups in the compound represented by formula I through this site.

The "substitution" in the present disclosure can be one or more. when there are multiple "substitutions", the "substitutions" can be the same or different.

The term "more" refers to 2, 3, 4 or 5.

The term "halogen" refers to fluorine, chlorine, bromine or iodine.

The term "alkyl" refers to straight or branched alkyl having specified number of carbon atoms. Examples of alkyl include methyl, ethyl, n-propyl, isopropyl, n-butyl, tert-butyl, isobutyl, sec-butyl, n-pentyl, n-hexyl, n-heptyl, n-octyl and similar alkyl groups.

The term "alkylcarbonyl" refers to the group —(C=O)—R$^X$, wherein R$^X$ is an alkyl as defined above.

The term "alkoxy" refers to group —O—R$^Y$, wherein R$^Y$ is alkyl as defined above.

The term "cycloalkyl" refers to a saturated monocyclic or polycyclic alkyl. The monocyclic cycloalkyl is preferably a monovalent saturated cyclic alkyl having 3 to 7 carbon atoms, more preferably 3 to 6 carbon atoms, such as cyclopropyl, cyclobutyl, cyclopentyl or cyclohexyl. Each ring of the polycyclic cycloalkyl is saturated, and can be a bicyclic or tricyclic cycloalkyl having 4 to 10 carbon atoms.

The term "heterocycloalkyl" refers to a saturated monocyclic or polycyclic group with heteroatoms. The monocyclic ring is preferably a 3 to 7 membered saturated monocyclic heterocycloalkyl containing 1, 2, or 3 heteroatoms independently selected from N, O, and S, and examples of the monocyclic ring include but are not limited to: pyrrolidinyl, tetrahydrofuryl, tetrahydropyranyl, tetrahydrothienyl, tetrahydropyridyl, tetrahydropyrrolyl, azetidinyl, thiazolidinyl, oxazolidinyl, piperidinyl, morpholinyl, thiomorpholinyl, piperazinyl, azepanyl, diazepanyl, oxazepanyl, dioxolanyl, dioxanyl, etc. The polycyclic ring is preferably an 8 to 10 membered saturated polycyclic heterocycloalkyl containing 1, 2, or 3 heteroatoms independently selected from N, O, and S on at least one ring and can be bicyclic or tricyclic. Examples of the polycyclic ring include but are not limited to octahydropyrrolo[1,2-a]pyrazinyl, (1R,5S)-3,8-diazabicyclo[3.2.1]octyl.

The term "aryl" refers to an aromatic group with a specified number of carbon atoms, preferably a monocyclic, bicyclic or tricyclic aromatic group. When it is bicyclic or tricyclic, each ring satisfies Huckel's rule. The C$_{6-10}$ aryl in the present disclosure refers to an aromatic group containing 6 to 10 carbon atoms, such as a phenyl or a naphthyl.

The term "heteroaryl" refers to an aromatic group containing heteroatoms, preferably, an aromatic 5 to 6 membered monocyclic ring or 9 to 10 membered bicyclic ring containing 1, 2 or 3 heteroatoms independently selected from nitrogen, oxygen and sulfur. The 5 to 6 membered monocyclic ring includes, but is not limited to, pyrrolyl, furyl, thienyl, imidazolyl, pyrazolyl, oxazolyl, isoxazolyl, thiazolyl, isothiazolyl, 1,2,3-triazolyl, 1,2,4-triazolyl, furazanyl, 1,2,3-oxadiazolyl, 1,2,4-oxadiazolyl, 1,2,5-oxadiazolyl, 1,3,4-oxadiazolyl, thiadiazolyl, dithiazolyl, tetrazolyl, pyridyl, pyranyl, thiopyranyl, diazinyl, pyrazinyl, pyrimidinyl, pyridazinyl, oxazinyl, thiazinyl, dioxinyl, dithiinyl, 1,2,3-triazinyl, 1,2,4-triazinyl, 1,3,5-triazinyl or tetrazinyl. The 9 to 10 membered bicyclic ring includes, but is not limited to, benzimidazolyl, indolyl, indazolyl, benzofuranyl, benzothiazolyl, benzisothiazolyl, benzoxazolyl, benzisoxazolyl, quinolinyl and isoquinolinyl.

On the basis of not departing from common knowledge in the art, the above-mentioned various preferred conditions can be combined in any manner, such that various preferred examples of the present disclosure are obtained.

Reagents and raw materials used in the present disclosure are all commercially available.

The positive effect of the present disclosure lies in:

(1) the fused ring pyrimidine amino compound of the present disclosure has a good inhibitory activity on DDRs, especially DDR2.

(2) the compound of the present disclosure has a good therapeutic effect on pulmonary inflammation and pulmonary fibrosis.

(3) further, the compound of the present disclosure has good selectivity to kinases and can reduce the occurrence of side effects.

DETAILED DESCRIPTION OF THE PREFERRED EMBODIMENT

Figure 1:
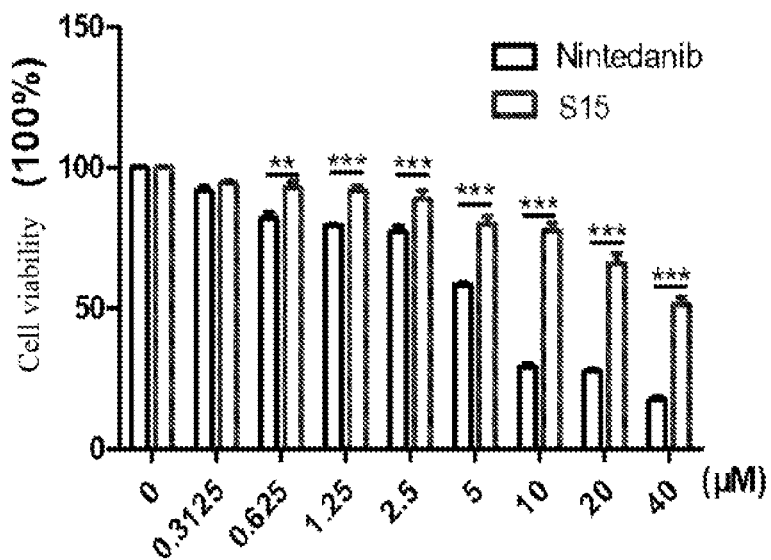
FIG. 1 shows the cytotoxic activity of the positive medicine Nintedanib and compound S15 on the lung fibroblast cell line MRC-5 in Effect example 3.

The present disclosure is further illustrated by the following examples, but the present disclosure is not limited thereto. The experimental methods in the examples below of which the specific conditions are not indicated are selected according to the conventional methods and conditions, or according to the commodity instructions.

Example 1: Synthesis of 6-bromo-N-(1-methyl-1H-pyrazol-4-yl)quinazolin-2-amine

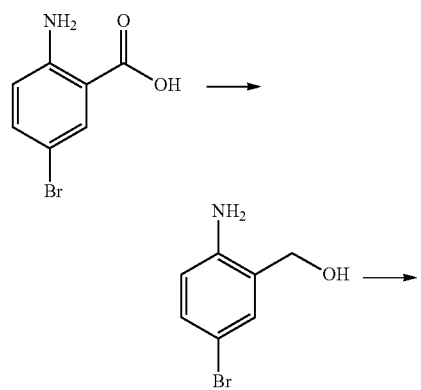

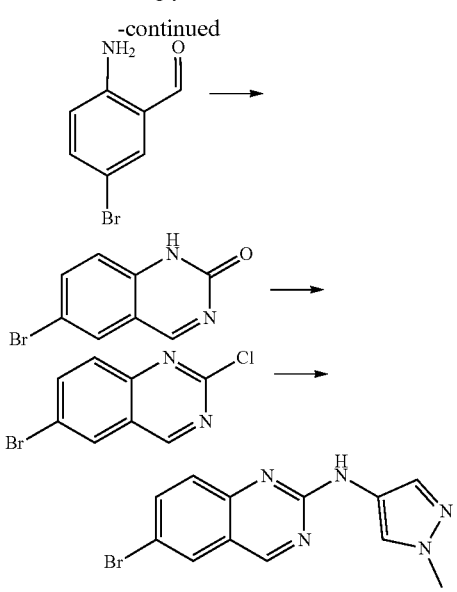

Step 1: Synthesis of (2-amino-5-bromophenyl)methanol 2-amino-5-bromobenzoic acid (10 g, 46.3 mmol) was weighed and dissolved in 80 ml dry tetrahydrofuran. A constant pressure dropping funnel was used to slowly add 1 M borane tetrahydrofuran solution (231 ml) dropwise to the reaction solution under ice bath conditions. After the dropwise addition was complete, the reaction solution was cooled to room temperature and stirred overnight. After the reaction was over, water was carefully added dropwise to the reaction solution for quenching, extracted with ethyl acetate, washed with water and a saturated sodium chloride solution, dried over anhydrous sodium sulfate and filtered, and the solvent was evaporated to dryness to obtain 9 g of white solid. The yield was 96%.

$^1$H NMR (400 MHz, Chloroform-d): δ 7.24-7.17 (m, 2H), 6.57 (d, J=8.3 Hz, 1H), 4.61 (s, 2H).

Step 2: Synthesis of 2-amino-5-bromobenzene(form)aldehyde

The intermediate (2-amino-5-bromophenyl)methanol (9 g, 44.54 mmol) and manganese dioxide (27 g, 312 mmol) were weighed and placed in 100 ml of dichloromethane, stirred at room temperature for 6 h. After the reaction was completed, the manganese dioxide was removed by suction filtration, the filter cake was washed with dichloromethane, the filtrate was combined, and the solvent was evaporated to dryness to obtain 7.2 g of a yellow-brown solid. The yield was 80%.

$^1$H NMR (400 MHz, Chloroform-d) δ: 9.79 (s, 1H), 7.58 (d, J=2.4, 1H), 7.37 (dd, J=8.8, 2.3, 1H), 6.56 (d, J=8.8, 1H), 6.14 (brs, 2H).

Step 3: Synthesis of 6-bromoquinazolin-2(1H)-one 2-amino-5-bromobenzene(form)aldehyde (3.7 g, 18.5 mmol) and urea (16.6 g, 277 mmol) was weighed, placed in a round bottom flask and heated to 180° C. in an oil bath. The solid was dissolved and stirred for 5 h to cool to room temperature. Water was added and stirred. At this time, a solid was precipitated, suction-filtered, washed with water, and dried to obtain a light yellow solid, 4 g of which was directly used in the next step. The yield was 96%.

Step 4: Synthesis of 6-bromo-2-chloroquinazoline

The intermediate obtained in the previous step was put directly into a round bottom flask, and 25 ml of phosphorus oxychloride was added. The reaction solution was placed in an oil bath at 110° C. for reflux heating for 6 hours, but after the reaction was completed, the reaction solution was cooled to room temperature. Ice water was added to the reaction system to carefully quench the reaction, and the resulting mixture was neutralized with saturated sodium carbonate solution, adjusted to PH 8 to 9, extracted 3 times with ethyl acetate, dried with anhydrous sodium sulfate and filtered, and the solvent was evaporated to dryness. The crude product was purified by silica gel chromatography to obtain 2 g of white solid. The yield was 46%.

$^1$H NMR (400 MHz, DMSO-d$_6$) δ 9.58 (s, 1H), 8.54 (s, 1H), 8.22 (d, J=8.9 Hz, 1H), 7.94 (d, J=9.0 Hz, 1H).

Step 5: Synthesis of 6-bromo-N-(1-methyl-1H-pyrazol-4-yl)quinazolin-2-amine

The intermediate (250 mg, 1.03 mmol) obtained in the previous step was weighed and placed into a round bottom flask, and 1-methyl-1H-pyrazol-4-amine (122.65 mg, 1.23 mmol) and trifluoroacetic acid (265 mg, 2.05 mmol) were added and dissolved in 30 ml of isopropanol. The reaction solution was placed on an oil bath at 85° C. and heated for 4 h. After the raw materials disappeared completely, the reaction was quenched by adding water to the reaction, extracted 3 times with ethyl acetate, dried with anhydrous sodium sulfate and filtered and the solvent was evaporated to dryness to obtain a crude product as a yellow solid, which was slurried with dichloromethane and purified to obtain a yellow solid (240 mg). The yield was 88%.

$^1$H NMR (400 MHz, DMSO-d6) δ 9.92 (s, 1H), 9.19 (s, 1H), 8.21 (s, 1H), 8.13 (s, 1H), 7.88 (dd, J=8.9, 2.1 Hz, 1H), 7.61 (d, J=7.6 Hz, 2H), 3.85 (s, 3H).

Example 2: Synthesis of Compound S1

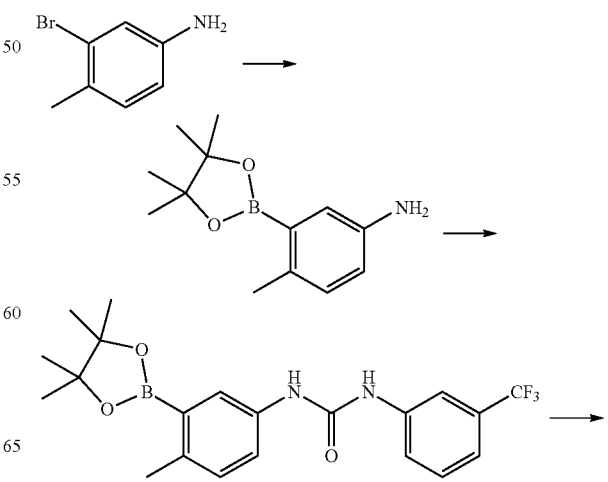

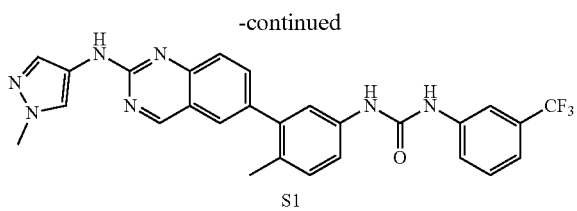

S1

Step 1: Synthesis of 4-methyl-3-(4,4,5,5-tetramethyl-1,3,2-dioxaborolan-2-yl)aniline The compound 3-bromo-4-methylaniline (10 g, 53.75 mmol) was weighed and placed in a Schlenk bottle and dissolved in 80 ml of dry dimethyl sulfoxide. Pinacol diborate (17.74 g, 69.87 mmol), potassium acetate (15.82 g, 161.25 mmol), and [1,1'-bis(diphenylphosphine)ferrocene] dichloropalladium dichloromethane complex (1.32 g, 1.61 mmol) were added, respectively. Vacuum pump and argon balloon were used to perform gas replacement to remove the air in the reaction system. After three replacements, the reaction system was protected with an argon balloon and placed in an oil bath at 80° C. for 3 hours of reaction. After the reaction was completed, the reaction system was allowed to be cooled to room temperature, and then saturated brine was added and extracted with ethyl acetate 3 times. The organic layer was dried with anhydrous sodium sulfate and filtered and the solvent was evaporated to dryness. The crude product was purified by silica gel column chromatography to obtain a brown solid (10.6 g). The yield was 84.6%.

$^1$H NMR (400 MHz, DMSO-d6) δ 6.94 (d, J=2.1 Hz, 1H), 6.82 (d, J=8.1 Hz, 1H), 6.55 (dd, J=8.0, 2.3 Hz, 1H), 4.82 (s, 2H), 2.28 (s, 3H), 1.28 (s, 12H).

Step 2: Synthesis of 1-(4-methyl-3-(4,4,5,5-tetramethyl-1,3,2-dioxaborolan-2-yl)phenyl)-3-(3-(trifluoromethyl)phenyl)urea The intermediate 4-methyl-3-(4,4,5,5-tetramethyl-1,3,2-dioxaborolan-2-yl)aniline (10 g, 42.9 mmol) was dissolved in dry tetrahydrofuran. 3-(trifluoromethyl)phenyl isocyanate (8.0 g, 42.9 mmol) was slowly added dropwise and stirred at room temperature for 3 hours. A white solid was precipitated out. After the reaction was completed, suction filtration was performed to obtain a white solid (14 g). The yield was 77%.

$^1$H NMR (400 MHz, DMSO-d6) δ 8.90 (s, 1H), 8.78 (s, 1H), 8.02 (s, 1H), 7.72 (s, 1H), 7.57 (d, J=8.9 Hz, 1H), 7.51 (t, J=8.0 Hz, 1H), 7.45 (dd, J=8.2, 2.0 Hz, 1H), 7.30 (d, J=7.7 Hz, 1H), 7.11 (d, J=8.1 Hz, 1H), 2.41 (s, 3H), 1.31 (s, 12H).

Step 3: Synthesis of 1-(4-methyl-3-(2-((1-methyl-1H-pyrazol-4-yl)amino)quinazolin-6-yl)phenyl)-3-(3-(trifluoromethyl)phenyl)urea (S1)

The compound 6-bromo-N-(1-methyl-1H-pyrazol-4-yl)quinazolin-2-amine (200 mg, 0.657 mmol) was weighed and placed in a Schlenk bottle and dissolved in 16 ml of dioxane and 4 ml of water. 1-(4-methyl-3-(4,4,5,5-tetramethyl-1,3,2-dioxaborolan-2-yl)phenyl)-3-(3-(trifluoromethyl)phenyl)urea (304 mg, 0.723 mmol), potassium carbonate (182 mg, 1.32 mmol), and [1,1'-bis(diphenylphosphine)ferrocene] dichloropalladium dichloromethane complex (16 mg, 0.020 mmol) were added, respectively. Vacuum pump and argon balloon were used to perform gas replacement to remove the air in the reaction system. After three replacements, the reaction system was protected with an argon balloon and placed in an oil bath at 80° C. for 3 hours of reaction. After the reaction was completed, the reaction system was allowed to be cooled to room temperature, and then saturated brine was added and extracted with ethyl acetate 3 times. The organic layer was dried with anhydrous sodium sulfate and filtered and the solvent was evaporated to dryness. The crude product was purified by silica gel column chromatography to obtain a yellow solid (260 mg). The yield was 76%.

$^1$H NMR (400 MHz, DMSO-d6) δ 9.82 (s, 1H), 9.28 (s, 1H), 9.07 (s, 1H), 8.83 (s, 1H), 8.24 (s, 1H), 8.04 (s, 1H), 7.85 (s, 1H), 7.79 (dd, J=8.7, 1.6 Hz, 1H), 7.72 (d, J=8.5 Hz, 1H), 7.63 (s, 1H), 7.57 (d, J=8.5 Hz, 1H), 7.53 (s, 1H), 7.50 (d, J=7.8 Hz, 1H), 7.34 (d, J=8.4 Hz, 1H), 7.31 (d, J=7.5 Hz, 1H), 7.26 (d, J=8.3 Hz, 1H), 3.87 (s, 3H), 2.24 (s, 3H).

HRMS m/z (ESI) found 518.1921 (M+H)$^+$, C27H23F3N7O$^+$ calcd for 518.1911, retention time 3.212 min, purity: >99%.

Example 3: Synthesis of Compound S2

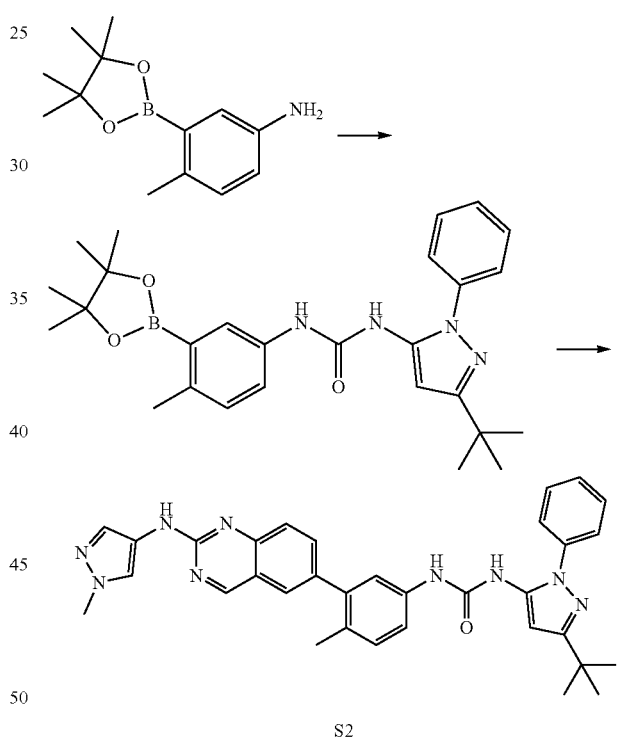

S2

Step 1: Synthesis of 1-(3-(tert-butyl)-1-phenyl-1H-pyrazol-5-yl)-3-(4-methyl-3-(4,4,5,5-tetramethyl-1,3,2-dioxaborolan-2-yl)phenyl)urea Triphosgene (84 mg, 0.283 mmol) was weighed and dissolved in dichloromethane. 3-(tert-butyl)-1-phenyl-1H-pyrazol-5-amine (184.71 mg, 0.858 mmol) was slowly added to the reaction solution under ice bath. After 30 minutes of reaction, 300 μL of DIPEA and 4-methyl-3-(4,4,5,5-tetramethyl-1,3,2-dioxaborolan-2-yl)aniline (200 mg, 0.858 mmol) were added to the reaction solution and stirred at room temperature for 6 h. A white solid was precipitated out. After the reaction was over, a white solid was obtained by suction filtration, and the filter cake was washed with diethyl ether. The yield was 86%.

¹H NMR (400 MHz, DMSO-d6) δ 9.03 (s, 1H), 8.25 (s, 1H), 7.66 (s, 1H), 7.53 (d, J=3.6 Hz, 4H), 7.41 (d, J=7.9 Hz, 2H), 7.07 (d, J=8.0 Hz, 1H), 6.38 (s, 1H), 2.38 (s, 3H), 1.29 (d, J=2.6 Hz, 22H).

Step 2: Synthesis of 1-(3-(tert-butyl)-1-phenyl-1H-pyrazol-5-yl)-3-(4-methyl-3-(2-((1-methyl-1H-pyrazol-4-yl)amino)quinazolin-6-yl)phenyl)urea (S2)

The compound 6-bromo-N-(1-methyl-1H-pyrazol-4-yl)quinazolin-2-amine (200 mg, 0.657 mmol) was weighed and placed in a Schlenk bottle and dissolved in 16 ml of dioxane and 4 ml of water. 1-(3-(tert-butyl)-1-phenyl-1H-pyrazol-5-yl)-3-(4-methyl-3-(4,4,5,5-tetramethyl-1,3,2-dioxaborolan-2-yl)phenyl)urea (312 mg, 0.657 mmol), potassium carbonate (182 mg, 1.32 mmol), and [1,1'-bis(diphenylphosphine)ferrocene] dichloropalladium dichloromethane complex (16 mg, 0.020 mmol) were added, respectively. Vacuum pump and argon balloon were used to perform gas replacement to remove the air in the reaction system. After three replacements, the reaction system was protected with an argon balloon and placed in an oil bath at 80° C. for 3 hours of reaction. After the reaction was completed, the reaction system was allowed to be cooled to room temperature, and then saturated brine was added and extracted with ethyl acetate 3 times. The organic layer was dried with anhydrous sodium sulfate and filtered and the solvent was evaporated to dryness. The crude product was purified by silica gel column chromatography to obtain a yellow solid (283 mg). The yield was 75%.

¹H NMR (400 MHz, DMSO-d6) δ 9.81 (s, 1H), 9.26 (s, 2H), 8.56 (s, 1H), 8.23 (s, 1H), 7.83 (s, 1H), 7.77 (dd, J=8.5, 2.1 Hz, 1H), 7.71 (d, J=8.9 Hz, 1H), 7.63 (s, 1H), 7.57-7.50 (m, 4H), 7.48 (d, J=2.1 Hz, 1H), 7.43-7.39 (m, 1H), 7.28 (dd, J=8.3, 2.1 Hz, 1H), 7.22 (d, J=8.3 Hz, 1H), 6.37 (s, 1H), 3.87 (s, 3H), 2.22 (s, 3H), 1.28 (s, 9H).

HRMS m/z (ESI) found 572.2893 (M+H)⁺, C33H34N9O⁺ calcd for 572.2881, >99% pure.

Example 4: Synthesis of Compound S4

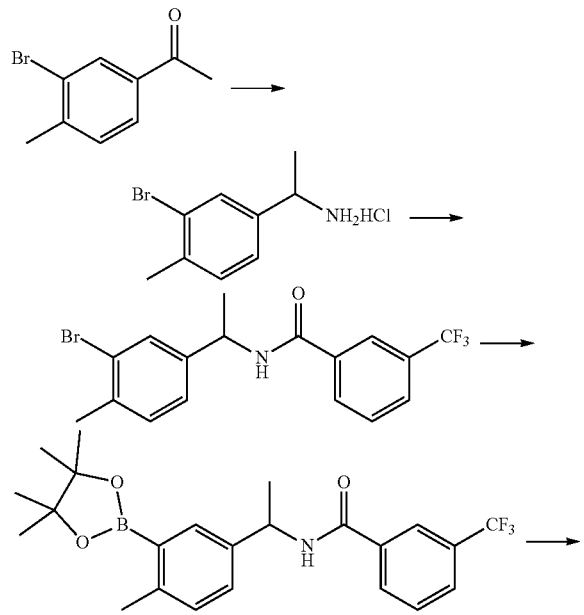

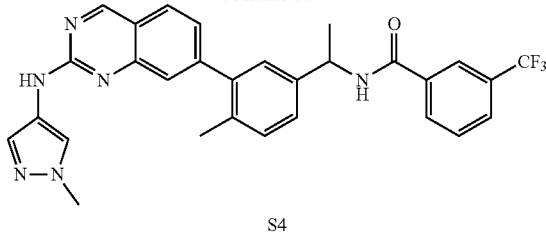

S4

Step 1: Synthesis of 1-(3-bromo-4-methylphenyl)ethane-1-amine hydrochloride 3-bromo-4-methylacetophenone (5 g, 23.47 mmol) was dissolved in 100 ml of anhydrous methanol, and 2 g of 4 A molecular sieve was added. Ammonium acetate solid (18 g, 234.7 mmol) was weighed, added to anhydrous ethyl alcohol in batches and stirred for 2 hours at room temperature, and then sodium cyanoborohydride (4.42 g, 70.4 mmol) was slowly added under ice bath condition. After the addition was completed, the resulting mixture was stirred for 48 hours at room temperature. After the raw materials were completely reacted, the resulting mixture was distilled to removed the solvent methanol under reduced pressure, extracted with ethyl acetate and washed with water to remove excess solids, the organic phase was collected, dried with anhydrous sodium sulfate, and distilled under reduced pressure to remove ethyl acetate. The obtained oily substance was added to a solution of diethyl ether in hydrochloric acid and sonicated. At this time, a large amount of white solid was precipitated out. Suction filtration was performed and the filter cake was washed with anhydrous diethyl ether to obtain a total of 4.8 g of white solid, with a yield of 81.7%.

Step 2: Synthesis of N-(1-(3-bromo-4-methylphenyl)ethyl)-3-(trifluoromethyl)benzamide The intermediate 1-(3-bromo-4-methylphenyl)ethane-1-amine hydrochloride (3 g, 11.97 mmol), HATU (5 g, 11.97 mmol) and DIPEA (4.64 g, 35.92 mmol) were weighed and placed in a round bottom flask. 50 ml of anhydrous N,N-dimethylformamide was added. After stirring for 30 min at room temperature, 3-trifluoromethylbenzoic acid (2.3 g, 11.97 mmol) was added dropwise to the reaction solution. The reaction solution was stirred at room temperature for 4 hours. After the reactants were reacted completely, saturated brine was added to the reaction solution and extracted with ethyl acetate 3 times. The organic layer was dried with anhydrous sodium sulfate and filtered and the solvent was evaporated to dryness. The crude product was purified by silica gel column chromatography to obtain a total of 4 g of yellow oily liquid. The yield was 86.5%.

¹H NMR (400 MHz, Chloroform-d) δ 8.04 (s, 1H), 7.97 (d, J=7.8 Hz, 1H), 7.77 (d, J=7.8 Hz, 1H), 7.58 (d, J=7.9 Hz, 1H), 7.57-7.55 (m, 1H), 7.28 (s, 1H), 7.24 (d, J=1.6 Hz, 1H), 7.23 (s, 1H), 5.31-5.26 (m, 1H), 2.39 (s, 3H), 1.61 (d, J=6.9 Hz, 3H).

Step 3: Synthesis of N-(1-(4-methyl-3-(4,4,5,5-tetramethyl-1,3,2-dioxaborolan-2-yl)phenyl)ethyl)-3-(trifluoromethyl)benzamide The intermediate N-(1-(3-bromo-4-methylphenyl)ethyl)-3-(trifluoromethyl)benzamide (3 g, 7.77 mmol) was weighed and placed in a Schlenk bottle and dissolved in 30 ml of dry dimethyl sulfoxide. Pinacol diborate (2.17 g, 8.54 mmol), potassium acetate (2.29 g, 23.30 mmol), and [1,1'-bis(diphenylphosphine)ferrocene] dichloropalladium dichloromethane complex (189 mg, 0.23 mmol) were added, respectively. Vacuum pump and argon balloon were used to perform gas replacement to remove the air in the reaction system. After three replacements, the reaction system was protected with an argon balloon and placed in an oil bath at 80° C. for 3 hours of reaction. After the reaction was completed, the reaction system was allowed to be cooled to room temperature, and then saturated brine was added and extracted with ethyl acetate 3 times. The organic layer was dried with anhydrous sodium sulfate and filtered and the solvent was evaporated to dryness. The crude product was purified by silica gel column chromatography to obtain a total of 3 g of white solid. The yield was 89%.

$^1$H NMR (400 MHz, Chloroform-d) δ 8.03 (s, 1H), 7.96 (d, J=7.7 Hz, 1H), 7.80 (d, J=2.0 Hz, 1H), 7.76 (d, J=8.5 Hz, 1H), 7.58 (t, J=7.8 Hz, 1H), 7.38 (dd, J=9.0, 1.1 Hz, 1H), 7.20 (d, J=7.9 Hz, 1H), 6.33 (d, J=9.1 Hz, 1H), 5.33 (p, J=7.6 Hz, 1H), 2.55 (s, 3H), 1.65 (d, J=6.9 Hz, 3H), 1.37 (s, 12H).

Step 4: Synthesis of N-(1-(4-methyl-3-(2-((1-methyl-1H-pyrazol-4-yl)amino)quinazolin-7-yl)phenyl)ethyl)-3-(Trifluoromethyl)benzamide (S4)

The compound 6-bromo-N-(1-methyl-1H-pyrazol-4-yl)quinazolin-2-amine (140 mg, 0.462 mmol) was weighed and placed in a Schlenk bottle and dissolved in 20 ml of dioxane and 4 ml of water. N-(1-(4-methyl-3-(4,4,5,5-tetramethyl-1,3,2-dioxaborolan-2-yl)phenyl)ethyl)-3-(trifluoromethyl)benzamide (200 mg, 0.462 mmol), potassium carbonate (138 mg, 0.923 mmol), and [1,1'-bis(diphenylphosphine)ferrocene] dichloropalladium dichloromethane complex (15 mg, 0.015 mmol) were added, respectively. Vacuum pump and argon balloon were used to perform gas replacement to remove the air in the reaction system. After three replacements, the reaction system was protected with an argon balloon and placed in an oil bath at 80° C. for 3 hours of reaction. After the reaction was completed, the reaction system was allowed to be cooled to room temperature, and then saturated brine was added and extracted with ethyl acetate 3 times. The organic layer was dried with anhydrous sodium sulfate and filtered and the solvent was evaporated to dryness. The crude product was purified by silica gel column chromatography to obtain 150 mg of yellow solid with a yield of 77%.

$^1$H NMR (400 MHz, DMSO-d6) δ 9.79 (s, 1H), 9.25 (s, 1H), 9.10 (d, J=8.0 Hz, 1H), 8.23 (s, 1H), 8.19 (d, J=7.9 Hz, 1H), 7.91 (d, J=7.4 Hz, 1H), 7.84 (d, J=1.9 Hz, 1H), 7.78 (dd, J=8.6, 2.0 Hz, 1H), 7.72 (t, J=7.9 Hz, 2H), 7.62 (s, 1H), 7.35 (s, 1H), 7.34 (d, J=1.7 Hz, 1H), 7.30 (d, J=8.5 Hz, 1H), 5.23 (p, J=7.8 Hz, 1H), 3.86 (s, 3H), 2.27 (s, 3H), 1.54 (d, J=7.0 Hz, 3H).

HRMS m/z (ESI) found 531.2118 (M+H)$^+$, C29H26F3N6O$^+$ calcd for 531.2115, >99% pure The compounds S5 to S8 in the following Examples 5 to 8 can be obtained according to the synthesis method in the above examples, only with the corresponding raw materials replaced.

Example 5: Synthesis of Compound S5

4-Methyl-3-(2-((1-methyl-1H-pyrazol-4-yl)amino)quinazolin-6-yl)-N-(1-(3-(trifluoromethyl)phenyl)ethyl)benzamide (S5)

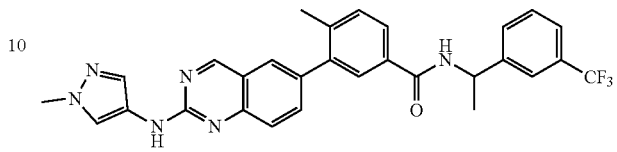

$^1$H NMR (400 MHz, DMSO-d6) δ 9.83 (s, 1H), 9.27 (s, 1H), 8.95 (d, J=7.6 Hz, 1H), 8.23 (s, 1H), 7.89 (d, J=4.0 Hz, 2H), 7.87-7.78 (m, 2H), 7.75 (s, 2H), 7.71 (d, J=7.4 Hz, 1H), 7.60 (dd, J=16.7, 8.0 Hz, 3H), 7.45 (d, J=8.0 Hz, 1H), 5.27 (p, J=8.0, 7.5 Hz, 1H), 3.87 (s, 3H), 2.34 (s, 3H), 1.51 (d, J=7.0 Hz, 3H).

HRMS m/z (ESI) found 531.212 (M+H)$^+$, C29H26F3N6O$^+$ calcd for 531.2115, >99% pure

Example 6: Synthesis of Compound S6

N-(1-(4-methyl-3-(2-((1-methyl-1H-pyrazol-4-yl)amino)quinazolin-6-yl)phenyl)propyl)-3-(trifluoromethyl)benzamide (S6)

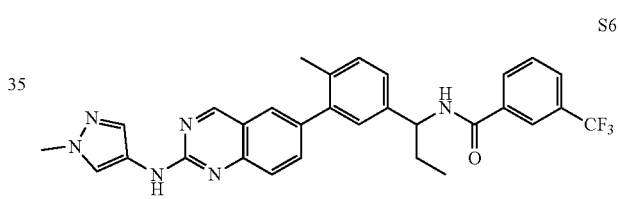

$^1$H NMR (400 MHz, DMSO-d6) δ 9.79 (s, 1H), 9.25 (s, 1H), 9.03 (d, J=8.6 Hz, 1H), 8.21 (s, 1H), 8.19 (d, J=7.9 Hz, 1H), 7.91 (d, J=7.7 Hz, 1H), 7.83 (s, 1H), 7.78 (d, J=8.6 Hz, 1H), 7.73 (t, J=7.4 Hz, 2H), 7.62 (s, 1H), 7.35 (s, 1H), 7.33 (s, 1H), 7.30 (d, J=7.8 Hz, 1H), 5.06-4.92 (m, 1H), 3.86 (s, 3H), 2.27 (s, 3H), 1.89 (qt, J=13.7, 6.6 Hz, 2H), 0.94 (t, J=7.2 Hz, 3H).

HRMS m/z (ESI) found 545.2284 (M+H)$^+$, C30H28F3N6O$^+$ calcd for 545.2271, >99% pure.

Example 7: Synthesis of Compound S7

4-methyl-3-(2-((1-methyl-1H-pyrazol-4-yl)amino)quinazolin-6-yl)-N-(3-(trifluoromethyl)benzyl)benzamide (S7)

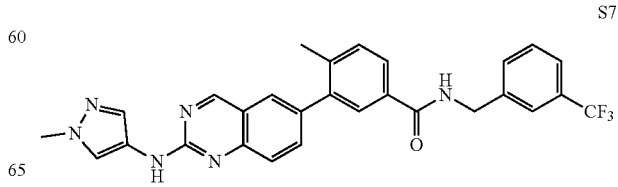

¹H NMR (400 MHz, DMSO-d6) δ 9.82 (s, 1H), 9.26 (s, 1H), 9.19 (t, J=5.9 Hz, 1H), 8.23 (s, 1H), 7.90 (d, J=1.9 Hz, 1H), 7.88 (d, J=1.6 Hz, 1H), 7.87-7.85 (m, 1H), 7.85-7.81 (m, 1H), 7.74 (d, J=8.9 Hz, 1H), 7.68 (s, 1H), 7.63 (t, J=8.0 Hz, 3H), 7.60-7.55 (m, 1H), 7.47 (d, J=7.9 Hz, 1H), 4.57 (d, J=5.8 Hz, 2H), 3.86 (s, 3H), 2.35 (s, 3H).

HRMS m/z (ESI) found 517.1948 (M+H)$^+$, C28H24F3N6O$^+$ calcd for 517.1958, >99% pure.

Example 8: Synthesis of Compound S8

N-(4-methyl-3-(2-((1-methyl-1H-pyrazol-4-yl)amino)quinazolin-6-yl)phenyl)-2-(3-(trifluoromethyl)phenyl)propionamide (S8)

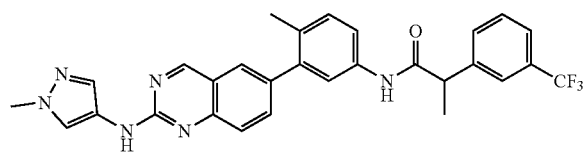 [SMILES: Cc1ccc(C(=O)NC(C)c2cccc(C(F)(F)F)c2)cc1-c1ccc2nc(Nc3cnn(C)c3)ncc2c1]

S8

¹H NMR (400 MHz, DMSO-d6) δ 10.21 (s, 1H), 9.81 (s, 1H), 9.25 (s, 1H), 8.22 (s, 1H), 7.82 (s, 1H), 7.75 (d, J=10.7 Hz, 2H), 7.70 (d, J=7.2 Hz, 2H), 7.63 (d, J=7.9 Hz, 2H), 7.60 (d, J=7.4 Hz, 2H), 7.49 (d, J=1.8 Hz, 1H), 7.26 (d, J=8.4 Hz, 1H), 3.96 (q, J=7.5 Hz, 1H), 3.86 (s, 3H), 2.22 (s, 3H), 1.46 (d, J=6.9 Hz, 3H).

HRMS m/z (ESI) found 531.2123 (M+H)$^+$, C29H26F3N6O$^+$ calcd for 531.2115, >99% pure.

Example 9: Synthesis of Compound S9

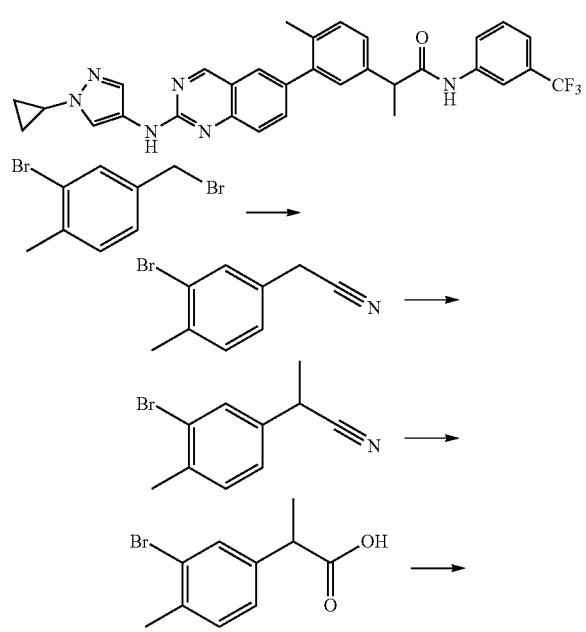

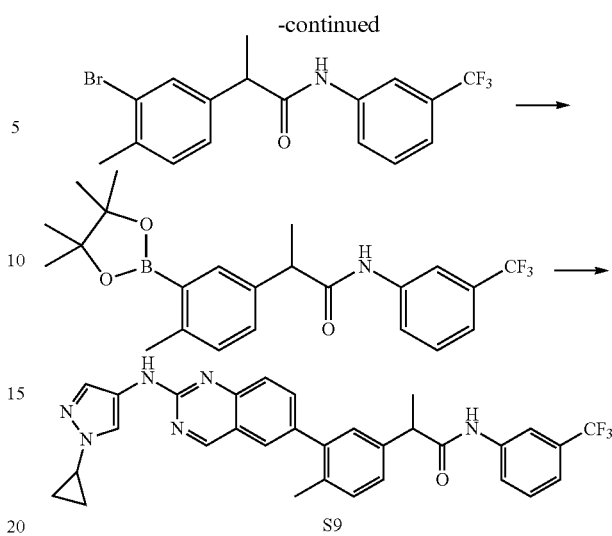

Step 1: Synthesis of 2-(3-bromo-4-methylphenyl)acetonitrile 2-bromo-4-(bromomethyl)-1-methylbenzene (5 g, 18.94 mmol) was dissolved in 30 ml of anhydrous acetonitrile. 18-crown ether-6 (15 g, 56.83 mmol) was added, and potassium cyanide (1.36 g, 20.84 mmol) was slowly added and stirred at room temperature for 6 hours.

After the raw materials were reacted completely, extraction was performed 3 times with ethyl acetate and water, the organic phase was collected, dried with anhydrous sodium sulfate and distilled under reduced pressure to remove ethyl acetate. The crude product was purified by silica gel column chromatography to obtain a total of 2 g of colorless oily liquid. The yield was 50%.

¹H NMR (400 MHz, Chloroform-d) δ 7.49 (d, J=1.4 Hz, 1H), 7.23 (d, J=7.8 Hz, 1H), 7.17 (d, J=7.8 Hz, 1H), 3.69 (s, 2H), 2.38 (s, 3H).

Step 2: Synthesis of 2-(3-bromo-4-methylphenyl)propionitrile

The intermediate 2-(3-bromo-4-methylphenyl)acetonitrile (1 g, 4.76 mmol) was dissolved in 10 ml of anhydrous DMF, and sodium hydride (60%, 209 mg, 5.24 mmol) was slowly added under ice bath condition. After stirring for 30 minutes under ice bath condition, iodomethane (675 mg, 4.76 mmol) was added dropwise to the reaction solution. After reacting for about 5 hours, the raw materials were reacted completely, and then extraction was performed 3 times with ethyl acetate and water. The organic phase was collected, dried with anhydrous sodium sulfate, and distilled under reduced pressure to remove ethyl acetate. The crude product was purified by silica gel column chromatography to obtain a total of 700 mg of yellow oily liquid. The yield was 66%.

1H NMR (400 MHz, Chloroform-d) δ 7.52 (d, J=1.8 Hz, 1H), 7.25 (d, J=7.9 Hz, 1H), 7.20 (dd, J=7.9, 1.9 Hz, 1H), 3.85 (q, J=7.3 Hz, 1H), 2.39 (s, 3H), 1.63 (d, J=7.3 Hz, 3H).

Step 3: Synthesis of 2-(3-bromo-4-methylphenyl)propionic acid

The intermediate 2-(3-bromo-4-methylphenyl)propionitrile (500 mg, 2.23 mmol) was dissolved in 20 ml of 4 N sodium hydroxide solution and stirred at 125° C. for 6 hours. After the yellow oily suspension disappeared completely, extraction was performed with ethyl acetate and water, the organic phase was discarded and the aqueous layer was retained. The aqueous layer was acidified with hydrochloric acid to PH=2 to 3, extracted with ethyl acetate, and the organic phase was collected, dried with anhydrous sodium sulfate and distilled under reduced pressure to remove ethyl acetate. A colorless oily liquid 400 mg was obtained. The yield was 74%.

$^1$H NMR (400 MHz, Chloroform-d) δ7.53 (s, 1H), 7.21 (s, 1H), 7.20 (s, 1H), 3.71 (q, J=7.0 Hz, 1H), 2.40 (s, 3H), 1.52 (d, J=7.0 Hz, 3H).

Step 4: Synthesis of 2-(3-bromo-4-methylphenyl)-N-(3-(trifluoromethyl)phenyl)propionamide The intermediate 2-(3-bromo-4-methylphenyl)propionic acid (300 mg, 1.23 mmol), HATU (516 mg, 1.36 mmol) and DIPEA (319 mg, 2.47 mmol) were weighed and placed in a round bottom flask, and 15 ml of anhydrous N,N-dimethylformamide was added. After stirring for 30 min at room temperature, m-aminotrifluorotoluene (199 mg, 1.23 mmol) was added dropwise to the reaction solution. The reaction solution was stirred at room temperature for 4 hours. After the reactants were reacted completely, saturated brine was added to the reaction solution and extracted with ethyl acetate 3 times. The organic layer was dried with anhydrous sodium sulfate and filtered and the solvent was evaporated to dryness. The crude product was purified by silica gel column chromatography to obtain a total of 400 mg of yellow oily liquid. The yield was 84%.

$^1$H NMR (400 MHz, Chloroform-d) δ 7.76 (s, 1H), 7.62 (d, J=8.0 Hz, 1H), 7.52 (s, 1H), 7.38 (t, J=7.9 Hz, 1H), 7.32 (d, J=7.7 Hz, 1H), 7.24 (d, J=7.9 Hz, 1H), 7.22-7.18 (m, 1H), 3.65 (q, J=7.1 Hz, 1H), 2.39 (s, 3H), 1.56 (d, J=7.1 Hz, 3H).

Step 5: Synthesis of 2-(4-methyl-3-(4,4,5,5-tetramethyl-1,3,2-dioxaborolan-2-yl)phenyl)-N-(3-(trifluoromethyl)phenyl)propionamide The intermediate 2-(3-bromo-4-methylphenyl)-N-(3-(trifluoromethyl)phenyl)propionamide (300 mg, 0.777 mmol) was weighed and placed in a Schlenk bottle and dissolved in 10 ml of dry dimethyl sulfoxide. Pinacol diborate (217 mg, 0.854 mmol), potassium acetate (229 mg, 2.33 mmol), and [1,1'-bis(diphenylphosphine)ferrocene] dichloropalladium dichloromethane complex (19 mg, 0.02 mmol) were added, respectively. Vacuum pump and argon balloon were used to perform gas replacement to remove the air in the reaction system. After three replacements, the reaction system was protected with an argon balloon and placed in an oil bath at 80° C. for 3 hours of reaction. After the reaction was completed, the reaction system was allowed to be cooled to room temperature, and then saturated brine was added and extracted with ethyl acetate 3 times. The organic layer was dried with anhydrous sodium sulfate and filtered and the solvent was evaporated to dryness. The crude product was purified by silica gel column chromatography to obtain a total of 270 mg of white solid. The yield was 80%.

$^1$H NMR (400 MHz, Chloroform-d) δ 7.74 (s, 1H), 7.70 (d, J=1.7 Hz, 1H), 7.59 (d, J=8.0 Hz, 1H), 7.40-7.27 (m, 4H), 7.20 (d, J=7.9 Hz, 1H), 3.70 (q, J=7.1 Hz, 1H), 2.54 (s, 3H), 1.57 (d, J=7.1 Hz, 3H), 1.26 (s, 12H).

Step 6: Synthesis of 2-(3-(2-((1-cyclopropyl-1H-pyrazol-4-yl)amino)quinazolin-6-yl)-4-methylphenyl)-N-(3-(trifluoromethyl)phenyl)propionamide (S9)

The intermediate 6-bromo-N-(1-cyclopropyl-1H-pyrazol-4-yl)quinazolin-2-amine (136 mg, 0.446 mmol, the synthesis method was the same as in the example 1 except that the raw materials were different) was weighed and placed in a Schlenk bottle and dissolved in 20 ml of dioxane and 4 ml of water. The intermediate 2-(4-methyl-3-(4,4,5,5-tetramethyl-1,3,2-dioxaborolan-2-yl)phenyl)-N-(3-(trifluoromethyl)phenyl) propionamide (200 mg, 0.446 mmol), potassium carbonate (123 mg, 0.892 mmol), and [1,1'-bis(diphenylphosphine)ferrocene] dichloropalladium dichloromethane complex (11 mg, 0.014 mmol) were added, respectively. Vacuum pump and argon balloon were used to perform gas replacement to remove the air in the reaction system. After three replacements, the reaction system was protected with an argon balloon and placed in an oil bath at 80° C. for 3 hours of reaction. After the reaction was completed, the reaction system was allowed to be cooled to room temperature, and then saturated brine was added and extracted with ethyl acetate 3 times. The organic layer was dried with anhydrous sodium sulfate and filtered and the solvent was evaporated to dryness. The crude product was purified by silica gel column chromatography to obtain a total of 175 mg of yellow solid. The yield was 77%.

$^1$H NMR (400 MHz, Chloroform-d) δ 9.04 (s, 1H), 8.19 (s, 1H), 7.80 (s, 1H), 7.74 (d, J=8.8 Hz, 1H), 7.71 (d, J=1.7 Hz, 1H), 7.70-7.66 (m, 2H), 7.62 (s, 1H), 7.58 (s, 1H), 7.47 (s, 1H), 7.39 (t, J=7.9 Hz, 1H), 7.33 (s, 3H), 7.23 (s, 1H), 3.76 (q, J=7.0 Hz, 1H), 3.61 (tt, J=7.3, 3.8 Hz, 1H), 2.30 (s, 3H), 1.63 (d, J=7.1 Hz, 3H), 1.17 (p, J=5.0 Hz, 2H), 1.06-0.99 (m, 2H).

The compounds in the following examples can be obtained according to the synthesis method in the above examples, only with the corresponding raw materials replaced.

Example 10: Synthesis of Compound S10

The synthesis method for the compound referred to that in Example 4.

N-(1-(4-cyclopropyl-3-(2-((1-cyclopropyl-1H-pyrazol-4-yl)amino)quinazolin-7-yl)phenyl)ethyl)-3-(trifluoromethyl)benzamide (S10)

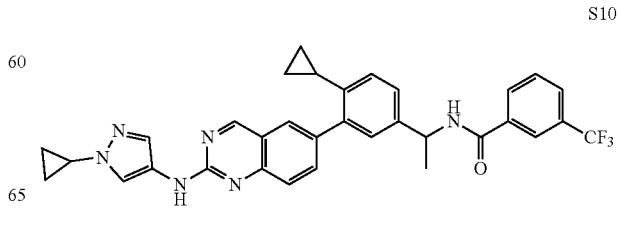

S10

¹H NMR (400 MHz, DMSO-d6) δ 9.78 (s, 1H), 9.27 (s, 1H), 9.09 (d, J=8.1 Hz, 1H), 8.27-8.21 (m, 2H), 8.19 (d, J=8.0 Hz, 1H), 7.93-7.88 (m, 2H), 7.86 (dd, J=8.6, 1.9 Hz, 1H), 7.72 (t, J=7.9 Hz, 2H), 7.62 (s, 1H), 7.37-7.32 (m, 2H), 7.01 (d, J=8.7 Hz, 1H), 5.22 (p, J=7.5, 7.0 Hz, 1H), 3.74 (tt, J=7.6, 4.1 Hz, 1H), 1.84 (ddt, J=12.4, 9.0, 4.2 Hz, 1H), 1.53 (d, J=7.0 Hz, 3H), 1.09-1.02 (m, 2H), 1.00-0.93 (m, 2H), 0.86-0.80 (m, 2H), 0.67 (q, J=4.9 Hz, 2H).

HRMS m/z (ESI) found 583.2438 (M+H)⁺, $C_{29}H_{27}F_3N_7O^+$ calcd for 583.2428, >99% pure

Example 11: Synthesis of Compound S11

The synthesis method for the compound referred to that in Example 4.

N-(1-(3-(2-((1-cyclopropyl-1H-pyrazol-4-yl)amino)quinazolin-7-yl)-4-methylphenyl)ethyl)-3-(trifluoromethyl)benzamide (S11)

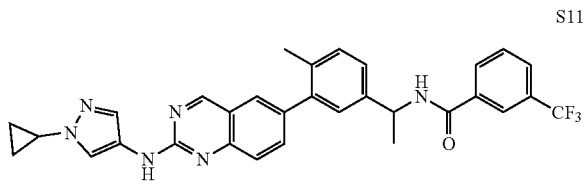 [SMILES: Cc1ccc(C(C)NC(=O)c2cccc(C(F)(F)F)c2)cc1-c1ccc2nc(Nc3cnn(C4CC4)c3)ncc2c1]

S11

¹H NMR (400 MHz, DMSO-d6) δ9.79 (s, 1H), 9.25 (s, 1H), 9.10 (d, J=8.0 Hz, 1H), 8.23 (s, 2H), 8.19 (d, J=7.9 Hz, 1H), 7.91 (d, J=7.7 Hz, 1H), 7.83 (s, 1H), 7.77 (dd, J=8.5, 1.9 Hz, 1H), 7.76-7.68 (m, 2H), 7.62 (s, 1H), 7.38-7.32 (m, 2H), 7.30 (d, J=8.4 Hz, 1H), 5.31-5.16 (m, 1H), 3.74 (tt, J=7.4, 3.9 Hz, 1H), 2.26 (s, 3H), 1.54 (d, J=7.0 Hz, 3H), 1.06 (dt, J=7.8, 3.8 Hz, 2H), 0.97 (dt, J=6.6, 3.0 Hz, 2H).

HRMS m/z (ESI) found 557.2277 (M+H)⁺, $C_{31}H_{28}F_3N_6O^+$ calcd for 557.2271, >99% pure.

Example 12: Synthesis of Compound S11-A and Compound S11-B

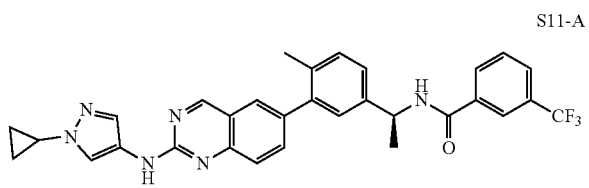

S11-A

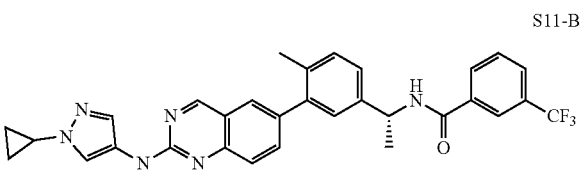

S11-B

The compound S11 has a chiral center and behaves as a pair of diastereomers. We used a chiral column for the chiral resolution of the compound Sit. The chiral column resolution conditions are shown in Table 1 below. Methanol and N,N-dimethylethylenediamine (volume ratio 100:0.5) are used as the mobile phase.

TABLE 1

| Chiral tesolution conditions for compound S11 | |
|---|---|
| Chiral column | Superchiral S-OJ |
| Chiral column size | 0.46 cm I.D. × 15 cm L, 5 um |
| Injection volume | 5 ul |
| Mobile phase | MeOH/DEA = 100/0.05 (v/v) |
| Flow rate | 0.9 ml/min |
| Wavelength | UV 220 nm |
| Temperature | 40° C. |

After resolution, a pair of diastereomers S11-A and S11-B were obtained. The ee values are shown in Table 2 below.

TABLE 2

Chiral column data for compound S11-A and compound S11-B

| No. | $t_R$(min) | Area | Area % | T. Plates | Tailing | ee value |
|---|---|---|---|---|---|---|
| S11-A | 3.903 | 4990552 | 99.9157 | 4351.762 | 1.087 | 98% |
| S11-B | 4.829 | 4685583 | 99.8157 | 2600.659 | 1.077 | 98% |

In the present disclosure, the S and R configurations were synthesized by chiral synthesis in the early stage, and the configuration of compounds S11-A and S11-B was determined by comparing the difference in activity.

The NMR and mass spectrum data of compound S11-A and S11-B were the same as those of compound S11.

Example 13: Chiral Synthesis of Compound S11-A' and Compound S11-B'

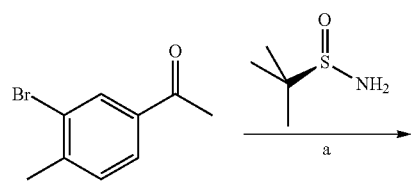

81
82
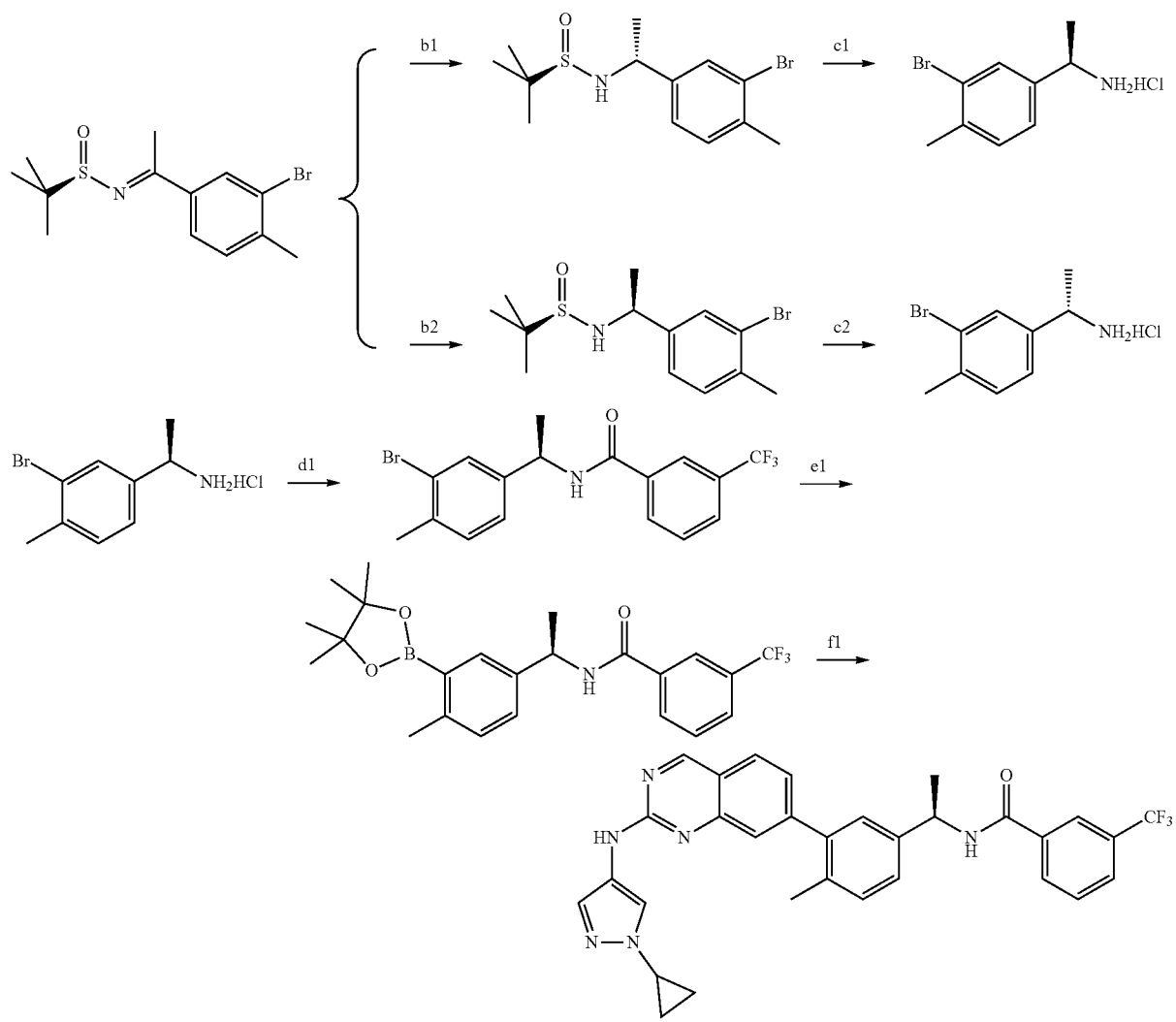

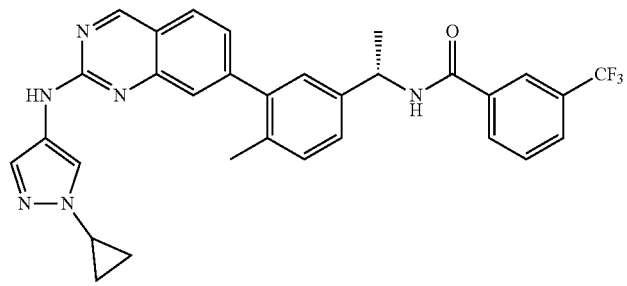

S11-A'

During the chiral synthesis, the operations of step a, step b1 and step b2 referred to the literature (DOI: 10.1021/jo0609834; 10.1021/jo0616512)

Other steps referred to the operation in Example 4, only with different raw materials replaced.

The NMR and MS data for the prepared compounds S11-A' and S11-B' were the same as those of Sit in Example 11.

The optical rotation and the inhibitory activity against DDR2 enzyme of the compounds S11-A and S11-B obtained by the resolution in Example 12, and the chirally synthesized compounds S11-A' and S11-B' in Example 13 were tested (referred to the operation in Effect example 1), and the results are shown in Table 3 below:

TABLE 3

Comparison of activity and optical rotation

|  | S11-A' (chiral synthesis) | S11-B' (chiral synthesis) | S11-A (resolution) | S11-B (resolution) |
| --- | --- | --- | --- | --- |
| Molecular activity comparison | 5.9 ± 0.3 nM | 20.2 ± 0.4 nM | 5.0 ± 0.1 nM | 14.4 ± 2.1 nM |
| Optical rotation comparison | 10.2 | −9.4 | 9.4 | −6.4 |

Results: It can be seen from the above table that the chirally synthesized compounds S11-A' and S11-B' in Example 13 have the same configuration as the compounds S11-A and S11-B obtained by resolution in Example 11, respectively.

Example 14: Synthesis of Compound S12

The synthesis method for the compound referred to that in Example 4.

N-(1-(4-Ethyl-3-(2-((1-methyl-1H-pyrazol-4-yl)amino)quinazolin-7-yl)phenyl)ethyl)-3-(trifluoromethyl)benzamide (S12)

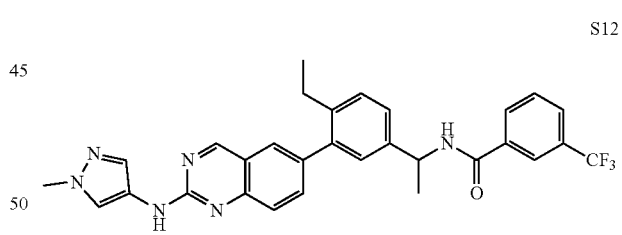

S12

$^1$H NMR (400 MHz, DMSO-d6) δ9.80 (s, 1H), 9.25 (s, 1H), 9.10 (d, J=7.9 Hz, 1H), 8.23 (s, 1H), 8.21 (s, 1H), 8.19 (s, 1H), 7.91 (d, J=7.9 Hz, 1H), 7.80 (s, 1H), 7.76-7.67 (m, 3H), 7.62 (s, 1H), 7.39 (dd, J=8.0, 1.7 Hz, 1H), 7.34 (d, J=8.0 Hz, 1H), 7.30 (s, 1H), 5.23 (p, J=7.2 Hz, 1H), 3.86 (s, 3H), 2.58 (q, J=7.6 Hz, 2H), 1.53 (d, J=7.0 Hz, 3H), 1.04 (t, J=7.5 Hz, 3H).

HRMS m/z (ESI) found 545.228 (M+H)$^+$, C30H28F3N6O$^+$ calcd for 545.2271, >99% pure.

Example 15: Synthesis of Compound S13

4-isopropyl-3-(2-((1-methyl-1H-pyrazol-4-yl)amino)quinazolin-6-yl)-N-(3-(trifluoromethyl)phenyl)benzamide (S13)

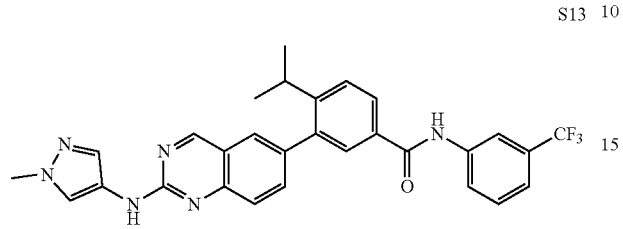

$^1$H NMR (400 MHz, DMSO-d6) δ 10.53 (s, 1H), 9.85 (s, 1H), 9.30 (s, 1H), 8.25 (s, 2H), 8.08 (d, J=8.0 Hz, 1H), 8.03 (d, J=8.9 Hz, 1H), 7.92 (s, 1H), 7.88 (s, 1H), 7.78 (s, 2H), 7.67 (d, J=8.5 Hz, 1H), 7.63 (d, J=9.9 Hz, 1H), 7.59 (d, J=8.0 Hz, 1H), 7.46 (d, J=7.6 Hz, 1H), 3.87 (s, 3H), 3.10 (p, J=7.1 Hz, 1H), 1.20 (d, J=6.7 Hz, 6H).

HRMS m/z (ESI) found 531.2109 (M+H)$^+$, C29H26F3N6O$^+$ calcd for 531.2115, >99% pure.

Example 16: Synthesis of Compound S14

4-cyclopropyl-3-(2-((1-methyl-1H-pyrazol-4-yl)amino)quinazolin-6-yl)-N-(3-(trifluoromethyl)phenyl)benzamide (S14)

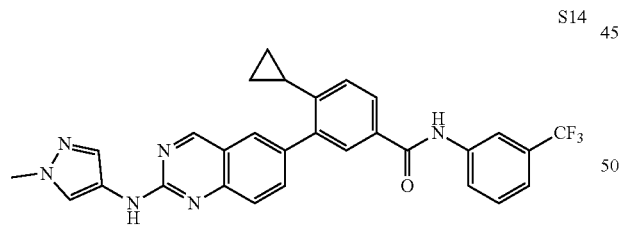

$^1$H NMR (400 MHz, DMSO-d6) δ 10.53 (s, 1H), 9.85 (s, 1H), 9.31 (s, 1H), 8.25 (s, 2H), 8.08 (d, J=8.5 Hz, 1H), 8.00 (d, J=7.6 Hz, 2H), 7.98-7.89 (m, 2H), 7.78 (d, J=10.3 Hz, 1H), 7.63 (d, J=7.5 Hz, 1H), 7.59 (d, J=8.2 Hz, 1H), 7.46 (d, J=7.8 Hz, 1H), 7.19 (d, J=8.3 Hz, 1H), 3.87 (s, 3H), 1.95 (td, J=8.6, 4.6 Hz, 1H), 0.97 (q, J=5.1, 3.8 Hz, 2H), 0.84 (q, J=5.1 Hz, 2H).

HRMS m/z (ESI) found 529.197 (M+H)$^+$, C29H24F3N6O$^+$ calcd for 529.1958, >99% pure.

Example 17: Synthesis of Compound S15

4-cyclopropyl-3-(2-((1-cyclopropyl-1H-pyrazol-4-yl)amino)quinazolin-6-yl)-N-(3-(trifluoromethyl)phenyl)benzamide (S15)

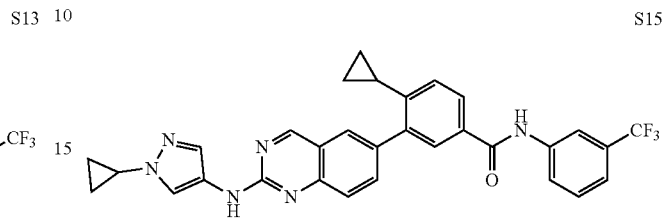

$^1$H NMR (400 MHz, DMSO-d6) δ 10.53 (s, 1H), 9.84 (s, 1H), 9.31 (s, 1H), 8.25 (s, 2H), 8.09 (d, J=8.1 Hz, 1H), 8.01 (s, 1H), 7.99 (s, 1H), 7.98-7.91 (m, 2H), 7.79 (d, J=7.0 Hz, 1H), 7.63 (d, J=7.1 Hz, 1H), 7.59 (d, J=8.5 Hz, 1H), 7.45 (d, J=7.5 Hz, 1H), 7.18 (d, J=8.2 Hz, 1H), 3.75 (s, 1H), 1.95 (p, J=6.4 Hz, 1H), 1.07 (s, 2H), 1.02-0.93 (m, 4H), 0.84 (d, J=3.5 Hz, 2H).

$^{13}$C NMR (126 MHz, DMSO-d6) δ 165.82, 162.78, 157.06, 150.98, 145.56, 141.12, 140.46, 136.38, 135.23, 131.72, 130.46, 130.30, 129.80 (d, J=31.5 Hz), 129.17, 128.60, 127.84, 125.68, 124.63 (d, J=272.1 Hz), 124.55, 124.24, 123.50, 120.32 (d, J=3.9 Hz), 120.27, 120.17, 116.86 (d, J=3.8 Hz), 33.15, 14.12, 10.83, 6.63.

Example 18: Synthesis of Compound S16

4-cyclopropyl-3-(2-((1-cyclopropyl-1H-pyrazol-4-yl)amino)quinazolin-6-yl)-N-(1-(3-(trifluoromethyl)phenyl)ethyl)benzamide (S16)

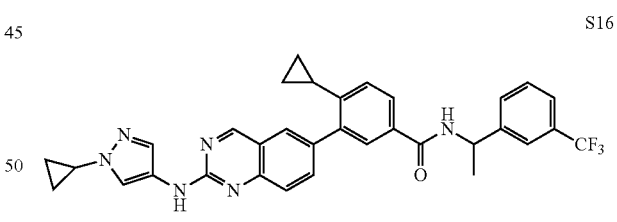

$^1$H NMR (400 MHz, DMSO-d6) δ 9.83 (s, 1H), 9.29 (s, 1H), 8.93 (d, J=8.1 Hz, 1H), 8.27 (s, 1H), 8.03-7.93 (m, 1H), 7.89 (dd, J=8.8, 2.0 Hz, 1H), 7.87 (d, J=1.6 Hz, 1H), 7.86-7.82 (m, 1H), 7.77 (d, J=6.8 Hz, 1H), 7.74 (s, 1H), 7.70 (d, J=7.2 Hz, 1H), 7.63 (s, 1H), 7.60-7.58 (m, 1H), 7.56 (d, J=7.5 Hz, 1H), 7.10 (d, J=8.2 Hz, 1H), 5.39-5.16 (m, 1H), 3.74 (tt, J=7.5, 4.0 Hz, 1H), 1.98-1.82 (m, 1H), 1.50 (d, J=7.0 Hz, 3H), 1.06-1.02 (m, 2H), 1.00-0.95 (m, 2H), 0.95-0.89 (m, 2H), 0.82-0.74 (m, 2H).

HRMS m/z (ESI) found 583.243 (M+H)$^+$, C33H30F3N6O$^+$ calcd for 583.2428, >99% pure.

Example 19: Synthesis of Compound S17

N-(4-cyclopropyl-3-(2-((1-cyclopropyl-1H-pyrazol-4-yl)amino)quinazolin-6-yl)phenyl)-2-(3-(trifluoromethyl)phenyl)propionamide (S17)

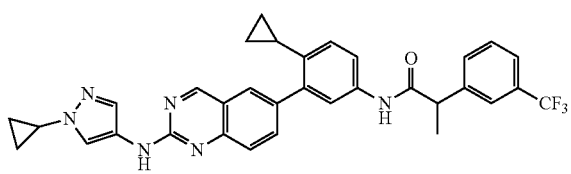

$^1$H NMR (400 MHz, DMSO-d6) δ 10.20 (s, 1H), 9.80 (s, 1H), 9.27 (s, 1H), 8.25 (s, 1H), 7.88 (d, J=1.6 Hz, 1H), 7.83 (dd, J=8.7, 1.9 Hz, 1H), 7.76-7.67 (m, 3H), 7.64 (s, 1H), 7.62-7.59 (m, 2H), 7.57 (d, J=7.5 Hz, 1H), 7.50 (dd, J=8.5, 2.1 Hz, 1H), 6.97 (d, J=8.6 Hz, 1H), 3.95 (q, J=7.2 Hz, 1H), 3.79-3.70 (m, 1H), 1.85-1.76 (m, 1H), 1.45 (d, J=7.0 Hz, 3H), 1.07-1.00 (m, 2H), 1.00-0.92 (m, 2H), 0.84-0.77 (m, 2H), 0.68-0.57 (m, 2H).

HRMS m/z (ESI) found 583.2433 (M+H)$^+$, C33H30F3N6O$^+$ calcd for 583.2428, >99% pure.

Example 20: Synthesis of Compound S18

4-cyclopropyl-3-(2-((1-cyclopropyl-1H-pyrazol-4-yl)amino)quinazolin-7-yl)-N-(1-(3-(trifluoromethyl)phenyl)ethyl)benzamide (S18)

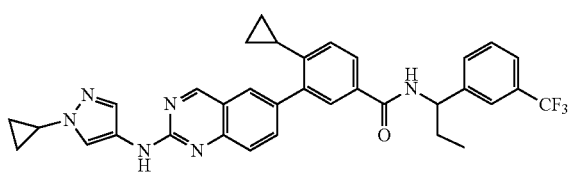

$^1$H NMR (400 MHz, DMSO-d6) δ9.82 (s, 1H), 9.29 (s, 1H), 8.86 (d, J=8.7 Hz, 1H), 8.26 (s, 1H), 7.96 (d, J=1.5 Hz, 1H), 7.89 (dd, J=8.8, 1.7 Hz, 1H), 7.87-7.81 (m, 2H), 7.81-7.73 (m, 2H), 7.70 (d, J=7.1 Hz, 1H), 7.62 (s, 1H), 7.59 (d, J=2.1 Hz, 1H), 7.56 (d, J=7.6 Hz, 1H), 7.11 (d, J=8.2 Hz, 1H), 5.08-4.94 (m, 1H), 3.74 (tt, J=7.7, 3.7 Hz, 1H), 1.93-1.84 (m, 2H), 1.84-1.76 (m, 1H), 1.05 (d, J=3.8 Hz, 2H), 0.98 (dt, J=9.6, 4.5 Hz, 2H), 0.91 (t, J=7.3 Hz, 5H), 0.81-0.75 (m, 2H).

$^{13}$C NMR (126 MHz, DMSO-d6) δ 166.08, 162.75, 157.05, 150.90, 146.09, 144.73, 141.04, 136.39, 135.44, 131.76, 131.33, 130.44, 129.76, 129.42 (d, J=31.0 Hz), 128.76, 128.47, 127.44, 125.60, 124.79 (d, J=272.5 Hz), 124.35, 123.92 123.50, 120.25, 120.13, 73.98, 55.09, 33.14, 29.25, 25.42, 11.77, 6.62.

HRMS m/z (ESI) found 597.2586 (M+H)$^+$, C34H32F3N6O$^+$ calcd for 597.2584, >99% pure.

Example 21: Synthesis of Compound S19

4-cyclopropyl-3-(2-((1-cyclopropyl-1H-pyrazol-4-yl)amino)quinazolin-7-yl)-N-(1-(3-(trifluoromethyl)phenyl)cyclopropyl)benzamide (S19)

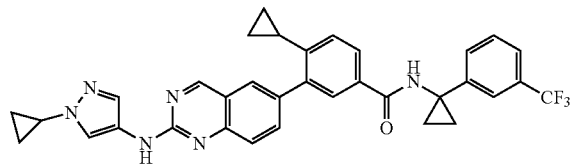

$^1$H NMR (400 MHz, DMSO-d6) δ 9.82 (s, 1H), 9.30 (d, J=7.1 Hz, 2H), 8.26 (s, 1H), 7.96 (s, 1H), 7.90 (d, J=8.5 Hz, 1H), 7.85 (d, J=13.2 Hz, 2H), 7.77 (s, 1H), 7.63 (s, 1H), 7.51 (d, J=8.3 Hz, 4H), 7.11 (d, J=8.2 Hz, 1H), 3.73 (d, J=8.1 Hz, 1H), 2.00-1.80 (m, 1H), 1.42-1.28 (m, 4H), 1.20 (m, 2H), 0.95 (m, 4H), 0.83-0.65 (m, 2H).

HRMS m/z (ESI) found 595.2420 (M+H)$^+$, C34H30F3N6O$^+$ calcd for 595.2519, >99% pure.

Example 22: Synthesis of Compound S20

3-(2-cyanopropane-2-yl)-N-(1-(3-(2-((1-cyclopropyl-1H-pyrazol-4-yl)amino)quinazolin-6-yl)-4-methylphenyl)ethyl)benzamide (S20)

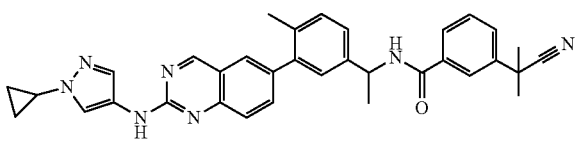

$^1$H NMR (400 MHz, DMSO-d6) δ 9.79 (s, 1H), 9.26 (s, 1H), 8.93 (d, J=8.0 Hz, 1H), 8.26 (s, 1H), 7.98 (t, J=1.6 Hz, 1H), 7.87 (d, J=8.9 Hz, 1H), 7.84 (d, J=1.7 Hz, 1H), 7.78 (dd, J=8.6, 2.0 Hz, 1H), 7.72 (d, J=6.7 Hz, 1H), 7.70-7.66 (m, 1H), 7.61 (s, 1H), 7.54 (d, J=7.8 Hz, 1H), 7.38-7.32 (m, 2H), 7.30 (d, J=8.1 Hz, 1H), 5.30-5.17 (m, 1H), 3.74 (tt, J=7.2, 3.8 Hz, 1H), 2.26 (s, 3H), 1.71 (s, 6H), 1.53 (d, J=7.0 Hz, 3H), 1.10-1.02 (m, 2H), 1.01-0.93 (m, 2H).

HRMS m/z (ESI) found 556.2803 (M+H)$^+$, C34H34N7O$^+$ calcd for 556.2819, >99% pure.

Example 23: Synthesis of Compound S21

3-(2-cyanopropane-2-yl)-N-(1-(4-methyl-3-(2-((1-methyl-1H-pyrazol-4-yl)amino)quinazolin-6-yl)phenyl)ethyl)benzamide (S21)

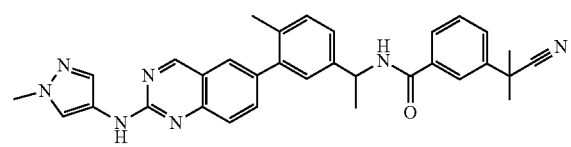

¹H NMR (400 MHz, DMSO-d6) δ 9.79 (s, 1H), 9.25 (s, 1H), 8.92 (d, J=8.0 Hz, 1H), 8.21 (s, 1H), 7.98 (s, 1H), 7.87 (d, J=7.7 Hz, 1H), 7.83 (s, 1H), 7.78 (dd, J=8.7, 1.9 Hz, 1H), 7.73-7.66 (m, 2H), 7.62 (s, 1H), 7.53 (t, J=7.8 Hz, 1H), 7.35 (s, 1H), 7.33 (d, J=1.8 Hz, 1H), 7.30 (d, J=7.8 Hz, 1H), 5.23 (p, J=7.7 Hz, 1H), 3.86 (s, 3H), 2.27 (s, 3H), 1.71 (s, 6H), 1.53 (d, J=7.0 Hz, 3H).

HRMS m/z (ESI) found 530.2666 (M+H)⁺, C32H32N7O⁺ calcd for 530.2663, >99% pure.

Example 24: Synthesis of Compound S22

N-(1-(4-methyl-3-(2-(phenylamino)quinazolin-6-yl)phenyl)ethyl)-3-(trifluoromethyl)benzamide (S22)

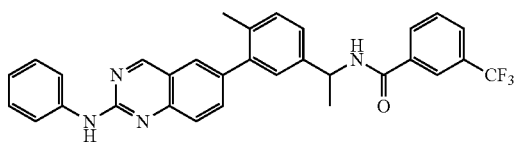

S22

¹H NMR (400 MHz, DMSO-d6) δ9.95 (s, 1H), 9.35 (s, 1H), 9.10 (d, J=7.9 Hz, 1H), 8.23 (s, 1H), 8.20 (d, J=7.9 Hz, 1H), 8.01 (d, J=7.8 Hz, 2H), 7.94-7.87 (m, 2H), 7.82 (dd, J=8.7, 2.0 Hz, 1H), 7.72 (dt, J=7.8, 3.5 Hz, 2H), 7.38-7.29 (m, 5H), 7.00 (t, J=7.3 Hz, 1H), 5.24 (p, J=7.3 Hz, 1H), 2.27 (s, 3H), 1.54 (d, J=7.1 Hz, 3H).

MS (ESI⁺) m/z 527.33[M+H]⁺.

Example 25: Synthesis of Compound S23

N-(1-(4-methyl-3-(2-(o-benzylamino)quinazolin-6-yl)phenyl)ethyl)-3-(trifluoromethyl)benzamide (S23)

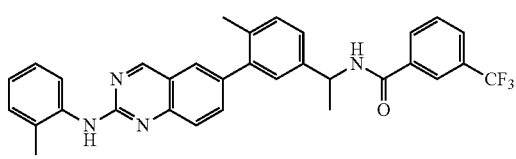

S23

¹H NMR (400 MHz, Chloroform-d) δ 9.11 (s, 1H), 8.37 (d, J=8.1 Hz, 1H), 8.05 (s, 1H), 7.98 (d, J=7.9 Hz, 1H), 7.76 (d, J=8.2 Hz, 2H), 7.73 (dd, J=8.7, 1.8 Hz, 1H), 7.67 (d, J=1.6 Hz, 1H), 7.57 (t, J=7.8 Hz, 1H), 7.35 (q, J=8.1 Hz, 4H), 7.27 (d, J=9.8 Hz, 2H), 7.17 (s, 1H), 7.09 (t, J=7.4 Hz, 1H), 5.39 (p, J=7.0 Hz, 1H), 2.41 (s, 3H), 2.31 (s, 3H), 1.68 (d, J=6.9 Hz, 3H).

MS (ESI⁺) m/z 541.33[M+H]⁺.

Example 26: Synthesis of Compound S24

N-(1-(3-(2-((4-ethylphenyl)amino)quinazolin-6-yl)-4-methylphenyl)ethyl)-3-(trifluoromethyl)benzamide (S24)

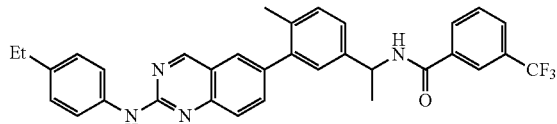

S24

¹H NMR (400 MHz, DMSO-d6) δ9.85 (s, 1H), 9.32 (s, 1H), 9.10 (d, J=8.0 Hz, 1H), 8.23 (s, 1H), 8.19 (d, J=8.0 Hz, 1H), 7.91 (d, J=8.3 Hz, 2H), 7.88 (d, J=2.5 Hz, 2H), 7.80 (dd, J=8.7, 2.0 Hz, 1H), 7.74 (d, J=7.7 Hz, 1H), 7.71-7.67 (m, 1H), 7.39-7.33 (m, 2H), 7.31 (d, J=8.4 Hz, 1H), 7.18 (d, J=8.5 Hz, 2H), 5.29-5.18 (m, 1H), 2.58 (q, J=7.4 Hz, 2H), 2.27 (s, 3H), 1.54 (d, J=7.0 Hz, 3H), 1.19 (t, J=7.6 Hz, 3H).

MS (ESI⁺) m/z 555.35[M+H]⁺.

Example 27: Synthesis of Compound S25

N-(1-(3-(2-((4-(dimethylamino)phenyl)amino)quinazolin-6-yl)-4-methylphenyl)ethyl)-3-(trifluoromethyl)benzamide (S25)

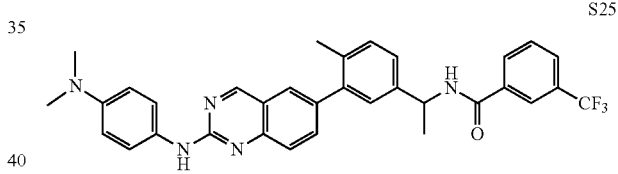

S25

¹H NMR (400 MHz, DMSO-d6) δ9.60 (s, 1H), 9.25 (s, 1H), 9.10 (d, J=8.0 Hz, 1H), 8.23 (s, 1H), 8.19 (d, J=7.8 Hz, 1H), 7.91 (d, J=8.2 Hz, 1H), 7.83 (s, 1H), 7.77 (d, J=8.7 Hz, 2H), 7.76-7.70 (m, 2H), 7.61 (d, J=8.5 Hz, 1H), 7.37-7.32 (m, 2H), 7.30 (d, J=8.6 Hz, 1H), 6.77 (d, J=6.7 Hz, 2H), 5.23 (p, J=6.6 Hz, 1H), 2.87 (s, 6H), 2.27 (s, 3H), 1.54 (d, J=7.0 Hz, 3H).

MS (ESI⁺) m/z 570.39[M+H]⁺.

Example 28: Synthesis of Compound S26

N-(1-(3-(2-((4-methoxyphenyl)amino)quinazolin-6-yl)-4-methylphenyl)ethyl)-3-(trifluoromethyl)benzamide (S26)

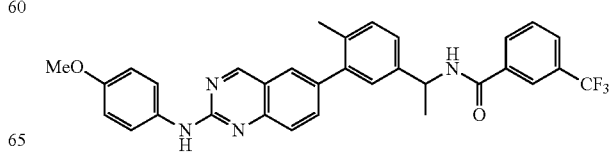

S26

¹H NMR (400 MHz, DMSO-d6) δ9.77 (s, 1H), 9.30 (s, 1H), 9.10 (d, J=8.2 Hz, 1H), 8.23 (s, 1H), 8.19 (d, J=7.8 Hz, 1H), 7.91 (d, J=8.0 Hz, 2H), 7.89-7.85 (m, 2H), 7.78 (dd, J=8.6, 2.0 Hz, 1H), 7.72 (t, J=7.7 Hz, 1H), 7.66 (d, J=8.6 Hz, 1H), 7.37-7.33 (m, 2H), 7.31 (d, J=8.5 Hz, 1H), 6.94 (d, J=9.1 Hz, 2H), 5.23 (p, J=7.3 Hz, 1H), 3.75 (s, 3H), 2.27 (s, 3H), 1.54 (d, J=7.0 Hz, 3H).
MS (ESI⁺) m/z 557.33[M+H]⁺.

Example 29: Synthesis of Compound S27

1-(1-(4-methyl-3-(2-((1-methyl-1H-pyrazol-4-yl)amino)quinazolin-6-yl)phenyl)ethyl)-3-(3-(trifluoromethyl)phenyl)urea (S27)

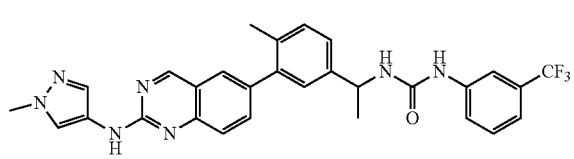

S27

¹H NMR (400 MHz, DMSO-d6) δ 9.79 (s, 1H), 9.25 (s, 1H), 8.77 (s, 1H), 8.22 (s, 1H), 7.97 (s, 1H), 7.84 (d, J=1.6 Hz, 1H), 7.79 (dd, J=8.7, 1.9 Hz, 1H), 7.71 (d, J=7.9 Hz, 1H), 7.62 (s, 1H), 7.48-7.41 (m, 2H), 7.35-7.26 (m, 3H), 7.22 (d, J=5.0 Hz, 1H), 6.90-6.74 (m, 1H), 4.87 (p, J=7.6 Hz, 1H), 3.86 (s, 3H), 2.27 (s, 3H), 1.44 (d, J=6.9 Hz, 3H).
¹³C NMR (126 MHz, DMSO-d6) δ 162.65, 157.00, 154.70, 150.82, 143.27, 141.66, 140.74, 136.09, 133.80, 130.96, 130.25, 130.20, 129.88 (d, J=31.2 Hz), 128.03, 127.62, 125.51, 124.70 (d, J=272.2 Hz), 123.69, 121.58, 121.08, 120.11, 117.73, 113.91, 48.94, 39.21, 23.57, 20.30.
HRMS m/z (ESI) found 546.2235 (M+H)⁺, C29H27F3N7O⁺ calcd for 546.2224, >99% pure.

Example 30: Synthesis of Compound S37

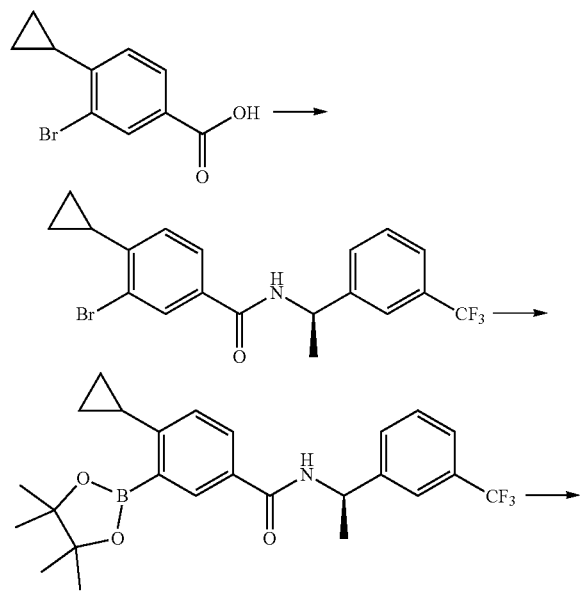

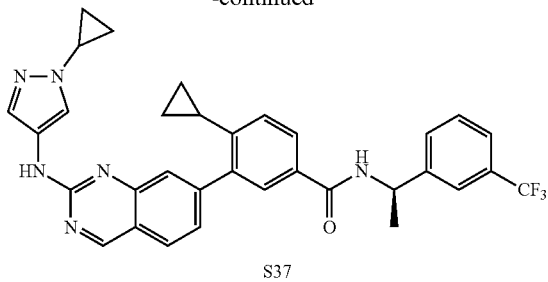

S37

The synthesis conditions for the compound referred to Example 4, wherein the raw material amine itself had chirality and was commercially available.
¹H NMR (400 MHz, DMSO-d₆) δ9.80 (s, 1H), 9.29 (s, 1H), 8.92 (d, J=7.7 Hz, 1H), 7.96 (d, J=2.1 Hz, 1H), 7.93-7.81 (m, 3H), 7.80-7.67 (m, 3H), 7.64-7.54 (m, 3H), 7.11 (d, J=8.2 Hz, 1H), 5.26 (p, J=7.1 Hz, 1H), 3.74 (tt, J=7.1, 3.5 Hz, 1H), 1.99-1.77 (m, 1H), 1.50 (d, J=7.0 Hz, 3H), 1.11-1.02 (m, 2H), 1.06-0.83 (m, 3H), 0.81-0.75 (m, 2H). ESI: 583[M+H].

Example 31: Synthesis of Compound S38

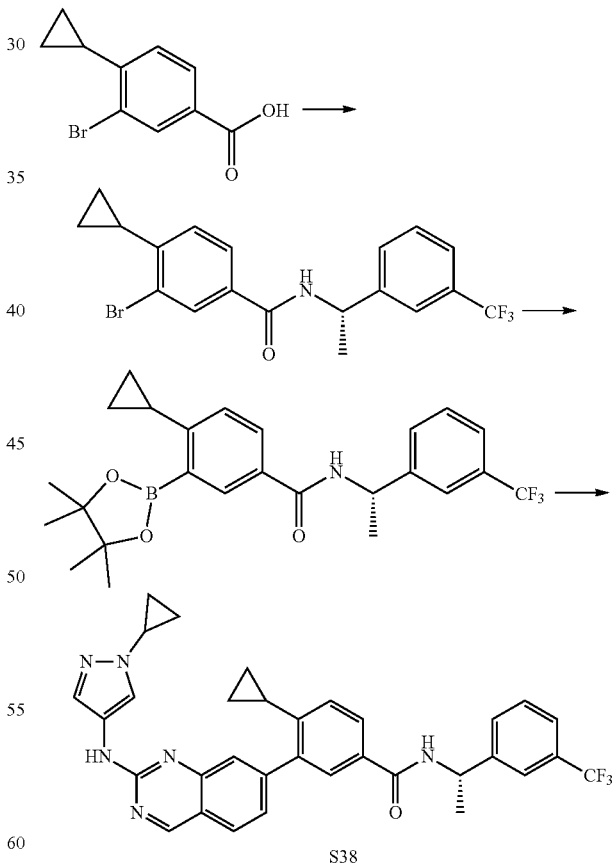

S38

The synthesis conditions for the compound referred to Example 4, wherein the raw material amine itself had chirality and was commercially available.
¹H NMR (400 MHz, DMSO-d₆) δ9.80 (s, 1H), 9.29 (s, 1H), 8.92 (d, J=7.7 Hz, 1H), 7.96 (d, J=2.1 Hz, 1H), 7.93-7.81 (m, 3H), 7.80-7.67 (m, 3H), 7.64-7.54 (m, 3H), 7.11 (d, J=8.2 Hz, 1H), 5.26 (p, J=7.1 Hz, 1H), 3.74 (tt, J=7.1, 3.5 Hz, 1H), 1.99-1.77 (m, 1H), 1.50 (d, J=7.0 Hz, 3H), 1.11-1.02 (m, 2H), 1.06-0.83 (m, 3H), 0.81-0.75 (m, 2H). ESI: 583 [M+H].

Example 32: Synthesis of Compound S39

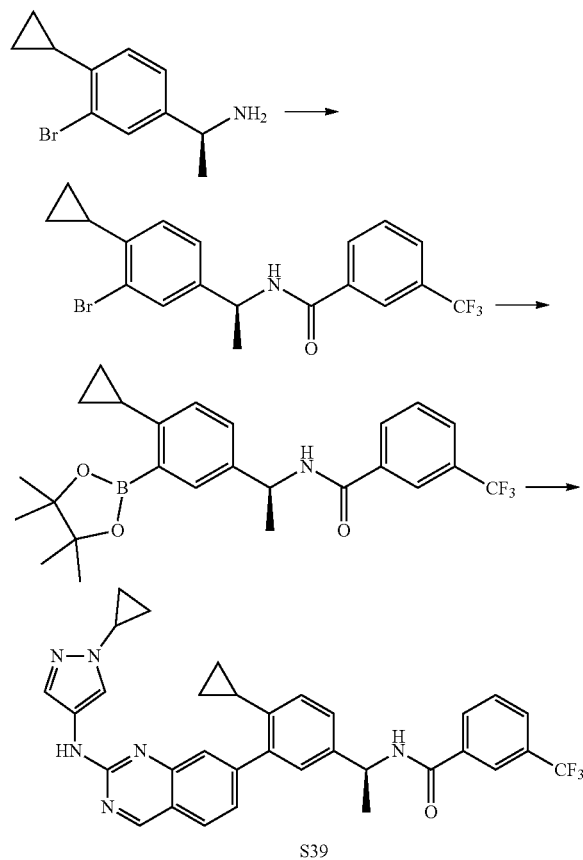

The synthesis conditions for the compound referred to Example 4, wherein the raw material amine itself had chirality and was commercially available.

$^1$H NMR (400 MHz, DMSO-d$_6$) δ9.78 (s, 1H), 9.27 (s, 1H), 9.09 (d, J=8.0 Hz, 1H), 8.23 (s, 1H), 8.19 (d, J=7.8 Hz, 1H), 7.94-7.88 (m, 2H), 7.86 (dd, J=8.6, 2.1 Hz, 1H), 7.77-7.68 (m, 2H), 7.63 (s, 1H), 7.39-7.32 (m, 2H), 7.01 (d, J=8.9 Hz, 1H), 5.23 (p, J=6.4 Hz, 1H), 3.78-3.69 (m, 1H), 1.91-1.79 (m, 1H), 1.54 (d, J=7.0 Hz, 3H), 1.11-0.98 (m, 2H), 1.02-0.92 (m, 2H), 0.89-0.77 (m, 1H), 0.71-0.63 (m, 2H). ESI: 583[M+H].

Example 33: Synthesis of Compound S40

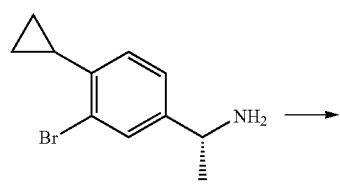

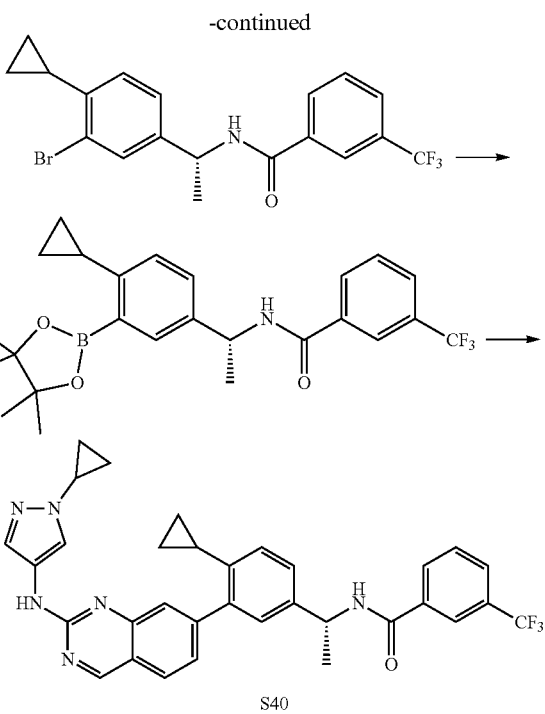

The synthesis conditions for the compound referred to Example 4, wherein the raw material amine itself had chirality and was commercially available.

$^1$H NMR (400 MHz, DMSO-d$_6$) δ9.77 (s, 1H), 9.26 (s, 1H), 9.08 (d, J=8.0 Hz, 1H), 8.22 (s, 1H), 8.20-8.16 (m, 1H), 7.94-7.88 (m, 2H), 7.85 (dd, J=8.6, 2.1 Hz, 1H), 7.76-7.68 (m, 2H), 7.61 (s, 1H), 7.38-7.30 (m, 2H), 7.01 (d, J=8.8 Hz, 1H), 5.22 (p, J=6.9 Hz, 1H), 3.78-3.68 (m, 1H), 1.90-1.76 (m, 1H), 1.53 (d, J=7.0 Hz, 3H), 1.09-1.02 (m, 2H), 1.02-0.93 (m, 2H), 0.90-0.75 (m, 2H), 0.72-0.62 (m, 2H). ESI: 583[M+H].

Example 34: Synthesis of Compound S41

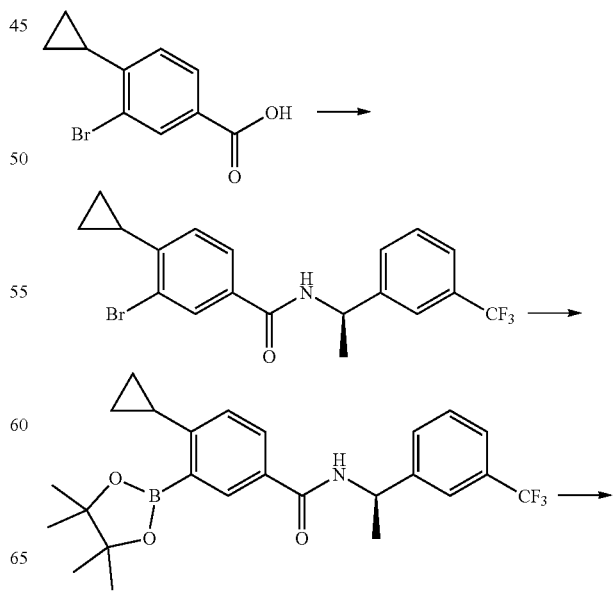

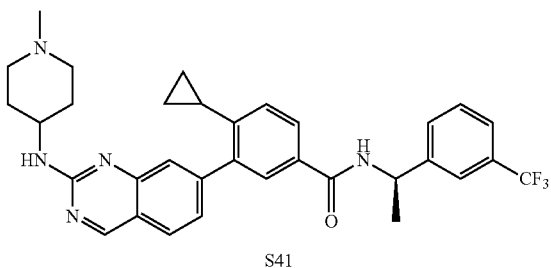

S41

The synthesis conditions for the compound referred to Example 4, wherein the raw material amine itself had chirality and was commercially available.

¹H NMR (400 MHz, DMSO-d₆) δ9.79 (s, 1H), 9.28 (s, 1H), 8.91 (d, J=8.2 Hz, 1H), 8.25 (s, 1H), 7.95 (d, J=2.1 Hz, 1H), 7.92-7.80 (m, 3H), 7.80-7.63 (m, 4H), 7.62-7.52 (m, 2H), 7.10 (d, J=8.2 Hz, 1H), 5.26 (p, J=6.9 Hz, 1H), 4.18-4.06 (m, 1H), 3.17 (d, J=5.2 Hz, 1H), 2.87 (d, J=10.3 Hz, 2H), 2.21 (s, 3H), 2.14-1.81 (m, 5H), 1.50 (d, J=7.1 Hz, 3H), 0.97-0.87 (m, 2H), 0.81-0.75 (m, 2H). ESI: 640[M+H].

Example 35: Synthesis of Compound S42

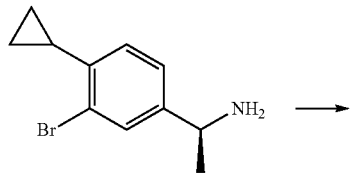

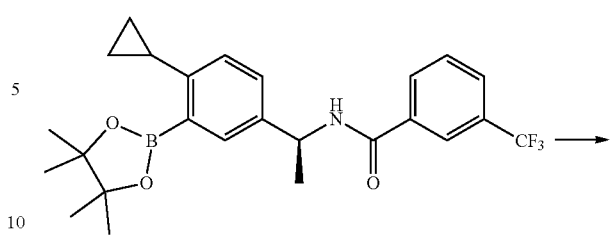

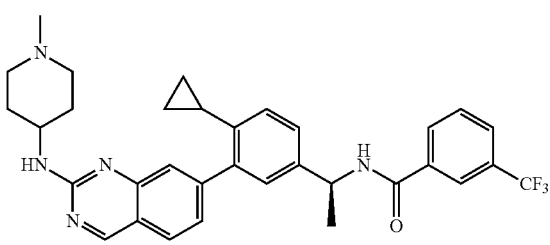

S42

The synthesis conditions for the compound referred to Example 4, wherein the raw material amine itself had chirality and was commercially available.

¹H NMR (400 MHz, DMSO-d₆) δ9.76 (s, 1H), 9.26 (s, 1H), 9.08 (d, J=8.1 Hz, 1H), 8.23 (s, 2H), 8.19 (d, J=7.9 Hz, 1H), 7.93-7.88 (m, 2H), 7.87-7.83 (m, 1H), 7.72 (t, J=7.8 Hz, 2H), 7.68 (s, 1H), 7.35 (d, J=6.7 Hz, 2H), 7.01 (d, J=8.9 Hz, 1H), 5.23 (p, J=6.8 Hz, 1H), 4.12 (p, J=8.0 Hz, 1H), 2.87 (d, J=11.7 Hz, 2H), 2.22 (s, 3H), 2.12-1.91 (m, 5H), 1.90-1.79 (m, 1H), 1.53 (d, J=7.1 Hz, 3H), 0.82 (dt, J=8.7, 3.1 Hz, 2H), 0.71-0.62 (m, 2H).

ESI: 640[M+H].

Example 36: Synthesis of Compound S43

The synthesis method for the compound referred to Example 4, and different raw materials were used.

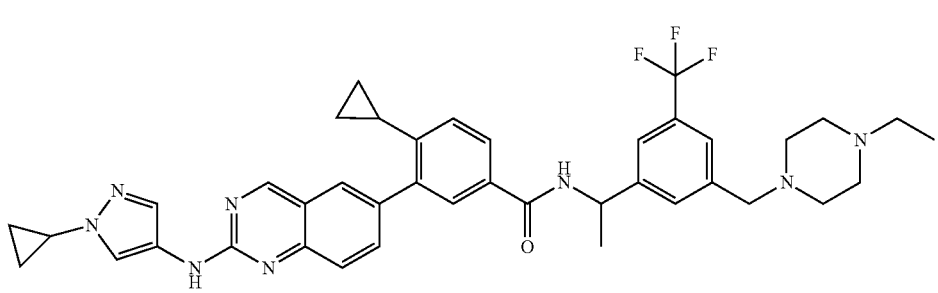

S43

¹H NMR (400 MHz, Methanol-d₄) δ 9.14 (s, 1H), 8.25 (s, 1H), 7.89-7.78 (m, 4H), 7.73 (d, J=9.2 Hz, 1H), 7.70 (s, 1H), 7.66 (s, 1H), 7.63 (s, 1H), 7.53 (s, 1H), 7.09 (d, J=8.8 Hz, 1H), 5.28 (q, J=7.0 Hz, 1H), 3.68-3.59 (m, 3H), 3.00-2.84 (m, 4H), 2.80 (q, J=7.2 Hz, 2H), 2.68-2.56 (m, 4H), 1.99-1.88 (m, 1H), 1.59 (d, J=7.1 Hz, 3H), 1.19 (t, J=7.3 Hz, 3H), 1.15-1.09 (m, 2H), 1.09-1.02 (m, 2H), 0.97-0.91 (m, 2H), 0.81-0.75 (m, 2H). ESI: 709[M+H].

Example 37: Synthesis of Compound S44

The synthesis method for the compound referred to Example 4, and different raw materials were used.

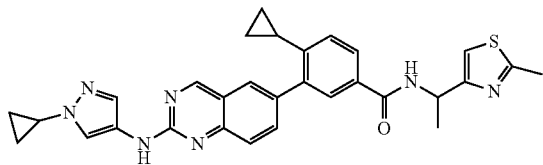

S44

¹H NMR (400 MHz, DMSO-d₆) δ9.78 (s, 1H), 9.28 (s, 1H), 8.78 (d, J=8.2 Hz, 1H), 8.23 (s, 1H), 7.94 (d, J=1.9 Hz, 1H), 7.92-7.81 (m, 3H), 7.80-7.69 (m, 1H), 7.61 (s, 1H), 7.19 (s, 1H), 7.08 (d, J=8.2 Hz, 1H), 5.33-5.21 (m, 1H), 3.79-3.66 (m, 1H), 2.61 (s, 3H), 1.93-1.84 (m, 1H), 1.49 (d, J=7.0 Hz, 3H), 1.11-1.01 (m, 2H), 1.00-0.87 (m, 4H), 0.76 (d, J=5.1 Hz, 2H). ESI: 536[M+H].

Example 38: Synthesis of Compound S45

The synthesis method for the compound referred to Example 4, and different raw materials were used.

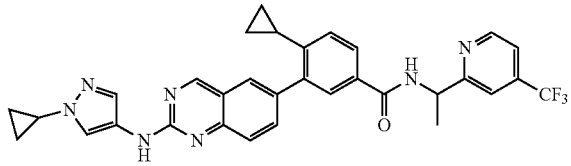

S45

¹H NMR (400 MHz, DMSO-d₆) δ9.79 (s, 1H), 9.28 (s, 1H), 8.94 (d, J=7.5 Hz, 1H), 8.80 (d, J=5.1 Hz, 1H), 7.95 (d, J=1.9 Hz, 1H), 7.92-7.81 (m, 3H), 7.75 (d, J=16.4 Hz, 2H), 7.68-7.57 (m, 2H), 7.10 (d, J=8.2 Hz, 1H), 5.29 (p, J=7.0 Hz, 1H), 3.78-3.66 (m, 1H), 1.95-1.83 (m, 1H), 1.52 (d, J=7.1 Hz, 3H), 1.09-0.98 (m, 2H), 0.98-0.89 (m, 5H), 0.80-0.73 (m, 2H). ESI: 584[M+H].

Example 39: Synthesis of Compound S46

The synthesis method for the compound referred to Example 4, and different raw materials were used.

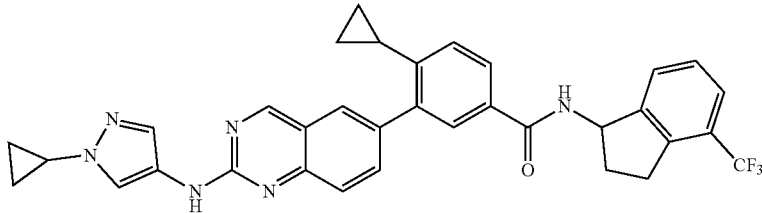

S46

¹H NMR (400 MHz, DMSO-d₆) δ 9.85-9.70 (m, 1H), 9.26 (s, 1H), 8.85 (d, J=8.3 Hz, 1H), 7.93 (d, J=2.0 Hz, 1H), 7.87 (dq, J=6.1, 2.0 Hz, 3H), 7.74 (d, J=8.7 Hz, 1H), 7.61 (s, 1H), 7.56 (d, J=7.7 Hz, 1H), 7.51 (d, J=7.6 Hz, 1H), 7.40 (t, J=7.7 Hz, 1H), 7.09 (d, J=8.8 Hz, 1H), 5.63 (q, J=8.1 Hz, 1H), 3.79-3.66 (m, 1H), 3.23-3.09 (m, 1H), 3.06-2.91 (m, 1H), 2.57-2.51 (m, 1H), 2.09-1.97 (m, 1H), 1.93-1.83 (m, 1H), 1.08-1.00 (m, 2H), 0.97-0.87 (m, 4H), 0.80-0.73 (m, 2H). ESI: 595[M+H].

Effect Example 1: DDR2 Enzyme Activity Test

Detection method: Enzyme-linked immunosorbent assay (ELISA)

Test receptor tyrosine kinase: DDR2

Test batch: 2 batches

Reagents, consumables and instruments:

The kinase used in the experiment was obtained by our laboratory using the insect baculovirus expression system to express and purify the recombinant protein containing the protein kinase region; polyglutamic acid-tyrosine peptide segment [Poly(Glu, Tyr) 4:1] and sodium vanadate were purchased from Sigma; the anti-phosphorylated monoclonal antibody PY99 was purchased from Santa Cruz; horseradish peroxidase labeled goat anti-murine secondary antibody was purchased from Calbiochem; ATP and OPD were purchased from Sangon Biotech (Shanghai) Co., Ltd.; the remaining reagents were purchased from Sinopharm Chemical Reagent Co., Ltd. The reaction ELISA plate (#2592) was purchased from Corning. The full-wavelength microplate reader for experiment reading was a product of Molecular Device, model: SpectraMax 190; the experimental water was distilled water produced by Sinopharm Group.

Compound Preparation:

The compound was centrifuged at 12,000 g for 5 min, and DMSO was added to prepare a 10-2M stock solution, which was vortexed evenly, then sonicated for 10 min and stored at −40° C. for later use. During the test, the compound was diluted with DMSO from the stock solution to 100 times the test concentration (the DMSO concentration in the system was 1%).

Test Method:

1) Enzyme reaction substrate Poly(Glu, Tyr) 4:1 was diluted to 20 µg/mL with potassium-free PBS (10 mM sodium phosphate buffer, 150 mM NaCl, pH 7.2-7.4), and the microtiter plate was coated with 125 µL/well and placed at 37° C. for 12-16 hours of reaction. The liquid in the well was discard. The plate was washed three times with T-PBS (potassium-free PBS containing 0.1% Tween-20, 200 µL/well), 5 minutes each time. The ELISA plate was dried in an oven at 37° C. for 1 to 2 hours.

2) Reaction buffer (50 mM HEPES pH 7.4, 50 mM $MgCl_2$, 0.5 mM $MnCl_2$, 0.2 mM $Na_3VO_4$, 1 mM DTT) diluted ATP solution (49 µL) was added to each well, 1 µL of the compound to be tested was added to each well, and then 50 µL of DDR2 kinase domain recombinant protein diluted in the reaction buffer was added to start the reaction. Two control wells without ATP were set in each experiment. The plate placed on a shaker (100 rpm) at 37° C. for 1 hour of reaction. The liquid in the well was discarded and the plate was washed three times with T-PBS.

3) Antibody PY99 dilution solution (the antibody was diluted 1:500 with T-PBS containing BSA 5 mg/mL) was added at 100 µL/well, and shaken on a shaker at 37° C. for 0.5 hour of reaction. The liquid in the well was discarded and the plate was washed three times with T-PBS.

4) Horseradish peroxidase labeled goat anti-murine secondary antibody dilution solution (the antibody is diluted 1:2000 with T-PBS containing BSA 5 mg/ml) was added at 100 µL/well, and shaken on a shaker at 37° C. for 0.5 hour of reaction. The liquid in the well was discarded and the plate was washed three times with T-PBS.

5) 2 mg/ml of OPD color developing solution [diluted with 0.1 M citric acid-sodium citrate buffer (pH=5.4) containing 0.03% $H_2O_2$] was added at 100 µL/well and reacted for 1 to 10 minutes at 25° C. in the dark.

6) 2M H2SO4 was added at 50 µL/well to stop the reaction, and a tunable wavelength microplate reader VERSAmax was used for reading at a wavelength of 490 nm.

7) Result analysis $$\text{Inhibition rate}(\%) = \left(1 - \frac{OD \text{ value of compound} - OD \text{ value of control well without enzyme}}{OD \text{ value of negative compound} - OD \text{ value of control well without enzyme}}\right) \times 100\%$$

The $IC_{50}$ value was obtained by four-parameter regression using the software that came with the microplate reader.

The analysis results are shown in Table 4 below

TABLE 4

| Compounds | R¹ | R² | R³ | L | DDR2 $IC_{50}$ |
|---|---|---|---|---|---|
| S1 | pyrazolyl-N-methyl | CH₃ | 3-CF₃-phenyl | –NH–C(O)–NH– (urea) | 6.6 ± 0.4 nM |
| S2 | pyrazolyl-N-methyl | CH₃ | 1-phenyl-3-tert-butyl-pyrazolyl | –NH–C(O)–NH– (urea) | 9.7 ± 0.6 nM |
| S4 | pyrazolyl-N-methyl | CH₃ | 3-CF₃-phenyl | –CH(CH₃)–NH–C(O)– | 4.1 ± 0.1 nM |
| S5 | pyrazolyl-N-methyl | CH₃ | 3-CF₃-phenyl | –C(O)–NH–CH(CH₃)– | 2.9 ± 0.8 nM |
| S6 | pyrazolyl-N-methyl | CH₃ | 3-CF₃-phenyl | –CH(CH₂CH₃)–NH–C(O)– | 5.0 ± 0.5 nM |

TABLE 4-continued

DDR2 enzyme activity test

| Compounds | R¹ | R² | R³ | L | DDR2 IC$_{50}$ |
|---|---|---|---|---|---|
| S7 | N-methylpyrazol-4-yl | CH$_3$ | 3-CF$_3$-phenyl | -C(O)NH-CH$_2$- | 1.3 ± 0.2 nM |
| S8 | N-methylpyrazol-4-yl | CH$_3$ | 3-CF$_3$-phenyl | -CH(CH$_3$)-NH-C(O)- | 2.2 ± 0.2 nM |
| S9 | N-cyclopropylpyrazol-4-yl | CH$_3$ | 3-CF$_3$-phenyl | -CH(CH$_3$)-C(O)-NH- | 2.7 ± 0.1 nM |
| S10 | N-cyclopropylpyrazol-4-yl | c-Pr | 3-CF$_3$-phenyl | -CH(CH$_3$)-NH-C(O)- | 35.5 ± 3.9 nM |
| S11 | N-cyclopropylpyrazol-4-yl | CH$_3$ | 3-CF$_3$-phenyl | -CH(CH$_3$)-NH-C(O)- | 4.3 ± 1.0 nM |
| S11-A | N-cyclopropylpyrazol-4-yl | CH$_3$ | 3-CF$_3$-phenyl | -(S)-CH(CH$_3$)-NH-C(O)- | 5.0 ± 0.1 nM |
| S11-B | N-cyclopropylpyrazol-4-yl | CH$_3$ | 3-CF$_3$-phenyl | -(R)-CH(CH$_3$)-NH-C(O)- | 14.4 ± 2.1 nM |
| S12 | N-methylpyrazol-4-yl | CH$_2$CH$_3$ | 3-CF$_3$-phenyl | -CH(CH$_3$)-NH-C(O)- | 14.6 ± 3.3 nM |
| S13 | N-methylpyrazol-4-yl | i-Pr | 3-CF$_3$-phenyl | -C(O)-NH-CH(CH$_3$)- | 5.4 ± 0.4 nM |
| S14 | N-methylpyrazol-4-yl | c-Pr | 3-CF$_3$-phenyl | -C(O)-NH-CH(CH$_3$)- | 4.3 ± 0.7 nM |

TABLE 4-continued

DDR2 enzyme activity test

| Compounds | R¹ | R² | R³ | L | DDR2 IC$_{50}$ |
|---|---|---|---|---|---|
| S15 | 1-cyclopropyl-pyrazol-4-yl | c-Pr | 3-CF₃-phenyl | -C(O)NH- | 6.1 ± 0.5 nM |
| S16 | 1-cyclopropyl-pyrazol-4-yl | c-Pr | 3-CF₃-phenyl | -C(O)NH-CH(CH₃)- | 38.3 ± 2.8 nM |
| S17 | 1-cyclopropyl-pyrazol-4-yl | c-Pr | 3-CF₃-phenyl | -NHC(O)CH(CH₃)- | 1.7 ± 0.3 nM |
| S18 | 1-cyclopropyl-pyrazol-4-yl | c-Pr | 3-CF₃-phenyl | -NHC(O)CH(Et)- | 3.7 ± 0.2 nM |
| S19 | 1-cyclopropyl-pyrazol-4-yl | c-Pr | 3-CF₃-phenyl | -C(O)NH-(1-cyclopropyl)- | 4.6 ± 0.3 nM |
| S20 | 1-cyclopropyl-pyrazol-4-yl | CH₃ | 3-(C(CH₃)₂CN)-phenyl | -CH(CH₃)NHC(O)- | 5.6 ± 0.3 nM |
| S27 | 1-methyl-pyrazol-4-yl | CH₃ | 3-CF₃-phenyl | -CH(CH₃)NHC(O)NH- | 8.7 ± 1.1 nM |
| S37 | 1-cyclopropyl-pyrazol-4-yl | c-Pr | 3-CF₃-phenyl | -C(O)NH-CH(CH₃)- (R) | 13.5 ± 7.2 nM |
| S38 | 1-cyclopropyl-pyrazol-4-yl | c-Pr | 3-CF₃-phenyl | -C(O)NH-CH(CH₃)- (S) | 100 nM |
| S39 | 1-cyclopropyl-pyrazol-4-yl | c-Pr | 3-CF₃-phenyl | -CH(CH₃)NHC(O)- (S) | 31.0 ± 5.8 nM |

TABLE 4-continued

DDR2 enzyme activity test

| Compounds | R¹ | R² | R³ | L | DDR2 IC$_{50}$ |
|---|---|---|---|---|---|
| S40 | 1-cyclopropyl-pyrazol-4-yl | c-Pr | 3-(CF$_3$)phenyl | -CH(CH$_3$)-NH-C(O)- | 336.2 ± 108.3 nM |
| S41 | 1-(1-methylpiperidin-4-yl)-pyrazol-4-yl | c-Pr | 3-(CF$_3$)phenyl | -C(O)-NH-CH(CH$_3$)- | 4.7 ± 0.01 nM |
| S42 | 1-(1-methylpiperidin-4-yl)-pyrazol-4-yl | c-Pr | 3-(CF$_3$)phenyl | -CH(CH$_3$)-NH-C(O)- | 8.2 ± 2.3 nM |
| S43 | 1-cyclopropyl-pyrazol-4-yl | c-Pr | 3-(CF$_3$)-5-((4-ethylpiperazin-1-yl)methyl)phenyl | -C(O)-NH-CH(CH$_3$)- | 57.6% (Inhibition rate at 0.1 μM) |
| S44 | 1-cyclopropyl-pyrazol-4-yl | c-Pr | 2-methylthiazol-4-yl | -C(O)-NH-CH(CH$_3$)- | 72.9% (Inhibition rate at 0.1 μM) |
| S45 | 1-cyclopropyl-pyrazol-4-yl | c-Pr | 4-(CF$_3$)pyridin-2-yl | -C(O)-NH-CH(CH$_3$)- | 68.4% (Inhibition rate at 0.1 μM) |
| S46 | 1-cyclopropyl-pyrazol-4-yl | c-Pr | 4-(CF$_3$)-2,3-dihydro-1H-inden-1-yl | -C(O)-NH-CH(CH$_3$)- | 47.7% (Inhibition rate at 0.1 μM) |

Effect Example 2: Selectivity Test of Compounds

Except that the enzyme was different, other test methods and conditions were the same as the DDR2 enzyme activity test method in Effect example 1.

IC50 test results are shown in Table 5 below (unit: nM), the compounds of the present disclosure S10, S12, S15, S16 and S18 have good selectivity for kinases.

4) 10 μL/well of MTS/PMS (20:1, Promega Corp) solution was added to each well containing 100 μL of culture medium, and then the plate was gently shaken. The plate was incubated at 37° C. for 2 to 4 hours.

5) M5 microplate reader (Molecular Device, USA) was used to measure the absorbance of the solution at 490 nm.

6) Data collection and result analysis: The OD value of each test well was subtracted from the OD value of the zero setting well or the OD value of the control well. The OD values of individual repetition wells were averaged.

TABLE 5

Enzyme selectivity test results

| | VEGFR-1 | PDGFR-α | PDGFR-β | C-Kit | Flt-3 | EGFR | ErbB2 |
|---|---|---|---|---|---|---|---|
| s18 | >1000 | >1000 | >1000 | >1000 | >1000 | >1000 | >1000 |
| s16 | >1000 | >1000 | >1000 | >1000 | >1000 | >1000 | >1000 |
| s10 | >1000 | >1000 | >1000 | >1000 | >1000 | >1000 | >1000 |
| s12 | >1000 | >1000 | >1000 | >1000 | >1000 | >1000 | >1000 |
| s15 | >1000 | >1000 | >1000 | >1000 | >1000 | >1000 | >1000 |

| | ErbB4 | Src | Abl | EPH-A2 | IGF-1R | AXL | Met |
|---|---|---|---|---|---|---|---|
| s18 | >1000 | >1000 | >1000 | >1000 | >1000 | >1000 | >1000 |
| s16 | >1000 | >1000 | >1000 | >1000 | >1000 | >1000 | >1000 |
| s10 | >1000 | >1000 | >1000 | >1000 | >1000 | >1000 | >1000 |
| s12 | >1000 | >1000 | >1000 | >1000 | >1000 | >1000 | >1000 |
| s15 | >10 | >100 | <10 | >10 | >1000 | >1000 | >1000 |

| | ALK | RET | FGFR-1 | FGFR-2 | FGFR-3 | FGFR-4 | KDR |
|---|---|---|---|---|---|---|---|
| s18 | >1000 | >1000 | >1000 | >1000 | >1000 | >1000 | >1000 |
| s16 | >1000 | >1000 | >1000 | >1000 | >1000 | >1000 | >1000 |
| s10 | >1000 | >1000 | >1000 | >1000 | >1000 | >1000 | >1000 |
| s12 | >1000 | >100 | >100 | >10 | >100 | >1000 | >1000 |
| s15 | >1000 | >1000 | >10 | — | — | — | <10 |

| | P38 MAPK |
|---|---|
| s18 | >1000 |
| s16 | >1000 |
| s10 | >1000 |
| s6 | >1000 |
| s15 | >1000 |

Effect Example 3: Cytotoxic Activity Test of Compound S15

Experimental objective: The cytotoxic activity of compound S15 on bronchial epithelial cell line Beas-2B and lung fibroblast cell line MRC-5 was tested.

1) The human bronchial epithelial cell line Beas-2B and the human embryonic lung fibroblast cell line MRC-5 were collected, and inoculated at a certain density (about 5000-10000 cells) on a 96-well plate (the edge wells were filled with sterile water or PBS). A control was set on each plate (100 μL of culture medium was added);

2) The plate was incubated overnight at 37° C., 5% $CO_2$. The plate was turned upside down and observed under the microscope.

3) The solutions of different concentrations of the compounds to be tested were added to each well, and a control well (culture medium and MTS solution with cells but no drug) and a blank well (without cells, medium and MTS solution) were set, 3 to 5 repetition wells were set for each group. Incubation was performed at 37° C. for 48-72 hours.

cell viability % =

$$\frac{\text{OD of cells treated with medicine} - \text{OD of blank}}{\text{OD of cotrol cells} - \text{OD of blank}} \times 100\%$$

Figure 2:
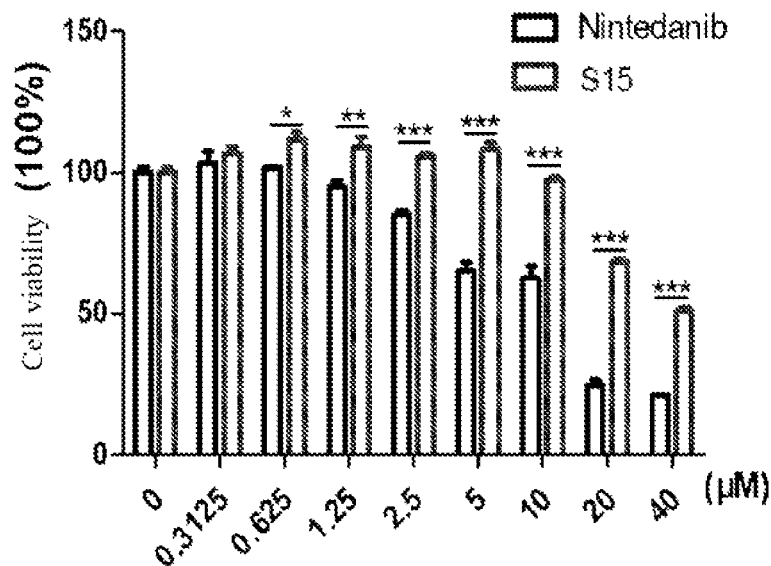
FIG. 2 shows the cytotoxic activity of the positive medicine Nintedanib and compound S15 on the bronchial epithelial cell line Beas-2B in Effect example 3.

Experimental results: FIG. 1 shows the test results of the cytotoxic activity of the positive medicine Nintedanib and the compound S15 on the lung fibroblast cell line MRC-5; FIG. 2 shows the test results of the cytotoxic activity of the positive medicine Nintedanib and the compound S15 on the bronchial epithelial cell line Beas-2B. It can be seen from FIG. 1 and FIG. 2 that Nintedanib shows significant cytotoxicity at a concentration of 5 μM, while compound S15 shows almost no toxicity on human bronchial epithelial cell line Beas-2B and lung fibroblast cell line MRC-5 at 10 μM. The above results indicate that the cytotoxicity of the compound S15 is much lower than that of the positive medicine nintedanib.

Effect Example 4: Evaluation of the Effects of Compound S15 on Lung Injury and Inflammation Caused by BLM Experimental objective: This group of experiments aimed to investigate the therapeutic potential of the compound S15 in acute lung injury and inflammation induced by bleomycin (BLM).

Experimental grouping (8 mice per group):

Model group (BLM): the mice received BLM (1.7 U/kg) via intratracheal instillation;

Compound S15 group (S15): this group was divided into three dose groups, namely 30, 60 and 90 mg/kg;

Positive control group (Nintedanib): Nintedanib administration group;

Negative control group (Control): only saline was used.

The experimental process of paraffin-embedded section of tissue:

1) Material acquisition: The fresh tissue was fixed in 4% paraformaldehyde for more than 24 hours. The tissue was removed from the fixative solution and trim the tissue at the target site. The trimmed tissue was marked and placed in the dehydration box for later use.

2) Dehydration: The dehydration box was put in the dehydrator and different concentration gradients of ethanol was used sequentially for dehydration. 75% ethanol (4 hours), 85% ethanol (2 hours), 90% ethanol (2 hours), 95% ethanol (1 hour), absolute ethanol I (30 minutes), absolute ethanol II (30 minutes), alcohol benzene (5-10 minutes), xylene I (5-10 minutes), xylene II (5-10 minutes), wax I (1 hour), wax II (1 hour), wax III (1 hour).

3) Embedment: The wax melted at high temperature was put into the embedding frame; before the wax was cooled and solidified, the tissue was taken out of the dehydration box, put into the embedding frame according to the requirements of the embedding surface, marked and cooled at −20° C. After completely solidified, the wax block was removed from the embedding frame and trimmed.

4) Section: The trimmed wax block was put on a paraffin microtome for sectioning. The section thickness was about 4 μm. The sections were floated on warm water at 40° C. of the flotation workstation and flatten. A glass slide was used to lift the tissue from the warm water, and put into a 60° C. oven for dryness. After the water was dried and the wax melted, the glass slide was taken out and stored at ambient temperature for later use.

Experimental process of HE staining of paraffin section

1) The section was put into xylene I (20 minutes), xylene II (20 minutes), absolute ethanol I (10 minutes), absolute ethanol II (10 minutes), 95% ethanol (5 minutes), 90% ethanol (5 minutes), 80% ethanol (5 minutes), 70% ethanol (5 minutes) in sequence, and washed with distilled water.

2) Staining nucleus with hematoxylin: The section was put into Harris hematoxylin for staining for 3 to 8 minutes, then washed with tap water, differentiated with 1% hydrochloric acid solution in ethanol for a few seconds, rinsed with tap water, turned blue with 0.6% ammonia water, and then rinsed with running water.

3) Staining cytoplasm with eosin: The section was placed in eosin staining solution for staining for 1 to 3 minutes.

4) Dehydration and sealing: The section was put into 95% ethanol I (5 minutes), 95% ethanol II (5 minutes), absolute ethanol I (5 minutes), absolute ethanol II (5 minutes), xylene I (5 minutes), xylene II (5 minutes) in sequence for dehydration and transparency. The section was taken out from xylene and dried for a while, and the section was sealed with neutral gum.

5) A microscope inspection was performed and images were collected for analysis.

6) Staining results: The nucleus was blue and the cytoplasm was red.

Morphological grading standard of mouse lung tissue (alveolitis grading):

1. Grade 0 (1 point): normal lung tissue;
2. Grade I (2 points): mild alveolitis, with infiltration with a small amount of inflammatory cells, and the alveolar septum is slightly widened;
3. Grade II (3 points): moderate alveolitis, with more inflammatory cells than Grade I, and more disordered alveolar morphology;
4. Grade III (4 points): severe alveolitis: a large number of inflammatory cells infiltrate, the lesion is diffuse, and the alveolar structure is completely destroyed;

(1) Histopathological Evaluation

Figure 3:
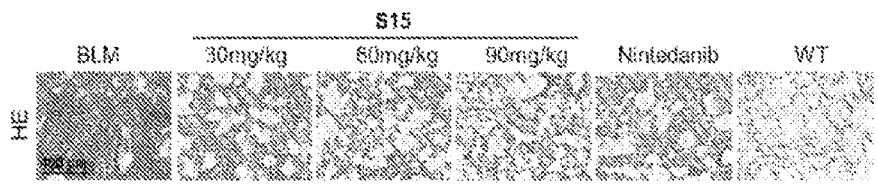
FIG. 3 shows the lung tissue section stained with H&E in Effect example 4.
Figure 4:
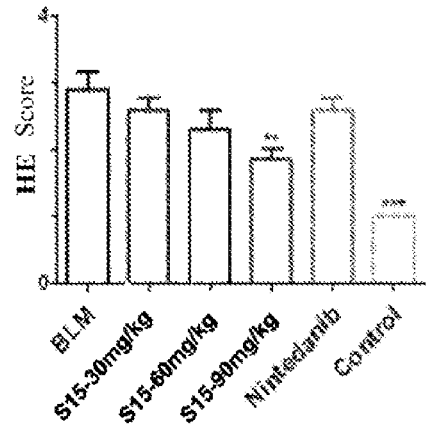
FIG. 4 shows the score of HE staining in Effect example 4.

The mouse model of BLM-induced lung injury is widely used in the study of idiopathic pulmonary fibrosis. On day 3 after oral administration of BLM (2 mg/kg), compound S15 was administered orally once a day (qd) in three dose groups of 30, 60, and 90 mg/kg for 12 days. Nintedanib was administered orally once a day (qd) in a single dose group of 30 mg/kg for 12 days. And then lung tissue sections were prepared and H&E staining was used for histopathological evaluation of mouse lung sections. As shown in FIG. 3 and FIG. 4, bleomycin induced severe lung injury, disappeared normal alveolar structure, significantly thickened alveolar wall, infiltration of a large number of inflammatory cells and focal fibrotic lesions, and the BLM-induced lung injury in the oral compound S15 and Nintedanib administration groups was improved significantly.

(2) Effect on the number of inflammatory cells and the concentration of related proteins 1. The determination of the total number of cells in BALF. The collected BALF was centrifuged at 1000 rpm at 4° C. for 10 minutes, and 25× Cocktail was added to the supernatant and stored at −80° C. for protein concentration detection and subsequent cytokine determination. The cell pellet was resuspend in 50 μL of saline. The total number of cells in BALF was determined with a cell counting instrument.

2. Determination of protein concentration. In the experiment, the BCA protein concentration determination kit (Beyotime) was used to determine the concentration of total protein in BALF. The experimental steps are as follows:

1). Preparation of Protein Standard a. 0.8 ml protein standard formulation solution was added to a tube of protein standard (20 mg BSA), dissolved and mixed thoroughly to prepare a protein standard solution at 25 mg/ml. After preparation, the protein standard solution can be used immediately and stored at −20° C.

b. An appropriate amount of 25 mg/ml of protein standard solution was taken and diluted to the target concentration of 0.5 mg/ml. Note that the protein sample and the standard should be diluted with the same solution, or the standard can be diluted with 0.9% NaCl or PBS. The diluted protein standard solution at 0.5 mg/ml can be stored for a long time at −20° C.

2). Formulation of BCA Working Solution

According to the number of samples, an appropriate amount of BCA working solution was formulated with BCA reagent A:BCA reagent B at a volume ratio of 50:1, and mixed thoroughly. And the working solution was stable within 24 hours at room temperature.

3). Protein Concentration Detection a. The standard was added to the standard wells of the 96-well plate at eight concentrations of 0 μl, 1 μl, 2 μl, 4 μl, 8 μl, 12 μl, 16 μl, and 20 μl, the standard was added and the dilution solution was diluted to 20 μl, equivalenting to standard concentrations of 0 mg/ml, 0.025 mg/ml, 0.05 mg/ml, 0.1 mg/ml, 0.2 mg/ml, 0.3 mg/ml, 0.4 mg/ml, 0.5 mg/ml, respectively.

b. An appropriate volume of sample was added to the sample well of the 96-well plate. If the sample was less than 20 μl, the standard diluent was added to make the volume up to 20 μl.

c. 200 μl of BCA working solution was added to each well and the plate was placed at 37° C. for 20-30 minutes.

d. The absorbance in the wavelength range of 540-595 nm was measured or a microplate reader was used to measure A562.

e. The protein concentration in the sample was calculated according to the sample volume used and standard curve.

Figure 5:
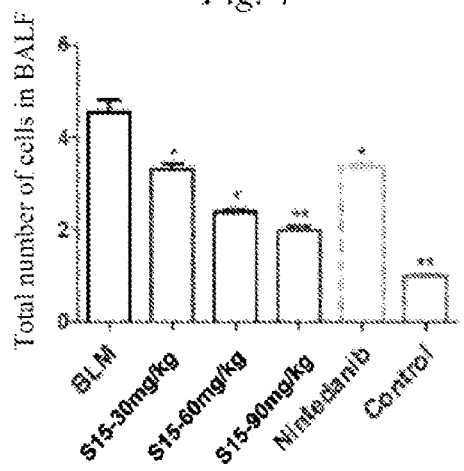
FIG. 5 shows the total number of cells in BALF in Effect Example 4.
Figure 6:
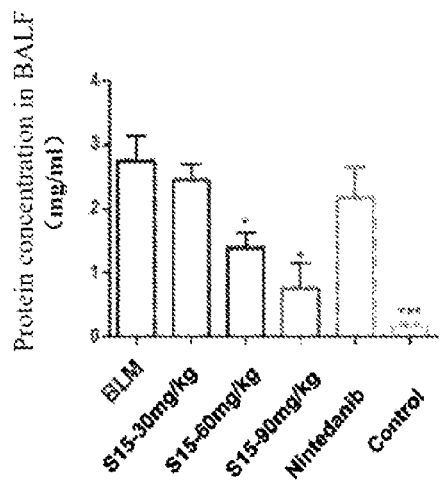
FIG. 6 shows the protein concentration in BALF in Effect Example 4.

Experimental results: The bronchoalveolar lavage fluid of each experimental group was separated. As shown in FIG. 5 and FIG. 6, BLM induction significantly increases the total number of inflammatory cells such as macrophages and neutrophils and protein concentration contained in BALF, while S15 can reduce the number of inflammatory cells and the concentration of related proteins in a dose-dependent manner.

(3) Evaluation of Inflammatory Response of Lung Injury

Alkaline phosphatase (ALP) level and lactate dehydrogenase (LDH) level. An automatic blood indicator analyzer and related kits (alkaline phosphatase assay kit and lactate dehydrogenase assay kit) were used to measure related indicators.

Figure 7:
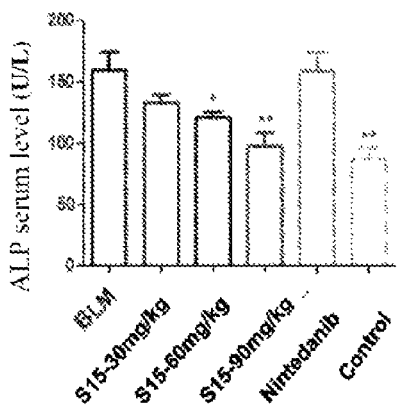
FIG. 7 shows the ALP serum level in Effect example 4.
Figure 8:
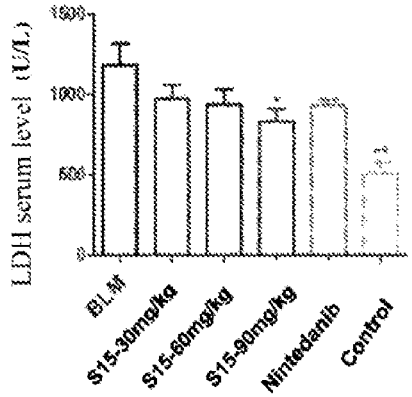
FIG. 8 shows the LDH serum level in Effect example 4.

Serum lactate dehydrogenase (LDH) and alkaline phosphatase (ALP) are important markers of inflammatory response of lung injury. It can be seen from FIG. 7 and FIG. 8 that bleomycin induces lung injury and significantly increase the serum lactate dehydrogenase and alkaline phosphatase levels. Compound S15 can inhibit the level of ALP more effectively than nintedanib. Compound S15 (90 mg/kg) can also effectively inhibit serum LDH level in the high dose group.

(4) Evaluation of mRNA Levels of Inflammatory Cytokines

The experiment used qRT-PCR technology to determine the mRNA levels of pro-inflammatory cytokines in lung tissue. Real-time quantitative PCR was used to detect the mRNA levels of TNF-α, IL-6, IL-1β, TGF-β and others.

1) Extraction of mRNA

About 30 mg of cryopreserved lung tissue was weighed and homogenized and lysed by adding 200 μL of Trizol (Takara, 9109 #). The fluid after the lysis in the well was collected by the RNA sterilization-grade pipette tip and transferred to the corresponding sterile EP tube. 400 μL of chloroform was added, shaken vigorously for 30 sec, and centrifuged for 15 minutes in a centrifuge at 4° C. at 12000 rpm. The upper aqueous layer was transferred to a new EP tube, an equal volume of isopropanol was used to precipitate the RNA in the aqueous phase, and the tube was allowed to stand at −20° C. for more than 1 hr. And then the tube was centrifuged for 15 min at 4° C. at 12000 rpm, and the supernatant was discarded. 75% ethanol was added to wash the RNA pellet, and then the tube was centrifuged for 15 min at 4° C. at 12000 rpm, and the supernatant was discarded. The tube was placed at room temperature for 10-20 min to dry the RNA pellet. 25-200 μL of RNase-free water was added for dissolution and stored at −80° C.

2) Reverse Transcription Synthesis of cDNA

PrimeScript™ RT Master Mix (Takara, RR036A) was selected for mRNA reverse transcription. Please refer to the instructions for the system. In short, 1 μg of mRNA was added to a 20 μL system, mixed and then kept at a constant temperature in a 37° C. water bath for 15 minutes, and then the enzyme was inactivated at 85° C. for 5 seconds. After centrifugation, double distilled water was used to dilute 10 times.

3) Real-Time Quantitative PCR Technology (QPCR)

Q-PCR technology used 2×SYBR Green qPCR Master Mix (B21202, Biomake), and the reaction system could be prepared according to the instruction (10 μL of 2×SYB-Green, 8.8 μL of cDNA template, 1.2 μL of 5 μM primer Mix). The reaction conditions are: pre-denaturation at 95° C. for 5 min, denaturation at 95° C. for 30 sec, annealing at 60° C. for 30 sec, and extension at 72° C. for 30 sec, the number of reaction cycles is 40 cycles. The primers involved are shown in Table 6 below:

TABLE 6

| Primers | | |
|---|---|---|
| Gene name | Primer 1 (5'-3') | Primer 2 (5'-3') |
| GAPDH | CATTTCCTGG TATGACAACGA | GTCTACATGGC AACTGTGAG |
| TNF-α | GGTGCCTATGT CTCAGCCTCTT | GCCATAGAACTG ATGAGAGGGAG |
| IL-6 | TACCACTTCAC AAGTCGGAGGC | CTGCAAGTGCA TCATCGTTGTTC |
| IL-1β | TGGACCTTCCA GGATGAGGAC | GTTCATCTCGGA GCCTGTAGTGA |
| α-SMA | CTGACAGAGGC ACCACTGAA | CATCTCCAGAGT CCAGCACA |
| TGF-1β | TGATACGCCTG AGTGGCTGTCT | CACAAGAGCAGT GAGCGCTGAA |
| Collagen 1 | GAGCGGAGAGT ACTGGATCG | TACTCGAACGGG AATCCATC |

Tumor necrosis factor-α (TNF-α), interleukin-1β (IL-1β), and interleukin-6 (IL-6) play an important role among many inflammatory cytokines. Among them, in the process of inflammatory response, TNF-α is the earliest and most important inflammatory mediator, can activate lymphocytes and neutrophils, increase the permeability of vascular endothelial cells, regulate the metabolic activity of other tissues and regulate the synthesis and release of other cytokines. The changes of IL-1β and IL-6 content can be consistent with the trend of severity of alveolar inflammation in HE staining. IL-6, as an inflammatory response trigger, can induce B cells to differentiate and produce antibodies, and then induce the activation, proliferation and differentiation of T cells to participate in the body's immune response. IL-1β is the main inducer of the pre-inflammatory immune response that plays the strongest role in the body and can mediate inflammation and post-injury repair and over-repair. Overexpression of IL-1β in macrophages can promote the proliferation of lung cancer cells.

Figure 9:
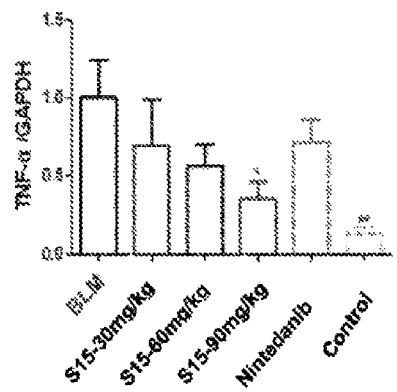
FIG. 9 shows the TNF-α mRNA level in Effect example 4.
Figure 10:
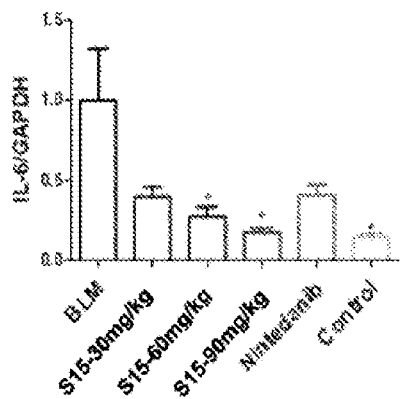
FIG. 10 shows the IL-6 mRNA level in Effect example 4.
Figure 11:
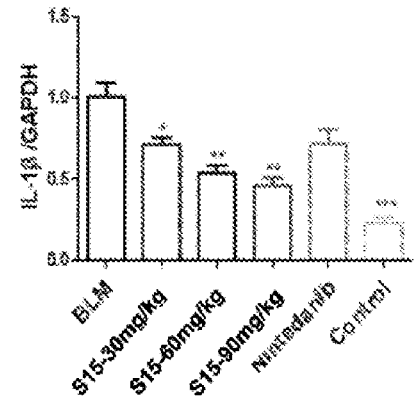
FIG. 11 shows the mRNA level of IL-10 in Effect example 4.

The results are shown in FIGS. 9 to 11. Compared with the control group (Control), BLN instillation can significantly increase the mRNA levels of TNF-α, IL-1β and IL-6 in the lung tissue. The compound S15 can significantly reduce the levels of pro-inflammatory cytokines in a dose-dependent manner.

From the above experimental results, it can be determined that the compound S15 can effectively reduce BLN-induced lung injury and inflammation. The same dose group of this compound shows a therapeutic effect equivalent to or even better than that of nintedanib, while the high dose group shows better therapeutic effect when it can be tolerated.

Effect Example 5: Effect of Compound S15 on Pulmonary Fibrosis Induced by Bleomycin The grouping of mice is the same as that in Effect example 2.

1) Dewaxing to water of the paraffin sections: the sections were put into xylene I (20 minutes)-xylene II (29 minutes)-absolute ethanol I (5 minutes)-absolute ethanol II (5 minutes)-75% ethanol (5 minutes), and then washed with tap water.

2) Potassium dichromate staining: the sections were soaked in potassium dichromate overnight and washed with tap water.

3) Iron hematoxylin staining: iron hematoxylin solution A and B were mixed in an equal ratio to form an iron hematoxylin staining solution, then the sections were put into iron hematoxylin for about 3 minutes, washed with tap water, differentiated with a solution of hydrochloric acid in ethanol, and then rinsed with tap water.

4) Ponceau red acid fuchsin staining: the sections were put into a Ponceau red acid fuchsin solution for 5 to 10 minutes and rinsed with tap water.

5) Phosphomolybdic acid staining: the sections were put into an aqueous phosphomolybdic acid solution for 1 to 3 minutes.

6) Aniline blue staining: after the phosphomolybdic acid staining, the sections were not washed with water, but directly put into an aniline blue staining solution for staining for 3 to 6 minutes.

7) Differentiation: the sections were differentiated with 1% glacial acetic acid, and dehydrated with two cylinders of absolute ethanol.

8) Transparency and sealing: the sections were placed in a third cylinder of absolute ethanol for 5 minutes and xylene for 5 minutes for transparency, and the sections were sealed with neutral gum.

9) A microscope inspection was performed and images were collected for analysis.

10) Interpretation of results: Muscle fibers, cellulose and red blood cells are red, and collagen fibers are blue.

Morphological Grading Standard of Mouse Lung Tissue (Pulmonary Fibrosis Grading):

1. Grade 0 (1 point): normal lung tissue, no or very small amount of filamentous collagen fibers;
2. Grade I (2 points): the collagen fibers are slightly increased and are in the shape of thin bundles;
3. Grade II (3 points): the collagen fibers are moderately increased, fused into a band, and the alveolar structure is disordered;
4. Grade III (4 points): the collagen fibers are obviously increased, are in the form of broadband or flaky, the alveoli are collapsed and fused, and disordered in structure.

After BLM induces early lung injury and inflammation, the lung would undergo abnormal repair and eventually lead to pulmonary fibrosis.

(1) Histopathological Evaluation and Immunohistochemistry Experiment

Figure 12:
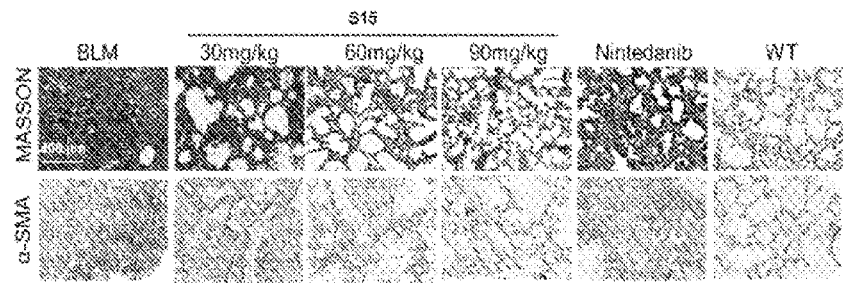
FIG. 12 shows the lung tissue section with MASSON staining and immunohistochemical staining of α-SMA in Effect example 5.
Figure 13:
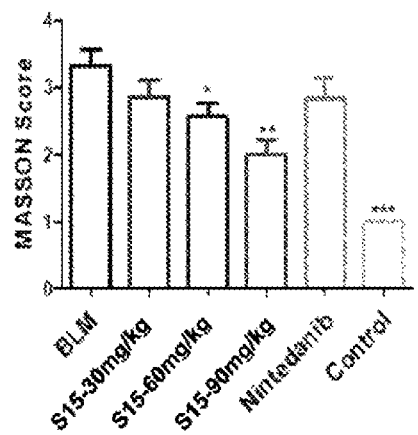
FIG. 13 shows the score of MASSON staining in Effect example 5.

On day 3 after oral administration of BLM (2 mg/kg), compound S15 was administered orally once a day (qd) in three dose groups of 30, 60, and 90 mg/kg for 12 days. Nintedanib was administered orally once a day (qd) in a single dose group of 30 mg/kg for 12 days. And then lung tissue sections were prepared, subjected to MASSON staining and α-SMA immunohistochemical staining, and histopathological evaluation of mouse lung sections was performed, as shown in FIG. 12 and FIG. 13. The results show that BLM can cause a large amount of collagen in the lung tissue of mice to accumulate in the alveolar septum. The collagen staining is obvious, and the alveolar structure almost completely disappears, the pulmonary interstitial fibroblasts increase to form pulmonary consolidation. The compound S15 can significantly reduce BLM-induced lung injury and inflammation, and can also reduce pulmonary fibrosis. Cells positive for expressing α-smooth muscle actin (α-SMA), myofibroblasts, are an important source of collagen, so α-SMA myofibroblasts are specific markers. The immunohistochemical experiment of α-SMA can also confirm that bleomycin can induce severe pulmonary fibrosis. Compound S15 can decrease the expression of collagen and α-SMA in a dose-dependent manner. In the administration group (compound S15 group and nintedanib group), the inflammatory cell infiltration in lung tissue of mice is lighter in the former and there are significantly fewer fibroblasts.

(2) Evaluation of Hydroxyproline Level

The change in hydroxyproline was determined by using a hydroxyproline detection kit, the steps are as follows:

1) The wet weights of the lung tissues in different groups were accurately weighed, and the lung tissues were placed in a 20 ml centrifuge tube after weighing.

2) 1 ml of hydrolysate was added to a 20 ml centrifuge tube and the tube was placed in boiling water at a constant temperature for 20 minutes.

3) The pH of the sample was adjusted to 6.0-8.0 with the reagents provided in the kit.

4) The reagents in the centrifuge tube were made up to 10 ml with distilled water, and mixed thoroughly.

5) 5 ml of hydrolysate was taken from the centrifuge tube, an appropriate amount of activated carbon was added, mixed thoroughly, centrifuged at 3500 rpm for 10 minutes in a centrifuge, and 1 ml of upper supernatant layer was taken for subsequent monitoring.

6) Reagents 1, 2, and 3 were added in order, mixed thoroughly, and then placed in a water bath at 60° C. for 15 minutes, then placed at room temperature for 5 minutes, and centrifuged in a centrifuge at 3500 rpm for 10 minutes. 100 μl of upper supernatant layer was taken and placed in a 96-well plate. Distilled water was used as the zero setting and the absorbance value of each sample at 550 nm wavelength was determined.

7) A standard curve was drew based on the absorbance of the standard, and used as a basis to determine the hydroxyproline content of each sample.

Figure 14:
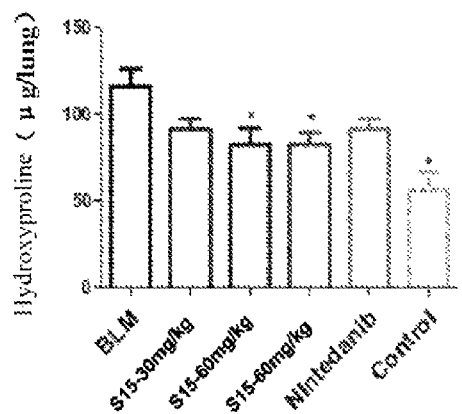
FIG. 14 shows the hydroxyproline level of the whole lung in Effect example 5.

Hydroxyproline is the main component of collagen, accounts for about 13% of the total amount of amino acids in collagen. Except for elastin, which contains a small amount of hydroxyproline (about 1%), all do not contain hydroxyproline. Therefore, hydroxyproline can be used as an important indicator of collagen tissue metabolism and also an important marker of fibrosis (FIG. 14). Compared with the BLM control group, the compound S15 can significantly reduce the level of hydroxyproline.

(3) Evaluation of TGF-β1 Expression Level

The expression level of active TGF-β1 in BALF was detected by using the TGF-β1 ELISA detection kit (Shanghai Wuhao Bio-Tech Co., Ltd). The steps are as follows:

1) 10 standard wells were set on the enzyme coated plate. After the standard was diluted, the volume in each well was 50 μl, and the concentration was 1800 ng/L, 1200 ng/L, 600 ng/L, 300 ng/L, 150 ng/L, respectively. The concentration was the same every two tubes.

2) Sample addition: a blank well (no sample and enzyme reagent) and a well for the sample to be tested were set, respectively. 40 μl of sample dilution solution was added to the well for the sample to be tested on the enzyme coated plate, and then 10 μl of the sample to be tested was added.

3) Incubation: the sample to be tested was sealed with a sealing film and then incubated at 37° C. for 30 minutes.

4) Solution preparation: the concentrated washing liquid (30 times (20 times of 48T)) was diluted 30 times (20 times of 48T) with distilled water for use.

5) Wash: the liquid was discarded and spun dry. Each well was filled with the washing liquid. After standing for 30 seconds, the washing liquid was discarded. This was repeated 5 times and pat dry.

6) Enzyme addition: 50 μl of enzyme reagent was added to each well, except for blank wells.

7) Incubation and wash: The operation was the same as above.

8) Color development: 50 μl of color developing agent A was added to each well, then 50 μl of color developing agent B was added and shaken gently to mix uniformly, and color development was performed at a constant temperature of 37° C. in the dark for about 15 minutes.

9) Stop: 50 μl of stop solution was added to each well to stop the reaction (the color changed from blue to yellow).

10) Determination: zero setting was performed using a blank well within 15 minutes after the reaction was stopped, and the absorbance (OD value) of each well was measured in sequence at a wavelength of 450 nm.

Figure 15:
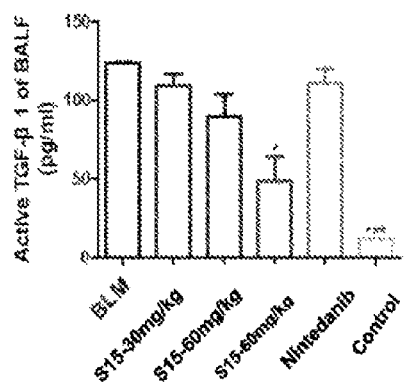
FIG. 15 shows the level of active TGF-β1 in BALF (EG) in Effect example 5.

TGF-β1 is considered to be an important main switch for inducing fibrosis progression during IPF, and is also the most important cytokine for inducing the activation of myofibroblasts, and is also the strongest known pro-fibrotic factor. TGF-β1 not only promotes the conversion of fibroblasts, endothelial cells and alveolar epithelial cells into myofibroblasts, but also is the most effective stimulant for the synthesis of collagen. TGF-β1 can increase the stability of collagen mRNA transcription and can inhibit the activity of collagenase, promote the over-expression of matrix metalloproteinase inhibitors on the fibrous foci to finally lead to the excessive deposition of collagen to accelerate the progress of fibrosis. This experiment investigated the inhibitory effect of compound S15 on TGF-β1 in bronchoalveolar lavage fluid. It can be seen from FIG. 15 that the compound S15 (90 mg/kg) can reduce the active TGF-β1 from 123 μg/ml to 48 pg/ml.

(4) Evaluation of mRNA Levels of Pulmonary Fibrosis-Related Markers

The experiment used qRT-PCR technology to determine the mRNA levels of fibrosis-related markers in lung tissue.

The experimental method was the same as that for the evaluation of the mRNA levels of inflammatory cytokines.

Figure 16:
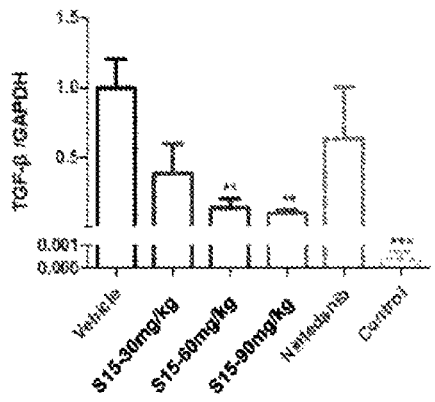
FIG. 16 shows the mRNA level of the fibrosis-related marker TGF-β1 in Effect example 5.
Figure 17:
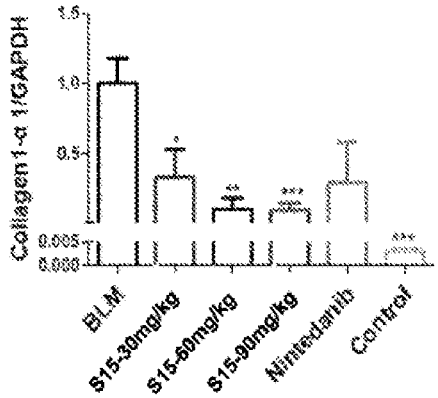
FIG. 17 shows the mRNA level of the fibrosis-related marker, Collagen1-α1 in Effect example 5.
Figure 18:
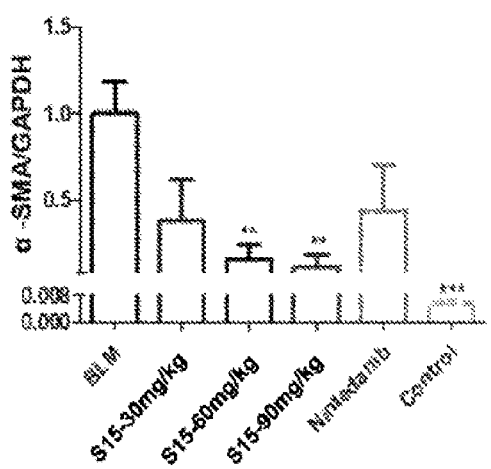
FIG. 18 shows the mRNA level of the fibrosis-related marker, α-SMA in Effect example 5.

S15 (60, 90 mg/kg) can reduce the expression of TGF-β1, Collagen1-α1 and α-SMA by about 90% (FIG. 16 to FIG. 18). Therefore, administration of S15 can slow down the process of BLM-induced pulmonary fibrosis or even has improvement effect, and its therapeutic effect on fibrosis was equivalent to or even better than that of Nintedanib.

Effect Example 6: The Effect of Compound S15 on the Activation of Lung Fibroblasts Induced by TGF-β1

(1) The Effect of TGF-β1 Stimulation on the Expression of DDR2, Fibronectin, α-SMA, Collagen1-α1 and GAPDH 1) Preparation of cell protein samples: the cell culture liquid was discarded, wash was performed once with PBS, and samples were collected by adding 1×SDS-Loading. after the samples were collected, they were placed in a metal bath at 100° C., and the samples were boiled for 10 minutes, and then the samples were stored at 4° C. for waiting for subsequent test.

2) Gel preparation and sample loading: according to the molecular weight of the detected protein, different concentrations of separation gel were selected. after filling the 1× electrophoresis buffer, an equal volume of protein sample 4 μl and protein marker were added on the far left to right in sequence.

3) Electrophoresis: the electrophoresis tank was put in a container of ice-water mixture, the liquid level was level with the electrophoresis tank, the current was set to the maximum value, the voltage was adjusted appropriately, and the sample electrophoresis was observed in real time. When the sample was in the concentrated gel, the voltage was set to 80 V; when the sample was electrophoresed to the separation gel, the voltage was increased to 120 V until the bromophenol blue was electrophoresed to reach the bottom of the gel, and the electrophoresis ended.

4) Transfer film: the gel and NC film were placed in the transfer buffer. The black part of the transfer clip was placed on the left side, and the sponge pad, filter paper, gel, NC film, filter paper, and sponge pad were placed on the top in sequence. After removing the air in the gap, the transfer clip clamped and was placed in the transfer tank for 1 to 2 hours under a voltage of 100 V according to the molecular weight of the protein of interest.

5) Ponceau red staining: the film was placed in the ponceau red staining solution and the electrophoretic transfer of the protein samples was observed. The position of the protein of interest was compared with that of the protein marker, and the excess NC film was cut off. TBST was used for quickly washing 3 times, about 5 minutes each time, until the redness of the NC film faded.

6) Blocking: 2 g of skimmed milk powder was weighed and placed in 40 ml TBST. After stirring evenly with a stirrer, the film was placed in the mixed solution and incubated at room temperature for about 1 hour.

7) Primary antibodies: all primary antibodies were diluted with TBST, and the respective dilution ratios were as follows: DDR2 (1:500); Fibronectin, α-SMA, GAPDH and other antibodies (1:1000). The mixed solution was incubated overnight at 4° C.

8) Secondary antibodies: the film with the primary antibodies was rewarmed and incubated for about half an hour, and then the primary antibodies were recovered and the film was washed quickly with TBST solution 3 times, 10 minutes each time. The film was placed in the corresponding secondary antibodies for incubation again. The dilution ratio of the secondary antibody dedicated for DDR2 was 1:5000; The dilution ratio for the rest of the secondary antibodies were 1:8000, ready for use. Incubation was performed for about 1 hour at room temperature.

9) Chemiluminescence: A detection kit (Genshare ultra-sensitive chemiluminescence substrate) was used to detect the protein on the film. The A and B color developing liquids were mixed in a volume ratio of 1:1 and then dripped onto the film immediately, and the Tanon chemiluminescence imager was used for image acquisition and analysis.

Figure 19:
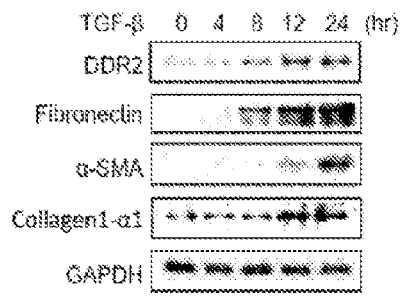
FIG. 19 shows the effect of TGF-β1 stimulation on the levels of DDR2, Fibronectin, α-SMA, Collagen1-α1 and α-SMA in MRC-5 in the Effect example 6.
Figure 20:
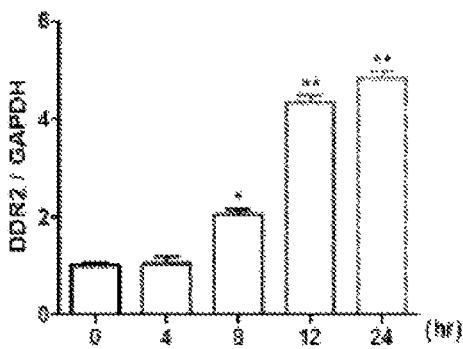
FIG. 20 shows the quantitative results of DDR2 normalized to GAPDH in Effect example 6.

TGF-β1 is a key mediator of fibrosis in many organ systems (including IPF). High expression of TGF-β1 can induce pulmonary fibrosis in animal models. We further studied the biological function of the compound S15 in the isolated primary lung fibroblasts of wild-type mice. Before TGF-β1 treatment, it can be seen that the expression levels of DDR2, Fibronectin, and α-SMA in lung fibroblasts were extremely low. After TGF-β1 stimulation induced lung fibroblasts for 4 hours, 8 hours, 12 hours and 48 hours, the expression levels of DDR2, Fibronectin, α-SMA and Collagen1-α1 were determined by Western Blot. From FIG. 19 and FIG. 20 above, it can be seen that the expression of DDR2 in MRC-5 gradually increased with the increase of TGF-β1 stimulation induction time, which is characterized that α-SMA, Collagen1-α1 and Fibronectin expression also continued to increase.

(2) The Inhibitory Effect of Compound S15 on MRC-5 Induced by TGF-β1

The experimental method was the same as that for the cytotoxic activity test experiment in Effect example 3.

Figure 21:
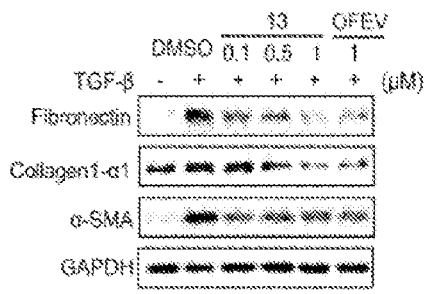
FIG. 21 shows the effect of Compound S15 and the positive medicine Nintedanib (OFEV) on the levels of DDR2, Fibronectin, α-SMA, Collagen1-α1 and α-SMA in MRC-5 in the Effect example 6.
Figure 22:
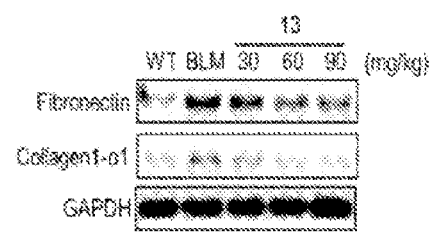
FIG. 22 shows the effect of different concentrations of compound S15 on the levels of Fibronectin, Collagen1-α1 and α-SMA in MRC-5 in the Effect example 6.

It was confirmed that the compound S15 can inhibit the activation of MRC-5 induced by TGF-β1 in a dose-dependent manner, and its effect was similar to or even better than that of nintedanib (FIG. 21). In addition, in primary lung fibroblasts isolated from different experimental groups of mice, the compound S15 can also inhibit the activation of myofibroblasts in a dose-dependent manner (FIG. 22).

(3) Study on the Molecular Mechanism of Compound S15 in Regulating the Biology of Pulmonary Myofibroblasts The experimental method was the same as that for the immunoblotting experiment.

Figure 23:
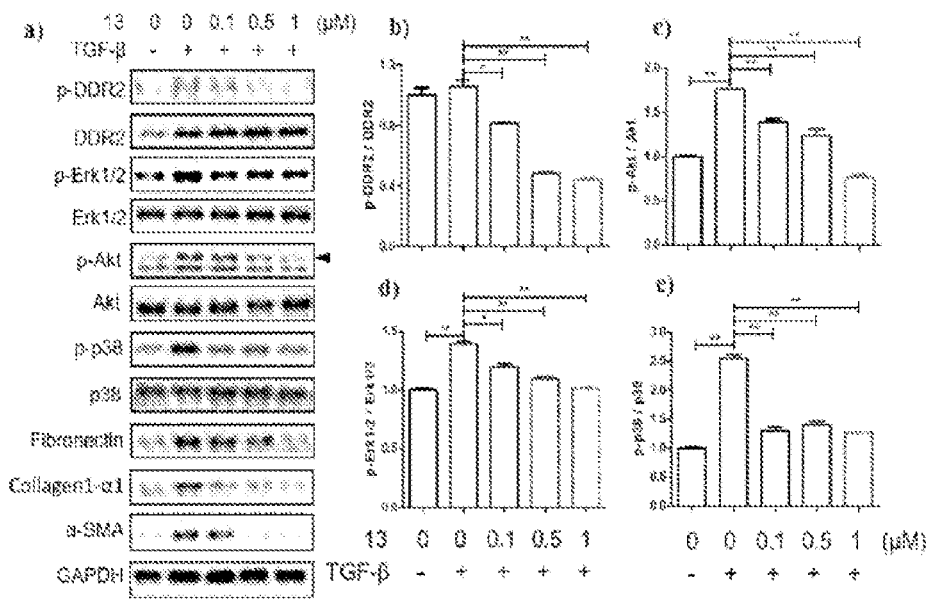
FIG. 23 shows the effect of compound S15 on the phosphorylation levels of DDR2, AKT, Erk1/2 and p38 in the Effect example 6. a) shows the effect of compound S15 on each cytokine and its phosphorylation level; b) shows the effect of compound S15 on the phosphorylation level of DDR2; c) shows the effect of compound S15 on the phosphorylation level of AKT; d) shows the effect of compound S15 on the phosphorylation level of Erk1/2; e) shows the effect of compound S15 on the phosphorylation level of p38.

Consistent with the in vitro molecular activity, the compound S15 can effectively inhibit the phosphorylation level of DDR2. In addition, the phosphorylation level of the main downstream mediators of TGF-β was analyzed by Western Blot. Compared with wild-type MRC-5, TGF-β1 treatment resulted in a significant increase in the phosphorylation levels of ERK1/2, Akt and p38. The above figure proved that the compound S15 can significantly inhibit the phosphorylation level of downstream ERK1/2, Akt and p38 by inhibiting the phosphorylation level of DDR2. (FIG. 23)

DDR2 can participate in the p38 and AKT non-classical activation pathway through TGF-β1, and DDR2 can regulate the formation of myofibroblasts through ERK1/2 in an activation manner. By studying the molecular mechanism of the compound S15 in regulating the biology of lung myofibroblasts, we believed that the compound S15 can inhibit the activation of myofibroblasts in the process of pulmonary fibrosis by inhibiting TGF-β induced ERK1/2 (an activation manner) and p38 and Akt (an non-activation manner).

Effect Example 7: The Effect of Chirally Resolved Compounds S11-A and S11-B of Compound S11 on BLM-Induced Pulmonary Inflammation and Pulmonary Fibrosis Experimental objective: This group of experiments aimed to investigate the therapeutic potential of the compound S11-A/S11-B in acute lung injury and inflammation induced by BLM.

Experimental grouping (8 mice per group):

Model group (Vehicle): the mice received BLM (1.7 U/kg) via intratracheal instillation;

Compound S15 group (S15): this group was divided into three dose groups, namely 30, 60 and 90 mg/kg;

Positive control group (Nintedanib): Nintedanib administration group;

Negative control group (WT): only saline was used.

(1) Histopathological Evaluation

Figure 24:
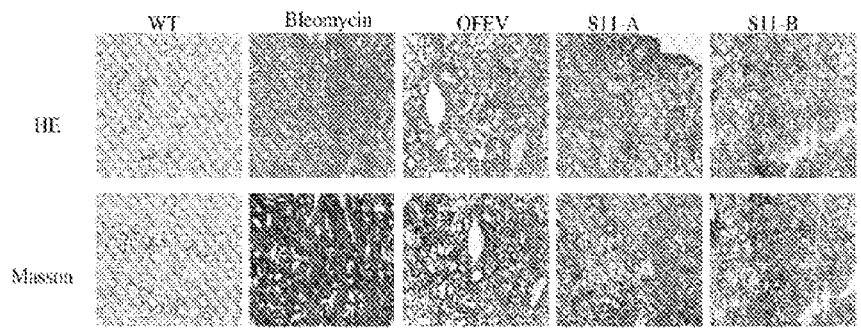
FIG. 24 shows the lung tissue section stained with H&E and MASSON in Effect example 7.
Figure 25:
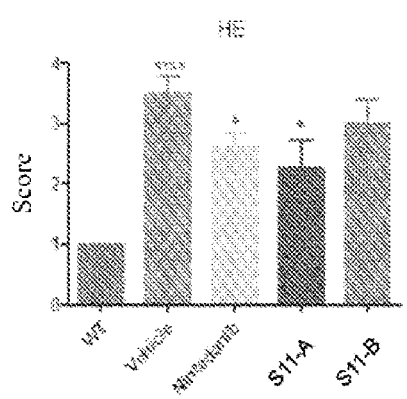
FIG. 25 shows the score of H&E staining in Effect example 7.

On day 3 after oral administration of BLM (1.7 U/kg), compound S11-A was administered orally once a day (qd) in three dose groups of 30 mg/kg for 12 days. Nintedanib was administered orally once a day (qd) in a single dose group of 30 mg/kg for 12 days. And then lung tissue sections were prepared and H&E staining (FIG. 24 and FIG. 25) was used for histopathological evaluation of mouse lung sections. The results showed that bleomycin induced severe lung injury, disordered normal alveolar structure, significantly thickened alveolar wall, infiltration of a large number of inflammatory cells and focal fibrotic lesions; In the oral S11-A and Nintedanib administration group, the lung injury induced by BLM was significantly improved.

Figure 26:
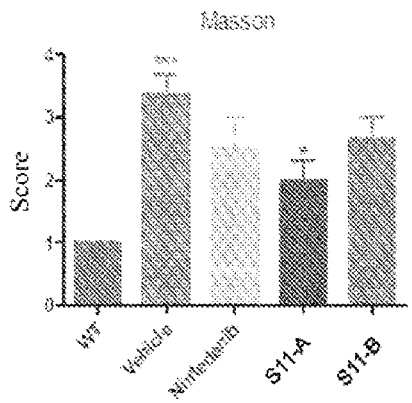
FIG. 26 shows the score of MASSON staining in Effect example 7.

On day 3 after oral administration of BLM (1.7 U/kg), compound S11-A was administered orally once a day (qd) in three dose groups of 30 mg/kg for 12 days. Nintedanib was administered orally once a day (qd) in a single dose group of 30 mg/kg for 12 days. And then lung tissue sections were prepared, and Masson trichrome staining (FIG. 24 and FIG. 26) was used for histopathological evaluation of mouse lung sections. The results showed: bleomycin can cause a large amount of collagen in the lung tissue of mice to accumulate in the alveolar septum. The collagen staining is obvious, and the alveolar structure almost completely disappears, the pulmonary interstitial fibroblasts increase to form pulmonary consolidation. Compared with nintedanib and S11-B, S11-A can significantly reduce BLM-induced lung injury and inflammation, and can also reduce pulmonary fibrosis.

(2) The Effect of Compound S11-A/S11-B on the Expression of Hydroxyproline Induced by BLM The experimental method was the same as the hydroxyproline level evaluation method in Effect example 5.

Figure 27:
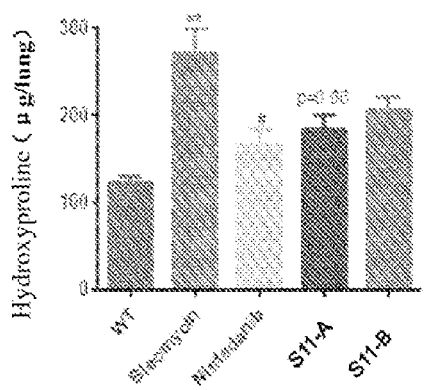
FIG. 27 shows the effects of compounds S11-A and S11-B on the level of hydroxyproline in the whole lung in Effect example 7.
Figure 28:
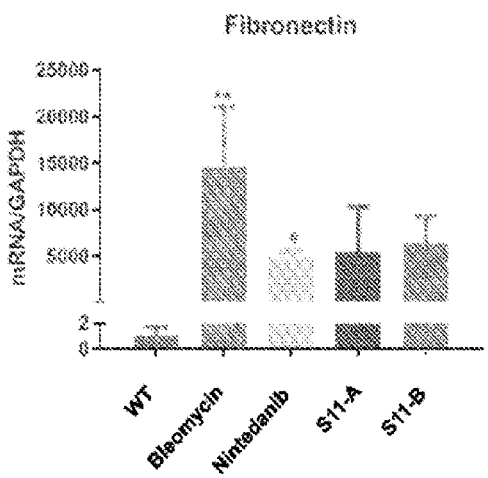
FIG. 28 shows the effects of compounds S11-A and S11-B on the mRNA level of Fibronectin in Effect example 7.
Figure 29:
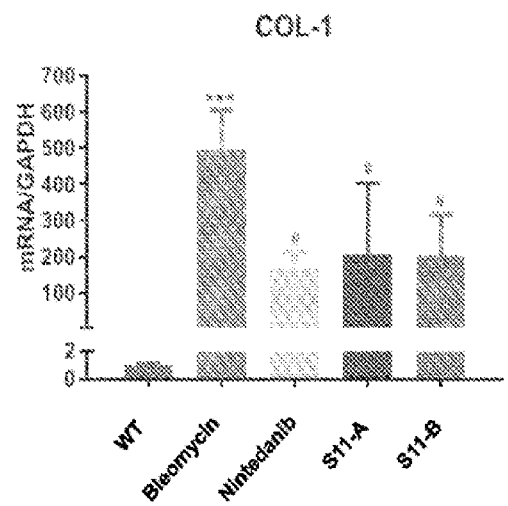
FIG. 29 shows the effects of compounds S11-A and S11-B on the mRNA level of COL-1 in Effect example 7.
Figure 30:
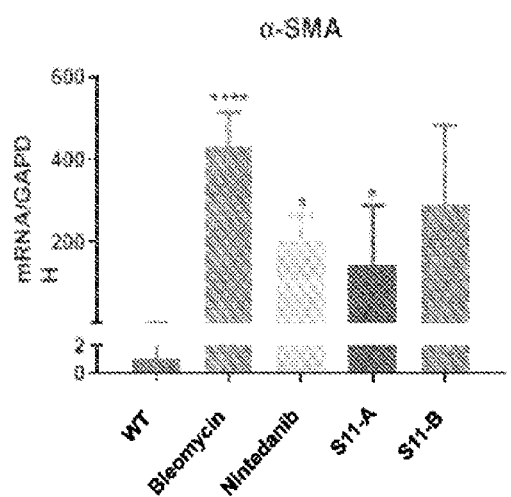
FIG. 30 shows the effects of compounds S11-A and S11-B on the mRNA level of α-SMA in Effect example 7.
Figure 31:
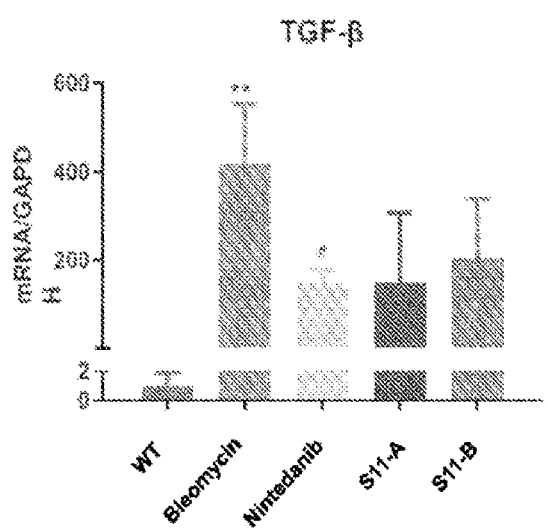
FIG. 31 shows the effects of compounds S11-A and S11-B on the mRNA level of TGF-β1 in Effect example 7.

Hydroxyproline is the main component of collagen, accounts for about 13% of the total amount of amino acids in collagen. Except for elastin, which contains a small amount of hydroxyproline (about 1%), all do not contain hydroxyproline. Therefore, hydroxyproline can be used as an important indicator of collagen tissue metabolism and also an important marker of fibrosis. It can be seen from FIG. 27 that the compound S11-A/S11-B can significantly reduce the level of hydroxyproline compared with the BLM group.

(3) The Effect of Compound S11-A/S11-B on the Expression Levels of Fibronectin, Collagen, α-SMA and TGF-β1 Induced by Bleomycin The experiment used qRT-PCR technology to determine the mRNA levels of fibrosis-related markers in lung tissue.

The experimental method was the same as that for the evaluation of the mRNA levels of inflammatory cytokines.

Experimental results: S11-A (30 mg/kg) can reduce the expression of TGF-β1, Collagen1-α1 and α-SMA by about 50% (FIG. 28 to FIG. 31). Therefore, administration of S11-A can slow down the process of BLM-induced pulmonary fibrosis or even has improvement effect, and its therapeutic effect on fibrosis was equivalent to or even better than that of nintedanib.

In the present disclosure, the bar group in FIGS. 1 to 31 represents the mean±SD; * represents P<0.05,  represents P<0.01, * represents P<0.001.

Comparative Example 1: Kinase Selectivity Test

The test method was the same as the DDR2 enzyme activity test method in Effect example 1, and the results are shown in Table 7 and Table 8 below.

TABLE 7

| Kinase | 1000 | 100 | 10 |
|---|---|---|---|
| VEGFR-1 | 70.4 | 68.4 | 52.6 |
| PDGFR-α | 89.5 | 83.2 | 43.4 |
| PDGFR-β | 85.7 | 86.1 | 62.4 |
| C-Kit | 88.6 | 84.9 | 52 |
| Flt-3 | 76.1 | 80.3 | 58 |
| EGFR | 2 | 0 | 0 |
| ErbB2 | 21.8 | 13.4 | 8.7 |
| ErbB4 | 80.6 | 79.2 | 58.7 |
| Src | 91.2 | 94 | 85.6 |
| Abl | 96.2 | 93.6 | 69.5 |
| ALK | 18.5 | 17.8 | 16.3 |
| RET | 97 | 97.2 | 93.9 |
| FGFR-1 | 100 | 100 | 62 |
| KDR | 100 | 100 | 75.3 |
| Met | 28.1 | 22.7 | 12 |
| DDR2 | 100 | 97.2 | 85 |
| EPH-A2 | 100 | 99.6 | 88.7 |
| IGF-1R | 1 | 2.8 | 4.8 |
| AXL | 91.4 | 80.1 | 74.5 |

TABLE 8

| Kinase | 1000 | 100 | 10 |
|---|---|---|---|
| VEGFR-1 | 44.6 | 48.7 | 0.0 |
| PDGFR-α | 78.6 | 75.2 | 58.1 |
| PDGFR-β | 53.4 | 51.8 | 35.0 |
| C-Kit | 31.7 | 30.4 | 10.3 |
| Flt-3 | 18.5 | 18.4 | 10.3 |
| EGFR | 15.2 | 0 | 1.7 |
| ErbB2 | 26.2 | 28.6 | 13.1 |
| ErbB4 | 16.1 | 18.3 | 10.0 |
| Src | 96.6 | 98.3 | 84.4 |
| Abl | 97.2 | 99.3 | 81.2 |
| ALK | 50.4 | 28.2 | 24.6 |
| RET | 79.4 | 83.6 | 51.9 |
| FGFR-1 | 95.4 | 75.1 | 27.1 |
| KDR | 92.2 | 76.4 | 38.8 |
| Met | 11 | 12.6 | -3.2 |
| EPH-A2 | 96.5 | 95.5 | 67.1 |
| IGF-1R | 5.9 | 9.0 | 7.2 |
| AXL | 21 | 0.5 | 0.4 |

What is claimed is:

1. A compound shown in formula I, a pharmaceutically acceptable salt thereof, a tautomer thereof, or a stereoisomer thereof, having a structure shown as below:

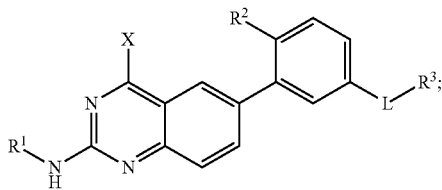

I wherein, X is hydrogen;

$R^3$ is unsubstituted or $R^{3-1}$ substituted $C_{6-10}$ aryl, unsubstituted or $R^{3-2}$ substituted 5 to 10 membered heteroaryl with 1 to 4 heteroatoms selected from one or more of N, O and S, or unsubstituted or $R^{3-3}$ substituted $C_{6-10}$ aryl-fused $C_{3-8}$ cycloalkyl;

$R^{3-1}$ and $R^{3-2}$ are independently hydroxyl, unsubstituted or $R^{3-1-1}$ substituted $C_{1-6}$ alkyl, $C_{1-6}$ alkoxy, or unsubstituted or $R^{3-1-4}$ substituted $C_{6-10}$ aryl;

$R^{3-3}$ is independently hydrogen or $C_{1-6}$ alkyl substituted with one or more halogens;

$R^{3-1-1}$ and $R^{3-1-4}$ are independently cyano, halogen, or unsubstituted or $R^{3-1-1-1}$ substituted 3 to 10 membered heterocycloalkyl with 1 to 3 heteroatoms selected from one or more of N, O and S;

$R^{3-1-1-1}$ is $C_{1-4}$ alkyl;

$R^2$ is methyl, ethyl, isopropyl or cyclopropyl;

when $R^2$ is methyl or ethyl, then L is —NH—CO—NH—, —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, —NH—CO—NH—CHR$^{4-6}$—, —CO—NH—CR$^{4-7}$R$^{4-8}$—

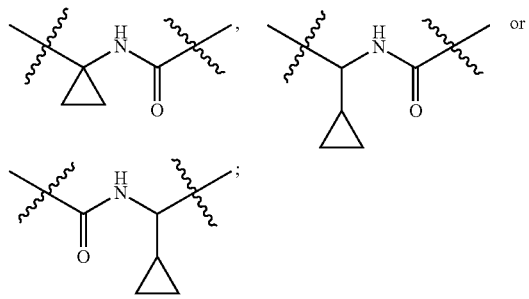

when $R^2$ is methyl or ethyl, then $R^1$ is unsubstituted or $R^{1-1}$ substituted $C_{6-10}$ aryl, or unsubstituted or $R^{1-2}$ substituted 5 to 10 membered heteroaryl with 1 to 4 heteroatoms selected from one or more of N, O and S;

when $R^2$ is isopropyl or cyclopropyl, then L is —CO—NH—, —NH—CO—, —NH—CO—NH—, —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, —NH—CO—NH—CHR$^{4-6}$—, —CO—NH—CR$^{4-7}$R$^{4-8}$—,

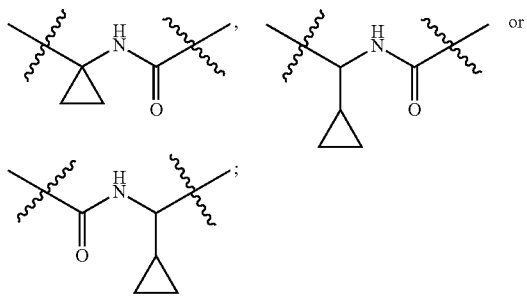

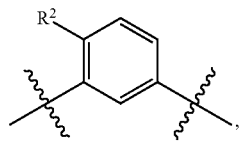

when $R^2$ is isopropyl or cyclopropyl, then $R^1$ is unsubstituted or $R^{1-1}$ substituted $C_{6-10}$ aryl, or unsubstituted or $R^{1-2}$ substituted 5 to 10 membered heteroaryl with 1 to 3 heteroatoms selected from one or more of N, O and S;

the left end of L is connected to

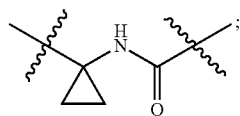 [SMILES: *C(=O)NC1(*)CC1]

and the right end is connected to $R^3$;

$R^{4-1}$, $R^{4-2}$, $R^{4-3}$, $R^{4-4}$, $R^{4-5}$, $R^{4-6}$, $R^{4-7}$ and $R^{4-8}$ are independently hydrogen, $C_{1-4}$ alkyl, or $R^{4-7}$ and $R^{4-8}$ together with the carbon atom therebetween form $C_{3-6}$ cycloalkyl;

$R^{1-1}$ and $R^{1-2}$ are independently unsubstituted or $R^{1-1-1}$ substituted $C_{1-6}$ alkyl, $C_{1-6}$ alkoxy, unsubstituted or $R^{1-1-2}$ substituted $C_{3-10}$ cycloalkyl, unsubstituted or $R^{1-1-3}$ substituted 3 to 10 membered heterocycloalkyl with 1 to 3 heteroatoms selected from one or more of N, O and S, or $NR^{1-1-4}R^{1-1-5}$;

$R^{1-1-1}$, $R^{1-1-2}$, $R^{1-1-3}$, $R^{1-1-4}$ and $R^{1-1-5}$ are independently hydroxyl or $C_{1-6}$ alkyl.

2. The compound shown in formula I, the pharmaceutically acceptable salt thereof, the tautomer thereof, or the stereoisomer thereof as defined in claim 1, wherein, X is hydrogen;

$R^3$ is unsubstituted or $R^{3-1}$ substituted $C_{6-10}$ aryl, or unsubstituted or $R^{3-2}$ substituted 5 to 10 membered heteroaryl with 1 to 4 heteroatoms selected from one or more of N, O and S;

$R^{3-1}$ and $R^{3-2}$ are independently hydroxyl, unsubstituted or $R^{3-1-1}$ substituted $C_{1-6}$ alkyl, $C_{1-6}$ alkoxy, or unsubstituted or $R^{3-1-4}$ substituted $C_{6-10}$ aryl;

$R^{3-1-1}$ and $R^{3-1-4}$ are independently cyano, halogen, or unsubstituted or $R^{3-1-1-1}$ substituted 3 to 10 membered heterocycloalkyl with 1 to 3 heteroatoms selected from one or more of N, O and S;

$R^{3-1-1-1}$ is $C_{1-4}$ alkyl;

$R^2$ is methyl, ethyl, isopropyl or cyclopropyl;

when $R^2$ is methyl or ethyl, then L is —NH—CO—NH—, —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, —NH—CO—NH—CHR$^{4-6}$—, —CO—NH—CR$^{4-7}$R$^{4-8}$— or

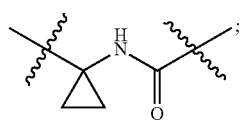

when $R^2$ is methyl or ethyl, then $R^1$ is unsubstituted or $R^{1-1}$ substituted $C_{6-10}$ aryl, or unsubstituted or $R^{1-2}$ substituted 5 to 10 membered heteroaryl with 1 to 4 heteroatoms selected from one or more of N, O and S;

when $R^2$ is isopropyl or cyclopropyl, then L is —CO—NH—, —NH—CO—, —NH—CO—NH—, —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, —NH—CO—NH—CHR$^{4-6}$—, —CO—NH—CR$^{4-7}$R$^{4-8}$— or

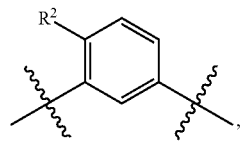

when $R^2$ is isopropyl or cyclopropyl, then $R^1$ is unsubstituted or $R^{1-1}$ substituted $C_{6-10}$ aryl, or unsubstituted or $R^{1-2}$ substituted 5 to 10 membered heteroaryl with 1 to 3 heteroatoms selected from one or more of N, O and S;

the left end of L is connected to and the right end is connected to $R^3$;

$R^{4-1}$, $R^{4-2}$, $R^{4-3}$, $R^{4-4}$, $R^{4-5}$, $R^{4-6}$, $R^{4-7}$ and $R^{4-8}$ are independently hydrogen, $C_{1-4}$ alkyl, or $R^{4-7}$ and $R^{4-8}$ together with the carbon atom therebetween form $C_{3-6}$ cycloalkyl;

$R^{1-1}$ and $R^{1-2}$ are independently unsubstituted or $R^{1-1-1}$ substituted $C_{1-6}$ alkyl, $C_{1-6}$ alkoxy, unsubstituted or $R^{1-1-2}$ substituted $C_{3-10}$ cycloalkyl, unsubstituted or $R^{1-1-3}$ substituted 3 to 10 membered heterocycloalkyl with 1 to 3 heteroatoms selected from one or more of N, O and S, or $NR^{1-1-4}R^{1-1-5}$;

$R^{1-1-1}$, $R^{1-1-2}$, $R^{1-1-3}$, $R^{1-1-4}$ and $R^{1-1-5}$ are independently hydroxyl or $C_{1-6}$ alkyl.

3. The compound shown in formula I, the pharmaceutically acceptable salt thereof, the tautomer thereof, or the stereoisomer thereof as defined in claim 1, wherein, in unsubstituted or $R^{3-1}$ substituted $C_{6-10}$ aryl, the $C_{6-10}$ aryl is phenyl;

or, in unsubstituted or $R^{3-2}$ substituted 5 to 10 membered heteroaryl with 1 to 4 heteroatoms selected from one or more of N, O and S, the heteroaryl is 5 to 6 membered heteroaryl with 1 to 4 heteroatoms selected from one or more of N, O and S;

or, in unsubstituted or $R^{3-1-1}$ substituted $C_{1-6}$ alkyl, the $C_{1-6}$ alkyl is $C_{1-4}$ alkyl;

or, in unsubstituted or $R^{3-1-4}$ substituted $C_{6-10}$ aryl, the $C_{6-10}$ aryl is phenyl;

or, in $R^{3-1-1}$, the halogen is fluorine, chlorine, bromine or iodine;

or, in $R^{3-1-4}$, the halogen is fluorine, chlorine, bromine or iodine;

or, when $R^2$ is methyl or ethyl, L

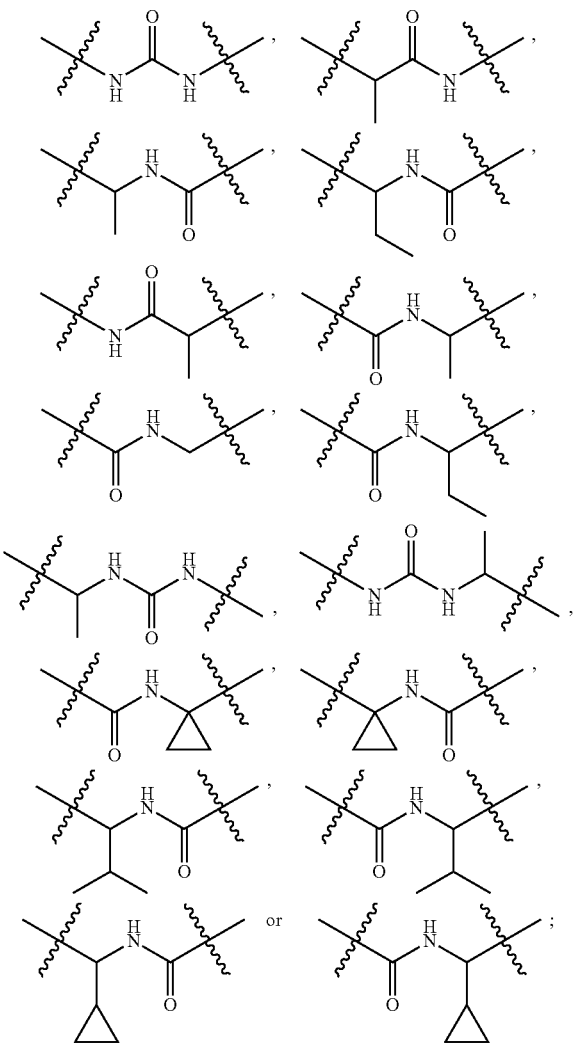

or, when $R^2$ is isopropyl or cyclopropyl, L

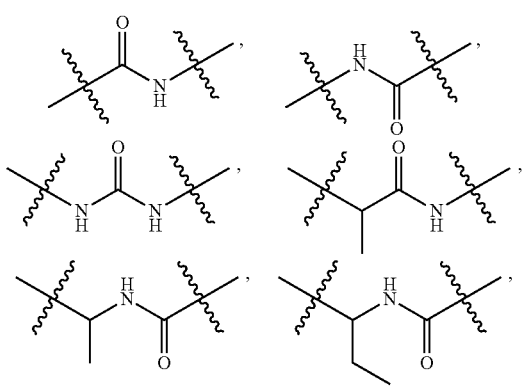

-continued

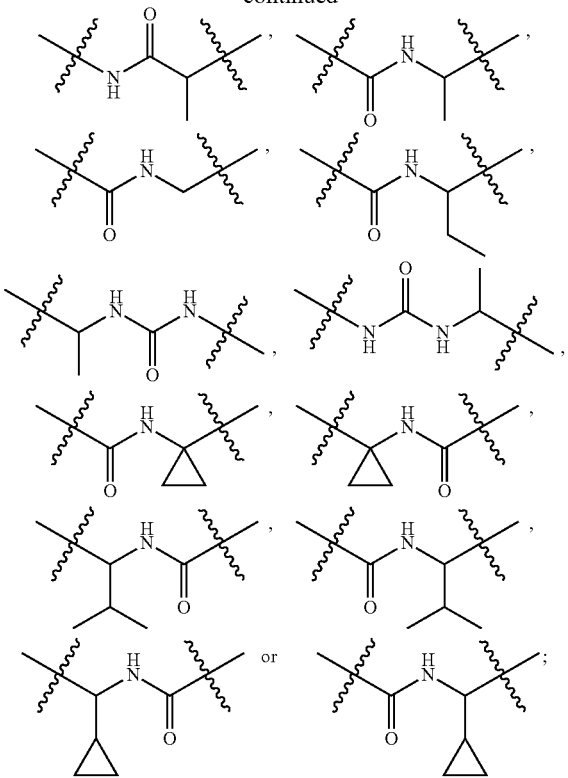

or, in unsubstituted or $R^{1-1}$ substituted $C_{6-10}$ aryl, the $C_{6-10}$ aryl is phenyl;

or, in unsubstituted or $R^{1-2}$ substituted 5 to 10 membered heteroaryl with 1 to 4 heteroatoms selected from one or more of N, O and S, the heteroaryl is 5 to 6 membered heteroaryl with 1 to 4 heteroatoms selected from one or more of N, O and S;

or, in unsubstituted or $R^{1-1-1}$ substituted $C_{1-6}$ alkyl, the $C_{1-6}$ alkyl is $C_{1-4}$ alkyl;

or, in $R^{1-1}$, the $C_{1-6}$ alkoxy is $C_{1-4}$ alkoxy;

or, in unsubstituted or $R^{1-1-2}$ substituted $C_{3-10}$ cycloalkyl, the $C_{3-10}$ cycloalkyl is $C_{3-6}$ cycloalkyl;

or, in $R^{1-2}$, the $C_{1-6}$ alkoxy is $C_{1-4}$ alkoxy;

or, in $R^{1-1-2}$, the $C_{1-6}$ alkyl is $C_{1-4}$ alkyl;

or, in $R^{1-1-4}$, the $C_{1-6}$ alkyl is $C_{1-4}$ alkyl;

or, in $R^{1-1-5}$, the $C_{1-6}$ alkyl is $C_{1-4}$ alkyl;

or, in $R^{4-1}$, $R^{4-2}$, $R^{4-3}$, $R^{4-4}$, $R^{4-5}$ and $R^{4-6}$, the $C_{1-4}$ alkyl is methyl, ethyl, propyl, isopropyl, n-butyl, isobutyl, sec-butyl or tert-butyl;

or, the $C_{3-6}$ cycloalkyl is cyclopropyl, cyclobutyl, cyclopentyl or cyclohexyl.

4. The compound shown in formula I, the pharmaceutically acceptable salt thereof, the tautomer thereof, or the stereoisomer thereof as defined in claim 1, wherein, in $R^{3-1}$ substituted $C_{6-10}$ aryl, the number of the $R^{3-1}$ is 1, 2, 3 or 4;

or, in unsubstituted or $R^{3-1}$ substituted $C_{6-10}$ aryl, the $R^{3-1}$ substituted $C_{6-10}$ aryl is

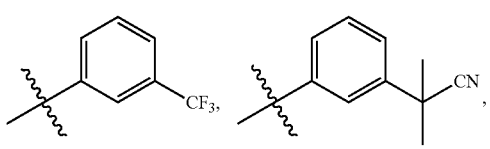

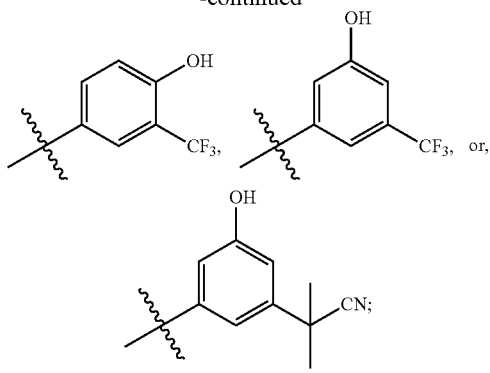

or, in $R^{3-2}$ substituted 5 to 10 membered heteroaryl with 1 to 4 heteroatoms selected from one or more of N, O and S, the number of the $R^{3-2}$ is 1, 2 or 3;

or, in unsubstituted or $R^{3-2}$ substituted 5 to 10 membered heteroaryl with 1 to 4 heteroatoms selected from one or more of N, O and S, the heteroaryl is pyrrolyl, furyl, thienyl, imidazolyl, pyrazolyl, oxazolyl, isoxazolyl, thiazolyl, isothiazolyl, 1,2,3-triazolyl, 1,2,4-triazolyl, furazanyl, 1,2,3-oxadiazolyl, 1,2,4-oxadiazolyl, 1,2,5-oxadiazolyl, 1,3,4-oxadiazolyl, thiadiazolyl, dithiazolyl, tetrazolyl, pyridyl, pyranyl, thiopyranyl, diazinyl, pyrazinyl, pyrimidinyl, pyridazinyl, oxazinyl, thiazinyl, dioxinyl, dithiinyl, 1,2,3-triazinyl, 1,2,4-triazinyl, 1,3,5-triazinyl or tetrazinyl;

or, in unsubstituted or $R^{3-2}$ substituted 5 to 10 membered heteroaryl with 1 to 4 heteroatoms selected from one or more of N, O and S, the $R^{3-2}$ substituted 5 to 10 membered heteroaryl with 1 to 4 heteroatoms selected from one or more of N, O and S is

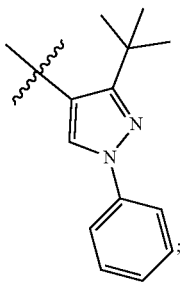 [SMILES: *c1cn(-c2ccccc2)nc1C(C)(C)C]

or, in $R^{3-1-1}$ substituted $C_{1-6}$ alkyl, the number of the $R^{3-1-1}$ is 1, 2 or 3;

or, in unsubstituted or $R^{3-1-1}$ substituted $C_{1-6}$ alkyl, the $C_{1-6}$ alkyl is methyl, ethyl, propyl, isopropyl, n-butyl, isobutyl, sec-butyl or tert-butyl;

or, in unsubstituted or $R^{3-1-1}$ substituted $C_{1-6}$ alkyl, the $R^{3-1-1}$ substituted $C_{1-6}$ alkyl is —$CF_3$, or

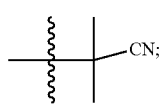

or, in $R^{3-1-4}$ substituted $C_{6-10}$ aryl, the number of the $R^{3-1-4}$ is 1, 2, 3 or 4;
or, in $R^{3-1-1}$ substituted $C_{1-6}$ alkyl, the number of the $R^{3-1-1}$ is 1, 2 or 3;

or, in unsubstituted or $R^{3-1-1}$ substituted $C_{1-6}$ alkyl, the $C_{1-6}$ alkyl is methyl, ethyl, propyl, isopropyl, n-butyl, isobutyl, sec-butyl or tert-butyl;

or, in unsubstituted or $R^{3-1-1}$ substituted $C_{1-6}$ alkyl, the $R^{3-1-1}$ substituted $C_{1-6}$ alkyl is —$CF_3$, or

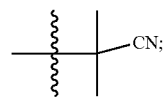

or, in $R^{3-1-4}$ substituted $C_{6-10}$ aryl, the number of the $R^{3-1-4}$ is 1, 2, 3 or 4;
or, in $R^{3-1-1}$, the halogen is fluorine;
or, in $R^{3-1-4}$, the halogen is fluorine;
or, in $R^{1-1}$ substituted $C_{6-10}$ aryl, the number of the $R^{1-1}$ is 1, 2, 3 or 4;
or, in unsubstituted or $R^{1-1}$ substituted $C_{6-10}$ aryl, the $R^{1-1}$ substituted $C_{6-10}$ aryl is

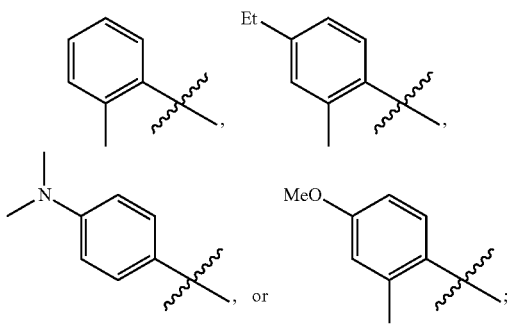

or, in $R^{1-2}$ substituted 5 to 10 membered heteroaryl with 1 to 4 heteroatoms selected from one or more of N, O and S, the number of the $R^{1-2}$ is 1, 2 or 3;

or, in unsubstituted or $R^{1-2}$ substituted 5 to 10 membered heteroaryl with 1 to 4 heteroatoms selected from one or more of N, O and S, the heteroaryl is pyrrolyl, furyl, thienyl, imidazolyl, pyrazolyl, oxazolyl, isoxazolyl, thiazolyl, isothiazolyl, 1,2,3-triazolyl, 1,2,4-triazolyl, furazanyl, 1,2,3-oxadiazolyl, 1,2,4-oxadiazolyl, 1,2,5-oxadiazolyl, 1,3,4-oxadiazolyl, thiadiazolyl, dithiazolyl, tetrazolyl, pyridyl, pyranyl, thiopyranyl, diazinyl, pyrazinyl, pyrimidinyl, pyridazinyl, oxazinyl, thiazinyl, dioxinyl, dithiinyl, 1,2,3-triazinyl, 1,2,4-triazinyl, 1,3,5-triazinyl or tetrazinyl;

or, in unsubstituted or $R^{1-2}$ substituted 5 to 10 membered heteroaryl with 1 to 4 heteroatoms selected from one or more of N, O and S, the $R^{1-2}$ substituted heteroaryl is

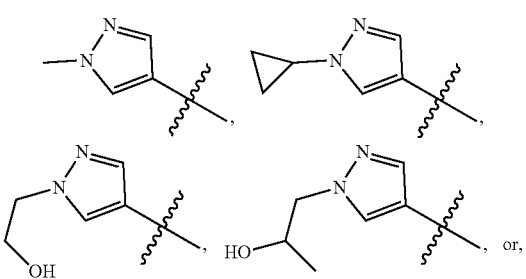

-continued

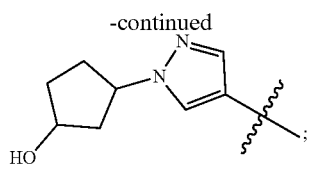

or, in $R^{1-1-1}$ substituted $C_{1-6}$ alkyl, the number of the $R^{1-1-1}$ is 1, 2 or 3;
or, in $R^{1-1-1}$ substituted $C_{1-6}$ alkyl, the $C_{1-6}$ alkyl is methyl, ethyl, propyl, isopropyl, n-butyl, isobutyl, sec-butyl or tert-butyl;
or, in $R^{1-1-1}$ substituted $C_{1-6}$ alkyl, the $R^{1-1-1}$ substituted $C_{1-6}$ alkyl is

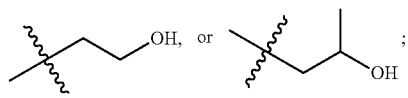

or, in $R^{1-1}$, the $C_{1-6}$ alkoxy is methoxy, ethoxy, propoxy, isopropoxy, n-butoxy, isobutoxy, sec-butoxy or tert-butoxy;
or, in $R^{1-1-2}$ substituted $C_{3-10}$ cycloalkyl, the number of the $R^{1-1-2}$ is 1, 2 or 3;
or, in unsubstituted or $R^{1-1-2}$ substituted $C_{3-10}$ cycloalkyl, the $C_{3-10}$ cycloalkyl is cyclopropyl, cyclobutyl, cyclopentyl or cyclohexyl;
or, in $R^{1-1-2}$ substituted $C_{3-10}$ cycloalkyl, the $R^{1-1-2}$ substituted $C_{3-10}$ cycloalkyl is

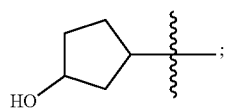 [SMILES: *C1CCC(O)C1]

or, the $-NR^{1-1-4}R^{1-1-5}$ is $-N(Me)_2$;
or, in $R^{1-1-1}$ substituted $C_{1-6}$ alkyl, the number of the $R^{1-1-1}$ is 1, 2 or 3;
or, in $R^{1-2}$, the $C_{1-6}$ alkoxy is methoxy, ethoxy, propoxy, isopropoxy, n-butoxy, isobutoxy, sec-butoxy or tert-butoxy;
or, in $R^{1-2-2}$ substituted $C_{3-10}$ cycloalkyl, the number of the $R^{1-1-2}$ is 1, 2 or 3;
or, in $R^{1-1-4}$, the $C_{1-6}$ alkyl is methyl;
or, in $R^{1-1-5}$, the $C_{1-6}$ alkyl is methyl;
or, in $R^{4-1}$, $R^{4-2}$, $R^{4-3}$, $R^{4-4}$, $R^{4-5}$ and $R^{4-6}$, the $C_{1-4}$ alkyl is methyl or ethyl;
or, the $C_{3-6}$ cycloalkyl is cyclopropyl.

5. The compound shown in formula I, the pharmaceutically acceptable salt thereof, the tautomer thereof, or the stereoisomer thereof as defined in claim 4, wherein, in unsubstituted or $R^{3-2}$ substituted 5 to 10 membered heteroaryl with 1 to 4 heteroatoms selected from one or more of N, O and S, the heteroaryl is pyrazolyl;
or, in unsubstituted or $R^{3-1-1}$ substituted $C_{1-6}$ alkyl, the $C_{1-6}$ alkyl is methyl, isopropyl or tert-butyl;
or, in unsubstituted or $R^{1-2}$ substituted 5 to 10 membered heteroaryl with 1 to 4 heteroatoms selected from one or more of N, O and S, the heteroaryl is pyrazolyl;
or, in unsubstituted or $R^{1-1-1}$ substituted $C_{1-6}$ alkyl, the $C_{1-6}$ alkyl is methyl, ethyl or isopropyl;
or, in $R^{1-1}$, the $C_{1-6}$ alkoxy is methoxy;
or, in unsubstituted or $R^{1-1-2}$ substituted $C_{3-10}$ cycloalkyl, the $C_{3-10}$ cycloalkyl is cyclopropyl or cyclopentyl;
or, in unsubstituted or $R^{1-1-1}$ substituted $C_{1-6}$ alkyl, the $C_{1-6}$ alkyl is methyl, ethyl or isopropyl;
or, in $R^{1-2}$, the $C_{1-6}$ alkoxy is methoxy.

6. The compound shown in formula I, the pharmaceutically acceptable salt thereof, the tautomer thereof, or the stereoisomer thereof as defined in claim 1, wherein, or, in unsubstituted or $R^{3-3}$ substituted $C_{6-10}$ aryl-fused $C_{3-8}$ cycloalkyl, the $C_{6-10}$ aryl is phenyl;
or, in unsubstituted or $R^{3-3}$ substituted $C_{6-10}$ aryl-fused $C_{3-8}$ cycloalkyl, the $C_{3-8}$ cycloalkyl is cyclopropyl, cyclobutyl, cyclopentyl or cyclohexyl;
or, in $C_{1-6}$ alkyl substituted with one or more halogens, the number of the halogen is 1, 2 or 3;
or, in $C_{1-6}$ alkyl substituted with one or more halogens, the halogens are fluorine, chlorine, bromine or iodine;
or, in $C_{1-6}$ alkyl substituted with one or more halogens, the $C_{1-6}$ alkyl is $C_{1-4}$ alkyl;
or, in unsubstituted or $R^{3-1-1-1}$ substituted 3 to 10 membered heterocycloalkyl with 1 to 3 heteroatoms selected from one or more of N, O and S, the heterocycloalkyl is 5 to 6 membered heterocycloalkyl with 1 or 2 heteroatoms selected from N;
or, in $R^{3-1-1-1}$ the $C_{1-4}$ alkyl is methyl, ethyl, propyl, isopropyl, n-butyl, isobutyl, sec-butyl or tert-butyl;
or, in unsubstituted or $R^{1-1-3}$ substituted 3 to 10 membered heterocycloalkyl with 1 to 3 heteroatoms selected from one or more of N, O and S, the 3 to 10 membered heterocycloalkyl with 1 to 3 heteroatoms selected from one or more of N, O and S is 5 to 6 membered heterocycloalkyl with 1 or 2 heteroatoms selected from N;
or, in $R^{1-1-3}$, the $C_{1-6}$ alkyl is $C_{1-4}$ alkyl.

7. The compound shown in formula I, the pharmaceutically acceptable salt thereof, the tautomer thereof, or the stereoisomer thereof as defined in claim 6, wherein, in $R^{3-3}$ substituted $C_{6-10}$ aryl-fused $C_{3-8}$ cycloalkyl, the number of the $R^{3-3}$ is 1, 2, 3 or 4;
or, in unsubstituted or $R^{3-3}$ substituted $C_{6-10}$ aryl-fused $C_{3-8}$ cycloalkyl, the $C_{3-8}$ cycloalkyl is cyclopentyl;
or, in $C_{1-6}$ alkyl substituted with one or more halogens, the halogens are fluorine;
or, in $C_{1-6}$ alkyl substituted with one or more halogens, the $C_{1-6}$ alkyl is methyl;
or, in unsubstituted or $R^{3-1-1-1}$ substituted 3 to 10 membered heterocycloalkyl with 1 to 3 heteroatoms selected from one or more of N, O and S, the heterocycloalkyl is piperazinyl;
or, in $R^{3-1-1-1}$, the $C_{1-4}$ alkyl is ethyl;
or, in $R^{1-1-3}$ substituted 3 to 10 membered heterocycloalkyl with 1 to 3 heteroatoms selected from one or more of N, O and S, the number of the $R^{1-1-3}$ is 1, 2 or 3;
or, in unsubstituted or $R^{1-1-3}$ substituted 3 to 10 membered heterocycloalkyl with 1 to 3 heteroatoms selected from one or more of N, O and S, the 3 to 10 membered heterocycloalkyl with 1 to 3 heteroatoms selected from one or more of N, O and S is piperidinyl;
or, in $R^{1-1-3}$, the $C_{1-6}$ alkyl is methyl.

8. The compound shown in formula I, the pharmaceutically acceptable salt thereof, the tautomer thereof, or the stereoisomer thereof as defined in claim 1, wherein,
$R^3$ is unsubstituted or $R^{3-1}$ substituted $C_{6-10}$ aryl, or unsubstituted or $R^{3-2}$ substituted 5 to 10 membered heteroaryl with 1 to 4 heteroatoms selected from one or more of N, O and S;
or, $R^{3-1}$ and $R^{3-2}$ are independently hydroxyl, unsubstituted or $R^{3-1-1}$ substituted $C_{1-6}$ alkyl, or unsubstituted or $R^{3-1-4}$ substituted phenyl;
or, $R^{3-1-1}$ and $R^{3-1-4}$ are independently cyano or halogen;
or, $R^1$ is unsubstituted or $R^{1-2}$ substituted 5 to 10 membered heteroaryl with 1 to 4 heteroatoms selected from one or more of N, O and S;
or, $R^{1-1-1}$, $R^{1-1-2}$, $R^{1-1-4}$ and $R^{1-1-5}$ are independently hydroxyl, or $C_{1-6}$ alkyl;
or, when $R^2$ is methyl or ethyl, L is —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, or —NH—CO—NH—CHR$^{4-6}$—;
or, when $R^2$ is isopropyl or cyclopropyl, L is —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, or —NH—CO—NH—CHR$^{4-6}$—.

9. The compound shown in formula I, the pharmaceutically acceptable salt thereof, the tautomer thereof, or the stereoisomer thereof as defined in claim 8, wherein, $R^{3-1}$ and $R^{3-2}$ are independently unsubstituted or $R^{3-1-1}$ substituted $C_{1-6}$ alkyl, or unsubstituted or $R^{3-1-4}$ substituted phenyl;
or, $R^{1-1-1}$, $R^{1-1-2}$, $R^{1-1-4}$ and $R^{1-1-5}$ are independently $C_{1-6}$ alkyl;
or, when $R^2$ is methyl or ethyl, L is —CHR$^{4-2}$—NH—CO—;
or, when $R^2$ is isopropyl or cyclopropyl, L is —CHR$^{4-2}$—NH—CO—.

10. The compound shown in formula I, the pharmaceutically acceptable salt thereof, the tautomer thereof, or the stereoisomer thereof as defined in claim 1, wherein,
$R^{1-2}$ is unsubstituted or $R^{1-1-1}$ substituted $C_{1-6}$ alkyl, unsubstituted or $R^{1-1-2}$ substituted $C_{3-10}$ cycloalkyl, unsubstituted or $R^{1-1-3}$ substituted 3 to 10 membered heterocycloalkyl with 1 to 3 heteroatoms selected from one or more of N and S, or NR$^{1-1-4}$R$^{1-1-5}$;
or, $R^{1-1-1}$, $R^{1-1-2}$, $R^{1-1-3}$, $R^{1-1-4}$ and $R^{1-1-5}$ are independently $C_{1-6}$ alkyl;
or, when the compound shown in formula I contains a chiral C atom, the C atom is in the S configuration or R configuration;
or, when L is —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH— or —NH—CO—NH—CHR$^{4-6}$—, the —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH— or —NH—CO—NH—CHR$^{4-6}$— is

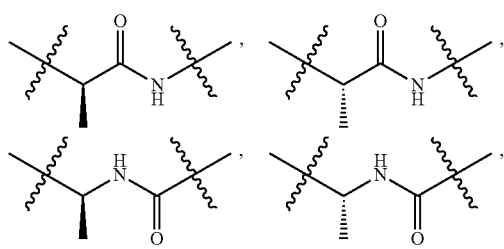

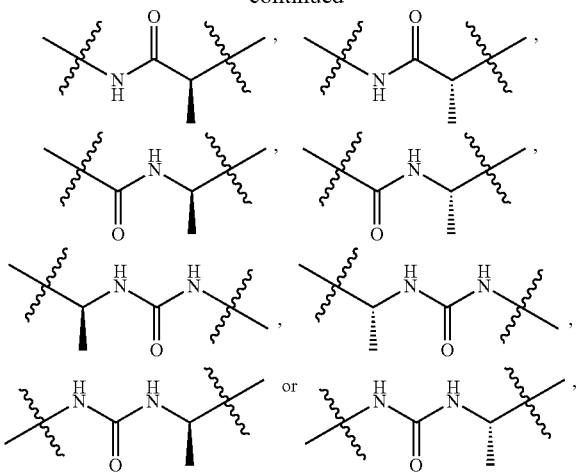

11. The compound shown in formula I, the pharmaceutically acceptable salt thereof, the tautomer thereof, or the stereoisomer thereof as defined in claim 10, wherein, when L is —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH— or —NH—CO—NH—CHR$^{4-6}$—, the —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH— or —NH—CO—NH—CHR$^{4-6}$— is

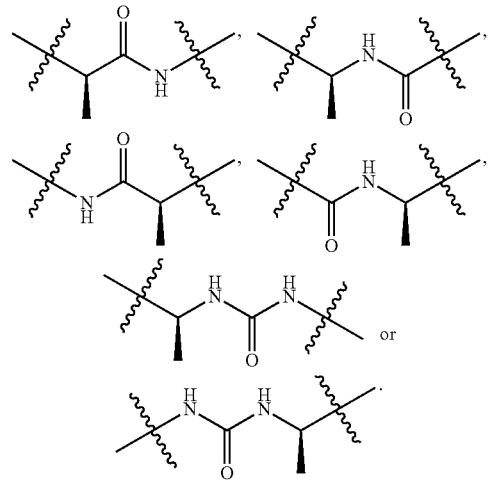

12. The compound shown in formula I, the pharmaceutically acceptable salt thereof, the tautomer thereof, or the stereoisomer thereof as defined in claim 1, wherein, the compound shown in formula I is any one of the following:
i) X is hydrogen;
$R^3$ is unsubstituted or $R^{3-1}$ substituted $C_{6-10}$ aryl, or unsubstituted or $R^{3-2}$ substituted 5 to 10 membered heteroaryl with 1 to 4 heteroatoms selected from one or more of N, O and S;
$R^{3-1}$ and $R^{3-2}$ are independently hydroxyl, unsubstituted or $R^{3-1-1}$ substituted $C_{1-6}$ alkyl, or unsubstituted or $R^{3-1-4}$ substituted $C_{6-10}$ aryl;
$R^{3-1-1}$ and $R^{3-1-4}$ are independently cyano or halogen;
$R^{1-1}$ and $R^{1-2}$ are independently unsubstituted or $R^{1-1-1}$ substituted $C_{1-6}$ alkyl, $C_{1-6}$ alkoxy, unsubstituted or $R^{1-1-2}$ substituted $C_{3-10}$ cycloalkyl, or NR$^{1-1-4}$R$^{1-1-5}$;

$R^{1-1-1}$, $R^{1-1-2}$, $R^{1-1-4}$ and $R^{1-1-5}$ are independently hydroxyl, or $C_{1-6}$ alkyl;

when $R^2$ is methyl or ethyl, then L is —NH—CO—NH—, —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, —NH—CO—NH—CHR$^{4-6}$—, or —CO—NH—CR$^{4-7}$R$^{4-8}$—;

when $R^2$ is isopropyl or cyclopropyl, then L is —CO—NH—, —NH—CO—, —NH—CO—NH—, —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, —NH—CO—NH—CHR$^{4-6}$—, or —CO—NH—CR$^{4-7}$R$^{4-8}$—;

$R^{4-1}$, $R^{4-2}$, $R^{4-3}$, $R^{4-4}$, $R^{4-5}$, $R^{4-6}$, $R^{4-7}$ and $R^{4-8}$ are independently hydrogen, $C_{1-4}$ alkyl, or $R^{4-7}$ and $R^{4-8}$ together with the carbon atom therebetween form $C_{3-6}$ cycloalkyl;

ii) X is hydrogen;

$R^3$ is unsubstituted or $R^{3-1}$ substituted $C_{6-10}$ aryl, or unsubstituted or $R^{3-2}$ substituted 5 to 10 membered heteroaryl with 1 to 4 heteroatoms selected from one or more of N, O and S;

$R^{3-1}$ and $R^{3-2}$ are independently hydroxyl, unsubstituted or $R^{3-1-1}$ substituted $C_{1-6}$ alkyl, or $R^{3-1-4}$ substituted $C_{6-10}$ aryl;

$R^{3-1-1}$ and $R^{3-1-4}$ are independently cyano or halogen;

$R^1$ is unsubstituted or $R^{1-2}$ substituted 5 to 10 membered heteroaryl with 1 to 3 heteroatoms selected from one or more of N, O and S;

$R^{1-2}$ is unsubstituted or $R^{1-1-1}$ substituted $C_{1-6}$ alkyl, $C_{1-6}$ alkoxy, unsubstituted or $R^{1-1-2}$ substituted $C_{3-10}$ cycloalkyl, or NR$^{1-1-4}$R$^{1-1-5}$;

$R^{1-1-1}$, $R^{1-1-2}$, $R^{1-1-4}$ and $R^{1-1-5}$ are independently hydroxyl, or $C_{1-6}$ alkyl;

when $R^2$ is methyl or ethyl, then L is —NH—CO—NH—, —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, —NH—CO—NH—CHR$^{4-6}$—, or —CO—NH—CR$^{4-7}$R$^{4-8}$—;

when $R^2$ is isopropyl or cyclopropyl, then L is —CO—NH—, —NH—CO—, —NH—CO—NH—, —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, —NH—CO—NH—CHR$^{4-6}$—, or —CO—NH—CR$^{4-7}$R$^{4-8}$—;

$R^{4-1}$, $R^{4-2}$, $R^{4-3}$, $R^{4-4}$, $R^{4-5}$, $R^{4-6}$, $R^{4-7}$ and $R^{4-8}$ are independently hydrogen, $C_{1-4}$ alkyl, or $R^{4-7}$ and $R^{4-8}$ together with the carbon atom therebetween form $C_{3-6}$ cycloalkyl;

iii) X is hydrogen;

$R^3$ is unsubstituted or $R^{3-1}$ substituted $C_{6-10}$ aryl, or unsubstituted or $R^{3-2}$ substituted 5 to 10 membered heteroaryl with 1 to 4 heteroatoms selected from one or more of N, O and S;

$R^{3-1}$ and $R^{3-2}$ are independently hydroxyl, unsubstituted or $R^{3-1-1}$ substituted $C_{1-6}$ alkyl, or $R^{3-1-4}$ substituted $C_{6-10}$ aryl;

$R^{3-1-1}$ and $R^{3-1-4}$ are independently cyano or halogen;

$R^{1-1}$ and $R^{1-2}$ are independently unsubstituted or $R^{1-1-1}$ substituted $C_{1-6}$ alkyl, $C_{1-6}$ alkoxy, unsubstituted or $R^{1-1-2}$ substituted $C_{3-10}$ cycloalkyl, or NR$^{1-1-4}$R$^{1-1-5}$;

$R^{1-1-1}$, $R^{1-1-2}$, $R^{1-1-4}$ and $R^{1-1-5}$ are independently hydroxyl, or $C_{1-6}$ alkyl;

when $R^2$ is methyl or ethyl, then L is —CHR$^{4-2}$—NH—CO—;

when $R^2$ is isopropyl or cyclopropyl, then L is —CHR$^{4-2}$—NH—CO—;

$R^{4-2}$ is hydrogen or $C_{1-4}$ alkyl;

iv) X is hydrogen;

$R^3$ is unsubstituted or $R^{3-1}$ substituted $C_{6-10}$ aryl, or unsubstituted or $R^{3-2}$ substituted 5 to 10 membered heteroaryl with 1 to 4 heteroatoms selected from one or more of N, O and S;

$R^{3-1}$ and $R^{3-2}$ are independently hydroxyl, unsubstituted or $R^{3-1-1}$ substituted $C_{1-6}$ alkyl, or unsubstituted or $R^{3-1-4}$ substituted $C_{6-10}$ aryl;

$R^{3-1-1}$ and $R^{3-1-4}$ are independently cyano or halogen;

$R^1$ is unsubstituted or $R^{1-1}$ substituted $C_{6-10}$ aryl, or unsubstituted or $R^{1-2}$ substituted 5 to 10 membered heteroaryl with 1 to 3 heteroatoms selected from one or more of N, O and S;

$R^{1-1}$ and $R^{1-2}$ are independently unsubstituted or $R^{1-1-1}$ substituted $C_{1-6}$ alkyl, $C_{1-6}$ alkoxy, unsubstituted or $R^{1-1-2}$ substituted $C_{3-10}$ cycloalkyl, or NR$^{1-1-4}$R$^{1-1-5}$;

$R^{1-1-1}$, $R^{1-1-2}$, $R^{1-1-4}$ and $R^{1-1-5}$ are independently hydroxyl, or $C_{1-6}$ alkyl;

$R^2$ is cyclopropyl;

L is —CO—NH—, —NH—CO—, —NH—CO—NH—, —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, —NH—CO—NH—CHR$^{4-6}$—, or —CO—NH—CR$^{4-7}$R$^{4-8}$—;

$R^{4-1}$, $R^{4-2}$, $R^{4-3}$, $R^{4-4}$, $R^{4-5}$, $R^{4-6}$, $R^{4-7}$ and $R^{4-8}$ are independently hydrogen, $C_{1-4}$ alkyl, or $R^{4-7}$ and $R^{4-8}$ together with the carbon atom therebetween form $C_{3-6}$ cycloalkyl;

v) X is hydrogen;

$R^3$ is unsubstituted or $R^{3-1}$ substituted $C_{6-10}$ aryl, or unsubstituted or $R^{3-2}$ substituted 5 to 10 membered heteroaryl with 1 to 4 heteroatoms selected from one or more of N, O and S;

$R^{3-1}$ and $R^{3-2}$ are independently hydroxyl, unsubstituted or $R^{3-1-1}$ substituted $C_{1-6}$ alkyl, or unsubstituted or $R^{3-1-4}$ substituted $C_{6-10}$ aryl;

$R^{3-1-1}$ and $R^{3-1-4}$ are independently cyano or halogen;

$R^1$ is unsubstituted or $R^{1-1}$ substituted $C_{6-10}$ aryl, or unsubstituted or $R^{1-2}$ substituted 5 to 10 membered heteroaryl with 1 to 3 heteroatoms selected from one or more of N, O and S;

$R^{1-1}$ and $R^{1-2}$ are independently unsubstituted or $R^{1-1-1}$ substituted $C_{1-6}$ alkyl, $C_{1-6}$ alkoxy, unsubstituted or $R^{1-1-2}$ substituted $C_{3-10}$ cycloalkyl, or NR$^{1-1-4}$R$^{1-1-5}$;

$R^{1-1-1}$, $R^{1-1-2}$, $R^{1-1-4}$ and $R^{1-1-5}$ are independently hydroxyl, or $C_{1-6}$ alkyl;

$R^2$ is isopropyl;

L is —CO—NH—, —NH—CO—, —NH—CO—NH—, —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, —NH—CO—NH—CHR$^{4-6}$—, or —CO—NH—CR$^{4-7}$R$^{4-8}$—;

$R^{4-1}$, $R^{4-2}$, $R^{4-3}$, $R^{4-4}$, $R^{4-5}$, $R^{4-6}$, $R^{4-7}$ and $R^{4-8}$ are independently hydrogen, $C_{1-4}$ alkyl, or $R^{4-7}$ and $R^{4-8}$ together with the carbon atom therebetween form $C_{3-6}$ cycloalkyl;

vi) X is hydrogen;

$R^3$ is unsubstituted or $R^{3-1}$ substituted $C_{6-10}$ aryl, or unsubstituted or $R^{3-2}$ substituted 5 to 10 membered heteroaryl with 1 to 4 heteroatoms selected from one or more of N, O and S;

$R^{3-1}$ and $R^{3-2}$ are independently unsubstituted or $R^{3-1-1}$ substituted $C_{1-6}$ alkyl, or unsubstituted or $R^{3-1-4}$ substituted $C_{6-10}$ aryl;

133

$R^{3-1-1}$ and $R^{3-1-4}$ are independently cyano or halogen;

$R^1$ is unsubstituted or $R^{1-2}$ substituted 5 to 10 membered heteroaryl with 1 to 3 heteroatoms selected from one or more of N, O and S;

$R^{1-2}$ is independently unsubstituted or $R^{1-1-1}$ substituted $C_{1-6}$ alkyl, unsubstituted or $R^{1-1-2}$ substituted $C_{3-10}$ cycloalkyl, or $NR^{1-1-4}R^{1-1-5}$;

$R^{1-1-1}$, $R^{1-1-2}$, $R^{1-1-4}$ and $R^{1-1-5}$ are independently $C_{1-6}$ alkyl;

when $R^2$ is methyl or ethyl, then L is —NH—CO—NH—, —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, —NH—CO—NH—CHR$^{4-6}$—, or —CO—NH—CR$^{4-7}$R$^{4-8}$—;

when $R^2$ is isopropyl or cyclopropyl, then L is —CO—NH—, —NH—CO—, —NH—CO—NH—, —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, —NH—CO—NH—CHR$^{4-6}$—, or —CO—NH—CR$^{4-7}$R$^{4-8}$—;

$R^{4-1}$, $R^{4-2}$, $R^{4-3}$, $R^{4-4}$, $R^{4-5}$, $R^{4-6}$, $R^{4-7}$ and $R^{4-8}$ are independently hydrogen, $C_{1-4}$ alkyl, or $R^{4-7}$ and $R^{4-8}$ together with the carbon atom attached thereto form $C_{3-6}$ cycloalkyl;

vii) X is hydrogen;

$R^3$ is unsubstituted or $R^{3-1}$ substituted $C_{6-10}$ aryl, or unsubstituted or $R^{3-2}$ substituted 5 to 10 membered heteroaryl with 1 to 4 heteroatoms selected from one or more of N, O and S;

$R^{3-1}$ and $R^{3-2}$ are independently unsubstituted or $R^{3-1-1}$ substituted $C_{1-6}$ alkyl, or unsubstituted or $R^{3-1-4}$ substituted $C_{6-10}$ aryl;

$R^{3-1-1}$ and $R^{3-1-4}$ are independently cyano or halogen;

$R^1$ is unsubstituted or $R^{1-2}$ substituted 5 to 10 membered heteroaryl with 1 to 3 heteroatoms selected from one or more of N, O and S;

$R^{1-2}$ is independently unsubstituted or $R^{1-1-1}$ substituted $C_{1-6}$ alkyl, unsubstituted or $R^{1-1-2}$ substituted $C_{3-10}$ cycloalkyl, or $NR^{1-1-4}R^{1-1-5}$;

$R^{1-1-1}$, $R^{1-1-2}$, $R^{1-1-4}$ and $R^{1-1-5}$ are independently $C_{1-6}$ alkyl;

$R^2$ is isopropyl or cyclopropyl;

L is —CO—NH—, —NH—CO—, —NH—CO—NH—, —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, —NH—CO—NH—CHR$^{4-6}$—, or —CO—NH—CR$^{4-7}$R$^{4-8}$—;

$R^{4-1}$, $R^{4-2}$, $R^{4-3}$, $R^{4-4}$, $R^{4-5}$, $R^{4-6}$, $R^{4-7}$ and $R^{4-8}$ are independently hydrogen, $C_{1-4}$ alkyl, or $R^{4-7}$ and $R^{4-8}$ together with the carbon atom therebetween form $C_{3-6}$ cycloalkyl; and viii) X is hydrogen;

$R^3$ is unsubstituted or $R^{3-1}$ substituted $C_{6-10}$ aryl, or unsubstituted or $R^{3-2}$ substituted 5 to 10 membered heteroaryl with 1 to 4 heteroatoms selected from one or more of N, O and S;

$R^{3-1}$ and $R^{3-2}$ are independently unsubstituted or $R^{3-1-1}$ substituted $C_{1-6}$ alkyl, or unsubstituted or $R^{3-1-4}$ substituted $C_{6-10}$ aryl;

$R^{3-1-1}$ and $R^{3-1-4}$ are independently cyano or halogen;

$R^1$ is unsubstituted or $R^{1-2}$ substituted 5 to 10 membered heteroaryl with 1 to 3 heteroatoms selected from one or more of N, O and S;

$R^{1-2}$ is independently unsubstituted or $R^{1-1-1}$ substituted $C_{1-6}$ alkyl, unsubstituted or $R^{1-1-2}$ substituted $C_{3-10}$ cycloalkyl, or $NR^{1-1-4}R^{1-1-5}$;

134

$R^{1-1-1}$, $R^{1-1-2}$, $R^{1-1-4}$ and $R^{1-1-5}$ are independently $C_{1-6}$ alkyl;

when $R^2$ is methyl or ethyl, then L is —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, or —NH—CO—NH—CHR$^{4-6}$—;

when $R^2$ is isopropyl or cyclopropyl, then L is —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, or —NH—CO—NH—CHR$^{4-6}$—;

$R^{4-1}$, $R^{4-2}$, $R^{4-3}$, $R^{4-4}$, $R^{4-5}$ and $R^{4-6}$ are independently hydrogen or $C_{1-4}$ alkyl.

13. The compound shown in formula I, the pharmaceutically acceptable salt thereof, the tautomer thereof, or the stereoisomer thereof as defined in claim 1, wherein, the compound shown in formula I is any one of the following:

i) X is hydrogen;

$R^3$ is unsubstituted or $R^{3-1}$ substituted $C_{6-10}$ aryl, unsubstituted or $R^{3-2}$ substituted 5 to 10 membered heteroaryl with 1 to 4 heteroatoms selected from one or more of N, O and S, or unsubstituted or $R^{3-3}$ substituted $C_{6-10}$ aryl-fused $C_{3-8}$ cycloalkyl;

$R^{3-1}$ and $R^{3-2}$ are independently unsubstituted or $R^{3-1-1}$ substituted $C_{1-6}$ alkyl, or unsubstituted or $R^{3-1-4}$ substituted $C_{6-10}$ aryl;

$R^{3-3}$ is hydrogen or $C_{1-6}$ alkyl substituted with one or more halogens;

$R^{3-1-1}$ and $R^{3-1-4}$ are independently cyano, halogen, or unsubstituted or $R^{3-1-1-1}$ substituted 3 to 10 membered heterocycloalkyl with 1 to 3 heteroatoms selected from one or more of N, O and S;

$R^{3-1-1-1}$ is $C_{1-4}$ alkyl;

$R^1$ is unsubstituted or $R^{1-2}$ substituted 5 to 10 membered heteroaryl with 1 to 3 heteroatoms selected from one or more of N, O and S;

$R^{1-2}$ is unsubstituted or $R^{1-1-1}$ substituted $C_{1-6}$ alkyl, unsubstituted or $R^{1-1-2}$ substituted $C_{3-10}$ cycloalkyl, unsubstituted or $R^{1-1-3}$ substituted 3 to 10 membered heterocycloalkyl with 1 to 3 heteroatoms selected from one or more of N, O and S, or $NR^{1-1-4}R^{1-1-5}$;

$R^{1-1-1}$, $R^{1-1-2}$, $R^{1-1-3}$, $R^{1-1-4}$ and $R^{1-1-5}$ are independently $C_{1-6}$ alkyl;

when $R^2$ is methyl or ethyl, then L is —NH—CO—NH—, —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, —NH—CO—NH—CHR$^{4-6}$—, or —CO—NH—CR$^{4-7}$R$^{4-8}$—;

when $R^2$ is isopropyl or cyclopropyl, then L is —CO—NH—, —NH—CO—, —NH—CO—NH—, —CHR$^{4-1}$—CO—NH—, —CHR$^{4-2}$—NH—CO—, —NH—CO—CHR$^{4-3}$—, —CO—NH—CHR$^{4-4}$—, —CHR$^{4-5}$—NH—CO—NH—, —NH—CO—NH—CHR$^{4-6}$—, or —CO—NH—CR$^{4-7}$R$^{4-8}$—;

$R^{4-1}$, $R^{4-2}$, $R^{4-3}$, $R^{4-4}$, $R^{4-5}$, $R^{4-6}$, $R^{4-7}$ and $R^{4-8}$ are independently hydrogen, $C_{1-4}$ alkyl, or $R^{4-7}$ and $R^{4-8}$ together with the carbon atom attached thereto form $C_{3-6}$ cycloalkyl;

ii) X is hydrogen;

$R^3$ is unsubstituted or $R^{3-1}$ substituted $C_{6-10}$ aryl, or unsubstituted or $R^{3-2}$ substituted 5 to 10 membered heteroaryl with 1 to 4 heteroatoms selected from one or more of N, O and S, or unsubstituted or $R^{3-3}$ substituted $C_{6-10}$ aryl-fused $C_{3-8}$ cycloalkyl;

$R^{3-1}$ and $R^{3-2}$ are independently unsubstituted or $R^{3-1-1}$ substituted $C_{1-6}$ alkyl, or unsubstituted or $R^{3-1-4}$ substituted $C_{6-10}$ aryl;

$R^{3-3}$ is hydrogen or $C_{1-6}$ alkyl substituted with one or more halogens;

$R^{3-1-1}$ and $R^{3-1-4}$ are independently cyano, halogen, or unsubstituted or $R^{3-1-1-1}$ substituted 3 to 10 membered heterocycloalkyl with 1 to 3 heteroatoms selected from one or more of N, O and S;

$R^{3-1-1-1}$ is $C_{1-4}$ alkyl;

$R^1$ is unsubstituted or $R^{1-2}$ substituted 5 to 10 membered heteroaryl with 1 to 3 heteroatoms selected from one or more of N, O and S;

$R^{1-2}$ is independently unsubstituted or $R^{1-1-1}$ substituted $C_{1-6}$ alkyl, unsubstituted or $R^{1-1-2}$ substituted $C_{3-10}$ cycloalkyl, unsubstituted or $R^{1-1-3}$ substituted 3 to 10 membered heterocycloalkyl with 1 to 3 heteroatoms selected from one or more of N, O and S, or $NR^{1-1-4}R^{1-1-5}$;

$R^{1-1-1}$, $R^{1-1-2}$, $R^{1-1-3}$, $R^{1-1-4}$ and $R^{1-1-5}$ are independently $C_{1-6}$ alkyl;

$R^2$ is isopropyl or cyclopropyl;

L is —CO—NH—, —NH—CO—, —NH—CO—NH—, —$CHR^{4-1}$—CO—NH—, —$CHR^{4-2}$—NH—CO—, —NH—CO—$CHR^{4-3}$—, —CO—NH—$CHR^{4-4}$—, —$CHR^{4-5}$—NH—CO—NH—, —NH—CO—NH—$CHR^{4-6}$—, or —CO—NH—$CR^{4-7}R^{4-8}$—;

$R^{4-1}$, $R^{4-2}$, $R^{4-3}$, $R^{4-4}$, $R^{4-5}$, $R^{4-6}$, $R^{4-7}$ and $R^{4-8}$ are independently hydrogen, $C_{1-4}$ alkyl, or $R^{4-7}$ and $R^{4-8}$ together with the carbon atom therebetween form $C_{3-6}$ cycloalkyl;

iii) X is hydrogen;

$R^3$ is unsubstituted or $R^{3-1}$ substituted $C_{6-10}$ aryl, or unsubstituted or $R^{3-2}$ substituted 5 to 10 membered heteroaryl with 1 to 4 heteroatoms selected from one or more of N, O and S;

$R^{3-1}$ and $R^{3-2}$ are independently unsubstituted or $R^{3-1-1}$ substituted $C_{1-6}$ alkyl, or unsubstituted or $R^{3-1-4}$ substituted $C_{6-10}$ aryl;

$R^{3-1-1}$ and $R^{3-1-4}$ are independently cyano, halogen, or unsubstituted or $R^{3-1-1-1}$ substituted 3 to 10 membered heterocycloalkyl with 1 to 3 heteroatoms selected from one or more of N, O and S;

$R^{3-1-1-1}$ is $C_{1-4}$ alkyl;

$R^1$ is unsubstituted or $R^{1-2}$ substituted 5 to 10 membered heteroaryl with 1 to 3 heteroatoms selected from one or more of N, O and S;

$R^{1-2}$ is independently unsubstituted or $R^{1-1-1}$ substituted $C_{1-6}$ alkyl, unsubstituted or $R^{1-1-2}$ substituted $C_{3-10}$ cycloalkyl, unsubstituted or $R^{1-1-3}$ substituted 3 to 10 membered heterocycloalkyl with 1 to 3 heteroatoms selected from one or more of N, O and S, or $NR^{1-1-4}R^{1-1-5}$;

$R^{1-1-1}$, $R^{1-1-2}$, $R^{1-1-3}$, $R^{1-1-4}$ and $R^{1-1-5}$ are independently $C_{1-6}$ alkyl;

when $R^2$ is methyl or ethyl, then L is —$CHR^{4-1}$—CO—NH—, —$CHR^{4-2}$—NH—CO—, —NH—CO—$CHR^{4-3}$—, —CO—NH—$CHR^{4-4}$—, —$CHR^{4-5}$—NH—CO—NH—, or —NH—CO—NH—$CHR^{4-6}$—;

when $R^2$ is isopropyl or cyclopropyl, then L is —$CHR^{4-1}$—CO—NH—, —$CHR^{4-2}$—NH—CO—, —NH—CO—$CHR^{4-3}$—, —CO—NH—$CHR^{4-4}$—, —$CHR^{4-5}$—NH—CO—NH—, or —NH—CO—NH—$CHR^{4-6}$—;

$R^{4-1}$, $R^{4-2}$, $R^{4-3}$, $R^{4-4}$, $R^{4-5}$ and $R^{4-6}$ are independently hydrogen or $C_{1-4}$ alkyl;

iv) X is hydrogen;

$R^3$ is unsubstituted or $R^{3-1}$ substituted $C_{6-10}$ aryl, or unsubstituted or $R^{3-2}$ substituted 5 to 10 membered heteroaryl with 1 to 4 heteroatoms selected from one or more of N, O and S;

$R^{3-1}$ and $R^{3-2}$ are independently unsubstituted or $R^{3-1-1}$ substituted $C_{1-6}$ alkyl, or unsubstituted or $R^{3-1-4}$ substituted $C_{6-10}$ aryl;

$R^{3-1-1}$ and $R^{3-1-4}$ are independently cyano or halogen;

$R^1$ is unsubstituted or $R^{1-2}$ substituted 5 to 10 membered heteroaryl with 1 to 3 heteroatoms selected from one or more of N, O and S;

$R^{1-2}$ is independently unsubstituted or $R^{1-1-1}$ substituted $C_{1-6}$ alkyl, unsubstituted or $R^{1-1-3}$ substituted 3 to 10 membered heterocycloalkyl with 1 to 3 heteroatoms selected from one or more of N, O and S, or unsubstituted or $R^{1-1-2}$ substituted $C_{3-10}$ cycloalkyl;

$R^{1-1-1}$, $R^{1-1-2}$ and $R^{1-1-3}$ are independently $C_{1-6}$ alkyl;

when $R^2$ is methyl, then L is —NH—CO—NH—, —$CHR^{4-1}$—CO—NH—, —$CHR^{4-2}$—NH—CO—, —NH—CO—$CHR^{4-3}$—, —CO—NH—$CHR^{4-4}$— or —$CHR^{4-5}$—NH—CO—NH—;

when $R^2$ is isopropyl or cyclopropyl, then L is —CO—NH—, —NH—CO—$CHR^{4-3}$—, —$CHR^{4-5}$—NH—CO—NH— or —CO—NH—$CR^{4-7}R^{4-8}$—;

$R^{4-1}$, $R^{4-2}$, $R^{4-3}$, $R^{4-4}$, $R^{4-5}$, $R^{4-6}$, $R^{4-7}$ and $R^{4-8}$ are independently hydrogen, $C_{1-4}$ alkyl, or $R^{4-7}$ and $R^{4-8}$ together with the carbon atom therebetween form $C_{3-6}$ cycloalkyl;

v) $R^1$ is unsubstituted or $R^{1-2}$ substituted 5 to 10 membered heteroaryl with 1 to 3 heteroatoms selected from one or more of N, O and S;

vi) $R^2$ is cyclopropyl; and vii) $R^2$ is isopropyl.

14. A compound, a pharmaceutically acceptable salt thereof, a tautomer thereof, or a stereoisomer thereof, wherein, the compound is any one of the following compounds:

S1

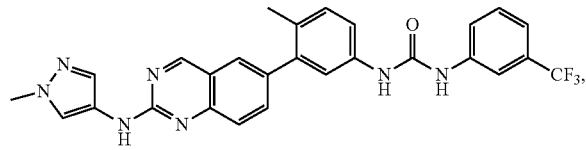

S2

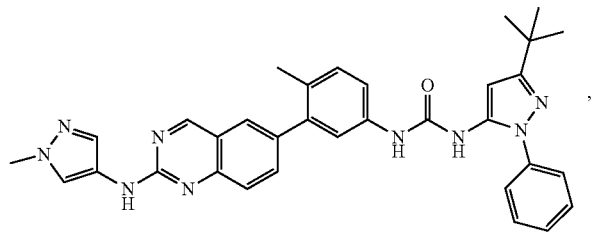

S4
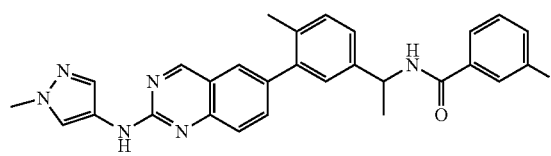
S5
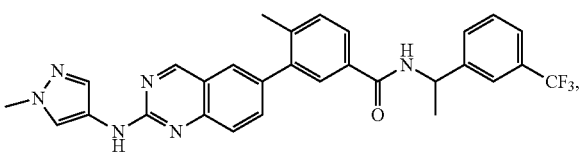
S6
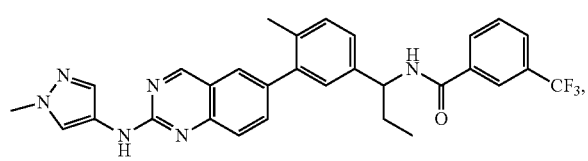
S7
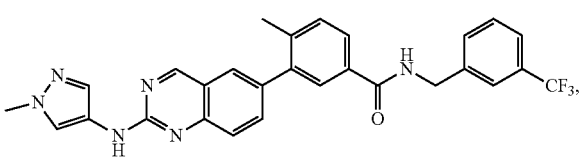
S8
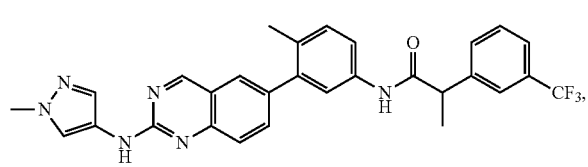
S9
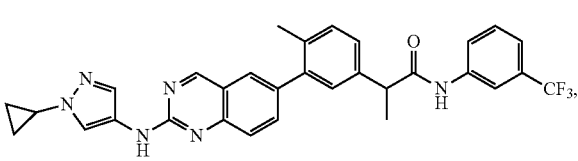
S10
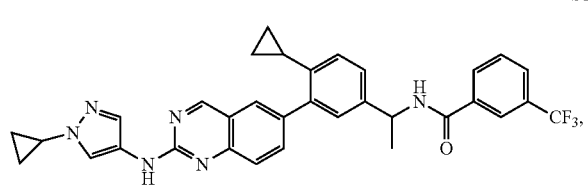
S11
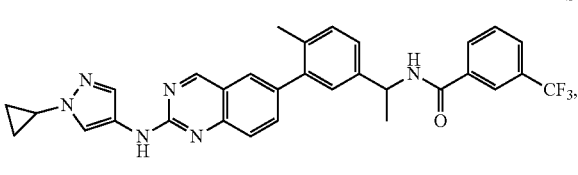
S12
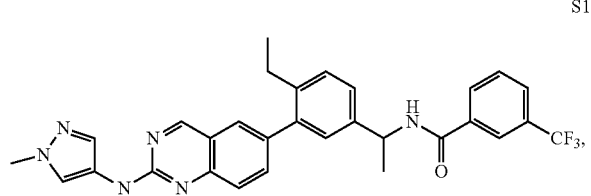
S13
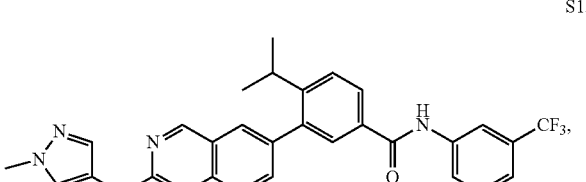
S14
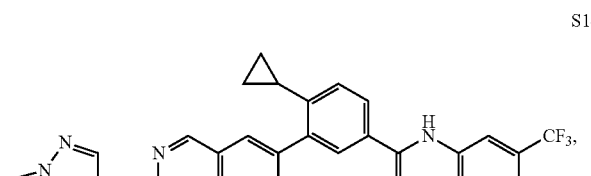
S15
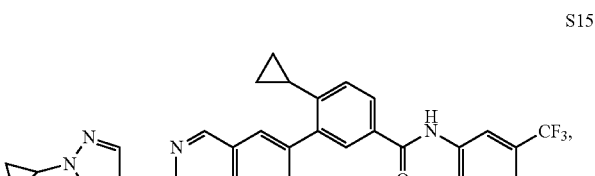
S16
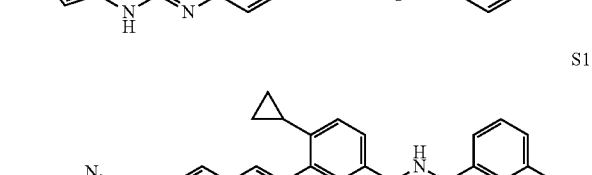
S17
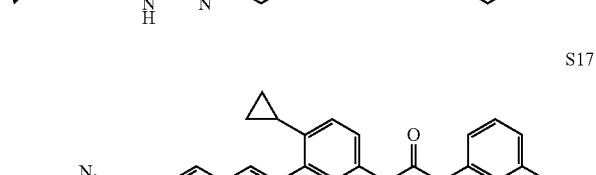
S18
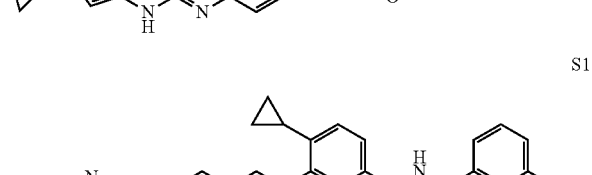
S19
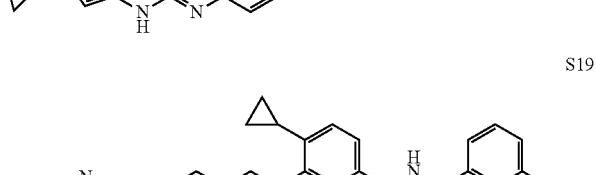

-continued
S20
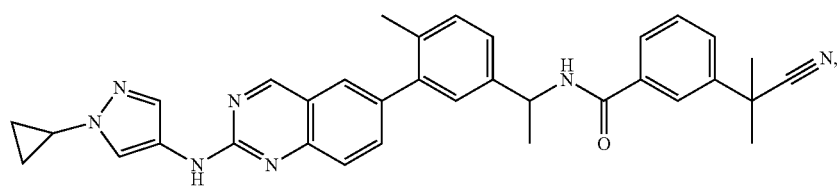
S21
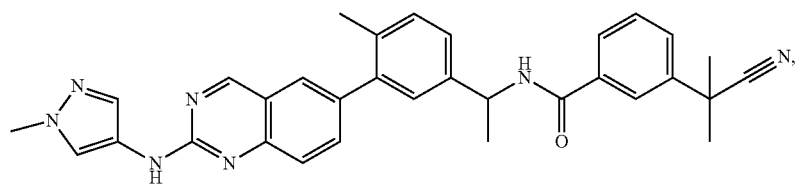
S22 S23
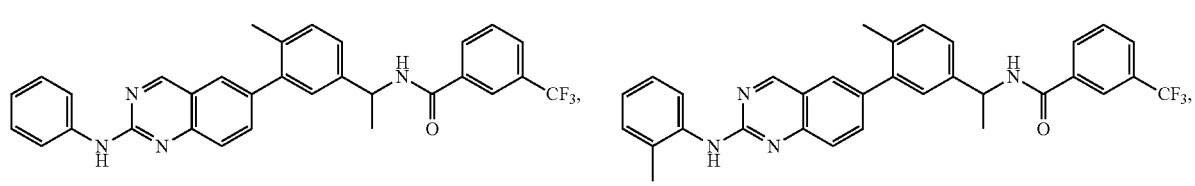
S24 S25
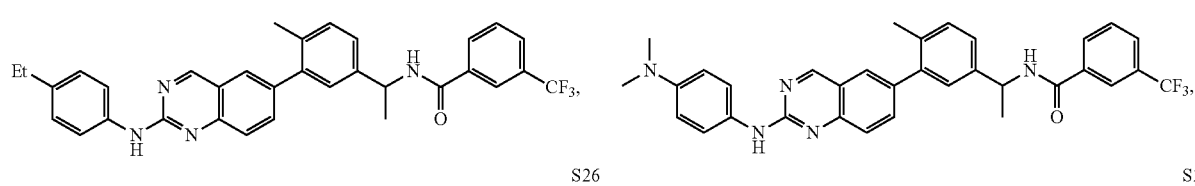
S26 S27
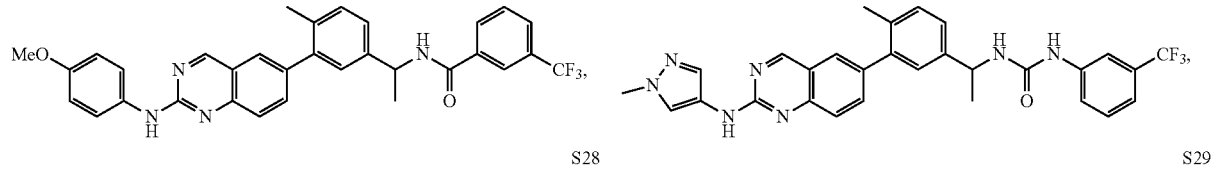
S28 S29
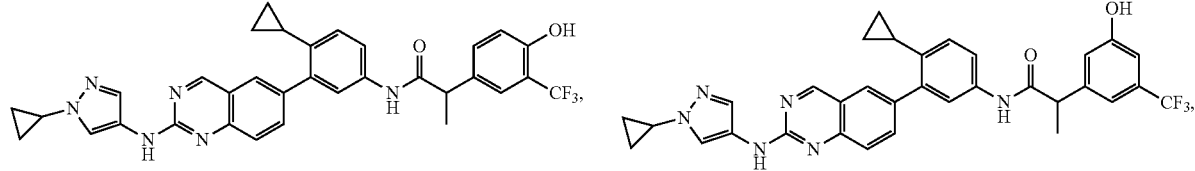
S30 S31
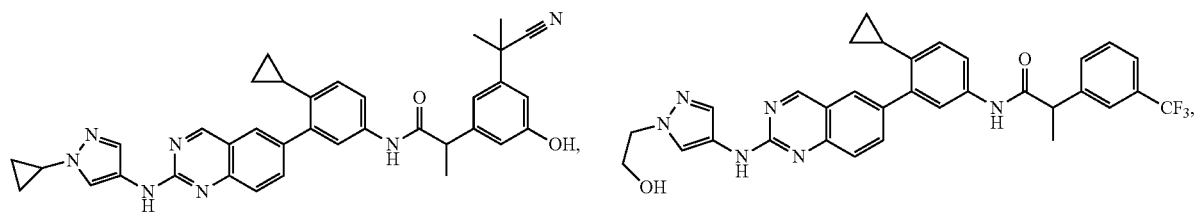
S32
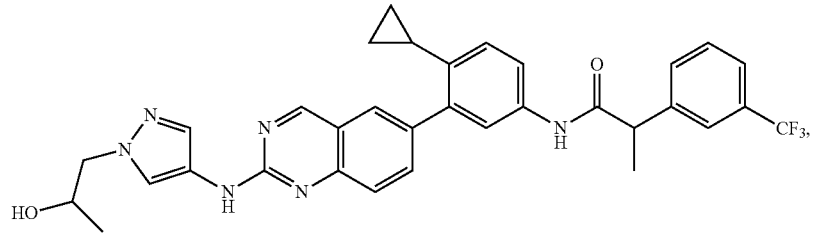

-continued
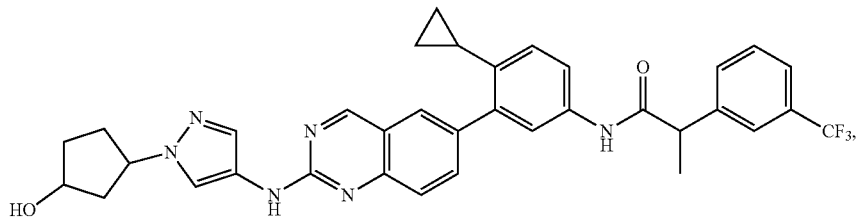
S33
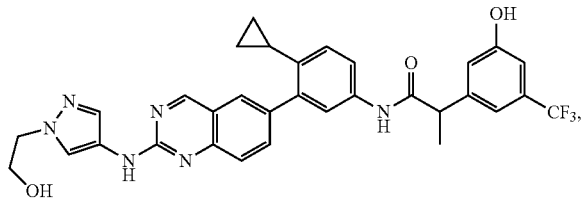
S34
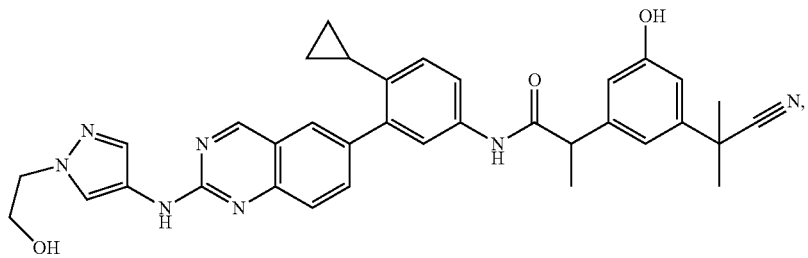
S35
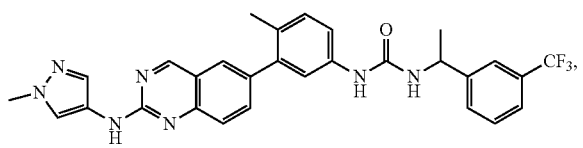
S36
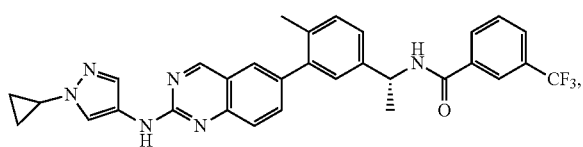
S11-A
S11-B
S37
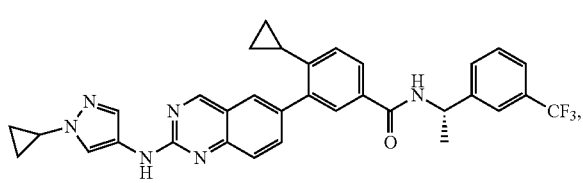
S38
S39
S40
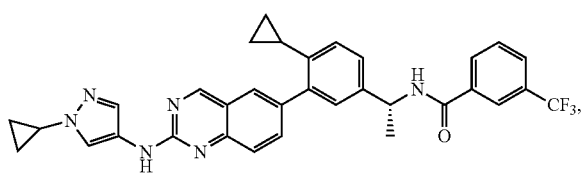

S41
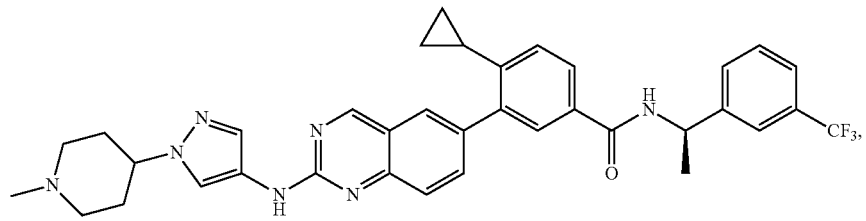
S42
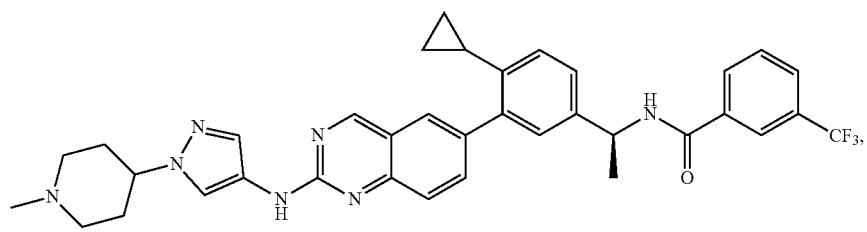
S43
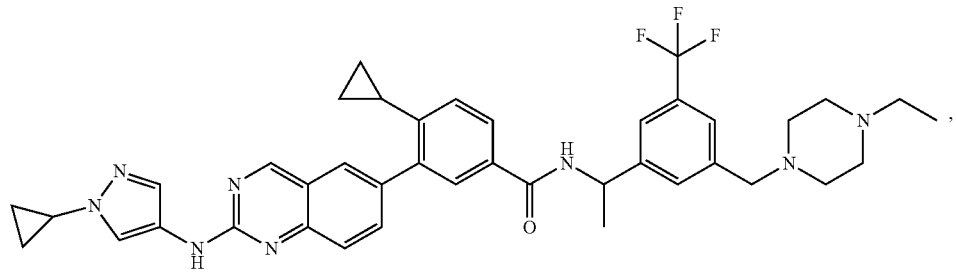
S44
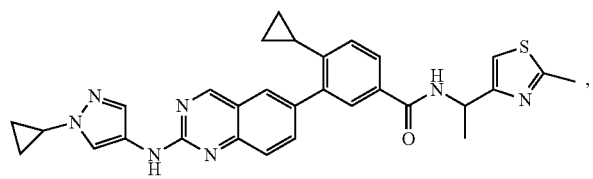
S45
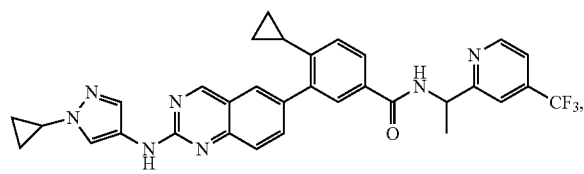
and
S46
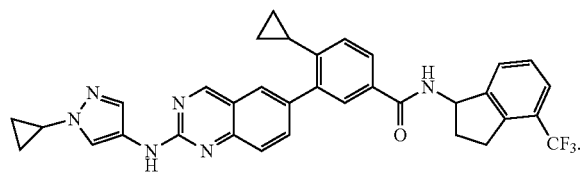

15. A method for preparing the compound shown in formula I as defined in claim 1, wherein, the method comprises the following step: in a solvent, under the action of a base and a palladium catalyst, a compound shown in formula II and a compound shown in formula III are subjected to the coupling reaction shown below;

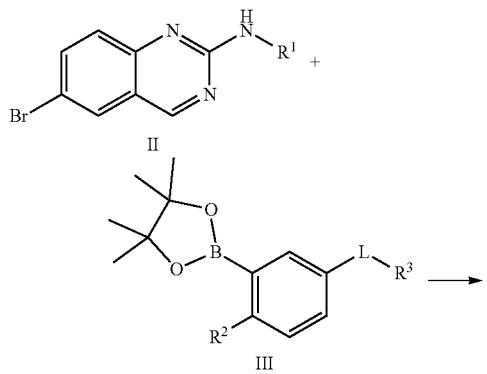

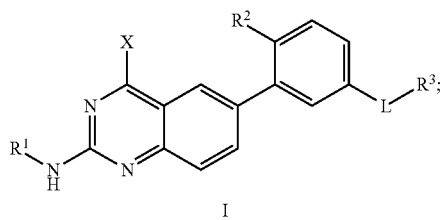

wherein, X, L, $R^1$, $R^2$ and $R^3$ are as defined in claim 1.

16. A pharmaceutical composition comprising the compound shown in formula I, the pharmaceutically acceptable salt thereof, the tautomer thereof, or the stereoisomer thereof as defined in claim 1, and pharmaceutical excipients.

* * * * *